United States Patent

Müller et al.

Patent Number: 5,814,633
Date of Patent: Sep. 29, 1998

[54] IMINOOXYMETHYLENE ANILIDES, PROCESS FOR PREPARING THE SAME AND THEIR USE

[75] Inventors: Bernd Müller, Frankenthal; Hubert Sauter, Mannheim; Franz Röhl, Schifferstadt; Eberhard Ammermann, Heppenheim; Gisela Lorenz, Hambach; Norbert Götz, Worms, all of Germany

[73] Assignee: BASF Aktiengesellschaft, Ludwigshafen, Germany

[21] Appl. No.: 849,087

[22] PCT Filed: Nov. 10, 1995

[86] PCT No.: PCT/EP95/04430

§ 371 Date: May 20, 1997

§ 102(e) Date: May 20, 1997

[87] PCT Pub. No.: WO96/16044

PCT Pub. Date: May 30, 1996

[30] Foreign Application Priority Data

Nov. 23, 1994 [DE] Germany .......... 44 41 676.8

[51] Int. Cl.[6] .............. C07D 239/32; C07D 213/84; A01N 43/48; A01N 43/64

[52] U.S. Cl. .......... 514/241; 514/242; 514/247; 514/255; 514/256; 514/261; 514/307; 514/311; 514/357; 514/411; 544/182; 544/215; 544/238; 544/277; 544/335; 544/358; 546/145; 546/175; 546/336; 548/505

[58] Field of Search .................. 544/182, 215, 544/238, 277, 335, 358; 546/145, 175, 336; 548/505; 514/241, 242, 247, 255, 256, 261, 307, 311, 357, 411

[56] References Cited

U.S. PATENT DOCUMENTS 5,342,837 8/1994 Clough et al. .......... 548/505

FOREIGN PATENT DOCUMENTS 2120163 10/1994 Canada .
619 301 10/1994 European Pat. Off. .
92/13830 8/1992 WIPO .
93/15046 8/1993 WIPO .

OTHER PUBLICATIONS

Derwent Abst. J 5 3116–378.
Synthesis of a series of 5–nitro . . . , Hrelia et al., Mutagenesis vol. 8, No. 3, pp. 183–188, 1993.

Primary Examiner—Zinna Northington Davis
Attorney, Agent, or Firm—Keil & Weinkauf

[57] ABSTRACT

Iminooxymephyleneanilides of the formula I

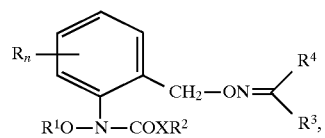

where the index and the substituents have the following meanings:

n is 0, 1, 2, 3 or 4;

R is nitro, cyano, halogen, unsubst. or subst. alkyl, alkenyl, alkynyl, alkoxy, alkenyloxy, alkynyloxy or an unsubst. or subst. bridge bonded to two adjacent ring atoms;

X is a direct bond or $CH_2$, O or $NR^a$;

$R^a$ is hydrogen, alkyl, alkenyl, alkynyl, cycloalkyl or cycloalkenyl;

$R^1$ is hydrogen, unsubst. or subst. alkyl, alkenyl, alkynyl, cycloalkyl, cycloalkenyl, alkylcarbonyl or alkoxycarbonyl;

$R^2$ is alkyl, alkenyl, alkynyl, cycloalkyl or cycloalkenyl, or in the case where X is $NR^a$, additionally hydrogen;

$R^3$ is hydrogen, cyano, halogen, alkyl, haloalkyl, alkoxy, haloalkoxy, alkylthio, haloalkylthio or cycloalkyl;

$R^4$ is a 6- to 10-membered mono- or bicyclic, substituted heteroaromatic ring system, and process and intermediates for their preparation and their use.

15 Claims, No Drawings

IMINOOXYMETHYLENE ANILIDES, PROCESS FOR PREPARING THE SAME AND THEIR USE

This is a National Stage Application under 35 U.S.C. §371, based on International Application No. PCT/EP 95/04,430, filed Nov. 10, 1995.

The present invention relates to iminooxymethyleneanilides of the formula I

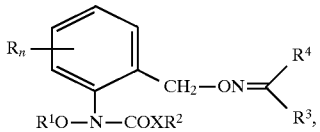

where the index and the substituents have the following meanings:

n is 0, 1, 2, 3 or 4, it being possible for the substituents R to be different if n is greater than 1;

R is nitro, cyano, halogen, unsubst. or subst. alkyl, alkenyl, alkynyl, alkoxy, alkenyloxy, alkynyloxy or in the case where n is 2 additionally an unsubst. or subst. bridge bonded to two adjacent ring atoms, which contains three or four members from the group consisting of 3 or 4 carbon atoms, and 2 or 3 carbon atoms and 1 or 2 nitrogen, oxygen and/or sulfur atoms, it being possible for this bridge, together with the ring to which it is bonded, to form a partially unsaturated or aromatic radical;

X is a direct bond or $CH_2$, O or $NR^a$;

$R^a$ is hydrogen, alkyl, alkenyl, alkynyl, cycloalkyl or cycloalkenyl;

$R^1$ is hydrogen, unsubst. or subst. alkyl, alkenyl, alkynyl, cycloalkyl, cycloalkenyl, alkylcarbonyl or alkoxycarbonyl;

$R^2$ is alkyl, alkenyl, alkyziyl, cycloalkyl or cycloalkenyl, or in the case where X is $NR^a$, additionally hydrogen;

$R^3$ is hydrogen, cyano, halogen, alkyl, haloalkyl, alkoxy, haloalkoxy, alkylthio, haloalkylthio or cycloalkyl;

$R^4$ is a 6- to 10-membered mono- or bicyclic, heteroaromatic ring system which is substituted by customary groups, and processes for their preparation and their use.

WO-A 93/15,046 discloses anilides having fungicidal activity.

It is an object of the present invention to make available active compounds having improved activity.

We have found that this object is achieved by the compounds I defined at the beginning. We have additionally found processes for their preparation, compositions containing them and methods for their use, in particular for controlling animal pests and harmful fungi.

The compounds I are obtainable by various methods. Compounds I, where $R^1$ is not hydrogen, are particularly advantageously obtained by reacting a methyleneanilide of the formula II with an oxime of the formula III or its salt.

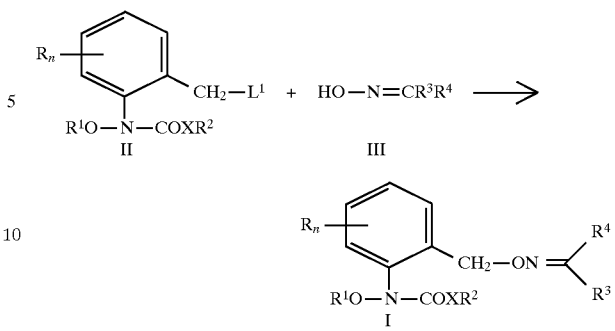

$L^1$ in the formula II is a leaving group, ie. a nucleophilically replaceable group such as halogen (eg. chlorine, bromine or iodine), or an alkyl- or arylsulfonate (eg. methylsulfonate, trifluoromethylsulfonate, phenylsulfonate or 4-methylphenylsulfonate).

The oximes III can also be used in the form of their salts, eg. with inorganic acids, such as hydrochlorides, hydrobromides, hydrosulfates and hydrophosphonates.

The reaction of the compounds II and III is customarily carried out at from 0° C. to 80° C., preferably 20° C. to 60° C., in an inert solvent in the presence of a base.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, alcohols such as methanol, ethanol, n-propanol, i-propanol, n-butanol and tert-butanol, ketones such as acetone and methyl ethyl ketone, and dimethyl sulfoxide, dimethylformamide, dimethylacetamide, 1,3-dimethylimidazolidin-2-one and 1,2-dimethyltetrahydro-2(1H)-pyrimidine, preferably methylene chloride, acetone, toluene, tert-butyl methyl ether and dimethylformamide. Mixtures of the solvents mentioned can also be used.

Suitable bases are generally inorganic compounds such as alkali metal and alkaline earth metal hydroxides (eg. lithium hydroxide, sodium hydroxide, potassium hydroxide and calcium hydroxide), alkali metal and alkaline earth metal oxides (eg. lithium oxide, sodium oxide, calcium oxide and magnesium oxide), alkali metal and alkaline earth metal hydrides (eg. lithium hydride, sodium hydride, potassium hydride and calcium hydride), alkali metal amides (eg. lithium amide, sodium amide and potassium amide), alkali metal and alkaline earth metal carbonates (eg. lithium carbonate and calcium carbonate) and also alkali metal hydrogen carbonates (eg. sodium hydrogen carbonate), organometallic compounds, in particular alkali metal alkyls (eg. methyllithium, butyllithium and phenyllithium), alkylmagnesium halides (eg. methylmagnesium chloride) and also alkali metal and alkaline earth metal alkoxides (eg. sodium methoxide, sodium ethoxide, potassium ethoxide, potassium tert-butoxide and dimethoxymagnesium), additionally organic bases, eg. tertiary amines such as trimethylamine, triethylamine, triisopropylethylamine and N-methylpiperidine, pyridine, substituted pyridines such as collidine, lutidine and 4-dimethylaminopyridine as well as bicyclic amines.

Particularly preferred bases are sodium hydroxide, potassium carbonate and potassium tert-butoxide.

The bases are in general used in an equimolar amount, in an excess or if appropriate as solvents.

It can be advantageous for the reaction to add a catalytic amount of a crown ether (eg. 18-crown-6 or 15-crown-5).

The reaction can also be carried out in two-phase systems consisting of a solution of alkali metal or alkaline earth metal hydroxides or carbonates in water and an organic phase (eg. aromatic and/or halogenated hydrocarbons). Suitable phase-transfer catalysts in this case are, for example, ammonium halides and tetrafluoroborates (eg. benzyltriethylammonium chloride, benzyltributylammonium bromide, tetrabutylammonium chloride, hexadecyltrimethylammonium bromide or tetrabutylammonium tetrafluoroborate) and phosphonium halides (eg. tetrabutylphosphonium chloride and tetraphenylphosphonium bromide).

The starting substances II needed for the preparation of the compounds I are disclosed in WO-A 93/15,046 or can be prepared by the methods described there.

The oximes III and their salts are disclosed in the literature [WO-A 92/13,830, WO-A 92/18,487, WO-A 94/08,968 and Comprehensive Heterocyclic Chemistry, Vol. 13, pp. 1–572 (1984); A. Weissberger et al., The Chemistry of Heterocyclic Compounds, Verlag John Wiley & Sons; E. Rodd, Heterocyclic Compounds, Vol. IV$^c$, Elsevier Publishing Company (1960); E. Rodd, Heterocyclic Compounds, Vol. IV$^b$, Elsevier Publishing Company (1959)] or can be prepared by the methods described there.

It can be advantageous for the reaction first to convert the oxime III or its salt with the base into the corresponding base, which is then reacted with the benzyl derivative II.

The compounds I can contain acidic or basic centers and accordingly form acid addition products or base addition products or salts.

Acids for acid addition products are, inter alia, mineral acids (eg. halohydric acids such as hydrochloric and hydrobromic acid, phosphoric acid, sulfuric acid, nitric acid), organic acids (eg. formic acid, acetic acid, oxalic acid, malonic acid, lactic acid, malic acid, succinic acid, tartaric acid, citric acid, salicylic acid, p-toluenesulfonic acid, dodecylbenzenesulfonic acid) or other proton-acidic compounds (eg. saccharin).

Alternatively, the compounds I, where $R^1$ is hydrogen, can be obtained by converting a nitrobenzene IV with an oxime III into the corresponding oxime ether V, reducing V in a manner known per se to the hydroxylamine VI and then reacting VI with an acylating agent VIIa or with an isocyanate VIIb or with a cyanate VIIc to give I.

$L^3$ in the formula VIIa is halogen (eg. chlorine, bromine or iodine), phenoxy or the group $R^2XCO_2$.

$M^+$ in the formula VIIc is an equivalent of a metal ion (eg. an alkali metal or alkaline earth metal ion such as sodium, potassium or calcium).

The reaction of the benzyl compounds IV with the oxime III is carried out in general and in particular by the methods of reaction of the benzyl compound II with the oximes III (see above).

The reduction of the nitroaromatics V to the hydroxylamines VI is carried out either using zinc (in a similar manner to Bamberger et al., Am. Chem. 316 (1901), 278) or using hydrogen in the presence of suitable catalysts, eg. platinum (similarly to EP 85 890).

The reaction of the hydroxylamines VI with the carbonyl compounds VIIa or VIIb or the cyanate VIIc is preferably carried out under alkaline conditions at from –40° to 60° C., preferably –10° to 30° C.

The preparation of the compounds I where $R^1$ is not hydrogen is carried out by reacting a compound of the formula I, where $R^1$ is hydrogen, in a manner known per se with a compound VIII.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, i-propanol, n-butanol and tert-butanol, ketones such as acetone and methyl ethyl ketone, and dimethyl sulfoxide, dimethylformamide, dimethylacetamide, 1,3-dimethylimidazolidin-2-one and 1,2-dimethyltetrahy-dro-2(1H)-pyrimidine, preferably methylene chloride, acetone, toluene, tert-butyl methyl ether and dimethylformamide. Mixtures of the solvents mentioned can also be used.

Preferred solvents are inert solvents, eg. toluene, methylene chloride, methyl t-butyl ether, acetonitrile, cyclohexane, acetone, tetrahydrofuran, dimethylformamide or N-methylpyrrolidone.

Suitable bases are generally inorganic compounds such as alkali metal and alkaline earth metal hydroxides (eg. lithium hydroxide, sodium hydroxide, potassium hydroxide and calcium hydroxide), alkali metal and alkaline earth metal

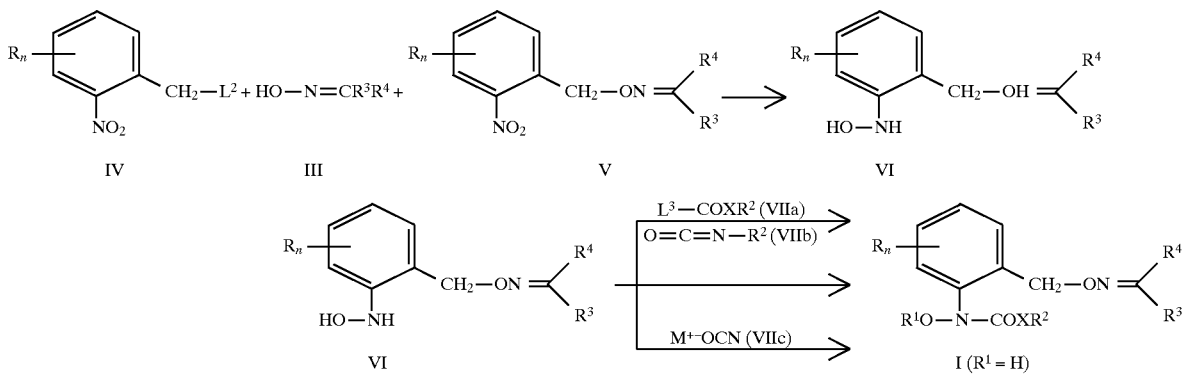

$L^2$ in the formula IV is a leaving group, ie. a nucleophilically replaceable group such as halogen (eg. chlorine, bromine or iodine), or an alkyl- or arylsulfonate (eg. methylsulfonate, trifluoromethylsulfonate, phenylsulfonate or 4-methylphenylsulfonate).

oxides (eg. lithium oxide, sodium oxide, calcium oxide and magnesium oxide), alkali metal and alkaline earth metal hydrides (eg. lithium hydride, sodium hydride, potassium hydride and calcium hydride), alkali metal amides (eg. lithium amide, sodium amide and potassium amide), alkali metal and alkaline earth metal carbonates (eg. lithium carbonate and calcium carbonate) and also alkali metal hydrogen carbonates (eg. sodium hydrogen carbonate), organometallic compounds, in particular alkali metal alkyls (eg. methyllithium, butyllithium and phenyllithium), alkylmagnesium halides (eg. methylmagnesium chloride) and also alkali metal and alkaline earth metal alkoxides (eg. sodium methoxide, sodium ethoxide, potassium ethoxide, potassium tert-butoxide and dimethoxymagnesium), additionally organic bases, eg. tertiary amines such as trimethylamine, triethylamine, triisopropylethylamine and N-methylpiperidine, pyridine, substituted pyridines such as collidine, lutidine and 4-dimethylaminopyridine as well as bicyclic amines.

Particularly preferred bases are triethylamine, morpholine, ethyldiisopropylamine, sodium hydroxide, potassium carbonate, potassium tert-butoxide, sodium carbonate, sodium hydrogen carbonate, potassium hydrogen carbonate, potassium phosphate, dipotassium hydrogen phosphate or potassium dihydrogen phosphate.

The bases are in general used in an equimolar amount, in an excess or if appropriate as solvents.

The reaction can also be carried out in two-phase systems consisting of a solution of alkali metal or alkaline earth metal hydroxides or carbonates in water and an organic phase (eg. aromatic and/or halogenated hydrocarbons). Suitable phase-transfer catalysts in this case are, for example, ammonium halides and tetrafluoroborates (eg. benzyltriethylammonium chloride, benzyltributylammonium bromide, tetrabutylammonium chloride, hexadecyltrimethylammonium bromide or tetrabutylammonium tetrafluoroborate) and phosphonium halides (eg. tetrabutylphosphonium chloride and tetraphenylphosphonium bromide).

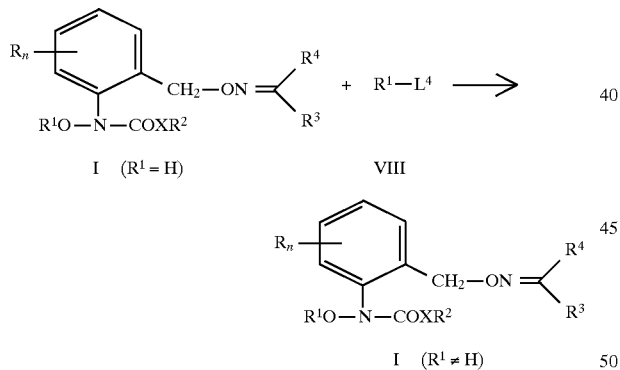

$L^4$ in the formula VIII is a leaving group, ie. a nucleophilically replaceable group such as halogen (eg. chlorine, bromine or iodine), phenoxy or an alkyl- or arylsulfonate (eg. methylsulfonate, trifluoromethylsulfonate, phenylsulfonate or 4-methylphenylsulfonate).

The reaction of the compounds I ($R^1$=H) to give the compounds I ($R^1 \neq H$) is carried out in general and in particular by the methods described for the reaction of the hydroxylamines VI to give the compounds I ($R^1$=H).

According to a further process, the compounds I are also obtained by first converting a methyleneanilide II with N-hydroxyphthalimide (IX) into the benzyl ether X, then hydrolyzing X with ammonia, hydrazine or an amine or with acid catalysis to the hydroxylamine ether XI and then reacting XI with a carbonyl compound XII to give I.

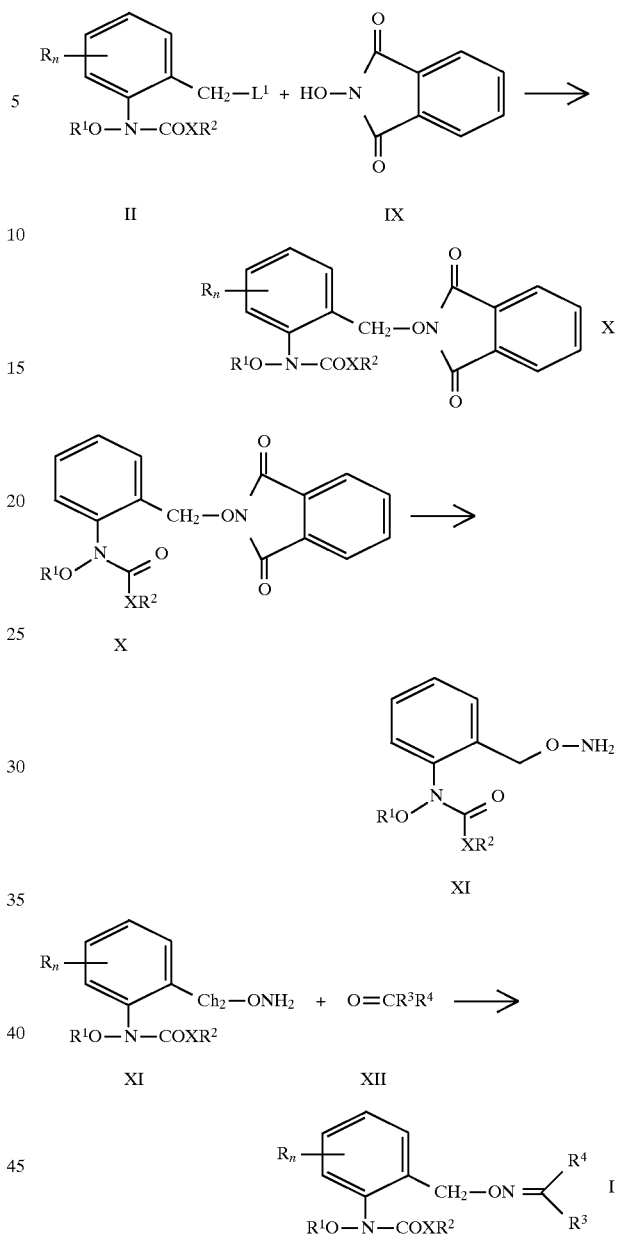

The reaction of the benzyl compound II with N-hydroxyphthalimide IX is carried out in general and in particular by the methods described for the reaction of the benzyl compounds II with the oximes III.

The reaction of the N-hydroxyphthalimide ether XI to give the benzyloxyamine XVa or its salts is carried out by the methods described in EP 463 488.

The reaction of the benzyloxyamine XI with the carbonyl compounds O=CR$^3$R$^4$ is carried out in general and in particular according to the conditions for the reaction of the benzyl compounds II with the oximes III.

Additionally, the reaction of the benzyloxyamine XI with the carbonyl compounds O=CR$^3$R$^4$ can also be carried out under neutral or acidic conditions.

Suitable acidic catalysts are mineral acids, eg. hydrochloric acid, sulfuric acid, phosphoric acid or nitric acid, or alternatively organic acids, eg. formic acid, acetic acid, propionic acid, triethylamine hydrochloride, p-toluenesulfonic acid, methanesulfonic acid, citric acid or acidic ion exchangers.

The compounds I, where X is NR$^a$, are additionally obtained, for example, by first converting a methyleneanilide of the formula IIa with an oxime III into the corresponding oxime ether XIII and then reacting XIII with an amine XIV to give I.

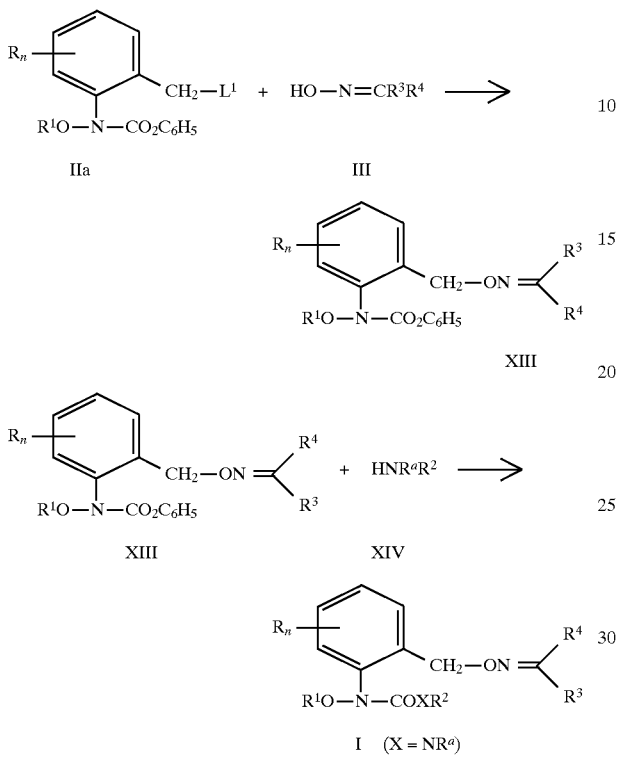

L$^1$ in the formula IIa is a leaving group, ie. a nucleophilically replaceable group such as halogen (eg. chlorine, bromine or iodine), or an alkyl- or arylsulfonate (eg. methylsulfonate, trifluoromethylsulfonate, phenylsulfonate or 4-methylphenylsulfonate).

The reaction of the methyleneanilides IIa with the oximes III is carried out in general and in particular by the methods of reaction of the benzyl compounds II with the oximes III.

The reaction of the compounds XIII with the amines of the formula HNR$^a$R$^2$ is carried out at from 0° C. to 100° C. in an inert solvent or in a solvent mixture.

Suitable solvents are, in particular, water, tert-butyl methyl ether and toluene or mixtures thereof. It can be advantageous to improve the solubility of the starting materials additionally to add one of the following solvents (as solubilizers): tetrahydrofuran, methanol, dimethylformamide or ethylene glycol ether.

The amines XIV are customarily employed in an excess of up to 100% based on the compounds XIII or can be used as solvents. With respect to the yield it can be advantageous to carry out the reaction under pressure.

Bases for base addition products are, inter alia, oxides, hydroxides, carbonates or hydrogencarbonates of alkali metals or alkaline earth metals (eg. potassium or sodium hydroxide or potassium or sodium carbonate) or ammonium compounds (eg. ammonium hydroxide).

Acids for acid addition products are, inter alia, mineral acids (eg. hydrohalic acids such as hydrochloric and hydrobromic acid, phosphoric acid, sulfuric acid, nitric acid), organic acids (eg. formic acid, acetic acid, oxalic acid, malonic acid, lactic acid, malic acid, succinic acid, tartaric acid, citric acid, salicylic acid, p-toluenesulfonic acid, dodecylbenzenesulfonic acid) or other proton-acidic compounds (eg. saccharin).

In the definitions of the symbols indicated in the above formulae, in some cases collective terms were used which are generally representative of the following substituents:

Halogen: fluorine, chlorine, bromine or iodine;

Alkyl: saturated, straight-chain or branched hydrocarbon radicals preferably having 1 to 10 carbon atoms, eg. methyl, ethyl, propyl, 1-methylethyl, butyl, 1-methylpropyl, 2-methylpropyl and 1,1-dimethylethyl;

Haloalkyl: straight-chain or branched alkyl groups preferably having 1 to 10 carbon atoms (as mentioned above), it being possible in these groups for the hydrogen atoms to be partly or completely replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkylcarbonyl: straight-chain or branched alkyl groups preferably having 1 to 10 carbon atoms (as mentioned above), which are bonded to the structure via a carbonyl group (—CO—);

Alkoxy: straight-chain or branched alkyl groups preferably having 1 to 10 carbon atoms (as mentioned above), which are bonded to the structure via an oxygen atom (—O—);

Haloalkoxy: straight-chain or branched haloalkyl groups preferably having 1 to 10 carbon atoms (as mentioned above), which are bonded to the structure via an oxygen atom (—O—);

Alkoxycarbonyl: straight-chain or branched alkoxy groups preferably having 1 to 10 carbon atoms (as mentioned above), which are bonded to the structure via a carbonyl group (—CO—);

Alkylthio: straight-chain or branched alkyl groups preferably having 1 to 10 carbon atoms (as mentioned above), which are bonded to the structure via a sulfur atom (—S—);

Haloalkylthio: straight-chain or branched haloalkyl groups preferably having 1 to 4 carbon atoms (as mentioned above), which are bonded to the structure via a sulfur atom (—S—);

Alkenyl: unsaturated, straight-chain or branched hydrocarbon radicals preferably having 2 to 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenyloxy: straight-chain or branched alkenyl groups preferably having 3 to 10 carbon atoms (as mentioned above), which are bonded to the structure via an oxygen atom (—O—);

Alkynyl: straight-chain or branched hydrocarbon groups preferably having 2 to 10 carbon atoms and a triple bond in any desired position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Alkynyloxy: straight-chain or branched alkynyl groups preferably having 3 to 10 carbon atoms (as mentioned above), which are bonded to the structure via an oxygen atom (—O—);

Cycloalkyl: mono- or bicyclic hydrocarbon radicals preferably having 3 to 10 carbon atoms, eg. $C_3$–$C_{10}$-(bi)cycloalkyl such as cyclopropyl, cyclobutyl, cyclopentyl, cyclohexyl, cycloheptyl, bornanyl, norbornanyl, dicyclohexyl, bicyclo[3.3.0]octyl, bicyclo[3.2.1]octyl, bicyclo[2.2.2]octyl or bicyclo[3.3.1]nonyl;

Cycloalkenyl: mono- or bicyclic hydrocarbon radicals preferably having 5 to 10 carbon atoms and a double bond in any desired ring position, eg. $C_5$–$C_{10}$-(bi)cycloalkenyl such as cyclopentenyl, cyclohexenyl, cycloheptenyl, bornenyl, norbornenyl, dicyclohexenyl and bicyclo[3.3.0]octenyl;

a bridge bonded to two adjacent ring atoms, which contains three or four members from the group consisting of 3 or 4 carbon atoms, and 2 or 3 carbon atoms and 1 or 2 nitrogen, oxygen and/or sulfur atoms, it being possible for this bridge, together with the ring to which it is bonded, to form a partially unsaturated or aromatic ring: eg. bridges which, with the ring to which they are bonded, for example form one of the following systems: quinolinyl, benzofuranyl and naphthyl;

Heterocyclyl: 3- to 8-membered saturated or unsaturated heterocycles, containing one to three nitrogen atoms and/or one or two oxygen or sulfur atoms, such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidiniyl, 4-imidazolidinyl, 1,2,4-oxazolidin-3-yl, 1,2,4-oxadiazolidin-5-yl, 1,2,4-thiadiazolidin-3-yl, 1,2,3-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydro-triazin-2-yl and 1,2,4-tetrahydrotriazin-3-yl, preferably 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3-dioxan-5-yl, 4-piperidinyl, 2-tetrahydropyranyl, 4-tetrahydropyranyl, morpholinyl or 2,6-dimethylmorpholinyl.

The bonding of the heteroaromatic or heterocyclic radical can be effected via a carbon atom or a nitrogen atom of the heteroaromatic or heterocyclic radical.

a 6- to 10-membered mono- or bicyclic, heteroaromatic ring system: 6-membered heteroaromatics which can additionally be benzofused or fused to a further 5- or 6-membered heteroaromatic ring system, eg.

5-membered heteroaryl, containing one to three nitrogen atoms: 5-membered ring heteroaryl groups which, besides carbon atoms, contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl, 1,2,3-triazolyl and 1,3,4-triazol-2-yl;

5-membered heteroaryl, containing one to four nitrogen atoms or one to three nitrogen atoms and a sulfur or an oxygen atom: 5-membered ring heteroaryl groups which, besides carbon atoms, can contain one to four nitrogen atoms or one to three nitrogen atoms and a sulfur or oxygen atom, or an oxygen or sulfur atom, as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered heteroaryl, containing one to three nitrogen atoms or a nitrogen atom and/or an oxygen or sulfur atom: 5-membered ring heteroaryl groups which, besides carbon atoms, can contain one to four nitrogen atoms, or one to three nitrogen atoms and a sulfur or oxygen atom or an oxygen or a sulfur atom as ring members, and in which two adjacent carbon ring members or a nitrogen and an adjacent carbon ring member can be bridged by a buta-1,3-diene-1,4-diyl group;

5-membered heteroaryl bonded via nitrogen, containing one to four nitrogen atoms, or benzo-fused 5-membered heteroaryl bonded via nitrogen, containing one to three nitrogen atoms: 5-membered ring heteroaryl groups which, besides carbon atoms, can contain one to four nitrogen atoms or one to three nitrogen atoms as ring members, and in which two adjacent carbon ring members or a nitrogen and an adjacent carbon ring member can be bridged by a buta-1,3-diene-1,4-diyl group, these rings being bonded to the structure via one of the nitrogen ring members;

6-membered heteroaryl. containing one to three or one to four nitrogen atoms: 6-membered ring heteroaryl groups which, besides carbon atoms, can contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

benzo- or hetero-fused 6-membered heteroaryl, containing one to three or one to four nitrogen atoms and/or an oxygen or sulfur atom: 6-membered ring heteroaryl groups which, besides carbon atoms, can contain one to three nitrogen atoms as ring members, and in which two adjacent carbon ring members or a nitrogen and an adjacent carbon ring member can be bridged by a buta-1,3-diene-1,4-diyl group or a 3- to 4-membered unsaturated chain which, besides carbon members, can contain, for example, nitrogen atoms and/or an oxygen or sulfur atom, eg. indolyl, quinolinyl, isoquinolinyl and purinyl.

or the corresponding oxy, thio, carbonyl or sulfonyl groups.

The addition of unsubst. or subst. with respect to alkyl, alkenyl and alkynyl groups is intended to express that these groups can be partially or completely halogenated, ie. that the hydrogen atoms of these groups can be partly or completely replaced by identical or different halogen atoms as mentioned above (preferably fluorine, chlorine or bromine) and/or can carry one to three (preferably one) of the following radicals:

cyano, nitro, hydroxyl, amino, formyl, carboxyl, aminocarbonyl, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, and $CR^{iii}= NOR^{iv}$, $R^{iii}$ being hydrogen, alkyl, alkenyl, alkynyl or cycloalkyl and $R^{iv}$ being alkyl, alkenyl, alkynyl or arylalkyl and said alkyl groups preferably containing 1 to 6 carbon atoms, in particular 1 to 4 carbon atoms, and the alkenyl or alkynyl groups preferably containing 2 to 6 carbon atoms and aryl in particular being phenyl which is unsubstituted or can be substituted by customary groups;

unsubstituted or customarily substituted cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

unsubstituted or customarily substituted aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino, hetarylalkyl-N-alkylamino, arylcarbonyl, aryloxycarbonyl, arylcarbonyloxy, arylaminocarbonyl, N-aryl-N-alkylaminocarbonyl, arylcarbonyl-N-alkylamino, aryloxycarbonylamino, hetarylcarbonyl, hetaryloxycarbonyl, hetarylcarbonyloxy, hetarylaminocarbonyl, N-hetaryl-N-alkylaminocarbonyl, hetarylcarbonyl-N-alkylamino and hetaryloxycarbonylamino, the aryl radicals preferably containing 6 to 10 ring members, in particular 6 ring members (phenyl), the hetaryl radicals in particular containing 5 or 6 ring members and the alkyl groups in these radicals preferably containing 1 to 6 carbon atoms, in particular 1 45 to 4 carbon atoms.

The addition of unsubst. or subst. with respect to the cyclic (saturated, unsaturated or aromatic) groups is intended to express that these groups can be partially or completely halogenated, ie. that the hydrogen atoms of these groups can be partly or completely replaced by identical or different halogen atoms such as mentioned above (preferably fluorine, chlorine or bromine, in particular fluorine or chlorine), and/or can carry one to four (in particular one to three) of the following radicals cyano, nitro, hydroxyl, amino, carboxyl, aminocarbonyl, alkyl, haloalkyl, alkenyl, haloalkenyl, alkenyloxy, haloalkenyloxy, alkynyl, haloalkynyl, alkynyloxy, haloalkynyloxy, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl- N-alkylamino, the alkyl groups in these radicals preferably containing 1 to 6 carbon atoms, in particular 1 to 4 carbon atoms, and said alkenyl or alkynyl groups in these radicals containing 2 to 8, preferably 2 to 6, in particular 2 to 4 carbon atoms;

and/or one to three (in particular one) of the following radicals unsubstituted or customarily substituted cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

unsubstituted or customarily substituted aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino, hetarylalkyl-N-alkylamino, arylcarbonyl, aryloxycarbonyl, arylcarbonyloxy, arylaminocarbonyl, Naryl-N-alkylaminocarbonyl, arylcarbonyl-N-alkylamino, aryloxycarbonylamino, hetarylcarbonyl, hetaryloxycarbonyl, hetarylcarbonyloxy, hetarylaminocarbonyl, N-hetaryl-N-alkylaminocarbonyl, hetarylcarbonyl-N-alkylamino and hetaryloxycarbonylamino, the aryl radicals preferably containing 6 to 10 ring members, in particular 6 ring members (phenyl), the hetaryl radicals in particular containing 5 or 6 ring members and the alkyl groups in these radicals preferably containing 1 to 6 carbon atoms, in particular 1 to 4 carbon atoms, and/or one or two (in particular one) of the following radicals formyl or $CR^{iii}=NOR^{iv}$, $R^{iii}$ being hydrogen, alkyl, alkenyl, cycloalkyl or alkynyl and Riv being alkyl, alkenyl, alkynyl and arylalkyl and said alkyl groups preferably containing 1 to 6 carbon atoms, in particular 1 to 4 carbon atoms, and the alkenyl or alkynyl groups preferably containing 2 to 6 carbon atoms and aryl in particular being phenyl which is unsubstituted or customarily substituted, or in which two adjacent C atoms of the cyclic systems can carry a $C_3$–$C_5$-alkylene, $C_3$–$C_5$-alkenylene, oxy-$C_2$–$C_4$-alkylene, oxy-$C_1$–$C_3$-alkyleneoxy, oxy-$C_2$–$C_4$-alkenylene, oxy-$C_2$–$C_4$-alkenyleneoxy or butadiendiyl group, it being possible for these bridges in turn to be partially or completely halogenated and/or to carry one to three, in particular one or two, of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

Customary groups which are suitable as substituents of $R^4$ are understood as meaning the radicals mentioned above as possible substituents of cyclic systems.

With respect to their biological action, preferred compounds I are those where n is 0 or 1, in particular 0.

In the case where n is 1, preferred compounds I are those where R is one of the following groups: fluorine, chlorine, cyano, methyl or methoxy.

Additionally, preferred compounds I where n is 1 are those where R is in the 3- or 6-position relative to the anilide nitrogen.

In addition, preferred compounds I are those where X is oxygen.

Additionally, particularly preferred compounds I are those where X is NH.

Equally, compounds I are particularly preferred where X is $CH_2$.

In addition, particularly preferred compounds I are those where X is a direct bond.

In addition, preferred compounds I are those where $R^1$ is $C_1$–$C_4$-alkyl, in particular methyl.

Additionally, particularly preferred compounds I are those where $R^1$ is hydrogen.

Equally, compounds I are particularly preferred where $R^1$ is allyl, propargyl or methoxymethyl.

In addition, preferred compounds I are those where $R^2$ is $C_1$–$C_4$-alkyl, in particular methyl.

Additionally, particularly preferred compounds I are those where $R^2$ is cyclopropyl.

Equally, compounds I are particularly preferred where $R^2$ is trifluoromethyl.

In addition, preferred compounds I are those where $R^3$ is $C_1$–$C_4$-alkyl, in particular methyl.

Additionally, particularly preferred compounds I are those where $R^3$ is cyclopropyl.

Equally, compounds I are particularly preferred where $R^3$ is cyano, trifluoromethyl, halogen, methoxy or methylthio.

In addition, preferred compounds I are those where $R^4$ is substituted pyrimidin-2-yl.

Additionally, particularly preferred compounds I are those where $R^4$ is substituted pyrimidin-4-yl.

Equally, compounds I are particularly preferred where $R^4$ is substituted pyrimidin-5-yl.

In addition, particularly preferred compounds I are those where $R^4$ is substituted pyridyl, 1,3,5-triazinyl or isoquinolinyl.

In addition, preferred compounds I are those where $R^4$ is substituted by pyridin-2-yl.

Additionally, particularly preferred compounds I are those where $R^4$ is substituted by cyano, halogen, $C_1$–$C_6$-alkyl, $C_2$–$C_6$-alkenyl, $C_2$–$C_6$-alkynyl, $C_1$–$C_6$-haloalkyl, $C_2$–$C_6$-haloalkenyl and $C_2$–$C_6$-haloalkynyl.

Equally, compounds I are particularly preferred where $R^4$ is substituted by $C_1$–$C_6$-alkoxy, $C_2$–$C_6$-alkenyloxy, $C_2$–$C_6$-alkynyloxy, $C_1$–$C_6$-haloalkoxy, $C_2$–$C_6$-haloalkenyloxy and $C_2$–$C_6$-haloalkynyloxy.

In addition, particularly preferred compounds I are those where $R^4$ is substituted by phenyl, phenoxy, hetaryl or hetaryloxy, it being possible for these groups in turn to be customarily substituted.

In particular, with respect to their use preferred compounds I are those compiled in the following tables. The groups mentioned for the substituents in these tables are additionally considered per se (independently of the combination in which they are mentioned) in each case to be a particular embodiment of the substituent concerned.

Table 1

Compounds of the formula I (n=0) where $R^1$ is hydrogen, $R^2X$ is methyl, $R^3$ is hydrogen and $R^4$ for a compound in each case corresponds to one line of Table A.

Table 2

Compounds of the formula I (n=0) where $R^1$ is hydrogen, $R^2X$ is ethyl, $R^3$ is hydrogen and $R^4$ for a compound in each case corresponds to one line of Table A.

Table 3

Compounds of the formula I (n=0) where $R^1$ is hydrogen, $R^2X$ is methoxy, $R^3$ is hydrogen and $R^4$ for a compound in each case corresponds to one line of Table A.

Table 4

Compounds of the formula I (n=0) where $R^1$ is hydrogen, $R^2X$ is ethoxy, $R^3$ is hydrogen and $R^4$ for a compound in each case corresponds to one line of Table A.

Table 5

Compounds of the formula I (n=0) where $R^1$ is hydrogen, $R^2X$ is methylamino, $R^3$ is hydrogen and $R^4$ for a compound in each case corresponds to one line of Table A.

Table 6

Compounds of the formula I (n=0) where $R^1$ is methyl, $R^2X$ is methyl, $R^3$ is hydrogen and $R^4$ for a compound in each case corresponds to one line of Table A.

Table 7

Compounds of the formula I (n=0) where $R^1$ is methyl, $R^2X$ is ethyl, $R^3$ is hydrogen and $R^4$ for a compound in each case corresponds to one line of Table A.

Table 8

Compounds of the formula I (n=0) where $R^1$ is methyl, $R^2X$ is methoxy, $R^3$ is hydrogen and $R^4$ for a compound in each case corresponds to one line of Table A.

Table 9

Compounds of the formula I (n=0) where $R^1$ is methyl, $R^2X$ is ethoxy, $R^3$ is hydrogen and $R^4$ for a compound in each case corresponds to one line of Table A.

Table 10

Compounds of the formula I (n=0) where $R^1$ is methyl, $R^2X$ is methylamino, $R^3$ is hydrogen and $R^4$ for a compound in each case corresponds to one line of Table A.

Table 11

Compounds of the formula I (n=0) where $R^1$ is ethyl, $R^2X$ is methyl, $R^3$ is hydrogen and $R^4$ for a compound in each case corresponds to one line of Table A.

Table 12

Compounds of the formula I (n=0) where $R^1$ is ethyl, $R^2X$ is ethyl, $R^3$ is hydrogen and $R^4$ for a compound in each case corresponds to one line of Table A.

Table 13

Compounds of the formula I (n=0) where $R^1$ is ethyl, $R^2X$ is methoxy, $R^3$ is hydrogen and $R^4$ for a compound in each case corresponds to one line of Table A.

Table 14

Compounds of the formula I (n=0) where $R^1$ is ethyl, $R^2X$ is ethoxy, $R^3$ is hydrogen and $R^4$ for a compound in each case corresponds to one line of Table A.

Table 15

Compounds of the formula I (n=0) where $R^1$ is ethyl, $R^2X$ is methylamino, $R^3$ is hydrogen and $R^4$ for a compound in each case corresponds to one line of Table A.

Table 16

Compounds of the formula I where $R_n$ is 3-chloro, $R^1$ is hydrogen, $R^2X$ is methyl, $R_3$ is hydrogen and $R^4$ for a compound in each case corresponds to one line of Table A.

Table 17

Compounds of the formula I where $R_n$ is 3-chloro, $R^1$ is hydrogen, $R^2X$ is ethyl, $R^3$ is hydrogen and $R^4$ for a compound in each case corresponds to one line of Table A.

Table 18

Compounds of the formula I where $R_n$ is 3-chloro, $R^1$ is hydrogen, $R^2X$ is methoxy, $R^3$ is hydrogen and $R^4$ for a compound in each case corresponds to one line of Table A.

Table 19

Compounds of the formula I where $R_n$ is 3-chloro, $R^1$ is hydrogen, $R^2X$ is ethoxy, $R^3$ is hydrogen and $R^4$ for a compound in each case corresponds to one line of Table A.

Table 20

Compounds of the formula I where $R_n$ is 3-chloro, $R^1$ is hydrogen, $R^2X$ is methylamino, $R^3$ is hydrogen and $R^4$ for a compound in each case corresponds to one line of Table A.

Table 21

Compounds of the formula I where $R_n$ is 3-chloro, $R^1$ is methyl, $R^2X$ is methyl, $R^3$ is hydrogen and $R^4$ for a compound in each case corresponds to one line of Table A.

Table 22

Compounds of the formula I where $R_n$ is 3-chloro, $R^1$ is methyl, $R^2X$ is ethyl, $R^3$ is hydrogen and $R^4$ for a compound in each case corresponds to one line of Table A.

Table 23

Compounds of the formula I where $R_n$ is 3-chloro, $R^1$ is methyl, $R^2X$ is methoxy, $R^3$ is hydrogen and $R^4$ for a compound in each case corresponds to one line of Table A.

Table 24

Compounds of the formula I where $R_n$ is 3-chloro, $R^1$ is methyl, $R^2X$ is ethoxy, $R^3$ is hydrogen and $R^4$ for a compound in each case corresponds to one line of Table A.

Table 25

Compounds of the formula I where $R_n$ is 3-chloro, $R^1$ is methyl, $R^2X$ is methylamino, $R^3$ is hydrogen and $R^4$ for a compound in each case corresponds to one line of Table A.

Table 26

Compounds of the formula I where $R_n$ is 3-chloro, $R^1$ is ethyl, $R^2X$ is methyl, $R^3$ is hydrogen and $R^4$ for a compound in each case corresponds to one line of Table A.

Table 27

Compounds of the formula I where $R_n$ is 3-chloro, $R^1$ is ethyl, $R^2X$ is ethyl, $R^3$ is hydrogen and $R^4$ for a compound in each case corresponds to one line of Table A.

Table 28

Compounds of the formula I where $R_n$ is 3-chloro, $R^1$ is ethyl, $R^2X$ is methoxy, $R^3$ is hydrogen and $R^4$ for a compound in each case corresponds to one line of Table A.

Table 29

Compounds of the formula I where $R_n$ is 3-chloro, $R^1$ is ethyl, $R^2X$ is ethoxy, $R^3$ is hydrogen and $R^4$ for a compound in each case corresponds to one line of Table A.

Table 30

Compounds of the formula I where $R_n$ is 3-chloro, $R^1$ is ethyl, $R^2X$ is methylamino, $R^3$ is hydrogen and $R^4$ for a compound in each case corresponds to one line of Table A.

Table 31

Compounds of the formula I (n=0) where $R^1$ is hydrogen, $R^2X$ is methyl, $R^3$ is cyano and $R^4$ for a compound in each case corresponds to one line of Table A.

Table 32

Compounds of the formula I (n=0) where $R^1$ is hydrogen, $R^2X$ is ethyl, $R^3$ is cyano and $R^4$ for a compound in each case corresponds to one line of Table A.

Table 33

Compounds of the formula I (n=0) where $R^1$ is hydrogen, $R^2X$ is methoxy, $R^3$ is cyano and $R^4$ for a compound in each case corresponds to one line of Table A.

Table 34

Compounds of the formula I (n=0) where $R^1$ is hydrogen, $R^2X$ is ethoxy, $R^3$ is cyano and $R^4$ for a compound in each case corresponds to one line of Table A.

Table 35

Compounds of the formula I (n=0) where $R^1$ is hydrogen, $R^2X$ is methylamino, $R^3$ is cyano and $R^4$ for a compound in each case corresponds to one line of Table A.

Table 36

Compounds of the formula I (n=0) where $R^1$ is methyl, $R^2X$ is methyl, $R^3$ is cyano and $R^4$ for a compound in each case corresponds to one line of Table A.

Table 37

Compounds of the formula I (n=0) where $R^1$ is methyl, $R^2X$ is ethyl, $R^3$ is cyano and $R^4$ for a compound in each case corresponds to one line of Table A.

Table 38

Compounds of the formula I (n=0) where $R^1$ is methyl, $R^2X$ is methoxy, $R^3$ is cyano and $R^4$ for a compound in each case corresponds to one line of Table A.

Table 39

Compounds of the formula I (n=0) where $R^1$ is methyl, $R^2X$ is ethoxy, $R^3$ is cyano and $R^4$ for a compound in each case corresponds to one line of Table A.

Table 40

Compounds of the formula I (n=0) where $R^1$ is methyl, $R^2X$ is methylamino, $R^3$ is cyano and $R^4$ for a compound in each case corresponds to one line of Table A.

Table 41

Compounds of the formula I (n=0) where $R^1$ is ethyl, $R^2X$ is methyl, $R^3$ is cyano and $R^4$ for a compound in each case corresponds to one line of Table A.

Table 42

Compounds of the formula I (n=0) where $R^1$ is ethyl, $R^2X$ is ethyl, $R^3$ is cyano and $R^4$ for a compound in each case corresponds to one line of Table A.

Table 43

Compounds of the formula I (n=0) where $R^1$ is ethyl, $R^2X$ is methoxy, $R^3$ is cyano and $R^4$ for a compound in each case corresponds to one line of Table A.

Table 44

Compounds of the formula I (n=0) where $R^1$ is ethyl, $R^2X$ is ethoxy, $R^3$ is cyano and $R^4$ for a compound in each case corresponds to one line of Table A.

Table 45

Compounds of the formula I (n=0) where $R^1$ is ethyl, $R^2X$ is methylamino, $R^3$ is cyano and $R^4$ for a compound in each case corresponds to one line of Table A.

Table 46

Compounds of the formula I where $R_n$ is 3-chloro, $R^1$ is hydrogen, $R^2X$ is methyl, $R^3$ is cyano and $R^4$ for a compound in each case corresponds to one line of Table A.

Table 47

Compounds of the formula I where $R_n$ is 3-chloro, $R^1$ is hydrogen, $R^2X$ is ethyl, $R^3$ is cyano and $R^4$ for a compound in each case corresponds to one line of Table A.

Table 48

Compounds of the formula I where $R_n$ is 3-chloro, $R^1$ is hydrogen, $R^2X$ is methoxy, $R^3$ is cyano and $R^4$ for a compound in each case corresponds to one line of Table A.

Table 49

Compounds of the formula I where $R_n$ is 3-chloro, $R^1$ is hydrogen, $R^2X$ is ethoxy, $R^3$ is cyano and $R^4$ for a compound in each case corresponds to one line of Table A.

Table 50

Compounds of the formula I where $R_n$ is 3-chloro, $R^1$ is hydrogen, $R^2X$ is methylamino, $R^3$ is cyano and $R^4$ for a compound in each case corresponds to one line of Table A.

Table 51

Compounds of the formula I where $R_n$ is 3-chloro, $R^1$ is methyl, $R^2X$ is methyl, $R^3$ is cyano and $R^4$ for a compound in each case corresponds to one line of Table A.

Table 52

Compounds of the formula I where $R_n$ is 3-chloro, $R^1$ is methyl, $R^2X$ is ethyl, $R^3$ is cyano and $R^4$ for a compound in each case corresponds to one line of Table A.

Table 53

Compounds of the formula I where $R_n$ is 3-chloro, $R^1$ is methyl, $R^2X$ is methoxy, $R^3$ is cyano and $R^4$ for a compound in each case corresponds to one line of Table A.

Table 54

Compounds of the formula I where $R_n$ is 3-chloro, $R^1$ is methyl, $R^2X$ is ethoxy, $R^3$ is cyano and $R^4$ for a compound in each case corresponds to one line of Table A.

Table 55

Compounds of the formula I where $R_n$ is 3-chloro, $R^1$ is methyl, $R^2X$ is methylamino, $R^3$ is cyano and $R^4$ for a compound in each case corresponds to one line of Table A.

Table 56

Compounds of the formula I where $R_n$ is 3-chloro, $R^1$ is ethyl, $R^2X$ is methyl, $R^3$ is cyano and $R^4$ for a compound in each case corresponds to one line of Table A.

Table 57

Compounds of the formula I where $R_n$ is 3-chloro, $R^1$ is ethyl, $R^2X$ is ethyl, $R^3$ is cyano and $R^4$ for a compound in each case corresponds to one line of Table A.

Table 58

Compounds of the formula I where $R_n$ is 3-chloro, $R^1$ is ethyl, $R^2X$ is methoxy, $R^3$ is cyano and $R^4$ for a compound in each case corresponds to one line of Table A.

Table 59

Compounds of the formula I where $R_n$ is 3-chloro, $R^1$ is ethyl, $R^2X$ is ethoxy, $R^3$ is cyano and $R^4$ for a compound in each case corresponds to one line of Table A.

Table 60

Compounds of the formula I where $R_n$ is 3-chloro, $R^1$ is ethyl, $R^2X$ is methylamino, $R^3$ is cyano and $R^4$ for a compound in each case corresponds to one line of Table A.

Table 61

Compounds of the formula I (n=0) where $R^1$ is hydrogen, $R^2X$ is methyl, $R^3$ is chloro and $R^4$ for a compound in each case corresponds to one line of Table A.

Table 62

Compounds of the formula I (n=0) where $R^1$ is hydrogen, $R^2X$ is ethyl, $R^3$ is chloro and $R^4$ for a compound in each case corresponds to one line of Table A.

Table 63

Compounds of the formula I (n=0) where $R^1$ is hydrogen, $R^2X$ is methoxy, $R^3$ is chloro and $R^4$ for a compound in each case corresponds to one line of Table A.

Table 64

Compounds of the formula I (n=0) where $R^1$ is hydrogen, $R^2X$ is ethoxy, $R^3$ is chloro and $R^4$ for a compound in each case corresponds to one line of Table A.

Table 65

Compounds of the formula I (n=0) where $R^1$ is hydrogen, $R^2X$ is methylamino, $R^3$ is chloro and $R^4$ for a compound in each case corresponds to one line of Table A.

Table 66

Compounds of the formula I (n=0) where $R^1$ is methyl, $R^2X$ is methyl, $R^3$ is chloro and $R^4$ for a compound in each case corresponds to one line of Table A.

Table 67

Compounds of the formula I (n=0) where $R^1$ is methyl, $R^2X$ is ethyl, $R^3$ is chloro and $R^4$ for a compound in each case corresponds to one line of Table A.

Table 68

Compounds of the formula I (n=0) where $R^1$ is methyl, $R^2X$ is methoxy, $R^3$ is chloro and $R^4$ for a compound in each case corresponds to one line of Table A.

Table 69

Compounds of the formula I (n=0) where $R^1$ is methyl, $R^2X$ is ethoxy, $R^3$ is chloro and $R^4$ for a compound in each case corresponds to one line of Table A.

Table 70

Compounds of the formula I (n=0) where $R^1$ is methyl, $R^2X$ is methylamino, $R^3$ is chloro and $R^4$ for a compound in each case corresponds to one line of Table A.

Table 71

Compounds of the formula I (n=0) where $R^1$ is ethyl, $R^2X$ is methyl, $R^3$ is chloro and $R^4$ for a compound in each case corresponds to one line of Table A.

Table 72

Compounds of the formula I (n=0) where $R^1$ is ethyl, $R^2X$ is ethyl, $R^3$ is chloro and $R^4$ for a compound in each case corresponds to one line of Table A.

Table 73

Compounds of the formula I (n=0) where $R^1$ is ethyl, $R^2X$ is methoxy, $R^3$ is chloro and $R^4$ for a compound in each case corresponds to one line of Table A.

Table 74

Compounds of the formula I (n=0) where $R^1$ is ethyl, $R^2X$ is ethoxy, $R^3$ is chloro and $R^4$ for a compound in each case corresponds to one line of Table A.

Table 75

Compounds of the formula I (n=0) where $R^1$ is ethyl, $R^2X$ is methylamino, $R^3$ is chloro and $R^4$ for a compound in each case corresponds to one line of Table A.

Table 76

Compounds of the formula I where $R_n$ is 3-chloro, $R^1$ is hydrogen, $R^2X$ is methyl, $R^3$ is chloro and $R^4$ for a compound in each case corresponds to one line of Table A.

Table 77

Compounds of the formula I where $R_n$ is 3-chloro, $R^1$ is hydrogen, $R^2X$ is ethyl, $R^3$ is chloro and $R^4$ for a compound in each case corresponds to one line of Table A.

Table 78

Compounds of the formula I where $R_n$ is 3-chloro, $R^1$ is hydrogen, $R^2X$ is methoxy, $R^3$ is chloro and $R^4$ for a compound in each case corresponds to one line of Table A.

Table 79

Compounds of the formula I where $R_n$ is 3-chloro, $R^1$ is hydrogen, $R^2X$ is ethoxy, $R^3$ is chloro and $R^4$ for a compound in each case corresponds to one line of Table A.

Table 80

Compounds of the formula I where $R_n$ is 3-chloro, $R^1$ is hydrogen, $R^2X$ is methylamino, $R^3$ is chloro and $R^4$ for a compound in each case corresponds to one line of Table A.

Table 81

Compounds of the formula I where $R_n$ is 3-chloro, $R^1$ is methyl, $R^2X$ is methyl, $R^3$ is chloro and $R^4$ for a compound in each case corresponds to one line of Table A.

Table 82

Compounds of the formula I where $R_n$ is 3-chloro, $R^1$ is methyl, $R^2X$ is ethyl, $R^3$ is chloro and $R^4$ for a compound in each case corresponds to one line of Table A.

Table 83

Compounds of the formula I where $R_n$ is 3-chloro, $R^1$ is methyl, $R^2X$ is methoxy, $R^3$ is chloro and $R^4$ for a compound in each case corresponds to one line of Table A.

Table 84

Compounds of the formula I where $R_n$ is 3-chloro, $R^1$ is methyl, $R^2X$ is ethoxy, $R^3$ is chloro and $R^4$ for a compound in each case corresponds to one line of Table A.

Table 85

Compounds of the formula I where $R_n$ is 3-chloro, $R^1$ is methyl, $R^2X$ is methylamino, $R^3$ is chloro and $R^4$ for a compound in each case corresponds to one line of Table A.

Table 86

Compounds of the formula I where $R_n$ is 3-chloro, $R^1$ is ethyl, $R^2X$ is methyl, $R^3$ is chloro and $R^4$ for a compound in each case corresponds to one line of Table A.

Table 87

Compounds of the formula I where $R_n$ is 3-chloro, $R^1$ is ethyl, $R^2X$ is ethyl, $R^3$ is chloro and $R^4$ for a compound in each case corresponds to one line of Table A.

Table 88

Compounds of the formula I where $R_n$ is 3-chloro, $R^1$ is ethyl, $R^2X$ is methoxy, $R^3$ is chloro and $R^4$ for a compound in each case corresponds to one line of Table A.

Table 89

Compounds of the formula I where $R_n$ is 3-chloro, $R^1$ is ethyl, $R^2X$ is ethoxy, $R^3$ is chloro and $R^4$ for a compound in each case corresponds to one line of Table A.

Table 90

Compounds of the formula I where $R_n$ is 3-chloro, $R^1$ is ethyl, $R^2X$ is methylamino, $R^3$ is chloro and $R^4$ for a compound in each case corresponds to one line of Table A.

Table 91

Compounds of the formula I (n=0) where $R^1$ is hydrogen, $R^2X$ is methyl, $R^3$ is methyl and $R^4$ for a compound in each case corresponds to one line of Table A.

Table 92

Compounds of the formula I (n=0) where $R^1$ is hydrogen, $R^2X$ is ethyl, $R^3$ is methyl and $R^4$ for a compound in each case corresponds to one line of Table A.

Table 93

Compounds of the formula I (n=0) where $R^1$ is hydrogen, $R^2X$ is methoxy, $R^3$ is methyl and $R^4$ for a compound in each case corresponds to one line of Table A.

Table 94

Compounds of the formula I (n=0) where $R^1$ is hydrogen, $R^2X$ is ethoxy, $R^3$ is methyl and $R^4$ for a compound in each case corresponds to one line of Table A.

Table 95

Compounds of the formula I (n=0) where $R^1$ is hydrogen, $R^2X$ is methylamino, $R^3$ is methyl and $R^4$ for a compound in each case corresponds to one line of Table A.

Table 96

Compounds of the formula I (n=0) where $R^1$ is methyl, $R^2X$ is methyl, $R^3$ is methyl and $R^4$ for a compound in each case corresponds to one line of Table A.

Table 97

Compounds of the formula I (n=0) where $R^1$ is methyl, $R^2X$ is ethyl, $R^3$ is methyl and $R^4$ for a compound in each case corresponds to one line of Table A.

Table 98

Compounds of the formula I (n=0) where $R^1$ is methyl, $R^2X$ is methoxy, $R^3$ is methyl and $R^4$ for a compound in each case corresponds to one line of Table A.

Table 99

Compounds of the formula I (n=0) where $R^1$ is methyl, $R^2X$ is ethoxy, $R^3$ is methyl and $R^4$ for a compound in each case corresponds to one line of Table A.

Table 100

Compounds of the formula I (n=0) where $R^1$ is methyl, $R^2X$ is methylamino, $R^3$ is methyl and $R^4$ for a compound in each case corresponds to one line of Table A.

Table 101

Compounds of the formula I (n=0) where $R^1$ is ethyl, $R^2X$ is methyl, $R^3$ is methyl and $R^4$ for a compound in each case corresponds to one line of Table A.

Table 102

Compounds of the formula I (n=0) where $R^1$ is ethyl, $R^2X$ is ethyl, $R^3$ is methyl and $R^4$ for a compound in each case corresponds to one line of Table A.

Table 103

Compounds of the formula I (n=0) where $R^1$ is ethyl, $R^2X$ is methoxy, $R^3$ is methyl and $R^4$ for a compound in each case corresponds to one line of Table A.

Table 104

Compounds of the formula I (n=0) where $R^1$ is ethyl, $R^2X$ is ethoxy, $R^3$ is methyl and $R^4$ for a compound in each case corresponds to one line of Table A.

Table 105

Compounds of the formula I (n=0) where $R^1$ is ethyl, $R^2X$ is methylamino, $R^3$ is methyl and $R^4$ for a compound in each case corresponds to one line of Table A.

Table 106

Compounds of the formula I where $R_n$ is 3-chloro, $R^1$ is hydrogen, $R^2X$ is methyl, $R^3$ is methyl and $R^4$ for a compound in each case corresponds to one line of Table A.

Table 107

Compounds of the formula I where $R_n$ is 3-chloro, $R^1$ is hydrogen, $R^2X$ is ethyl, $R^3$ is methyl and $R^4$ for a compound in each case corresponds to one line of Table A.

Table 108

Compounds of the formula I where $R_n$ is 3-chloro, $R^1$ is hydrogen, $R^2X$ is methoxy, $R^3$ is methyl and $R^4$ for a compound in each case corresponds to one line of Table A.

Table 109

Compounds of the formula I where $R_n$ is 3-chloro, $R^1$ is hydrogen, $R^2X$ is ethoxy, $R^3$ is methyl and $R^4$ for a compound in each case corresponds to one line of Table A.

Table 110

Compounds of the formula I where $R_n$ is 3-chloro, $R^1$ is hydrogen, $R^2X$ is methylamino, $R^3$ is methyl and $R^4$ for a compound in each case corresponds to one line of Table A.

Table 111

Compounds of the formula I where $R_n$ is 3-chloro, $R^1$ is methyl, $R^2X$ is methyl, $R^3$ is methyl and $R^4$ for a compound in each case corresponds to one line of Table A.

Table 112

Compounds of the formula I where $R_n$ is 3-chloro, $R^1$ is methyl, $R^2X$ is ethyl, $R^3$ is methyl and $R^4$ for a compound in each case corresponds to one line of Table A.

Table 113

Compounds of the formula I where $R_n$ is 3-chloro, $R^1$ is methyl, $R^2X$ is methoxy, $R^3$ is methyl and $R^4$ for a compound in each case corresponds to one line of Table A.

Table 114

Compounds of the formula I where $R_n$ is 3-chloro, $R^1$ is methyl, $R^2X$ is ethoxy, $R^3$ is methyl and $R^4$ for a compound in each case corresponds to one line of Table A.

Table 115

Compounds of the formula I where $R_n$ is 3-chloro, $R^1$ is methyl, $R^2X$ is methylamino, $R^3$ is methyl and $R^4$ for a compound in each case corresponds to one line of Table A.

Table 116

Compounds of the formula I where $R_n$ is 3-chloro, $R^1$ is ethyl, $R^2X$ is methyl, $R^3$ is methyl and $R^4$ for a compound in each case corresponds to one line of Table A.

Table 117

Compounds of the formula I where $R_n$ is 3-chloro, $R^1$ is ethyl, $R^2X$ is ethyl, $R^3$ is methyl and $R^4$ for a compound in each case corresponds to one line of Table A.

Table 118

Compounds of the formula I where $R_n$ is 3-chloro, $R^1$ is ethyl, $R^2X$ is methoxy, $R^3$ is methyl and $R^4$ for a compound in each case corresponds to one line of Table A.

Table 119

Compounds of the formula I where $R_n$ is 3-chloro, $R^1$ is ethyl, $R^2X$ is ethoxy, $R^3$ is methyl and $R^4$ for a compound in each case corresponds to one line of Table A.

Table 120

Compounds of the formula I where $R_n$ is 3-chloro, $R^1$ is ethyl, $R^2X$ is methylamino, $R^3$ is methyl and $R^4$ for a compound in each case corresponds to one line of Table A.

Table 121

Compounds of the formula I (n=0) where $R^1$ is hydrogen, $R^2X$ is methyl, $R^3$ is ethyl and $R^4$ for a compound in each case corresponds to one line of Table A.

Table 122

Compounds of the formula I (n=0) where $R^1$ is hydrogen, $R^2X$ is ethyl, $R^3$ is ethyl and $R^4$ for a compound in each case corresponds to one line of Table A.

Table 123

Compounds of the formula I (n=0) where $R^1$ is hydrogen, $R^2X$ is methoxy, $R^3$ is ethyl and $R^4$ for a compound in each case corresponds to one line of Table A.

Table 124

Compounds of the formula I (n=0) where $R^1$ is hydrogen, $R^2X$ is ethoxy, $R^3$ is ethyl and $R^4$ for a compound in each case corresponds to one line of Table A.

Table 125

Compounds of the formula I (n=0) where $R^1$ is hydrogen, $R^2X$ is methylamino, $R^3$ is ethyl and $R^4$ for a compound in each case corresponds to one line of Table A.

Table 126

Compounds of the formula I (n=0) where $R^1$ is methyl, $R^2X$ is methyl, $R^3$ is ethyl and $R^4$ for a compound in each case corresponds to one line of Table A.

Table 127

Compounds of the formula I (n=0) where $R^1$ is methyl, $R^2X$ is ethyl, $R^3$ is ethyl and $R^4$ for a compound in each case corresponds to one line of Table A.

Table 128

Compounds of the formula I (n=0) where $R^1$ is methyl, $R^2X$ is methoxy, $R^3$ is ethyl and $R^4$ for a compound in each case corresponds to one line of Table A.

Table 129

Compounds of the formula I (n=0) where $R^1$ is methyl, $R^2X$ is ethoxy, $R^3$ is ethyl and $R^4$ for a compound in each case corresponds to one line of Table A.

Table 130

Compounds of the formula I (n=0) where $R^1$ is methyl, $R^2X$ is methylamino, $R^3$ is ethyl and $R^4$ for a compound in each case corresponds to one line of Table A.

Table 131

Compounds of the formula I (n=0) where $R^1$ is ethyl, $R^2X$ is methyl, $R^3$ is ethyl and $R^4$ for a compound in each case corresponds to one line of Table A.

Table 132

Compounds of the formula I (n=0) where $R^1$ is ethyl, $R^2X$ is ethyl, $R^3$ is ethyl and $R^4$ for a compound in each case corresponds to one line of Table A.

Table 133

Compounds of the formula I (n=0) where $R^1$ is ethyl, $R^2X$ is methoxy, $R^3$ is ethyl and $R^4$ for a compound in each case corresponds to one line of Table A.

Table 134

Compounds of the formula I (n=0) where $R^1$ is ethyl, $R^2X$ is ethoxy, $R^3$ is ethyl and $R^4$ for a compound in each case corresponds to one line of Table A.

Table 135

Compounds of the formula I (n=0) where $R^1$ is ethyl, $R^2X$ is methylamino, $R^3$ is ethyl and $R^4$ for a compound in each case corresponds to one line of Table A.

Table 136

Compounds of the formula I where $R_n$ is 3-chloro, $R^1$ is hydrogen, $R^2X$ is methyl, $R^3$ is ethyl and $R^4$ for a compound in each case corresponds to one line of Table A.

Table 137

Compounds of the formula I where $R_n$ is 3-chloro, $R^1$ is hydrogen, $R^2X$ is ethyl, $R^3$ is ethyl and $R^4$ for a compound in each case corresponds to one line of Table A.

Table 138

Compounds of the formula I where $R_n$ is 3-chloro, $R^1$ is hydrogen, $R^2X$ is methoxy, $R^3$ is ethyl and $R^4$ for a compound in each case corresponds to one line of Table A.

Table 139

Compounds of the formula I where $R_n$ is 3-chloro, $R^1$ is hydrogen, $R^2X$ is ethoxy, $R^3$ is ethyl and $R^4$ for a compound in each case corresponds to one line of Table A.

Table 140

Compounds of the formula I where $R_n$ is 3-chloro, $R^1$ is hydrogen, $R^2X$ is methylamino, $R^3$ is ethyl and $R^4$ for a compound in each case corresponds to one line of Table A.

Table 141

Compounds of the formula I where $R_n$ is 3-chloro, $R^1$ is methyl, $R^2X$ is methyl, $R^3$ is ethyl and $R^4$ for a compound in each case corresponds to one line of Table A.

Table 142

Compounds of the formula I where $R_n$ is 3-chloro, $R^1$ is methyl, $R^2X$ is ethyl, $R^3$ is ethyl and $R^4$ for a compound in each case corresponds to one line of Table A.

Table 143

Compounds of the formula I where $R_n$ is 3-chloro, $R^1$ is methyl, $R^2X$ is methoxy, $R^3$ is ethyl and $R^4$ for a compound in each case corresponds to one line of Table A.

Table 144

Compounds of the formula I where $R_n$ is 3-chloro, $R^1$ is methyl, $R^2X$ is ethoxy, $R^3$ is ethyl and $R^4$ for a compound in each case corresponds to one line of Table A.

Table 145

Compounds of the formula I where $R_n$ is 3-chloro, $R^1$ is methyl, $R^2X$ is methylamino, $R^3$ is ethyl and $R^4$ for a compound in each case corresponds to one line of Table A.

Table 146

Compounds of the formula I where $R_n$ is 3-chloro, $R^1$ is ethyl, $R^2X$ is methyl, $R^3$ is ethyl and $R^4$ for a compound in each case corresponds to one line of Table A.

Table 147

Compounds of the formula I where $R_n$ is 3-chloro, $R^1$ is ethyl, $R^2X$ is ethyl, $R^3$ is ethyl and $R^4$ for a compound in each case corresponds to one line of Table A.

Table 148

Compounds of the formula I where $R_n$ is 3-chloro, $R^1$ is ethyl, $R^2X$ is methoxy, $R^3$ is ethyl and $R^4$ for a compound in each case corresponds to one line of Table A.

Table 149

Compounds of the formula I where $R_n$ is 3-chloro, $R^1$ is ethyl, $R^2X$ is ethoxy, $R^3$ is ethyl and $R^4$ for a compound in each case corresponds to one line of Table A.

Table 150

Compounds of the formula I where $R_n$ is 3-chloro, $R^1$ is ethyl, $R^2X$ is methylamino, $R^3$ is ethyl and $R^4$ for a compound in each case corresponds to one line of Table A.

Table 151

Compounds of the formula I (n=0) where $R^1$ is hydrogen, $R^2X$ is methyl, $R^3$ is isopropyl and $R^4$ for a compound in each case corresponds to one line of Table A.

Table 152

Compounds of the formula I (n=0) where $R^1$ is hydrogen, $R^2X$ is ethyl, $R^3$ is isopropyl and $R^4$ for a compound in each case corresponds to one line of Table A.

Table 153

Compounds of the formula I (n=0) where $R^1$ is hydrogen, $R^2X$ is methoxy, $R^3$ is isopropyl and $R^4$ for a compound in each case corresponds to one line of Table A.

Table 154

Compounds of the formula I (n=0) where $R^1$ is hydrogen, $R^2X$ is ethoxy, $R^3$ is isopropyl and $R^4$ for a compound in each case corresponds to one line of Table A.

Table 155

Compounds of the formula I (n=0) where $R^1$ is hydrogen, $R^2X$ is methylamino, $R^3$ is isopropyl and $R^4$ for a compound in each case corresponds to one line of Table A.

Table 156

Compounds of the formula I (n=0) where $R^1$ is methyl, $R^2X$ is methyl, $R^3$ is isopropyl and $R^4$ for a compound in each case corresponds to one line of Table A.

Table 157

Compounds of the formula I (n=0) where $R^1$ is methyl, $R^2X$ is ethyl, $R^3$ is isopropyl and $R^4$ for a compound in each case corresponds to one line of Table A.

Table 158

Compounds of the formula I (n=0) where $R^1$ is methyl, $R^2X$ is methoxy, $R^3$ is isopropyl and $R^4$ for a compound in each case corresponds to one line of Table A.

Table 159

Compounds of the formula I (n=0) where $R^1$ is methyl, $R^2X$ is ethoxy, $R^3$ is isopropyl and $R^4$ for a compound in each case corresponds to one line of Table A.

Table 160

Compounds of the formula I (n=0) where $R^1$ is methyl, $R^2X$ is methylamino, $R^3$ is isopropyl and $R^4$ for a compound in each case corresponds to one line of Table A.

Table 161

Compounds of the formula I (n=0) where $R^1$ is ethyl, $R^2X$ is methyl, $R^3$ is isopropyl and $R^4$ for a compound in each case corresponds to one line of Table A.

Table 162

Compounds of the formula I (n=0) where $R^1$ is ethyl, $R^2X$ is ethyl, $R^3$ is isopropyl and $R^4$ for a compound in each case corresponds to one line of Table A.

Table 163

Compounds of the formula I (n=0) where $R^1$ is ethyl, $R^2X$ is methoxy, $R^3$ is isopropyl and $R^4$ for a compound in each case corresponds to one line of Table A.

Table 164

Compounds of the formula I (n=0) where $R^1$ is ethyl, $R^2X$ is ethoxy, $R^3$ is isopropyl and $R^4$ for a compound in each case corresponds to one line of Table A.

Table 165

Compounds of the formula I (n=0) where $R^1$ is ethyl, $R^2X$ is methylamino, $R^3$ is isopropyl and $R^4$ for a compound in each case corresponds to one line of Table A.

Table 166

Compounds of the formula I where $R_n$ is 3-chloro, $R^1$ is hydrogen, $R^2X$ is methyl, $R^3$ is isopropyl and $R^4$ for a compound in each case corresponds to one line of Table A.

Table 167

Compounds of the formula I where $R_n$ is 3-chloro, $R^1$ is hydrogen, $R^2X$ is ethyl, $R^3$ is isopropyl and $R^4$ for a compound in each case corresponds to one line of Table A.

Table 168

Compounds of the formula I where $R_n$ is 3-chloro, $R^1$ is hydrogen, $R^2X$ is methoxy, $R^3$ is isopropyl and $R^4$ for a compound in each case corresponds to one line of Table A.

Table 169

Compounds of the formula I where $R_n$ is 3-chloro, $R^1$ is hydrogen, $R^2X$ is ethoxy, $R^3$ is isopropyl and $R^4$ for a compound in each case corresponds to one line of Table A.

Table 170

Compounds of the formula I where $R_n$ is 3-chloro, $R^1$ is hydrogen, $R^2X$ is methylamino, $R^3$ is isopropyl and $R^4$ for a compound in each case corresponds to one line of Table A.

Table 171

Compounds of the formula I where $R_n$ is 3-chloro, $R^1$ is methyl, $R^2X$ is methyl, $R^3$ is isopropyl and $R^4$ for a compound in each case corresponds to one line of Table A.

Table 172

Compounds of the formula I where $R_n$ is 3-chloro, $R^1$ is methyl, $R^2X$ is ethyl, $R^3$ is isopropyl and $R^4$ for a compound in each case corresponds to one line of Table A.

Table 173

Compounds of the formula I where $R_n$ is 3-chloro, $R^1$ is methyl, $R^2X$ is methoxy, $R^3$ is isopropyl and $R^4$ for a compound in each case corresponds to one line of Table A.

Table 174

Compounds of the formula I where $R_n$ is 3-chloro, $R^1$ is methyl, $R^2X$ is ethoxy, $R^3$ is isopropyl and $R^4$ for a compound in each case corresponds to one line of Table A.

Table 175

Compounds of the formula I where $R_n$ is 3-chloro, $R^1$ is methyl, $R^2X$ is methylamino, $R^3$ is isopropyl and $R^4$ for a compound in each case corresponds to one line of Table A.

Table 176

Compounds of the formula I where $R_n$ is 3-chloro, $R^1$ is ethyl, $R^2X$ is methyl, $R^3$ is isopropyl and $R^4$ for a compound in each case corresponds to one line of Table A.

Table 177

Compounds of the formula I where $R_n$ is 3-chloro, $R^1$ is ethyl, $R^2X$ is ethyl, $R^3$ is isopropyl and $R^4$ for a compound in each case corresponds to one line of Table A.

Table 178

Compounds of the formula I where $R_n$ is 3-chloro, $R^1$ is ethyl, $R^2X$ is methoxy, $R^3$ is isopropyl and $R^4$ for a compound in each case corresponds to one line of Table A.

Table 179

Compounds of the formula I where $R_n$ is 3-chloro, $R^1$ is ethyl, $R^2X$ is ethoxy, $R^3$ is isopropyl and $R^4$ for a compound in each case corresponds to one line of Table A.

Table 180

Compounds of the formula I where $R_n$ is 3-chloro, $R^1$ is ethyl, $R^2X$ is methylamino, $R^3$ is isopropyl and $R^4$ for a compound in each case corresponds to one line of Table A.

Table 181

Compounds of the formula I (n=0) where $R^1$ is hydrogen, $R^2X$ is methyl, $R^3$ is trifluoromethyl and $R^4$ for a compound in each case corresponds to one line of Table A.

Table 182

Compounds of the formula I (n=0) where $R^1$ is hydrogen, $R^2X$ is ethyl, $R^3$ is trifluoromethyl and $R^4$ for a compound in each case corresponds to one line of Table A.

Table 183

Compounds of the formula I (n=0) where $R^1$ is hydrogen, $R^2X$ is methoxy, $R^3$ is trifluoromethyl and $R^4$ for a compound in each case corresponds to one line of Table A.

Table 184

Compounds of the formula I (n=0) where $R^1$ is hydrogen, $R^2X$ is ethoxy, $R^3$ is trifluoromethyl and $R^4$ for a compound in each case corresponds to one line of Table A.

Table 185

Compounds of the formula I (n=0) where $R^1$ is hydrogen, $R^2X$ is methylamino, $R^3$ is trifluoromethyl and $R^4$ for a compound in each case corresponds to one line of Table A.

Table 186

Compounds of the formula I (n=0) where $R^1$ is methyl, $R^2X$ is ethyl, $R^3$ is trifluoromethyl and $R^4$ for a compound in each case corresponds to one line of Table A.

Table 187

Compounds of the formula I (n=0) where $R^1$ is methyl, $R^2X$ is ethyl, $R^3$ is trifluoromethyl and $R^4$ for a compound in each case corresponds to one line of Table A.

Table 188

Compounds of the formula I (n=0) where $R^1$ is methyl, $R^2X$ is methoxy, $R^3$ is trifluoromethyl and $R^4$ for a compound in each case corresponds to one line of Table A.

Table 189

Compounds of the formula I (n=0) where $R^1$ is methyl, $R^2X$ is ethoxy, $R^3$ is trifluoromethyl and $R^4$ for a compound in each case corresponds to one line of Table A.

Table 190

Compounds of the formula I (n=0) where $R^1$ is methyl, $R^2X$ is methylamino, $R^3$ is trifluoromethyl and $R^4$ for a compound in each case corresponds to one line of Table A.

Table 191

Compounds of the formula I (n=0) where $R^1$ is ethyl, $R^2X$ is methyl, $R^3$ is trifluoromethyl and $R^4$ for a compound in each case corresponds to one line of Table A.

Table 192

Compounds of the formula I (n=0) where $R^1$ is ethyl, $R^2X$ is ethyl, $R^3$ is trifluoromethyl and $R^4$ for a compound in each case corresponds to one line of Table A.

Table 193

Compounds of the formula I (n=0) where $R^1$ is ethyl, $R^2X$ is methoxy, $R^3$ is trifluoromethyl and $R^4$ for a compound in each case corresponds to one line of Table A.

Table 194

Compounds of the formula I (n=0) where $R^1$ is ethyl, $R^2X$ is ethoxy, $R^3$ is trifluoromethyl and $R^4$ for a compound in each case corresponds to one line of Table A.

Table 195

Compounds of the formula I (n=0) where $R^1$ is ethyl, $R^2X$ is ethylamino, $R^3$ is trifluoromethyl and $R^4$ for a compound in each case corresponds to one line of Table A.

Table 196

Compounds of the formula I where $R_n$ is 3-chloro, $R^1$ is hydrogen, $R^2X$ is methyl, $R^3$ is trifluoromethyl and $R^4$ for a compound in each case corresponds to one line of Table A.

Table 197

Compounds of the formula I where $R_n$ is 3-chloro, $R^1$ is hydrogen, $R^2X$ is ethyl, $R^3$ is trifluoromethyl and $R^4$ for a compound in each case corresponds to one line of Table A.

Table 198

Compounds of the formula I where $R_n$ is 3-chloro, $R^1$ is hydrogen, $R^2X$ is methoxy, $R^3$ is trifluoromethyl and $R^4$ for a compound in each case corresponds to one line of Table A.

Table 199

Compounds of the formula I where $R_n$ is 3-chloro, $R^1$ is hydrogen, $R^2X$ is ethoxy, $R^3$ is trifluoromethyl and $R^4$ for a compound in each case corresponds to one line of Table A.

Table 200

Compounds of the formula I where $R_n$ is 3-chloro, $R^1$ is hydrogen, $R^2X$ is methylamino, $R^3$ is trifluoromethyl and $R^4$ for a compound in each case corresponds to one line of Table A.

Table 201

Compounds of the formula I where $R_n$ is 3-chloro, $R^1$ is methyl, $R^2X$ is methyl, $R^3$ is trifluoromethyl and $R^4$ for a compound in each case corresponds to one line of Table A.

Table 202

Compounds of the formula I where $R_n$ is 3-chloro, $R^1$ is methyl, $R^2X$ is ethyl, $R^3$ is trifluoromethyl and $R^4$ for a compound in each case corresponds to one line of Table A.

Table 203

Compounds of the formula I where $R_n$ is 3-chloro, $R^1$ is methyl, $R^2X$ is methoxy, $R^3$ is trifluoromethyl and $R^4$ for a compound in each case corresponds to one line of Table A.

Table 204

Compounds of the formula I where $R_n$ is 3-chloro, $R^1$ is methyl, $R^2X$ is ethoxy, $R^3$ is trifluoromethyl and $R^4$ for a compound in each case corresponds to one line of Table A.

Table 205

Compounds of the formula I where $R_n$ is 3-chloro, $R^1$ is methyl, $R^2X$ is methylamino, $R^3$ is trifluoromethyl and $R^4$ for a compound in each case corresponds to one line of Table A.

Table 206

Compounds of the formula I where $R_n$ is 3-chloro, $R^1$ is ethyl, $R^2X$ is methyl, $R^3$ is trifluoromethyl and $R^4$ for a compound in each case corresponds to one line of Table A.

Table 207

Compounds of the formula I where $R_n$ is 3-chloro, $R^1$ is ethyl, $R^2X$ is ethyl, $R^3$ is trifluoromethyl and $R^4$ for a compound in each case corresponds to one line of Table A.

Table 208

Compounds of the formula I where $R_n$ is 3-chloro, $R^1$ is ethyl, $R^2X$ is methoxy, $R^3$ is trifluoromethyl and $R^4$ for a compound in each case corresponds to one line of Table A.

Table 209

Compounds of the formula I where $R_n$ is 3-chloro, $R^1$ is ethyl, $R^2X$ is ethoxy, $R^3$ is trifluoromethyl and $R^4$ for a compound in each case corresponds to one line of Table A.

Table 210

Compounds of the formula I where $R_n$ is 3-chloro, $R^1$ is ethyl, $R^2X$ is methylamino, $R^3$ is trifluoromethyl and $R^4$ for a compound in each case corresponds to one line of Table A.

Table 211

Compounds of the formula I (n=0) where $R^1$ is hydrogen, $R^2X$ is methyl, $R^3$ is methoxy and $R^4$ for a compound in each case corresponds to one line of Table A.

Table 212

Compounds of the formula I (n=0) where $R^1$ is hydrogen, $R^2X$ is ethyl, $R^3$ is methoxy and $R^4$ for a compound in each case corresponds to one line of Table A.

Table 213

Compounds of the formula I (n=0) where $R^1$ is hydrogen, $R^2X$ is methoxy, $R^3$ is methoxy and $R^4$ for a compound in each case corresponds to one line of Table A.

Table 214

Compounds of the formula I (n=0) where $R^1$ is hydrogen, $R^2X$ is ethoxy, $R^3$ is methoxy and $R^4$ for a compound in each case corresponds to one line of Table A.

Table 215

Compounds of the formula I (n=0) where $R^1$ is hydrogen, $R^2X$ is methylamino, $R^3$ is methoxy and $R^4$ for a compound in each case corresponds to one line of Table A.

Table 216

Compounds of the formula I (n=0) where $R^1$ is methyl, $R^2X$ is methyl, $R^3$ is methoxy and $R^4$ for a compound in each case corresponds to one line of Table A.

Table 217

Compounds of the formula I (n=0) where $R^1$ is methyl, $R^2X$ is ethyl, $R^3$ is methoxy and $R^4$ for a compound in each case corresponds to one line of Table A.

Table 218

Compounds of the formula I (n=0) where $R^1$ is methyl, $R^2X$ is methoxy, $R^3$ is methoxy and $R^4$ for a compound in each case corresponds to one line of Table A.

Table 219

Compounds of the formula I (n=0) where $R^1$ is methyl, $R^2X$ is ethoxy, $R^3$ is methoxy and $R^4$ for a compound in each case corresponds to one line of Table A.

Table 220

Compounds of the formula I (n=0) where $R^1$ is methyl, $R^2X$ is methylamino, $R^3$ is methoxy and $R^4$ for a compound in each case corresponds to one line of Table A.

Table 221

Compounds of the formula I (n=0) where $R^1$ is ethyl, $R^2X$ is methyl, $R^3$ is methoxy and $R^4$ for a compound in each case corresponds to one line of Table A.

Table 222

Compounds of the formula I (n=0) where $R^1$ is ethyl, $R^2X$ is ethyl, $R^3$ is methoxy and $R^4$ for a compound in each case corresponds to one line of Table A.

Table 223

Compounds of the formula I (n=0) where $R^1$ is ethyl, $R^2X$ is methoxy, $R^3$ is methoxy and $R^4$ for a compound in each case corresponds to one line of Table A.

Table 224

Compounds of the formula I (n=0) where $R^1$ is ethyl, $R^2X$ is ethoxy, $R^3$ is methoxy and $R^4$ for a compound in each case corresponds to one line of Table A.

Table 225

Compounds of the formula I (n=0) where $R^1$ is ethyl, $R^2X$ is methylamino, $R^3$ is methoxy and $R^4$ for a compound in each case corresponds to one line of Table A.

Table 226

Compounds of the formula I where $R_n$ is 3-chloro, $R^1$ is hydrogen, $R^2X$ is methyl, $R^3$ is methoxy and $R^4$ for a compound in each case corresponds to one line of Table A.

Table 227

Compounds of the formula I where $R_n$ is 3-chloro, $R^1$ is hydrogen, $R^2X$ is ethyl, $R^3$ is methoxy and $R^4$ for a compound in each case corresponds to one line of Table A.

Table 228

Compounds of the formula I where $R_n$ is 3-chloro, $R^1$ is hydrogen, $R^2X$ is methoxy, $R^3$ is methoxy and $R^4$ for a compound in each case corresponds to one line of Table A.

Table 229

Compounds of the formula I where $R_n$ is 3-chloro, $R^1$ is hydrogen, $R^2X$ is ethoxy, $R^3$ is methoxy and $R^4$ for a compound in each case corresponds to one line of Table A.

Table 230

Compounds of the formula I where $R_n$ is 3-chloro, $R^1$ is hydrogen, $R^2X$ is methylamino, $R^3$ is methoxy and $R^4$ for a compound in each case corresponds to one line of Table A.

Table 231

Compounds of the formula I where $R_n$ is 3-chloro, $R^1$ is methyl, $R^2X$ is methyl, $R^3$ is methoxy and $R^4$ for a compound in each case corresponds to one line of Table A.

Table 232

Compounds of the formula I where $R_n$ is 3-chloro, $R^1$ is methyl, $R^2X$ is ethyl, $R^3$ is methoxy and $R^4$ for a compound in each case corresponds to one line of Table A.

Table 233

Compounds of the formula I where $R_n$ is 3-chloro, $R^1$ is methyl, $R^2X$ is methoxy, $R^3$ is methoxy and $R^4$ for a compound in each case corresponds to one line of Table A.

Table 234

Compounds of the formula I where $R_n$ is 3-chloro, $R^1$ is methyl, $R^2X$ is ethoxy, $R^3$ is methoxy and $R^4$ for a compound in each case corresponds to one line of Table A.

Table 235

Compounds of the formula I where $R_n$ is 3-chloro, $R^1$ is methyl, $R^2X$ is methylamino, $R^3$ is methoxy and $R^4$ for a compound in each case corresponds to one line of Table A.

Table 236

Compounds of the formula I where $R_n$ is 3-chloro, $R^1$ is ethyl, $R^2X$ is methyl, $R^3$ is methoxy and $R^4$ for a compound in each case corresponds to one line of Table A.

Table 237

Compounds of the formula I where $R_n$ is 3-chloro, $R^1$ is ethyl, $R^2X$ is ethyl, $R^3$ is methoxy and $R^4$ for a compound in each case corresponds to one line of Table A.

Table 238

Compounds of the formula I where $R_n$ is 3-chloro, $R^1$ is ethyl, $R^2X$ is methoxy, $R^3$ is methoxy and $R^4$ for a compound in each case corresponds to one line of Table A.

Table 239

Compounds of the formula I where $R_n$ is 3-chloro, $R^1$ is ethyl, $R^2X$ is ethoxy, $R^3$ is methoxy and $R^4$ for a compound in each case corresponds to one line of Table A.

Table 240

Compounds of the formula I where $R_n$ is 3-chloro, $R^1$ is ethyl, $R^2X$ is methylamino, $R^3$ is methoxy and $R^4$ for a compound in each case corresponds to one line of Table A.

Table 241

Compounds of the formula I (n=0) where $R^1$ is hydrogen, $R^2X$ is methyl, $R^3$ is ethoxy and $R^4$ for a compound in each case corresponds to one line of Table A.

Table 242

Compounds of the formula I (n=0) where $R^1$ is hydrogen, $R^2X$ is ethyl, $R^3$ is ethoxy and $R^4$ for a compound in each case corresponds to one line of Table A.

Table 243

Compounds of the formula I (n=0) where $R^1$ is hydrogen, $R^2X$ is methoxy, $R^3$ is ethoxy and $R^4$ for a compound in each case corresponds to one line of Table A.

Table 244

Compounds of the formula I (n=0) where $R^1$ is hydrogen, $R^2X$ is ethoxy, $R^3$ is ethoxy and $R^4$ for a compound in each case corresponds to one line of Table A.

Table 245

Compounds of the formula I (n=0) where $R^1$ is hydrogen, $R^2X$ is methylamino, $R^3$ is ethoxy and $R^4$ for a compound in each case corresponds to one line of Table A.

Table 246

Compounds of the formula I (n=0) where $R^1$ is methyl, $R^2X$ is methyl, $R^3$ is ethoxy and $R^4$ for a compound in each case corresponds to one line of Table A.

Table 247

Compounds of the formula I (n=0) where $R^1$ is methyl, $R^2X$ is ethyl, $R^3$ is ethoxy and $R^4$ for a compound in each case corresponds to one line of Table A.

Table 248

Compounds of the formula I (n=0) where $R^1$ is methyl, $R^2X$ is methoxy, $R^3$ is ethoxy and $R^4$ for a compound in each case corresponds to one line of Table A.

Table 249

Compounds of the formula I (n=0) where $R^1$ is methyl, $R^2X$ is ethoxy, $R^3$ is ethoxy and $R^4$ for a compound in each case corresponds to one line of Table A.

Table 250

Compounds of the formula I (n=0) where $R^1$ is methyl, $R^2X$ is methylamino, $R^3$ is ethoxy and $R^4$ for a compound in each case corresponds to one line of Table A.

Table 251

Compounds of the formula I (n=0) where $R^1$ is ethyl, $R^2X$ is methyl, $R^3$ is ethoxy and $R^4$ for a compound in each case corresponds to one line of Table A.

Table 252

Compounds of the formula I (n=0) where $R^1$ is ethyl, $R^2X$ is ethyl, $R^3$ is ethoxy and $R^4$ for a compound in each case corresponds to one line of Table A.

Table 253

Compounds of the formula I (n=0) where $R^1$ is ethyl, $R^2X$ is methoxy, $R^3$ is ethoxy and $R^4$ for a compound in each case corresponds to one line of Table A.

Table 254

Compounds of the formula I (n=0) where $R^1$ is ethyl, $R^2X$ is ethoxy, $R^3$ is ethoxy and $R^4$ for a compound in each case corresponds to one line of Table A.

Table 255

Compounds of the formula I (n=0) where $R^1$ is ethyl, $R^2X$ is methylamino, $R^3$ is ethoxy and $R^4$ for a compound in each case corresponds to one line of Table A.

Table 256

Compounds of the formula I where $R_n$ is 3-chloro, $R^1$ is hydrogen, $R^2X$ is methyl, $R^3$ is ethoxy and $R^4$ for a compound in each case corresponds to one line of Table A.

Table 257

Compounds of the formula I where $R_n$ is 3-chloro, $R^1$ is hydrogen, $R^2X$ is ethyl, $R^3$ is ethoxy and $R^4$ for a compound in each case corresponds to one line of Table A.

Table 258

Compounds of the formula I where $R_n$ is 3-chloro, $R^1$ is hydrogen, $R^2X$ is methoxy, $R^3$ is ethoxy and $R^4$ for a compound in each case corresponds to one line of Table A.

Table 259

Compounds of the formula I where $R_n$ is 3-chloro, $R^1$ is hydrogen, $R^2X$ is ethoxy, $R^3$ is ethoxy and $R^4$ for a compound in each case corresponds to one line of Table A.

Table 260

Compounds of the formula I where $R_n$ is 3-chloro, $R^1$ is hydrogen, $R^2X$ is methylamino, $R^3$ is ethoxy and $R^4$ for a compound in each case corresponds to one line of Table A.

Table 261

Compounds of the formula I where $R_n$ is 3-chloro, $R^1$ is methyl, $R^2X$ is methyl, $R^3$ is ethoxy and $R^4$ for a compound in each case corresponds to one line of Table A.

Table 262

Compounds of the formula I where $R_n$ is 3-chloro, $R^1$ is methyl, $R^2X$ is ethyl, $R^3$ is ethoxy and $R^4$ for a compound in each case corresponds to one line of Table A.

Table 263

Compounds of the formula I where $R_n$ is 3-chloro, $R^1$ is methyl, $R^2X$ is methoxy, $R^3$ is ethoxy and $R^4$ for a compound in each case corresponds to one line of Table A.

Table 264

Compounds of the formula I where $R_n$ is 3-chloro, $R^1$ is methyl, $R^2X$ is ethoxy, $R^3$ is ethoxy and $R^4$ for a compound in each case corresponds to one line of Table A.

Table 265

Compounds of the formula I where $R_n$ is 3-chloro, $R^1$ is methyl, $R^2X$ is methylamino, $R^3$ is ethoxy and $R^4$ for a compound in each case corresponds to one line of Table A.

Table 266

Compounds of the formula I where $R_n$ is 3-chloro, $R^1$ is ethyl, $R^2X$ is methyl, $R^3$ is ethoxy and $R^4$ for a compound in each case corresponds to one line of Table A.

Table 267

Compounds of the formula I where $R_n$ is 3-chloro, $R^1$ is ethyl, $R^2X$ is ethyl, $R^3$ is ethoxy and $R^4$ for a compound in each case corresponds to one line of Table A.

Table 268

Compounds of the formula I where $R_n$ is 3-chloro, $R^1$ is ethyl, $R^2X$ is methoxy, $R^3$ is ethoxy and $R^4$ for a compound in each case corresponds to one line of Table A.

Table 269

Compounds of the formula I where $R_n$ is 3-chloro, $R^1$ is ethyl, $R^2X$ is ethoxy, $R^3$ is ethoxy and $R^4$ for a compound in each case corresponds to one line of Table A.

Table 270

Compounds of the formula I where $R_n$ is 3-chloro, $R^1$ is ethyl, $R^2X$ is methylamino, $R^3$ is ethoxy and $R^4$ for a compound in each case corresponds to one line of Table A.

Table 271

Compounds of the formula I (n=0) where $R^1$ is hydrogen, $R^2X$ is ethyl, $R^3$ is difluoromethoxy and $R^4$ for a compound in each case corresponds to one line of Table A.

Table 272

Compounds of the formula I (n=0) where $R^1$ is hydrogen, $R^2X$ is ethyl, $R^3$ is difluoromethoxy and $R^4$ for a compound in each case corresponds to one line of Table A.

Table 273

Compounds of the formula I (n=0) where $R^1$ is hydrogen, $R^2X$ is methoxy, $R^3$ is difluoromethoxy and $R^4$ for a compound in each case corresponds to one line of Table A.

Table 274

Compounds of the formula I (n=0) where $R^1$ is hydrogen, $R^2X$ is ethoxy, $R^3$ is difluoromethoxy and $R^4$ for a compound in each case corresponds to one line of Table A.

Table 275

Compounds of the formula I (n=0) where $R^1$ is hydrogen, $R^2X$ is methylamino, $R^3$ is difluoromethoxy and $R^4$ for a compound in each case corresponds to one line of Table A.

Table 276

Compounds of the formula I (n=0) where $R^1$ is methyl, $R^2X$ is methyl, $R^3$ is difluoromethoxy and $R^4$ for a compound in each case corresponds to one line of Table A.

Table 277

Compounds of the formula I (n=0) where $R^1$ is methyl, $R^2X$ is ethyl, $R^3$ is difluoromethoxy and $R^4$ for a compound in each case corresponds to one line of Table A.

Table 278

Compounds of the formula I (n=0) where $R^1$ is methyl, $R^2X$ is methoxy, $R^3$ is difluoromethoxy and $R^4$ for a compound in each case corresponds to one line of Table A.

Table 279

Compounds of the formula I (n=0) where $R^1$ is methyl, $R^2X$ is ethoxy, $R^3$ is difluoromethoxy and $R^4$ for a compound in each case corresponds to one line of Table A.

Table 280

Compounds of the formula I (n=0) where $R^1$ is methyl, $R^2X$ is methylamino, $R^3$ is difluoromethoxy and $R^4$ for a compound in each case corresponds to one line of Table A.

Table 281

Compounds of the formula I (n=0) where $R^1$ is ethyl, $R^2X$ is methyl, $R^3$ is difluoromethoxy and $R^4$ for a compound in each case corresponds to one line of Table A.

Table 282

Compounds of the formula I (n=0) where $R^1$ is ethyl, $R^2X$ is ethyl, $R^3$ is difluoromethoxy and $R^4$ for a compound in each case corresponds to one line of Table A.

Table 283

Compounds of the formula I (n=0) where $R^1$ is ethyl, $R^2X$ is methoxy, $R^3$ is difluoromethoxy and $R^4$ for a compound in each case corresponds to one line of Table A.

Table 284

Compounds of the formula I (n=0) where $R^1$ is ethyl, $R^2X$ is ethoxy, $R^3$ is difluoromethoxy and $R^4$ for a compound in each case corresponds to one line of Table A.

Table 285

Compounds of the formula I (n=0) where $R^1$ is ethyl, $R^2X$ is methylamino, $R^3$ is difluoromethoxy and $R^4$ for a compound in each case corresponds to one line of Table A.

Table 286

Compounds of the formula I where $R_n$ is 3-chloro, $R^1$ is hydrogen, $R^2X$ is methyl, $R^3$ is difluoromethoxy and $R^4$ for a compound in each case corresponds to one line of Table A.

Table 287

Compounds of the formula I where $R_n$ is 3-chloro, $R^1$ is hydrogen, $R^2X$ is ethyl, $R^3$ is difluoromethoxy and $R^4$ for a compound in each case corresponds to one line of Table A.

Table 288

Compounds of the formula I where $R_n$ is 3-chloro, $R^1$ is hydrogen, $R^2X$ is methoxy, $R^3$ is difluoromethoxy and $R^4$ for a compound in each case corresponds to one line of Table A.

Table 289

Compounds of the formula I where $R_n$ is 3-chloro, $R^1$ is hydrogen, $R^2X$ is ethoxy, $R^3$ is difluoromethoxy and $R^4$ for a compound in each case corresponds to one line of Table A.

Table 290

Compounds of the formula I where $R_n$ is 3-chloro, $R^1$ is hydrogen, $R^2X$ is methylamino, $R^3$ is difluoromethoxy and $R^4$ for a compound in each case corresponds to one line of Table A.

Table 291

Compounds of the formula I where $R_n$ is 3-chloro, $R^1$ is methyl, $R^2X$ is methyl, $R^3$ is difluoromethoxy and $R^4$ for a compound in each case corresponds to one line of Table A.

Table 292

Compounds of the formula I where $R_n$ is 3-chloro, $R^1$ is methyl, $R^2X$ is ethyl, $R^3$ is difluoromethoxy and $R^4$ for a compound in each case corresponds to one line of Table A.

Table 293

Compounds of the formula I where $R_n$ is 3-chloro, $R^1$ is methyl, $R^2X$ is methoxy, $R^3$ is difluoromethoxy and $R^4$ for a compound in each case corresponds to one line of Table A.

Table 294

Compounds of the formula I where $R_n$ is 3-chloro, $R^1$ is methyl, $R^2X$ is ethoxy, $R^3$ is difluoromethoxy and $R^4$ for a compound in each case corresponds to one line of Table A.

Table 295

Compounds of the formula I where $R_n$ is 3-chloro, $R^1$ is methyl, $R^2X$ is methylamino, $R^3$ is difluoromethoxy and $R^4$ for a compound in each case corresponds to one line of Table A.

Table 296

Compounds of the formula I where $R_n$ is 3-chloro, $R^1$ is ethyl, $R^2X$ is methyl, $R^3$ is difluoromethoxy and $R^4$ for a compound in each case corresponds to one line of Table A.

Table 297

Compounds of the formula I where $R_n$ is 3-chloro, $R^1$ is ethyl, $R^2X$ is ethyl, $R^3$ is difluoromethoxy and $R^4$ for a compound in each case corresponds to one line of Table A.

Table 298

Compounds of the formula I where $R_n$ is 3-chloro, $R^1$ is ethyl, $R^2X$ is methoxy, $R^3$ is difluoromethoxy and $R^4$ for a compound in each case corresponds to one line of Table A.

Table 299

Compounds of the formula I where $R_n$ is 3-chioro, $R^1$ is ethyl, $R^2X$ is ethoxy, $R^3$ is difluoromethoxy and $R^4$ for a compound in each case corresponds to one line of Table A.

Table 300

Compounds of the formula I where $R_n$ is 3-chloro, $R^1$ is ethyl, $R^2X$ is methylamino, $R^3$ is difluoromethoxy and $R^4$ for a compound in each case corresponds to one line of Table A.

Table 301

Compounds of the formula I (n=0) where $R^1$ is hydrogen, $R^2X$ is methyl, $R^3$ is methylthio and $R^4$ for a compound in each case corresponds to one line of Table A.

Table 302

Compounds of the formula I (n=0) where $R^1$ is hydrogen, $R^2X$ is ethyl, $R^3$ is methylthio and $R^4$ for a compound in each case corresponds to one line of Table A.

Table 303

Compounds of the formula I (n=0) where $R^1$ is hydrogen, $R^2X$ is methoxy, $R^3$ is methylthio and $R^4$ for a compound in each case corresponds to one line of Table A.

Table 304

Compounds of the formula I (n=0) where $R^1$ is hydrogen, $R^2X$ is ethoxy, $R^3$ is methylthio and $R^4$ for a compound in each case corresponds to one line of Table A.

Table 305

Compounds of the formula I (n=0) where $R^1$ is hydrogen, $R^2X$ is methylamino, $R^3$ is methylthio and $R^4$ for a compound in each case corresponds to one line of Table A.

Table 306

Compounds of the formula I (n=0) where $R^1$ is methyl, $R^2X$ is methyl, $R^3$ is methylthio and $R^4$ for a compound in each case corresponds to one line of Table A.

Table 307

Compounds of the formula I (n=0) where $R^1$ is methyl, $R^2X$ is ethyl, $R^3$ is methylthio and $R^4$ for a compound in each case corresponds to one line of Table A.

Table 308

Compounds of the formula I (n=0) where $R^1$ is methyl, $R^2X$ is methoxy, $R^3$ is methylthio and $R^4$ for a compound in each case corresponds to one line of Table A.

Table 309

Compounds of the formula I (n=0) where $R^1$ is methyl, $R^2X$ is ethoxy, $R^3$ is methylthio and $R^4$ for a compound in each case corresponds to one line of Table A.

Table 310

Compounds of the formula I (n=0) where $R^1$ is methyl, $R^2X$ is methylamino, $R^3$ is methylthio and $R^4$ for a compound in each case corresponds to one line of Table A.

Table 311

Compounds of the formula I (n=0) where $R^1$ is ethyl, $R^2X$ is methyl, $R^3$ is methylthio and $R^4$ for a compound in each case corresponds to one line of Table A.

Table 312

Compounds of the formula I (n=0) where $R^1$ is ethyl, $R^2X$ is ethyl, $R^3$ is methylthio and $R^4$ for a compound in each case corresponds to one line of Table A.

Table 313

Compounds of the formula I (n=0) where $R^1$ is ethyl, $R^2X$ is methoxy, $R^3$ is methylthio and $R^4$ for a compound in each case corresponds to one line of Table A.

Table 314

Compounds of the formula I (n=0) where $R^1$ is ethyl, $R^2X$ is ethoxy, $R^3$ is methylthio and $R^4$ for a compound in each case corresponds to one line of Table A.

Table 315

Compounds of the formula I (n=0) where $R^1$ is ethyl, $R^2X$ is methylamino, $R^3$ is methylthio and $R^4$ for a compound in each case corresponds to one line of Table A.

Table 316

Compounds of the formula I where $R_n$ is 3-chloro, $R^1$ is hydrogen, $R^2X$ is methyl, $R^3$ is methylthio and $R^4$ for a compound in each case corresponds to one line of Table A.

Table 317

Compounds of the formula I where $R_n$ is 3-chloro, $R^1$ is hydrogen, $R^2X$ is ethyl, $R^3$ is methylthio and $R^4$ for a compound in each case corresponds to one line of Table A.

Table 318

Compounds of the formula I where $R_n$ is 3-chloro, $R^1$ is hydrogen, $R^2X$ is methoxy, $R^3$ is methylthio and $R^4$ for a compound in each case corresponds to one line of Table A.

Table 319

Compounds of the formula I where $R_n$ is 3-chloro, $R^1$ is hydrogen, $R^2X$ is ethoxy, $R^3$ is methylthio and $R^4$ for a compound in each case corresponds to one line of Table A.

Table 320

Compounds of the formula I where $R_n$ is 3-chloro, $R^1$ is hydrogen, $R^2X$ is methylamino, $R^3$ is methylthio and $R^4$ for a compound in each case corresponds to one line of Table A.

Table 321

Compounds of the formula I where $R_n$ is 3-chloro, $R^1$ is methyl, $R^2X$ is methyl, $R^3$ is methylthio and $R^4$ for a compound in each case corresponds to one line of Table A.

Table 322

Compounds of the formula I where $R_n$ is 3-chloro, $R^1$ is methyl, $R^2X$ is ethyl, $R^3$ is methylthio and $R^4$ for a compound in each case corresponds to one line of Table A.

Table 323

Compounds of the formula I where $R_n$ is 3-chloro, $R^1$ is methyl, $R^2X$ is methoxy, $R^3$ is methylthio and $R^4$ for a compound in each case corresponds to one line of Table A.

Table 324

Compounds of the formula I where $R_n$ is 3-chloro, $R^1$ is methyl, $R^2X$ is ethoxy, $R^3$ is methylthio and $R^4$ for a compound in each case corresponds to one line of Table A.

Table 325

Compounds of the formula I where $R_n$ is 3-chloro, $R^1$ is methyl, $R^2X$ is methylamino, $R^3$ is methylthio and $R^4$ for a compound in each case corresponds to one line of Table A.

Table 326

Compounds of the formula I where $R_n$ is 3-chloro, $R^1$ is ethyl, $R^2X$ is methyl, $R^3$ is methylthio and $R^4$ for a compound in each case corresponds to one line of Table A.

Table 327

Compounds of the formula I where $R_n$ is 3-chloro, $R^1$ is ethyl, $R^2X$ is ethyl, $R^3$ is methylthio and $R^4$ for a compound in each case corresponds to one line of Table A.

Table 328

Compounds of the formula I where $R_n$ is 3-chloro, $R^1$ is ethyl, $R^2X$ is methoxy, $R^3$ is methylthio and $R^4$ for a compound in each case corresponds to one line of Table A.

Table 329

Compounds of the formula I where $R_n$ is 3-chloro, $R^1$ is ethyl, $R^2X$ is ethoxy, $R^3$ is methylthio and $R^4$ for a compound in each case corresponds to one line of Table A.

Table 330

Compounds of the formula I where $R_n$ is 3-chloro, $R^1$ is ethyl, $R^2X$ is methylamino, $R^3$ is methylthio and $R^4$ for a compound in each case corresponds to one line of Table A.

Table 331

Compounds of the formula I (n=0) where $R^1$ is hydrogen, $R^2X$ is methyl, $R^3$ is ethylthio and $R^4$ for a compound in each case corresponds to one line of Table A.

Table 332

Compounds of the formula I (n=0) where $R^1$ is hydrogen, $R^2X$ is ethyl, $R^3$ is ethylthio and $R^4$ for a compound in each case corresponds to one line of Table A.

Table 333

Compounds of the formula I (n=0) where $R^1$ is hydrogen, $R^2X$ is methoxy, $R^3$ is ethylthio and $R^4$ for a compound in each case corresponds to one line of Table A.

Table 334

Compounds of the formula I (n=0) where $R^1$ is hydrogen, $R^2X$ is ethoxy, $R^3$ is ethylthio and $R^4$ for a compound in each case corresponds to one line of Table A.

Table 335

Compounds of the formula I (n=0) where $R^1$ is hydrogen, $R^2X$ is methylamino, $R^3$ is ethylthio and $R^4$ for a compound in each case corresponds to one line of Table A.

Table 336

Compounds of the formula I (n=0) where $R^1$ is methyl, $R^2X$ is methyl, $R^3$ is ethylthio and $R^4$ for a compound in each case corresponds to one line of Table A.

Table 337

Compounds of the formula I (n=0) where $R^1$ is methyl, $R^2X$ is ethyl, $R^3$ is ethylthio and $R^4$ for a compound in each case corresponds to one line of Table A.

Table 338

Compounds of the formula I (n=0) where $R^1$ is methyl, $R^2X$ is methoxy, $R^3$ is ethylthio and $R^4$ for a compound in each case corresponds to one line of Table A.

Table 339

Compounds of the formula I (n=0) where $R^1$ is methyl, $R^2X$ is ethoxy, $R^3$ is ethylthio and $R^4$ for a compound in each case corresponds to one line of Table A.

Table 340

Compounds of the formula I (n=0) where $R^1$ is methyl, $R^2X$ is methylamino, $R^3$ is ethylthio and $R^4$ for a compound in each case corresponds to one line of Table A.

Table 341

Compounds of the formula I (n=0) where $R^1$ is ethyl, $R^2X$ is methyl, $R^3$ is ethylthio and $R^4$ for a compound in each case corresponds to one line of Table A.

Table 342
Compounds of the formula I (n=0) where $R^1$ is ethyl, $R^2X$ is ethyl, $R^3$ is ethylthio and $R^4$ for a compound in each case corresponds to one line of Table A.

Table 343
Compounds of the formula I (n=0) where $R^1$ is ethyl, $R^2X$ is methoxy, $R^3$ is ethylthio and $R^4$ for a compound in each case corresponds to one line of Table A.

Table 344
Compounds of the formula I (n=0) where $R^1$ is ethyl, $R^2X$ is ethoxy, $R^3$ is ethylthio and $R^4$ for a compound in each case corresponds to one line of Table A.

Table 345
Compounds of the formula I (n=0) where $R^1$ is ethyl, $R^2X$ is methylamino, $R^3$ is ethylthio and $R^4$ for a compound in each case corresponds to one line of Table A.

Table 346
Compounds of the formula I where $R_n$ is 3-chloro, $R^1$ is hydrogen, $R^2X$ is methyl, $R^3$ is ethylthio and $R^4$ for a compound in each case corresponds to one line of Table A.

Table 347
Compounds of the formula I where $R_n$ is 3-chloro, $R^1$ is hydrogen, $R^2X$ is ethyl, $R^3$ is ethylthio and $R^4$ for a compound in each case corresponds to one line of Table A.

Table 348
Compounds of the formula I where $R_n$ is 3-chloro, $R^1$ is hydrogen, $R^2X$ is methoxy, $R^3$ is ethylthio and $R^4$ for a compound in each case corresponds to one line of Table A.

Table 349
Compounds of the formula I where $R_n$ is 3-chloro, $R^1$ is hydrogen, $R^2X$ is ethoxy, $R^3$ is ethylthio and $R^4$ for a compound in each case corresponds to one line of Table A.

Table 350
Compounds of the formula I where $R_n$ is 3-chloro, $R^1$ is hydrogen, $R^2X$ is methylamino, $R^3$ is ethylthio and $R^4$ for a compound in each case corresponds to one line of Table A.

Table 351
Compounds of the formula I where $R_n$ is 3-chloro, $R^1$ is methyl, $R^2X$ is methyl, $R^3$ is ethylthio and $R^4$ for a compound in each case corresponds to one line of Table A.

Table 352
Compounds of the formula I where $R_n$ is 3-chloro, $R^1$ is methyl, $R^2X$ is ethyl, $R^3$ is ethylthio and $R^4$ for a compound in each case corresponds to one line of Table A.

Table 353
Compounds of the formula I where $R_n$ is 3-chloro, $R^1$ is methyl, $R^2X$ is methoxy, $R^3$ is ethylthio and $R^4$ for a compound in each case corresponds to one line of Table A.

Table 354
Compounds of the formula I where $R_n$ is 3-chloro, $R^1$ is methyl, $R^2X$ is ethoxy, $R^3$ is ethylthio and $R^4$ for a compound in each case corresponds to one line of Table A.

Table 355
Compounds of the formula I where $R_n$ is 3-chloro, $R^1$ is methyl, $R^2X$ is methylamino, $R^3$ is ethylthio and $R^4$ for a compound in each case corresponds to one line of Table A.

Table 356
Compounds of the formula I where $R_n$ is 3-chloro, $R^1$ is ethyl, $R^2X$ is methyl, $R^3$ is ethylthio and $R^4$ for a compound in each case corresponds to one line of Table A.

Table 357
Compounds of the formula I where $R_n$ is 3-chloro, $R^1$ is ethyl, $R^2X$ is ethyl, $R^3$ is ethylthio and $R^4$ for a compound in each case corresponds to one line of Table A.

Table 358
Compounds of the formula I where $R_n$ is 3-chloro, $R^1$ is ethyl, $R^2X$ is methoxy, $R^3$ is ethylthio and $R^4$ for a compound in each case corresponds to one line of Table A.

Table 359
Compounds of the formula I where $R_n$ is 3-chloro, $R^1$ is ethyl, $R^2X$ is ethoxy, $R^3$ is ethylthio and $R^4$ for a compound in each case corresponds to one line of Table A.

Table 360
Compounds of the formula I where $R_n$ is 3-chloro, $R^1$ is ethyl, $R^2X$ is methylamino, $R^3$ is ethylthio and $R^4$ for a compound in each case corresponds to one line of Table A.

Table 361
Compounds of the formula I (n=0) where $R^1$ is hydrogen, $R^2X$ is methyl, $R^3$ is cyclopropyl and $R^4$ for a compound in each case corresponds to one line of Table A.

Table 362
Compounds of the formula I (n=0) where $R^1$ is hydrogen, $R^2X$ is ethyl, $R^3$ is cyclopropyl and $R^4$ for a compound in each case corresponds to one line of Table A.

Table 363
Compounds of the formula I (n=0) where $R^1$ is hydrogen, $R^2X$ is methoxy, $R^3$ is cyclopropyl and $R^4$ for a compound in each case corresponds to one line of Table A.

Table 364
Compounds of the formula I (n=0) where $R^1$ is hydrogen, $R^2X$ is ethoxy, $R^3$ is cyclopropyl and $R^4$ for a compound in each case corresponds to one line of Table A.

Table 365
Compounds of the formula I (n=0) where $R^1$ is hydrogen, $R^2X$ is methylamino, $R^3$ is cyclopropyl and $R^4$ for a compound in each case corresponds to one line of Table A.

Table 366
Compounds of the formula I (n=0) where $R^1$ is methyl, $R^2X$ is methyl, $R^3$ is cyclopropyl and $R^4$ for a compound in each case corresponds to one line of Table A.

Table 367
Compounds of the formula I (n=0) where $R^1$ is methyl, $R^2X$ is ethyl, $R^3$ is cyclopropyl and $R^4$ for a compound in each case corresponds to one line of Table A.

Table 368

Compounds of the formula I (n=0) where $R^1$ is methyl, $R^2X$ is methoxy, $R^3$ is cyclopropyl and $R^4$ for a compound in each case corresponds to one line of Table A.

Table 369

Compounds of the formula I (n=0) where $R^1$ is methyl, $R^2X$ is ethoxy, $R^3$ is cyclopropyl and $R^4$ for a compound in each case corresponds to one line of Table A.

Table 370

Compounds of the formula I (n=0) where $R^1$ is methyl, $R^2X$ is methylamino, $R^3$ is cyclopropyl and $R^4$ for a compound in each case corresponds to one line of Table A.

Table 371

Compounds of the formula I (n=0) where $R^1$ is ethyl, $R^2X$ is methyl, $R^3$ is cyclopropyl and $R^4$ for a compound in each case corresponds to one line of Table A.

Table 372

Compounds of the formula I (n=0) where $R^1$ is ethyl, $R^2X$ is ethyl, $R^3$ is cyclopropyl and $R^4$ for a compound in each case corresponds to one line of Table A.

Table 373

Compounds of the formula I (n=0) where $R^1$ is ethyl, $R^2X$ is methoxy, $R^3$ is cyclopropyl and $R^4$ for a compound in each case corresponds to one line of Table A.

Table 374

Compounds of the formula I (n=0) where $R^1$ is ethyl, $R^2X$ is ethoxy, $R^3$ is cyclopropyl and $R^4$ for a compound in each case corresponds to one line of Table A.

Table 375

Compounds of the formula I (n=0) where $R^1$ is ethyl, $R^2X$ is methylamino, $R^3$ is cyclopropyl and $R^4$ for a compound in each case corresponds to one line of Table A.

Table 376

Compounds of the formula I where $R_n$ is 3-chloro, $R^1$ is hydrogen, $R^2X$ is methyl, $R^3$ is cyclopropyl and $R^4$ for a compound in each case corresponds to one line of Table A.

Table 377

Compounds of the formula I where $R_n$ is 3-chloro, $R^1$ is hydrogen, $R^2X$ is ethyl, $R^3$ is cyclopropyl and $R^4$ for a compound in each case corresponds to one line of Table A.

Table 378

Compounds of the formula I where $R_n$ is 3-chloro, $R^1$ is hydrogen, $R^2X$ is methoxy, $R^3$ is cyclopropyl and $R^4$ for a compound in each case corresponds to one line of Table A.

Table 379

Compounds of the formula I where $R_n$ is 3-chloro, $R^1$ is hydrogen, $R^2X$ is ethoxy, $R^3$ is cyclopropyl and $R^4$ for a compound in each case corresponds to one line of Table A.

Table 380

Compounds of the formula I where $R_n$ is 3-chloro, $R^1$ is hydrogen, $R^2X$ is methylamino, $R^3$ is cyclopropyl and $R^4$ for a compound in each case corresponds to one line of Table A.

Table 381

Compounds of the formula I where $R_n$ is 3-chloro, $R^1$ is methyl, $R^2X$ is methyl, $R^3$ is cyclopropyl and $R^4$ for a compound in each case corresponds to one line of Table A.

Table 382

Compounds of the formula I where $R_n$ is 3-chloro, $R^1$ is methyl, $R^2X$ is ethyl, $R^3$ is cyclopropyl and $R^4$ for a compound in each case corresponds to one line of Table A.

Table 383

Compounds of the formula I where $R_n$ is 3-chloro, $R^1$ is methyl, $R^2X$ is methoxy, $R^3$ is cyclopropyl and $R^4$ for a compound in each case corresponds to one line of Table A.

Table 384

Compounds of the formula I where $R_n$ is 3-chloro, $R^1$ is methyl, $R^2X$ is ethoxy, $R^3$ is cyclopropyl and $R^4$ for a compound in each case corresponds to one line of Table A.

Table 385

Compounds of the formula I where $R_n$ is 3-chloro, $R^1$ is methyl, $R^2X$ is methylamino, $R^3$ is cyclopropyl and $R^4$ for a compound in each case corresponds to one line of Table A.

Table 386

Compounds of the formula I where $R_n$ is 3-chloro, $R^1$ is ethyl, $R^2X$ is methyl, $R^3$ is cyclopropyl and $R^4$ for a compound in each case corresponds to one line of Table A.

Table 387

Compounds of the formula I where $R_n$ is 3-chloro, $R^1$ is ethyl, $R^2X$ is ethyl, $R^3$ is cyclopropyl and $R^4$ for a compound in each case corresponds to one line of Table A.

Table 388

Compounds of the formula I where $R_n$ is 3-chloro, $R^1$ is ethyl, $R^2X$ is methoxy, $R^3$ is cyclopropyl and $R^4$ for a compound in each case corresponds to one line of Table A.

Table 389

Compounds of the formula I where $R_n$ is 3-chloro, $R^1$ is ethyl, $R^2X$ is ethoxy, $R^3$ is cyclopropyl and $R^4$ for a compound in each case corresponds to one line of Table A.

Table 390

Compounds of the formula I where $R_n$ is 3-chloro, $R^1$ is ethyl, $R^2X$ is methylamino, $R^3$ is cyclopropyl and $R^4$ for a compound in each case corresponds to one line of Table A.

Table 391

Compounds of the formula I where $R_n$ is 6-methyl, $R^1$ is hydrogen, $R^2X$ is methyl, $R^3$ is methyl and $R^4$ for a compound in each case corresponds to one line of Table A.

Table 392

Compounds of the formula I where $R_n$ is 6-methyl, $R^1$ is hydrogen, $R^2X$ is ethyl, $R^3$ is methyl and $R^4$ for a compound in each case corresponds to one line of Table A.

Table 393

Compounds of the formula I where $R_n$ is 6-methyl, $R^1$ is hydrogen, $R^2X$ is methoxy, $R^3$ is methyl and $R^4$ for a compound in each case corresponds to one line of Table A.

Table 394

Compounds of the formula I where $R_n$ is 6-methyl, $R^1$ is hydrogen, $R^2X$ is ethoxy, $R^3$ is methyl and $R^4$ for a compound in each case corresponds to one line of Table A.

Table 395

Compounds of the formula I where $R_n$ is 6-methyl, $R^1$ is hydrogen, $R^2X$ is methylamino, $R^3$ is methyl and $R^4$ for a compound in each case corresponds to one line of Table A.

Table 396

Compounds of the formula I where $R_n$ is 6-methyl, $R^1$ is methyl, $R^2X$ is methyl, $R^3$ is methyl and $R^4$ for a compound in each case corresponds to one line of Table A.

Table 397

Compounds of the formula I where $R_n$ is 6-methyl, $R^1$ is methyl, $R^2X$ is ethyl, $R^3$ is methyl and $R^4$ for a compound in each case corresponds to one line of Table A.

Table 398

Compounds of the formula I where $R_n$ is 6-methyl, $R^1$ is methyl, $R^2X$ is methoxy, $R^3$ is methyl and $R^4$ for a compound in each case corresponds to one line of Table A.

Table 399

Compounds of the formula I where $R_n$ is 6-methyl, $R^1$ is methyl, $R^2X$ is ethoxy, $R^3$ is methyl and $R^4$ for a compound in each case corresponds to one line of Table A.

Table 400

Compounds of the formula I where $R_n$ is 6-methyl, $R^1$ is methyl, $R^2X$ is methylamino, $R^3$ is methyl and $R^4$ for a compound in each case corresponds to one line of Table A.

Table 401

Compounds of the formula I where $R_n$ is 6-methyl, $R^1$ is ethyl, $R^2X$ is methyl, $R^3$ is methyl and $R^4$ for a compound in each case corresponds to one line of Table A.

Table 402

Compounds of the formula I where $R_n$ is 6-methyl, $R^1$ is ethyl, $R^2X$ is ethyl, $R^3$ is methyl and $R^4$ for a compound in each case corresponds to one line of Table A.

Table 403

Compounds of the formula I where $R_n$ is 6-methyl, $R^1$ is ethyl, $R^2X$ is methoxy, $R^3$ is methyl and $R^4$ for a compound in each case corresponds to one line of Table A.

Table 404

Compounds of the formula I where $R_n$ is 6-methyl, $R^1$ is ethyl, $R^2X$ is ethoxy, $R^3$ is methyl and $R^4$ for a compound in each case corresponds to one line of Table A.

Table 405

Compounds of the formula I where $R_n$ is 6-methyl, $R^1$ is ethyl, $R^2X$ is methylamino, $R^3$ is methyl and $R^4$ for a compound in each case corresponds to one line of Table A.

Table 406

Compounds of the formula I where $R_n$ is 3-chloro, $R^1$ is hydrogen, $R^2X$ is methyl, $R^3$ is cyclopentyl and $R^4$ for a compound in each case corresponds to one line of Table A.

Table 407

Compounds of the formula I where $R_n$ is 3-chloro, $R^1$ is hydrogen, $R^2X$ is ethyl, $R^3$ is cyclopentyl and $R^4$ for a compound in each case corresponds to one line of Table A.

Table 408

Compounds of the formula I where $R_n$ is 3-chloro, $R^1$ is hydrogen, $R^2X$ is methoxy, $R^3$ is cyclopentyl and $R^4$ for a compound in each case corresponds to one line of Table A.

Table 409

Compounds of the formula I where $R_n$ is 3-chloro, $R^1$ is hydrogen, $R^2X$ is ethoxy, $R^3$ is cyclopentyl and $R^4$ for a compound in each case corresponds to one line of Table A.

Table 410

Compounds of the formula I where $R_n$ is 3-chloro, $R^1$ is hydrogen, $R^2X$ is methylamino, $R^3$ is cyclopentyl and $R^4$ for a compound in each case corresponds to one line of Table A.

Table 411

Compounds of the formula I where $R_n$ is 3-chloro, $R^1$ is methyl, $R^2X$ is methyl, $R^3$ is cyclopentyl and $R^4$ for a compound in each case corresponds to one line of Table A.

Table 412

Compounds of the formula I where $R_n$ is 3-chloro, $R^1$ is methyl, $R^2X$ is ethyl, $R^3$ is cyclopentyl and $R^4$ for a compound in each case corresponds to one line of Table A.

Table 413

Compounds of the formula I where $R_n$ is 3-chloro, $R^1$ is methyl, $R^2X$ is methoxy, $R^3$ is cyclopentyl and $R^4$ for a compound in each case corresponds to one line of Table A.

Table 414

Compounds of the formula I where $R_n$ is 3-chloro, $R^1$ is methyl, $R^2X$ is ethoxy, $R^3$ is cyclopentyl and $R^4$ for a compound in each case corresponds to one line of Table A.

Table 415

Compounds of the formula I where $R_n$ is 3-chloro, $R^1$ is methyl, $R^2X$ is methylamino, $R^3$ is cyclopentyl and $R^4$ for a compound in each case corresponds to one line of Table A.

Table 416

Compounds of the formula I where $R_n$ is 3-chloro, $R^1$ is ethyl, $R^2X$ is methyl, $R^3$ is cyclopentyl and $R^4$ for a compound in each case corresponds to one line of Table A.

Table 417

Compounds of the formula I where $R_n$ is 3-chloro, $R^1$ is ethyl, $R^2X$ is ethyl, $R^3$ is cyclopentyl and $R^4$ for a compound in each case corresponds to one line of Table A.

Table 418

Compounds of the formula I where $R_n$ is 3-chloro, $R^1$ is ethyl, $R^2X$ is methoxy, $R^3$ is cyclopentyl and $R^4$ for a compound in each case corresponds to one line of Table A.

Table 419

Compounds of the formula I where $R_n$ is 3-chloro, $R^1$ is ethyl, $R^2X$ is ethoxy, $R^3$ is cyclopentyl and $R^4$ for a compound in each case corresponds to one line of Table A.

Table 420

Compounds of the formula I where $R_n$ is 3-chloro, $R^1$ is ethyl, $R^2X$ is methylamino, $R^3$ is cyclopentyl and $R^4$ for a compound in each case corresponds to one line of Table A.

Table 421

Compounds of the formula I (n=0) where $R^1$ is hydrogen, $R^2X$ is methyl, $R^3$ is cyclohexyl and $R^4$ for a compound in each case corresponds to one line of Table A.

Table 422

Compounds of the formula I (n=0) where $R^1$ is hydrogen, $R^2X$ is ethyl, $R^3$ is cyclohexyl and $R^4$ for a compound in each case corresponds to one line of Table A.

Table 423

Compounds of the formula I (n=0) where $R^1$ is hydrogen, $R^2X$ is methoxy, $R^3$ is cyclohexyl and $R^4$ for a compound in each case corresponds to one line of Table A.

Table 424

Compounds of the formula I (n=0) where $R^1$ is hydrogen, $R^2X$ is ethoxy, $R^3$ is cyclohexyl and $R^4$ for a compound in each case corresponds to one line of Table A.

Table 425

Compounds of the formula I (n=0) where $R^1$ is hydrogen, $R^2X$ is methylamino, $R^3$ is cyclohexyl and $R^4$ for a compound in each case corresponds to one line of Table A.

Table 426

Compounds of the formula I (n=0) where $R^1$ is methyl, $R^2X$ is methyl, $R^3$ is cyclohexyl and $R^4$ for a compound in each case corresponds to one line of Table A.

Table 427

Compounds of the formula I (n=0) where $R^1$ is methyl, $R^2X$ is ethyl, $R^3$ is cyclohexyl and $R^4$ for a compound in each case corresponds to one line of Table A.

Table 428

Compounds of the formula I (n=0) where $R^1$ is methyl, $R^2X$ is ethoxy, $R^3$ is cyclohexyl and $R^4$ for a compound in each case corresponds to one line of Table A.

Table 429

Compounds of the formula I (n=0) where $R^1$ is methyl, $R^2X$ is ethoxy, $R^3$ is cyclohexyl and $R^4$ for a compound in each case corresponds to one line of Table A.

Table 430

Compounds of the formula I (n=0) where $R^1$ is methyl, $R^2X$ is methylamino, $R^3$ is cyclohexyl and $R^4$ for a compound in each case corresponds to one line of Table A.

Table 431

Compounds of the formula I (n=0) where $R^1$ is ethyl, $R^2X$ is methyl, $R^3$ is cyclohexyl and $R^4$ for a compound in each case corresponds to one line of Table A.

Table 432

Compounds of the formula I (n=0) where $R^1$ is ethyl, $R^2X$ is ethyl, $R^3$ is cyclohexyl and $R^4$ for a compound in each case corresponds to one line of Table A.

Table 433

Compounds of the formula I (n=0) where $R^1$ is ethyl, $R^2X$ is methoxy, $R^3$ is cyclohexyl and $R^4$ for a compound in each case corresponds to one line of Table A.

Table 434

Compounds of the formula I (n=0) where $R^1$ is ethyl, $R^2X$ is ethoxy, $R^3$ is cyclohexyl and $R^4$ for a compound in each case corresponds to one line of Table A.

Table 435

Compounds of the formula I (n=0) where $R^1$ is ethyl, $R^2X$ is methylamino, $R^3$ is cyclohexyl and $R^4$ for a compound in each case corresponds to one line of Table A.

Table 436

Compounds of the formula I where $R_n$ is 3-chloro, $R^1$ is hydrogen, $R^2X$ is methyl, $R^3$ is cyclohexyl and $R^4$ for a compound in each case corresponds to one line of Table A.

Table 437

Compounds of the formula I where $R_n$ is 3-chloro, $R^1$ is hydrogen, $R^2X$ is ethyl, $R^3$ is cyclohexyl and $R^4$ for a compound in each case corresponds to one line of Table A.

Table 438

Compounds of the formula I where $R_n$ is 3-chloro, $R^1$ is hydrogen, $R^2X$ is methoxy, $R^3$ is cyclohexyl and $R^4$ for a compound in each case corresponds to one line of Table A.

Table 439

Compounds of the formula I where $R_n$ is 3-chloro, $R^1$ is hydrogen, $R^2X$ is ethoxy, $R^3$ is cyclohexyl and $R^4$ for a compound in each case corresponds to one line of Table A.

Table 440

Compounds of the formula I where $R_n$ is 3-chloro, $R^1$ is hydrogen, $R^2X$ is methylamino, $R^3$ is cyclohexyl and $R^4$ for a compound in each case corresponds to one line of Table A.

Table 441

Compounds of the formula I where $R_n$ is 3-chloro, $R^1$ is methyl, $R^2X$ is methyl, $R^3$ is cyclohexyl and $R^4$ for a compound in each case corresponds to one line of Table A.

Table 442

Compounds of the formula I where $R_n$ is 3-chloro, $R^1$ is methyl, $R^2X$ is ethyl, $R^3$ is cyclohexyl and $R^4$ for a compound in each case corresponds to one line of Table A.

Table 443

Compounds of the formula I where $R_n$ is 3-chloro, $R^1$ is methyl, $R^2X$ is methoxy, $R^3$ is cyclohexyl and $R^4$ for a compound in each case corresponds to one line of Table A.

Table 444

Compounds of the formula I where $R_n$ is 3-chloro, $R^1$ is methyl, $R^2X$ is ethoxy, $R^3$ is cyclohexyl and $R^4$ for a compound in each case corresponds to one line of Table A.

Table 445

Compounds of the formula I where $R_n$ is 3-chloro, $R^1$ is methyl, $R^2X$ is methylamino, $R^3$ is cyclohexyl and $R^4$ for a compound in each case corresponds to one line of Table A.

Table 446

Compounds of the formula I where $R_n$ is 3-chloro, $R^1$ is ethyl, $R^2X$ is methyl, $R^3$ is cyclohexyl and $R^4$ for a compound in each case corresponds to one line of Table A.

Table 447

Compounds of the formula I where $R_n$ is 3-chloro, $R^1$ is ethyl, $R^2X$ is ethyl, $R^3$ is cyclohexyl and $R^4$ for a compound in each case corresponds to one line of Table A.

Table 448

Compounds of the formula I where $R_n$ is 3-chloro, $R^1$ is ethyl, $R^2X$ is methoxy, $R^3$ is cyclohexyl and $R^4$ for a compound in each case corresponds to one line of Table A.

Table 449

Compounds of the formula I where $R_n$ is 3-chloro, $R^1$ is ethyl, $R^2X$ is ethoxy, $R^3$ is cyclohexyl and $R^4$ for a compound in each case corresponds to one line of Table A.

Table 450

Compounds of the formula I where $R_n$ is 3-chloro, $R^1$ is ethyl, $R^2X$ is methylamino, $R^3$ is cyclohexyl and $R^4$ for a compound in each case corresponds to one line of Table A.

TABLE A

| No. | $R^4$ |
|---|---|
| 1 | 3-$CH_3$-pyridin-2-yl |
| 2 | 4-$CH_3$-pyridin-2-yl |
| 3 | 5-$CH_3$-pyridin-2-yl |
| 4 | 6-$CH_3$-pyridin-2-yl |
| 5 | 3-$CH_2CH_3$-pyridin-2-yl |
| 6 | 4-$CH_2CH_3$-pyridin-2-yl |
| 7 | 5-$CH_2CH_3$-pyridin-2-yl |
| 8 | 6-$CH_2CH_3$-pyridin-2-yl |
| 9 | 3-$CF_3$-pyridin-2-yl |
| 10 | 4-$CF_3$-pyridin-2-yl |
| 11 | 5-$CF_3$-pyridin-2-yl |
| 12 | 6-$CF_3$-pyridin-2-yl |
| 13 | 3-$OCH_3$-pyridin-2-yl |
| 14 | 4-$OCH_3$-pyridin-2-yl |
| 15 | 5-$OCH_3$-pyridin-2-yl |
| 16 | 6-$OCH_3$-pyridin-2-yl |
| 17 | 3-$OCH_2CH_3$-pyridin-2-yl |
| 18 | 4-$OCH_2CH_3$-pyridin-2-yl |
| 19 | 5-$OCH_2CH_3$-pyridin-2-yl |
| 20 | 6-$OCH_2CH_3$-pyridin-2-yl |
| 21 | 3-$OCH(CH_3)_2$-pyridin-2-yl |
| 22 | 4-$OCH(CH_3)_2$-pyridin-2-yl |
| 23 | 5-$OCH(CH_3)_2$-pyridin-2-yl |
| 24 | 6-$OCH(CH_3)_2$-pyridin-2-yl |
| 25 | 3-$OCH_2CH_2OCH_3$-pyridin-2-yl |
| 26 | 4-$OCH_2CH_2OCH_3$-pyridin-2-yl |
| 27 | 5-$OCH_2CH_2OCH_3$-pyridin-2-yl |
| 28 | 6-$OCH_2CH_2OCH_3$-pyridin-2-yl |
| 29 | 3-$OCH_2CF_3$-pyridin-2-yl |
| 30 | 4-$OCH_2CF_3$-pyridin-2-yl |
| 31 | 5-$OCH_2CF_3$-pyridin-2-yl |
| 32 | 6-$OCH_2CF_3$-pyridin-2-yl |
| 33 | 3-$NO_2$-pyridin-2-yl |
| 34 | 4-$NO_2$-pyridin-2-yl |
| 35 | 5-$NO_2$-pyridin-2-yl |
| 36 | 6-$NO_2$-pyridin-2-yl |
| 37 | 3-CN-pyridin-2-yl |
| 38 | 4-CN-pyridin-2-yl |
| 39 | 5-CN-pyridin-2-yl |
| 40 | 6-CN-pyridin-2-yl |
| 41 | 4-C(O)$NH_2$-pyridin-2-yl |
| 42 | 5-C(O)$NH_2$-pyridin-2-yl |
| 43 | 6-C(O)$NH_2$-pyridin-2-yl |

TABLE A-continued

| No. | $R^4$ |
|---|---|
| 44 | 4-C(S)$NH_2$-pyridin-2-yl |
| 45 | 5-C(S)$NH_2$-pyridin-2-yl |
| 46 | 6-C(S)$NH_2$-pyridin-2-yl |
| 47 | 3-$CO_2CH_3$-pyridin-2-yl |
| 48 | 4-$CO_2CH_3$-pyridin-2-yl |
| 49 | 5-$CO_2CH_3$-pyridin-2-yl |
| 50 | 6-$CO_2CH_3$-pyridin-2-yl |
| 51 | 4-[2-Cl—$C_6H_4$]-pyridin-2-yl |
| 52 | 5-[2-Cl—$C_6H_4$]-pyridin-2-yl |
| 53 | 6-[2-Cl—$C_6H_4$]-pyridin-2-yl |
| 54 | 4-[1-$CH_3$-imidazol-2-yl]pyridin-2-yl |
| 55 | 5-[1-$CH_3$-imidazol-2-yl]pyridin-2-yl |
| 56 | 6-[1-$CH_3$-imidazol-2-yl]pyridin-2-yl |
| 57 | 4-$CF_3$, 3-$OCH_3$-pyridin-2-yl |
| 58 | 4-$CF_3$, 6-$OCH_3$-pyridin-2-yl |
| 59 | 4-$CF_3$, 3-$OCH_2CH_3$-pyridin-2-yl |
| 60 | 4-$CF_3$, 6-$OCH_2CH_3$-pyridin-2-yl |
| 61 | 4-$CF_3$, 3-$OCH_2CF_3$-pyridin-2-yl |
| 62 | 4-$CF_3$, 6-$OCH_2CF_3$-pyridin-2-yl |
| 63 | 2-$CH_3$-pyridin-3-yl |
| 64 | 4-$CH_3$-pyridin-3-yl |
| 65 | 5-$CH_3$-pyridin-3-yl |
| 66 | 6-$CH_3$-pyridin-3-yl |
| 67 | 2-$CH_2CH_3$-pyridin-3-yl |
| 68 | 4-$CH_2CH_3$-pyridin-3-yl |
| 69 | 5-$CH_2CH_3$-pyridin-3-yl |
| 70 | 6-$CH_2CH_3$-pyridin-3-yl |
| 71 | 2-$CF_3$-pyridin-3-yl |
| 72 | 4-$CF_3$-pyridin-3-yl |
| 73 | 5-$CF_3$-pyridin-3-yl |
| 74 | 6-$CF_3$-pyridin-3-yl |
| 75 | 2-$OCH_3$-pyridin-3-yl |
| 76 | 4-$OCH_3$-pyridin-3-yl |
| 77 | 5-$OCH_3$-pyridin-3-yl |
| 78 | 6-$OCH_3$-pyridin-3-yl |
| 79 | 2-$OCH_2CH_3$-pyridin-3-yl |
| 80 | 4-$OCH_2CH_3$-pyridin-3-yl |
| 81 | 5-$OCH_2CH_3$-pyridin-3-yl |
| 82 | 6-$OCH_2CH_3$-pyridin-3-yl |
| 83 | 2-$CH_3$-pyridin-4-yl |
| 84 | 3-$CH_3$-pyridin-4-yl |
| 85 | 2-$CH_2CH_3$-pyridin-4-yl |
| 86 | 3-$CH_2CH_3$-pyridin-4-yl |
| 87 | 2-$CF_3$-pyridin-4-yl |
| 88 | 3-$CF_3$-pyridin-4-yl |
| 89 | 2-$OCH_3$-pyridin-4-yl |
| 90 | 3-$OCH_3$-pyridin-4-yl |
| 91 | 2-$OCH_2CH_3$-pyridin-4-yl |
| 92 | 3-$OCH_2CH_3$-pyridin-4-yl |
| 93 | 4-$CH_3$-pyridin-2-yl |
| 94 | 5-$CH_3$-pyrimidin-2-yl |
| 95 | 4-$CH_2CH_3$-pyrimidin-2-yl |
| 96 | 5-$CH_2CH_3$-pyrimidin-2-yl |
| 97 | 4-$CH(CH_3)_2$-pyrimidin-2-yl |
| 98 | 5-$CH(CH_3)_2$-pyrimidin-2-yl |
| 99 | 4-$CH(CH_3)CH_2CH_3$-pyrimidin-2-yl |
| 100 | 5-$CH(CH_3)CH_2CH_3$-pyrimidin-2-yl |
| 101 | 4-$CF_3$-pyrimidin-2-yl |
| 102 | 5-$CF_3$-pyrimidin-2-yl |
| 103 | 4-CH=$CH_2$-pyrimidin-2-yl |
| 104 | 5-CH=$CH_2$-pyrimidin-2-yl |
| 105 | 4-CH=$CHCH_3$-pyrimidin-2-yl |
| 106 | 5-CH=$CHCH_3$-pyrimidin-2-yl |
| 107 | 4-CH=CHCl-pyrimidin-2-yl |
| 108 | 5-CH=CHCl-pyrimidin-2-yl |
| 109 | 4-C≡CH-pyrimidin-2-yl |
| 110 | 5-C≡CH-pyrimidin-2-yl |
| 111 | 4-$CH_2$C≡CH-pyrimidin-2-yl |
| 112 | 5-$CH_2$C≡CH-pyrimidin-2-yl |
| 113 | 4-$CH_2$C≡$CCH_3$-pyrimidin-2-yl |
| 114 | 5-$CH_2$C≡$CCH_3$-pyrimidin-2-yl |
| 115 | 4-cyclopropyl-pyrimidin-2-yl |
| 116 | 5-cyclopropyl-pyrimidin-2-yl |
| 117 | 4-cyclopentyl-pyrimidin-2-yl |
| 118 | 5-cyclopentyl-pyrimidin-2-yl |
| 119 | 4-$OCH_3$-pyrimidin-2-yl |
| 120 | 5-$OCH_3$-pyrimidin-2-yl |

TABLE A-continued

| No. | R⁴ |
|---|---|
| 121 | 4-OCH₂CH₃-pyrimidin-2-yl |
| 122 | 5-OCH₂CH₃-pyrimidin-2-yl |
| 123 | 4-OCH₂CH₂CH₃-pyrimidin-2-yl |
| 124 | 5-OCH₂CH₂CH₃-pyrimidin-2-yl |
| 125 | 4-OCH(CH₃)₂-pyrimidin-2-yl |
| 126 | 5-OCH(CH₃)₂-pyrimidin-2-yl |
| 127 | 4-OCH₂CH₂CH₂CH₃-pyrimidin-2-yl |
| 128 | 5-OCH₂CH₂CH₂CH₃-pyrimidin-2-yl |
| 129 | 4-OCH(CH₃)CH₂CH₃-pyrimidin-2-yl |
| 130 | 5-OCH(CH₃)CH₂CH₃-pyrimidin-2-yl |
| 131 | 4-OCH₂CH(CH₃)₂-pyrimidin-2-yl |
| 132 | 5-OCH₂CH(CH₃)₂-pyrimidin-2-yl |
| 133 | 4-OC(CH₃)₃-pyrimidin-2-yl |
| 134 | 5-OC(CH₃)₃-pyrimidin-2-yl |
| 135 | 4-OCH(CH₃)CH₂CH₂CH₃-pyrimidin-2-yl |
| 136 | 5-OCH(CH₃)CH₂CH₂CH₃-pyrimidin-2-yl |
| 137 | 4-OCH₂OCH₃-pyrimidin-2-yl |
| 138 | 5-OCH₂OCH₃-pyrimidin-2-yl |
| 139 | 4-OCH₂OCH₂CH₃-pyrimidin-2-yl |
| 140 | 5-OCH₂OCH₂CH₃-pyrimidin-2-yl |
| 141 | 4-OCH(CH₃)OCH₃-pyrimidin-2-yl |
| 142 | 5-OCH(CH₃)OCH₃-pyrimidin-2-yl |
| 143 | 4-OCH(CH₃)OCH₂CH₃-pyrimidin-2-yl |
| 144 | 5-OCH(CH₃)OCH₂CH₃-pyrimidin-2-yl |
| 145 | 4-OCH₂CH₂OCH₃-pyrimidin-2-yl |
| 146 | 5-OCH₂CH₂OCH₃-pyrimidin-2-yl |
| 147 | 4-OCH₂CH₂OCH₂CH₃-pyrimidin-2-yl |
| 148 | 5-OCH₂CH₂OCH₂CH₃-pyrimidin-2-yl |
| 149 | 4-OCH₂CH₂OCH(CH₃)₂-pyrimidin-2-yl |
| 150 | 5-OCH₂CH₂OCH(CH₃)₂-pyrimidin-2-yl |
| 151 | 4-OCH₂CH₂SCH₃-pyrimidin-2-yl |
| 152 | 5-OCH₂CH₂SCH₃-pyrimidin-2-yl |
| 153 | 4-OCH₂CH₂SO₂CH₃-pyrimidin-2-yl |
| 154 | 5-OCH₂CH₂SO₂CH₃-pyrimidin-2-yl |
| 155 | 4-OCH₂CH₂SCH(CH₃)₂-pyrimidin-2-yl |
| 156 | 5-OCH₂CH₂SCH(CH₃)₂-pyrimidin-2-yl |
| 157 | 4-OCH₂CH₂CN-pyrimidin-2-yl |
| 158 | 5-OCH₂CH₂CN-pyrimidin-2-yl |
| 159 | 4-OCH₂CH₂SCH₂CH₂CN-pyrimidin-2-yl |
| 160 | 5-OCH₂CH₂SCH₂CH₂CN-pyrimidin-2-yl |
| 161 | 4-OCH₂CH₂OC₆H₅-pyrimidin-2-yl |
| 162 | 5-OCH₂CH₂OC₆H₅-pyrimidin-2-yl |
| 163 | 4-OCH₂CH₂OCH₂C₆H₅-pyrimidin-2-yl |
| 164 | 5-OCH₂CH₂OCH₂C₆H₅-pyrimidin-2-yl |
| 165 | 4-OCH₂CH₂N(CH₃)₂-pyrimidin-2-yl |
| 166 | 5-OCH₂CH₂N(CH₃)₂-pyrimidin-2-yl |
| 167 | 4-OCH₂CH₂CONH₂-pyrimidin-2-yl |
| 168 | 5-OCH₂CH₂CONH₂-pyrimidin-2-yl |
| 169 | 4-OCH₂CH₂CO₂CH₂CH₂CH₃-pyrimidin-2-yl |
| 170 | 5-OCH₂CH₂CO₂CH₂CH₂CH₃-pyrimidin-2-yl |
| 171 | 4-OCH(CH₃)CH₂OCH₃-pyrimidin-2-yl |
| 172 | 5-OCH(CH₃)CH₂OCH₃-pyrimidin-2-yl |
| 173 | 4-OCH(CH₃)CH₂CO₂CH₃-pyrimidin-2-yl |
| 174 | 5-OCH(CH₃)CH₂CO₂CH₃-pyrimidin-2-yl |
| 175 | 4-OCH(CH₃)CH₂CO₂CH₂CH₃-pyrimidin-2-yl |
| 176 | 5-OCH(CH₃)CH₂CO₂CH₂CH₃-pyrimidin-2-yl |
| 177 | 4-OCH₂CH(CH₃)CO₂CH₃-pyrimidin-2-yl |
| 178 | 5-OCH₂CH(CH₃)CO₂CH₃-pyrimidin-2-yl |
| 179 | 4-OCH₂C(=O)CH₃-pyrimidin-2-yl |
| 180 | 5-OCH₂C(=O)CH₃-pyrimidin-2-yl |
| 181 | 4-OCH₂C(=O)CH₂CH₃-pyrimidin-2-yl |
| 182 | 5-OCH₂C(=O)CH₂CH₃-pyrimidin-2-yl |
| 183 | 4-OCH₂CO₂CH₃-pyrimidin-2-yl |
| 184 | 5-OCH₂CO₂CH₃-pyrimidin-2-yl |
| 185 | 4-OCH₂CO₂CH₂CH₃-pyrimidin-2-yl |
| 186 | 5-OCH₂CO₂CH₂CH₃-pyrimidin-2-yl |
| 187 | 4-OCH₂C(=O)NH₂-pyrimidin-2-yl |
| 188 | 5-OCH₂C(=O)NH₂-pyrimidin-2-yl |
| 189 | 4-OCH₂C(=O)NHCH₃-pyrimidin-2-yl |
| 190 | 5-OCH₂C(=O)NHCH₃-pyrimidin-2-yl |
| 191 | 4-OCH₂C(=O)SCH₃-pyrimidin-2-yl |
| 192 | 5-OCH₂C(=O)SCH₃-pyrimidin-2-yl |
| 193 | 4-OCH(CH₃)C(=O)NH₂-pyrimidin-2-yl |
| 194 | 5-OCH(CH₃)C(=O)NH₂-pyrimidin-2-yl |
| 195 | 4-OCH(CH₃)C(=O)NHCH₃-pyrimidin-2-yl |
| 196 | 5-OCH(CH₃)C(=O)NHCH₃-pyrimidin-2-yl |
| 197 | 4-OCH(CH₃)C(=O)NHNH₂-pyrimidin-2-yl |
| 198 | 5-OCH(CH₃)C(=O)NHNH₂-pyrimidin-2-yl |
| 199 | 4-OCH(CH₃)CO₂CH₃-pyrimidin-2-yl |
| 200 | 5-OCH(CH₃)CO₂CH₃-pyrimidin-2-yl |
| 201 | 4-OCH(CH₃)CO₂CH₂CH₃-pyrimidin-2-yl |
| 202 | 5-OCH(CH₃)CO₂CH₂CH₃-pyrimidin-2-yl |
| 203 | 4-OCH(CH₃)C(=O)CH₃-pyrimidin-2-yl |
| 204 | 5-OCH(CH₃)C(=O)CH₃-pyrimidin-2-yl |
| 205 | 4-OCH(CH₃)C(=O)CH₂CH₃-pyrimidin-2-yl |
| 206 | 5-OCH(CH₃)C(=O)CH₂CH₃-pyrimidin-2-yl |
| 207 | 4-OCH(CH₃)CH₂C(=O)CH₃-pyrimidin-2-yl |
| 208 | 5-OCH(CH₃)CH₂C(=O)CH₃-pyrimidin-2-yl |
| 209 | 4-OCH(CH₃)CH₂OC(CH₃)₃-pyrimidin-2-yl |
| 210 | 5-OCH(CH₃)CH₂OC(CH₃)₃-pyrimidin-2-yl |
| 211 | 4-OCH(CH₃)CH₂OCH₂CH₃-pyrimidin-2-yl |
| 212 | 5-OCH(CH₃)CH₂OCH₂CH₃-pyrimidin-2-yl |
| 213 | 4-OCH(CH₃)CH₂O(CH₃)₂CH₃-pyrimidin-2-yl |
| 214 | 5-OCH(CH₃)CH₂O(CH₃)₂CH₃-pyrimidin-2-yl |
| 215 | 4-OCH(CH₃)CH₂OCH₂CH=CH₂-pyrimidin-2-yl |
| 216 | 5-OCH(CH₃)CH₂OCH₂CH=CH₂-pyrimidin-2-yl |
| 217 | 4-O(CH₂)₃OCH₃-pyrimidin-2-yl |
| 218 | 5-O(CH₂)₃OCH₃-pyrimidin-2-yl |
| 219 | 4-O(CH₂)₃OCH₂CH₃-pyrimidin-2-yl |
| 220 | 5-O(CH₂)₃OCH₂CH₃-pyrimidin-2-yl |
| 221 | 4-O(CH₂)₃OCH(CH₃)₂-pyrimidin-2-yl |
| 222 | 5-O(CH₂)₃OCH(CH₃)₂-pyrimidin-2-yl |
| 223 | 4-O(CH₂)₃OC₆H₅-pyrimidin-2-yl |
| 224 | 5-O(CH₂)₃OC₆H₅-pyrimidin-2-yl |
| 225 | 4-O(CH₂)₃OCH₂C₆H₅-pyrimidin-2-yl |
| 226 | 5-O(CH₂)₃OCH₂C₆H₅-pyrimidin-2-yl |
| 227 | 4-OCH(CH₂CH₃)CH₂OCH₃-pyrimidin-2-yl |
| 228 | 5-OCH(CH₂CH₃)CH₂OCH₃-pyrimidin-2-yl |
| 229 | 4-OCH(CH₂CH₃)CH₂CH₂OCH₃-pyrimidin-2-yl |
| 230 | 5-OCH(CH₂CH₃)CH₂CH₂OCH₃-pyrimidin-2-yl |
| 231 | 4-OCH(CH₂CH₃)CH₂CH₂OCH₂CH₃-pyrimidin-2-yl |
| 232 | 5-OCH(CH₂CH₃)CH₂CH₂OCH₂CH₃-pyrimidin-2-yl |
| 233 | 4-O[(CH₂)₃O]₂CH₃-pyrimidin-2-yl |
| 234 | 5-O[(CH₂)₃O]₂CH₃-pyrimidin-2-yl |
| 235 | 4-OCH₂CH(CH₃)CH₂OCH₃-pyrimidin-2-yl |
| 236 | 5-OCH₂CH(CH₃)CH₂OCH₃-pyrimidin-2-yl |
| 237 | 4-OCH₂CH(CH₃)CH₂OCH₂CH₃-pyrimidin-2-yl |
| 238 | 5-OCH₂CH(CH₃)CH₂OCH₂CH₃-pyrimidin-2-yl |
| 239 | 4-OCH(CH₂Cl)CH₂OCH₃-pyrimidin-2-yl |
| 240 | 5-OCH(CH₂Cl)CH₂OCH₃-pyrimidin-2-yl |
| 241 | 4-OCH(CH₂Cl)CH₂OCH₂CH₃-pyrimidin-2-yl |
| 242 | 5-OCH(CH₂Cl)CH₂OCH₂CH₃-pyrimidin-2-yl |
| 243 | 4-OCH(CH₂Cl)CH₂OCH(CH₃)₂-pyrimidin-2-yl |
| 244 | 5-OCH(CH₂Cl)CH₂OCH(CH₃)₂-pyrimidin-2-yl |
| 245 | 4-OCH(CH₂Cl)CH₂OCH₂CH=CH₂-pyrimidin-2-yl |
| 246 | 5-OCH(CH₂Cl)CH₂OCH₂CH=CH₂-pyrimidin-2-yl |
| 247 | 4-OCH[CH₂OCH₃]₂-pyrimidin-2-yl |
| 248 | 5-OCH[CH₂OCH₃]₂-pyrimidin-2-yl |
| 249 | 4-OCH[CH₂OCH₂CH₃]₂-pyrimidin-2-yl |
| 250 | 5-OCH[CH₂OCH₂CH₃]₂-pyrimidin-2-yl |
| 251 | 4-OCCl₃-pyrimidin-2-yl |
| 252 | 5-OCCl₃-pyrimidin-2-yl |
| 253 | 4-OCHF₂-pyrimidin-2-yl |
| 254 | 5-OCHF₂-pyrimidin-2-yl |
| 255 | 4-OCF₃-pyrimidin-2-yl |
| 256 | 5-OCF₃-pyrimidin-2-yl |
| 257 | 4-OCF₂CHF₂-pyrimidin-2-yl |
| 258 | 5-OCF₂CHF₂-pyrimidin-2-yl |
| 259 | 4-OCH₂CF₃-pyrimidin-2-yl |
| 260 | 5-OCH₂CF₃-pyrimidin-2-yl |
| 261 | 4-OCH₂CHF₂-pyrimidin-2-yl |
| 262 | 5-OCH₂CHF₂-pyrimidin-2-yl |
| 263 | 4-O(CH₂)₃F-pyrimidin-2-yl |
| 264 | 5-O(CH₂)₃F-pyrimidin-2-yl |
| 265 | 4-OCH(CH₃)CF₃-pyrimidin-2-yl |
| 266 | 5-OCH(CH₃)CF₃-pyrimidin-2-yl |
| 267 | 4-O(CH₂)₄F-pyrimidin-2-yl |
| 268 | 5-O(CH₂)₄F-pyrimidin-2-yl |
| 269 | 4-O(CH₂)₃CF₃-pyrimidin-2-yl |
| 270 | 5-O(CH₂)₃CF₃-pyrimidin-2-yl |
| 271 | 4-OCH(CH₃)CF₂CF₃-pyrimidin-2-yl |
| 272 | 5-OCH(CH₃)CF₂CF₃-pyrimidin-2-yl |
| 273 | 4-OCH(CH₃)CF₂CHF₂-pyrimidin-2-yl |
| 274 | 5-OCH(CH₃)CF₂CHF₂-pyrimidin-2-yl |

TABLE A-continued

| No. | R⁴ |
|---|---|
| 275 | 4-OCH₂CF₂CHFCH₃-pyrimidin-2-yl |
| 276 | 5-OCH₂CF₂CHFCH₃-pyrimidin-2-yl |
| 277 | 4-OCH₂(CF₂)₂CF₃-pyrimidin-2-yl |
| 276 | 5-OCH₂(CF₂)₂CF₃-pyrimidin-2-yl |
| 279 | 4-O(CF₂)₃CF₃-pyrimidin-2-yl |
| 280 | 5-O(CF₂)₃CF₃-pyrimidin-2-yl |
| 281 | 4-OCH₂CF₂CHF₂-pyrimidin-2-yl |
| 282 | 5-OCH₂CF₂CHF₂-pyrimidin-2-yl |
| 283 | 4-CH₂CH=CH₂-pyrimidin-2-yl |
| 284 | 5-CH₂CH=CH₂-pyrimidin-2-yl |
| 285 | 4-CH₂C(CH₃)=CH₂-pyrimidin-2-yl |
| 286 | 5-CH₂C(CH₃)=CH₂-pyrimidin-2-yl |
| 287 | 4-OCH₂CH=CHCH₃-pyrimidin-2-yl |
| 288 | 5-OCH₂CH=CHCH₃-pyrimidin-2-yl |
| 289 | 4-O(CH₂)₂CH=CH₂-pyrimidin-2-yl |
| 290 | 5-O(CH₂)₂CH=CH₂-pyrimidin-2-yl |
| 291 | 4-OCH₂C(CH₃)=CH₂-pyrimidin-2-yl |
| 292 | 5-OCH₂C(CH₃)=CH₂-pyrimidin-2-yl |
| 293 | 4-OCH(CH₃)CH=CH₂-pyrimidin-2-yl |
| 294 | 5-OCH(CH₃)CH=CH₂-pyrimidin-2-yl |
| 295 | 4-OCH₂C≡CH-pyrimidin-2-yl |
| 296 | 5-OCH₂C≡CH-pyrimidin-2-yl |
| 297 | 4-OCH₂C≡CCH₃-pyrimidin-2-yl |
| 298 | 5-OCH₂C≡CCH₃-pyrimidin-2-yl |
| 299 | 4-O(CH₂)₂C≡CH-pyrimidin-2-yl |
| 300 | 5-O(CH₂)₂C≡CH-pyrimidin-2-yl |
| 301 | 4-SCH₃-pyrimidin-2-yl |
| 302 | 5-SCH₃-pyrimidin-2-yl |
| 303 | 4-SCH₂CH₃-pyrimidin-2-yl |
| 304 | 5-SCH₂CH₃-pyrimidin-2-yl |
| 305 | 4-OC₆H₅-pyrimidin-2-yl |
| 306 | 5-OC₆H₅-pyrimidin-2-yl |
| 307 | 4-OCH₂C₆H₅-pyrimidin-2-yl |
| 308 | 5-OCH₂C₆H₅-pyrimidin-2-yl |
| 309 | 4-NO₂-pyrimidin-2-yl |
| 310 | 5-NO₂-pyrimidin-2-yl |
| 311 | 4-NHCH₃-pyrimidin-2-yl |
| 312 | 5-NHCH₃-pyrimidin-2-yl |
| 313 | 4-N(CH₃)₂-pyrimidin-2-yl |
| 314 | 5-N(CH₃)₂-pyrimidin-2-yl |
| 315 | 4-N(CH₃)C₂H₅-pyrimidin-2-yl |
| 316 | 5-N(CH₃)C₂H₅-pyrimidin-2-yl |
| 317 | 4-NHCH₂CF₃-pyrimidin-2-yl |
| 318 | 5-NHCH₂CF₃-pyrimidin-2-yl |
| 319 | 4-F-pyrimidin-2-yl |
| 320 | 5-F-pyrimidin-2-yl |
| 321 | 4-Cl-pyrimidin-2-yl |
| 322 | 5-Cl-pyrimidin-2-yl |
| 323 | 4-OH-pyrimidin-2-yl |
| 324 | 5-OH-pyrimidin-2-yl |
| 325 | 4-CN-pyrimidin-2-yl |
| 326 | 5-CN-pyrimidin-2-yl |
| 327 | 4-C(O)NH₂-pyrimidin-2-yl |
| 328 | 5-C(O)NH₂-pyrimidin-2-yl |
| 329 | 4-C(S)NH₂-pyrimidin-2-yl |
| 330 | 5-C(S)NH₂-pyrimidin-2-yl |
| 331 | 4-CO₂CH₃-pyrimidin-2-yl |
| 332 | 5-CO₂CH₃-pyrimidin-2-yl |
| 333 | 4-ON=C(CH₃)₂-pyrimidin-2-yl |
| 334 | 5-ON=C(CH₃)₂-pyrimidin-2-yl |
| 335 | 4-[O-cyclopropyl]pyrimidin-2-yl |
| 336 | 5-[O-cyclopropyl]pyrimidin-2-yl |
| 337 | 4-[O-cyclobutyl]pyrimidin-2-yl |
| 338 | 5-[O-cyclobutyl]pyrimidin-2-yl |
| 339 | 4-[O-cyclopentyl]pyrimidin-2-yl |
| 340 | 5-[O-cyclopentyl]pyrimidin-2-yl |
| 341 | 4-[O-cyclohexyl]pyrimidin-2-yl |
| 342 | 5-[O-cyclohexyl]pyrimidin-2-yl |
| 343 | 4-[OCH₂-cyclopropyl]pyrimidin-2-yl |
| 344 | 5-[OCH₂-cyclopropyl]pyrimidin-2-yl |
| 345 | 5-F, 4-[OCH₂-cyclopropyl]pyrimidin-2-yl |
| 346 | 4-F, 5-[OCH₂-cyclopropyl]pyrimidin-2-yl |
| 347 | 5-CH₃, 4-[OCH₂-cyclopropyl]pyrimidin-2-yl |
| 348 | 4-CH₃, 5-[OCH₂-cyclopropyl]pyrimidin-2-yl |
| 349 | 5-CF₃, 4-[OCH₂-cyclopropyl]pyrimidin-2-yl |
| 350 | 4-CF₃, 5-[OCH₂-cyclopropyl]pyrimidin-2-yl |
| 351 | 4-[OCH(CH₃)-cyclopropyl]pyrimidin-2-yl |
| 352 | 5-[OCH(CH₃)-cyclopropyl]pyrimidin-2-yl |
| 353 | 5-F, 4-[OCH(CH₃)-cyclopropyl]pyrimidin-2-yl |
| 354 | 4-F, 5-[OCH(CH₃)-cyclopropyl]pyrimidin-2-yl |
| 355 | 5-CH₃, 4-[OCH(CH₃)-cyclopropyl]pyrimidin-2-yl |
| 356 | 4-CH₃, 5-[OCH(CH₃)-cyclopropyl]pyrimidin-2-yl |
| 357 | 5-CF₃, 4-[OCH(CH₃)-cyclopropyl]pyrimidin-2-yl |
| 358 | 4-CF₃, 5-[OCH(CH₃)-cyclopropyl]pyrimidin-2-yl |
| 359 | 4-[O-(1-CH₃-cyclopropyl)]pyrimidin-2-yl |
| 360 | 5-[O-(1-CH₃-cyclopropyl)]pyrimidin-2-yl |
| 361 | 5-F, 4-[O-(1-CH₃-cyclopropyl)]pyrimidin-2-yl |
| 362 | 4-F, 5-[O-(1-CH₃-cyclopropyl)]pyrimidin-2-yl |
| 363 | 5-CH₃, 4-[O-(1-CH₃-cyclopropyl)]pyrimidin-2-yl |
| 364 | 4-CH₃, 5-[O-(1-CH₃-cyclopropyl)]pyrimidin-2-yl |
| 365 | 5-CF₃, 4-[O-(1-CH₃-cyclopropyl)]pyrimidin-2-yl |
| 366 | 4-CF₃, 5-[O-(1-CH₃-cyclopropyl)]pyrimidin-2-yl |
| 367 | 4-[OCH₂-(1-CH₃-cyclopropyl)]pyrimidin-2-yl |
| 368 | 5-[OCH₂-(1-CH₃-cyclopropyl)]pyrimidin-2-yl |
| 369 | 5-F, 4-[OCH₂-(1-CH₃-cyclopropyl)]pyrimidin-2-yl |
| 370 | 4-F, 5-[OCH₂-(1-CH₃-cyclopropyl)]pyrimidin-2-yl |
| 371 | 5-CH₃, 4-[OCH₂-(1-CH₃-cyclopropyl)]pyrimidin-2-yl |
| 372 | 4-CH₃, 5-[OCH₂-(1-CH₃-cyclopropyl)]pyrimidin-2-yl |
| 373 | 5-CF₃, 4-[OCH₂-(1-CH₃-cyclopropyl)]pyrimidin-2-yl |
| 374 | 4-CF₃, 5-[OCH₂-(1-CH₃-cyclopropyl)]pyrimidin-2-yl |
| 375 | 4-[OCH₂-(2-CH₃-cyclopropyl)]pyrimidin-2-yl |
| 376 | 5-[OCH₂-(2-CH₃-cyclopropyl)]pyrimidin-2-yl |
| 377 | 5-F, 4-[OCH₂-(2-CH₃-cyclopropyl)]pyrimidin-2-yl |
| 378 | 4-F, 5-[OCH₂-(2-CH₃-cyclopropyl)]pyrimidin-2-yl |
| 379 | 5-CH₃, 4-[OCH₂-(2-CH₃-cyclopropyl)]pyrimidin-2-yl |
| 380 | 4-CH₃, 5-[OCH₂-(2-CH₃-cyclopropyl)]pyrimidin-2-yl |
| 381 | 5-CF₃, 4-[OCH₂-(2-CH₃-cyclopropyl)]pyrimidin-2-yl |
| 382 | 4-CF₃, 5-[OCH₂-(2-CH₃-cyclopropyl)]pyrimidin-2-yl |
| 383 | 4-[OCH₂-(tetrahydropyran-2-yl)]pyrimidin-2-yl |
| 384 | 5-[OCH₂-(tetrahydropyran-2-yl)]pyrimidin-2-yl |
| 385 | 5-F, 4-[OCH₂-(tetrahydropyran-2-yl)]pyrimidin-2-yl |
| 386 | 4-F, 5-[OCH₂-(tetrahydropyran-2-yl)]pyrimidin-2-yl |
| 387 | 5-CH₃, 4-[OCH₂-(tetrahydropyran-2-yl)]pyrimidin-2-yl |
| 388 | 4-CH₃, 5-[OCH₂-(tetrahydropyran-2-yl)]pyrimidin-2-yl |
| 389 | 5-CF₃, 4-[OCH₂-(tetrahydropyran-2-yl)]pyrimidin-2-yl |
| 390 | 4-CF₃, 5-[OCH₂-(tetrahydropyran-2-yl)]pyrimidin-2-yl |
| 391 | 4-[OCH₂-(furan-2-yl)]pyrimidin-2-yl |
| 392 | 5-[OCH₂-(furan-2-yl)]pyrimidin-2-yl |
| 393 | 5-F, 4-[OCH₂-(furan-2-yl)]pyrimidin-2-yl |
| 394 | 4-F, 5-[OCH₂-(furan-2-yl)]pyrimidin-2-yl |
| 395 | 5-CH₃, 4-[OCH₂-(furan-2-yl)]pyrimidin-2-yl |
| 396 | 4-CH₃, 5-[OCH₂-(furan-2-yl)]pyrimidin-2-yl |
| 397 | 5-CF₃, 4-[OCH₂-(furan-2-yl)]pyrimidin-2-yl |
| 398 | 4-CF₃, 5-[OCH₂-(furan-2-yl)]pyrimidin-2-yl |
| 399 | 4-[OCH₂-(furan-3-yl)]pyrimidin-2-yl |
| 400 | 5-[OCH₂-(furan-3-yl)]pyrimidin-2-yl |
| 401 | 5-F, 4-[OCH₂-(furan-3-yl)]pyrimidin-2-yl |
| 402 | 4-F, 5-[OCH₂-(furan-3-yl)]pyrimidin-2-yl |
| 403 | 5-CH₃, 4-[OCH₂-(furan-3-yl)]pyrimidin-2-yl |
| 404 | 4-CH₃, 5-[OCH₂-(furan-3-yl)]pyrimidin-2-yl |
| 405 | 5-CF₃, 4-[OCH₂-(furan-3-yl)]pyrimidin-2-yl |
| 406 | 4-CF₃, 5-[OCH₂-(furan-3-yl)]pyrimidin-2-yl |
| 407 | 4-[OCH₂-(tetrahydrofuran-3-yl)]pyrimidin-2-yl |
| 408 | 5-[OCH₂-(tetrahydrofuran-3-yl)]pyrimidin-2-yl |
| 409 | 5-F, 4-[OCH₂-(tetrahydrofuran-3-yl)]pyrimidin-2-yl |
| 410 | 4-F, 5-[OCH₂-(tetrahydrofuran-3-yl)]pyrimidin-2-yl |
| 411 | 5-CH₃, 4-[OCH₂-(tetrahydrofuran-3-yl)]pyrimidin-2-yl |
| 412 | 4-CH₃, 5-[OCH₂-(tetrahydrofuran-3-yl)]pyrimidin-2-yl |
| 413 | 5-CF₃, 4-[OCH₂-(tetrahydrofuran-3-yl)]pyrimidin-2-yl |
| 414 | 4-CF₃, 5-[OCH₂-(tetrahydrofuran-3-yl)]pyrimidin-2-yl |
| 415 | 4-[OCH₂-(tetrahydrofuran-2-yl)]pyrimidin-2-yl |
| 416 | 5-[OCH₂-(tetrahydrofuran-2-yl)]pyrimidin-2-yl |
| 417 | 5-F, 4-[OCH₂-(tetrahydrofuran-2-yl)]pyrimidin-2-yl |
| 418 | 4-F, 5-[OCH₂-(tetrahydrofuran-2-yl)]pyrimidin-2-yl |
| 419 | 5-CH₃, 4-[OCH₂-(tetrahydrofuran-2-yl)]pyrimidin-2-yl |
| 420 | 4-CH₃, 5-[OCH₂-(tetrahydrofuran-2-yl)]pyrimidin-2-yl |
| 421 | 5-CF₃, 4-[OCH₂-(tetrahydrofuran-2-yl)]pyrimidin-2-yl |
| 422 | 4-CF₃, 5-[OCH₂-(tetrahydrofuran-2-yl)]pyrimidin-2-yl |
| 423 | 4-[O-(tetrahydropyran-4-yl)]pyrimidin-2-yl |
| 424 | 5-[O-(tetrahydropyran-4-yl)]pyrimidin-2-yl |
| 425 | 5-F, 4-[O-(tetrahydropyran-4-yl)]pyrimidin-2-yl |
| 426 | 4-F, 5-[O-(tetrahydropyran-4-yl)]pyrimidin-2-yl |
| 427 | 5-CH₃, 4-[O-(tetrahydropyran-4-yl)]pyrimidin-2-yl |
| 429 | 4-CH₃, 5-[O-(tetrahydropyran-4-yl)]pyrimidin-2-yl |

TABLE A-continued

| No. | R⁴ |
|---|---|
| 429 | 5-CF₃, 4-[O-(tetrahydropyran-4-yl)]pyrimidin-2-yl |
| 430 | 4-CF₃, 5-[O-(tetrahydropyran-4-yl)]pyrimidin-2-yl |
| 431 | 4-[2-Cl—C₆H₄]pyrimidin-2-yl |
| 432 | 5-[2-Cl—C₆H₄]pyrimidin-2-yl |
| 433 | 5-F, 4-[2-Cl—C₆H₄]pyrimidin-2-yl |
| 434 | 4-F, 5-[2-Cl—C₆H₄]pyrimidin-2-yl |
| 435 | 5-CH₃, 4-[2-Cl—C₆H₄]pyrimidin-2-yl |
| 436 | 4-CH₃, 5-[2-Cl—C₆H₄]pyrimidin-2-yl |
| 437 | 5-CF₃, 4-[2-Cl—C₆H₄]pyrimidin-2-yl |
| 438 | 4-CF₃, 5-[2-Cl—C₆H₄]pyrimidin-2-yl |
| 439 | 4-[OCH₂-(pyridin-2-yl)]pyrimidin-2-yl |
| 440 | 5-[OCH₂-(pyridin-2-yl)]pyrimidin-2-yl |
| 441 | 5-F, 4-[OCH₂-(pyridin-2-yl)]pyrimidin-2-yl |
| 442 | 4-F, 5-[OCH₂-(pyridin-2-yl)]pyrimidin-2-yl |
| 443 | 5-CH₃, 4-[OCH₂-(pyridin-2-yl)]pyrimidin-2-yl |
| 444 | 4-CH₃, 5-[OCH₂-(pyridin-2-yl)]pyrimidin-2-yl |
| 445 | 5-CF₃, 4-[OCH₂-(pyridin-2-yl)]pyrimidin-2-yl |
| 446 | 4-CF₃, 5-[OCH₂-(pyridin-2-yl)]pyrimidin-2-yl |
| 447 | 4-[OCH₂-(pyridin-3-yl)]pyrimidin-2-yl |
| 448 | 5-[OCH₂-(pyridin-3-yl)]pyrimidin-2-yl |
| 449 | 5-F, 4-[OCH₂-(pyridin-3-yl)]pyrimidin-2-yl |
| 450 | 4-F, 5-[OCH₂-(pyridin-3-yl)]pyrimidin-2-yl |
| 451 | 5-CH₃, 4-[OCH₂-(pyridin-3-yl)]pyrimidin-2-yl |
| 452 | 4-CH₃, 5-[OCH₂-(pyridin-3-yl)]pyrimidin-2-yl |
| 453 | 5-CF₃, 4-[OCH₂-(pyridin-3-yl)]pyrimidin-2-yl |
| 454 | 4-CF₃, 5-[OCH₂-(pyridin-3-yl)]pyrimidin-2-yl |
| 455 | 4-[morpholin-4-yl]pyrimidin-2-yl |
| 456 | 5-[morpholin-4-yl]pyrimidin-2-yl |
| 457 | 4-[1-CH₃-imidazol-2-yl]pyrimidin-2-yl |
| 458 | 5-[1-CH₃-imidazol-2-yl]pyrimidin-2-yl |
| 459 | 5-F, 4-[1-CH₃-imidazol-2-yl]pyrimidin-2-yl |
| 460 | 4-F, 5-[1-CH₃-imidazol-2-yl]pyrimidin-2-yl |
| 461 | 5-CH₃, 4-[1-CH₃-imidazol-2-yl]pyrimidin-2-yl |
| 462 | 4-CH₃, 5-[1-CH₃-imidazol-2-yl]pyrimidin-2-yl |
| 463 | 5-CF₃, 4-[1-CH₃-imidazol-2-yl]pyrimidin-2-yl |
| 464 | 4-CF₃, 5-[1-CH₃-imidazol-2-yl]pyrimidin-2-yl |
| 465 | 4-[1,2,4-triazol-1-yl]pyrimidin-2-yl |
| 466 | 5-[1,2,4-triazol-1-yl]pyrimidin-2-yl |
| 467 | 5-F, 4-[1,2,4-triazol-1-yl]pyrimidin-2-yl |
| 468 | 4-F, 5-[1,2,4-triazol-1-yl]pyrimidin-2-yl |
| 469 | 5-CH₃, 4-[1,2,4-triazol-1-yl]pyrimidin-2-yl |
| 470 | 4-CH₃, 5-[1,2,4-triazol-1-yl]pyrimidin-2-yl |
| 471 | 5-CF₃, 4-[1,2,4-triazol-1-yl]pyrimidin-2-yl |
| 472 | 4-CF₃, 5-[1,2,4-triazol-1-yl]pyrimidin-2-yl |
| 473 | 4,5-Cl₂-pyrimidin-2-yl |
| 474 | 4,6-Cl₂-pyrimidin-2-yl |
| 475 | 4,5-(CH₃)₂-pyrimidin-2-yl |
| 476 | 4,6-(CH₃)₂-pyrimidin-2-yl |
| 477 | 4,5-(OCH₃)₂-pyrimidin-2-yl |
| 478 | 4,6-(OCH₃)₂-pyrimidin-2-yl |
| 479 | 4,5-(OCH₂CH₃)₂-pyrimidin-2-yl |
| 480 | 4,6-(OCH₂CH₃)₂-pyrimidin-2-yl |
| 481 | 4-F, 5-CH₃-pyrimidin-2-yl |
| 482 | 4-F, 6-CH₃-pyrimidin-2-yl |
| 483 | 5-F, 4-CH₃-pyrimidin-2-yl |
| 484 | 6-F, 4-CH₃-pyrimidin-2-yl |
| 485 | 4-F, 5-OCH₃-pyrimidin-2-yl |
| 486 | 4-F, 6-OCH₃-pyrimidin-2-yl |
| 487 | 5-F, 4-OCH₃-pyrimidin-2-yl |
| 488 | 6-F, 4-OCH₃-pyrimidin-2-yl |
| 489 | 4-F, 5-OCH₂CH₃-pyrimidin-2-yl |
| 490 | 4-F, 6-OCH₂CH₃-pyrimidin-2-yl |
| 491 | 5-F, 4-OCH₂CH₃-pyrimidin-2-yl |
| 492 | 6-F, 4-OCH₂CH₃-pyrimidin-2-yl |
| 493 | 4-F, 5-OCH₂CF₃-pyrimidin-2-yl |
| 494 | 4-F, 6-OCH₂CF₃-pyrimidin-2-yl |
| 495 | 5-F, 4-OCH₂CF₃-pyrimidin-2-yl |
| 496 | 6-F, 4-OCH₂CF₃-pyrimidin-2-yl |
| 497 | 4-F, 5-OCH(CH₃)₂-pyrimidin-2-yl |
| 498 | 4-F, 6-OCH(CH₃)₂-pyrimidin-2-yl |
| 499 | 5-F, 4-OCH(CH₃)₂-pyrimidin-2-yl |
| 500 | 6-F, 4-OCH(CH₃)₂-pyrimidin-2-yl |
| 501 | 4-Cl, 5-CH₃-pyrimidin-2-yl |
| 502 | 4-Cl, 6-CH₃-pyrimidin-2-yl |
| 503 | 5-Cl, 4-CH₃-pyrimidin-2-yl |
| 504 | 6-Cl, 4-CH₃-pyrimidin-2-yl |
| 505 | 4-Cl, 5-OCH₃-pyrimidin-2-yl |
| 506 | 4-Cl, 6-OCH₃-pyrimidin-2-yl |
| 507 | 5-Cl, 4-OCH₃-pyrimidin-2-yl |
| 508 | 6-Cl, 4-OCH₃-pyrimidin-2-yl |
| 509 | 4-Cl, 5-OCH₂CH₃-pyrimidin-2-yl |
| 510 | 4-Cl, 6-OCH₂CH₃-pyrimidin-2-yl |
| 511 | 5-Cl, 4-OCH₂CH₃-pyrimidin-2-yl |
| 512 | 6-Cl, 4-OCH₂CH₃-pyrimidin-2-yl |
| 513 | 4-Cl, 5-OCH₂CF₃-pyrimidin-2-yl |
| 514 | 4-Cl, 6-OCH₂CF₃-pyrimidin-2-yl |
| 515 | 5-Cl, 4-OCH₂CF₃-pyrimidin-2-yl |
| 516 | 6-Cl, 4-OCH₂CF₃-pyrimidin-2-yl |
| 517 | 4-Cl, 5-OCH(CH₃)₂-pyrimidin-2-yl |
| 518 | 4-Cl, 6-OCH(CH₃)₂-pyrimidin-2-yl |
| 519 | 5-Cl, 4-OCH(CH₃)₂-pyrimidin-2-yl |
| 520 | 6-Cl, 4-OCH(CH₃)₂-pyrimidin-2-yl |
| 521 | 4-CH₃, 5-OCH₃-pyrimidin-2-yl |
| 522 | 4-CH₃, 6-OCH₃-pyrimidin-2-yl |
| 523 | 5-CH₃, 4-OCH₃-pyrimidin-2-yl |
| 524 | 6-CH₃, 4-OCH₃-pyrimidin-2-yl |
| 525 | 6-CH₃, 4-OCH₂CH₃-pyrimidin-2-yl |
| 526 | 5-CH₃, 4-OCH₂CH₃-pyrimidin-2-yl |
| 527 | 4-CH₃, 5-OCH₂CH₃-pyrimidin-2-yl |
| 528 | 4-CH₃, 6-OCH₂CH₃-pyrimidin-2-yl |
| 529 | 4-CH₃, 5-OCH₂CF₃-pyrimidin-2-yl |
| 530 | 4-CH₃, 6-OCH₂CF₃-pyrimidin-2-yl |
| 531 | 5-CH₃, 4-OCH₂CF₃-pyrimidin-2-yl |
| 532 | 6-CH₃, 4-OCH₂CF₃-pyrimidin-2-yl |
| 533 | 4-CH₃, 5-OCH(CH₃)₂-pyrimidin-2-yl |
| 534 | 4-CH₃, 6-OCH(CH₃)₂-pyrimidin-2-yl |
| 535 | 5-CH₃, 4-OCH(CH₃)₂-pyrimidin-2-yl |
| 536 | 6-CH₃, 4-OCH(CH₃)₂-pyrimidin-2-yl |
| 537 | 4-CH₃, 5-OCH₂CH=CH₂-pyrimidin-2-yl |
| 538 | 4-CH₃, 6-OCH₂CH=CH₂-pyrimidin-2-yl |
| 539 | 5-CH₃, 4-OCH₂CH=CH₂-pyrimidin-2-yl |
| 540 | 6-CH₃, 4-OCH₂CH=CH₂-pyrimidin-2-yl |
| 541 | 4-CH₃, 5-CO₂CH₃-pyrimidin-2-yl |
| 542 | 4-CH₃, 6-CO₂CH₃-pyrimidin-2-yl |
| 543 | 4-CH₃, 5-CF₃-pyrimidin-2-yl |
| 544 | 4-CH₃, 6-CF₃-pyrimidin-2-yl |
| 545 | 5-CH₃, 4-CF₃-pyrimidin-2-yl |
| 546 | 6-CH₃, 4-CF₃-pyrimidin-2-yl |
| 547 | 4-CF₃, 5-OCH₃-pyrimidin-2-yl |
| 548 | 4-CF₃, 6-OCH₃-pyrimidin-2-yl |
| 549 | 5-CF₃, 4-OCH₃-pyrimidin-2-yl |
| 550 | 6-CF₃, 4-OCH₃-pyrimidin-2-yl |
| 551 | 4-CF₃, 5-OCH₃-pyrimidin-2-yl |
| 552 | 4-CF₃, 6-OCH₃-pyrimidin-2-yl |
| 553 | 5-CF₃, 4-OCH₃-pyrimidin-2-yl |
| 554 | 6-CF₃, 4-OCH₃-pyrimidin-2-yl |
| 555 | 4-CF₃, 5-OCH₂CH₃-pyrimidin-2-yl |
| 556 | 4-CF₃, 6-OCH₂CH₃-pyrimidin-2-yl |
| 557 | 5-CF₃, 4-OCH₂CH₃-pyrimidin-2-yl |
| 558 | 6-CF₃, 4-OCH₂CH₃-pyrimidin-2-yl |
| 559 | 4-CF₃, 5-OCH₂CF₃-pyrimidin-2-yl |
| 560 | 4-CF₃, 6-OCH₂CF₃-pyrimidin-2-yl |
| 561 | 5-CF₃, 4-OCH₂CF₃-pyrimidin-2-yl |
| 562 | 6-CF₃, 4-OCH₂CF₃-pyrimidin-2-yl |
| 563 | 4-OCH₃, 5-OCH₂CH₃-pyrimidin-2-yl |
| 564 | 4-OCH₃, 6-OCH₂CH₃-pyrimidin-2-yl |
| 565 | 5-OCH₃, 4-OCH₂CH₃-pyrimidin-2-yl |
| 566 | 6-OCH₃, 4-OCH₂CH₃-pyrimidin-2-yl |
| 567 | 4-OCH₃, 5-OCH₂CF₃-pyrimidin-2-yl |
| 568 | 4-OCH₃, 6-OCH₂CF₃-pyrimidin-2-yl |
| 569 | 5-OCH₃, 4-OCH₂CF₃-pyrimidin-2-yl |
| 570 | 6-OCH₃, 4-OCH₂CF₃-pyrimidin-2-yl |
| 571 | 4-OCH₃, 5-OCH(CH₃)-pyrimidin-2-yl |
| 572 | 4-OCH₃, 6-OCH(CH₃)-pyrimidin-2-yl |
| 573 | 5-OCH₃, 4-OCH(CH₃)-pyrimidin-2-yl |
| 574 | 6-OCH₃, 4-OCH(CH₃)-pyrimidin-2-yl |
| 575 | 4-OCH₂CH₃, 5-CH₂OCH₂CH₃-pyrimidin-2-yl |
| 576 | 4-OCH₂CH₃, 6-CH₂OCH₂CH₃-pyrimidin-2-yl |
| 577 | 5-OCH₂CH₃, 4-CH₂OCH₂CH₃-pyrimidin-2-yl |
| 578 | 6-OCH₂CH₃, 4-CH₂OCH₂CH₃-pyrimidin-2-yl |
| 579 | 4-NO₂, 5-CH₃-pyrimidin-2-yl |
| 580 | 4-NO₂, 6-CH₃-pyrimidin-2-yl |
| 581 | 5-NO₂, 4-CH₃-pyrimidin-2-yl |
| 582 | 6-NO₂, 4-CH₃-pyrimidin-2-yl |

TABLE A-continued

| No. | R⁴ |
|---|---|
| 583 | 4-NO₂, 5-OCH₃-pyrimidin-2-yl |
| 584 | 4-NO₂, 6-OCH₃-pyrimidin-2-yl |
| 585 | 5-NO₂, 4-OCH₃-pyrimidin-2-yl |
| 586 | 6-NO₂, 4-OCH₃-pyrimidin-2-yl |
| 587 | 4-NO₂, 5-OCH₂CH₃-pyrimidin-2-yl |
| 588 | 4-NO₂, 6-OCH₂CH₃-pyrimidin-2-yl |
| 589 | 5-NO₂, 4-OCH₂CH₃-pyrimidin-2-yl |
| 590 | 6-NO₂, 4-OCH₂CH₃-pyrimidin-2-yl |
| 591 | 4-NO₂, 5-OCH(CH₃)₂-pyrimidin-2-yl |
| 592 | 4-NO₂, 6-OCH(CH₃)₂-pyrimidin-2-yl |
| 593 | 5-NO₂, 4-OCH(CH₃)₂-pyrimidin-2-yl |
| 594 | 6-NO₂, 4-OCH(CH₃)₂-pyrimidin-2-yl |
| 595 | 4-NO₂, 5-OCH₂CF₃-pyrimidin-2-yl |
| 596 | 4-NO₂, 6-OCH₂CF₃-pyrimidin-2-yl |
| 597 | 5-NO₂, 4-OCH₂CF₃-pyrimidin-2-yl |
| 598 | 6-NO₂, 4-OCH₂CF₃-pyrimidin-2-yl |
| 599 | 4-CN, 5-CH₃-pyrimidin-2-yl |
| 600 | 4-CN, 6-CH₃-pyrimidin-2-yl |
| 601 | 5-CN, 4-CH₃-pyrimidin-2-yl |
| 602 | 6-CN, 4-CH₃-pyrimidin-2-yl |
| 603 | 4-CN, 5-OCH₃-pyrimidin-2-yl |
| 604 | 4-CN, 6-OCH₃-pyrimidin-2-yl |
| 605 | 5-CN, 4-OCH₃-pyrimidin-2-yl |
| 606 | 6-CN, 4-OCH₃-pyrimidin-2-yl |
| 607 | 4-CN, 5-OCH₂CH₃-pyrimidin-2-yl |
| 609 | 4-CN, 6-OCH₂CH₃-pyrimidin-2-yl |
| 609 | 5-CN, 4-OCH₂CH₃-pyrimidin-2-yl |
| 610 | 6-CN, 4-OCH₂CH₃-pyrimidin-2-yl |
| 611 | 4-CN, 5-OCH(CH₃)₂-pyrimidin-2-yl |
| 612 | 4-CN, 6-OCH(CH₃)₂-pyrimidin-2-yl |
| 613 | 5-CN, 4-OCH(CH₃)₂-pyrimidin-2-yl |
| 614 | 6-CN, 4-OCH(CH₃)₂-pyrimidin-2-yl |
| 615 | 4-CN, 5-OCH₂CF₃-pyrimidin-2-yl |
| 616 | 4-CN, 6-OCH₂CF₃-pyrimidin-2-yl |
| 617 | 5-CN, 4-OCH₂CF₃-pyrimidin-2-yl |
| 618 | 6-CN, 4-OCH₂CF₃-pyrimidin-2-yl |
| 619 | 5,6-(CH₃)₂, 4-OCH₃-pyrimidin-2-yl |
| 620 | 2-CH₃-pyrimidin-4-yl |
| 621 | 5-CH₃-pyrimidin-4-yl |
| 622 | 6-CH₃-pyrimidin-4-yl |
| 623 | 2-CH₂CH₃-pyrimidin-4-yl |
| 624 | 5-CH₂CH₃-pyrimidin-4-yl |
| 625 | 6-CH₂CH₃-pyrimidin-4-yl. |
| 626 | 2-CH(CH₃)₂-pyrimidin-4-yl |
| 627 | 5-CH(CH₃)₂-pyrimidin-4-yl |
| 628 | 6-CH(CH₃)₂-pyrimidin-4-yl |
| 629 | 2-CH(CH₃)CH₂CH₃-pyrimidin-4-yl |
| 630 | 5-CH(CH₃)CH₂CH₃-pyrimidin-4-yl |
| 631 | 6-CH(CH₃)CH₂CH₃-pyrimidin-4-yl |
| 632 | 2-CF₃-pyrimidin-4-yl |
| 633 | 5-CF₃-pyrimidin-4-yl |
| 634 | 6-CF₃-pyrimidin-4-yl |
| 635 | 2-CH=CH₂-pyrimidin-4-yl |
| 636 | 5-CH=CH₂-pyrimidin-4-yl |
| 637 | 6-CH=CH₂-pyrimidin-4-yl |
| 638 | 2-CH=CHCH₃-pyrimidin-4-yl |
| 639 | 5-CH=CHCH₃-pyrimidin-4-yl |
| 640 | 6-CH=CHCH₃-pyrimidin-4-yl |
| 641 | 2-CH=CHCl-pyrimidin-4-yl |
| 642 | 5-CH=CHCl-pyrimidin-4-yl |
| 643 | 6-CH=CHCl-pyrimidin-4-yl |
| 644 | 2-C≡CH-pyrimidin-4-yl |
| 645 | 5-C≡CH-pyrimidin-4-yl |
| 646 | 6-C≡CH-pyrimidin-4-yl |
| 647 | 2-CH₂C≡CH-pyrimidin-4-yl |
| 648 | 5-CH₂C≡CH-pyrimidin-4-yl |
| 649 | 6-CH₂C≡CH-pyrimidin-4-yl |
| 650 | 2-CH₂C≡CCH₃-pyrimidin-4-yl |
| 651 | 5-CH₂C≡CCH₃-pyrimidin-4-yl |
| 652 | 6-CH₂C≡CCH₃-pyrimidin-4-yl |
| 653 | 2-cyclopropyl-pyrimidin-4-yl |
| 654 | 5-cyclopropyl-pyrimidin-4-yl |
| 655 | 6-cyclopropyl-pyrimidin-4-yl |
| 656 | 2-cyclopentyl-pyrimidin-4-yl |
| 657 | 5-cyclopentyl-pyrimidin-4-yl |
| 658 | 6-cyclopentyl-pyrimidin-4-yl |
| 659 | 2-OCH₃-pyrimidin-4-yl |
| 660 | 5-OCH₃-pyrimidin-4-yl |
| 661 | 6-OCH₃-pyrimidin-4-yl |
| 662 | 2-OCH₂CH₃-pyrimidin-4-yl |
| 663 | 5-OCH₂CH₃-pyrimidin-4-yl |
| 664 | 6-OCH₂CH₃-pyrimidin-4-yl |
| 665 | 2-OCH₂CH₂CH₃-pyrimidin-4-yl |
| 666 | 5-OCH₂CH₂CH₃-pyrimidin-4-yl |
| 667 | 6-OCH₂CH₂CH₃-pyrimidin-4-yl |
| 668 | 2-OCH(CH₃)₂-pyrimidin-4-yl |
| 669 | 5-OCH(CH₃)₂-pyrimidin-4-yl |
| 670 | 6-OCH(CH₃)₂-pyrimidin-4-yl |
| 671 | 2-OCH₂CH₂CH₂CH₃-pyrimidin-4-yl |
| 672 | 5-OCH₂CH₂CH₂CH₃-pyrimidin-4-yl |
| 673 | 6-OCH₂CH₂CH₂CH₃-pyrimidin-4-yl |
| 674 | 2-OCH(CH₃)CH₂CH₃-pyrimidin-4-yl |
| 675 | 5-OCH(CH₃)CH₂CH₃-pyrimidin-4-yl |
| 676 | 6-OCH(CH₃)CH₂CH₃-pyrimidin-4-yl |
| 677 | 2-OCH₂CH(CH₃)₂-pyrimidin-4-yl |
| 678 | 5-OCH₂CH(CH₃)₂-pyrimidin-4-yl |
| 679 | 6-OCH₂CH(CH₃)₂-pyrimidin-4-yl |
| 680 | 2-OC(CH₃)₃-pyrimidin-4-yl |
| 681 | 5-OC(CH₃)₃-pyrimidin-4-yl |
| 662 | 6-OC(CH₃)₃-pyrimidin-4-yl |
| 683 | 2-OCH(CH₃)CH₂CH₂CH₃-pyrimidin-4-yl |
| 684 | 5-OCH(CH₃)CH₂CH₂CH₃-pyrimidin-4-yl |
| 685 | 6-OCH(CH₃)CH₂CH₂CH₃-pyrimidin-4-yl |
| 686 | 2-OCH₂OCH₃-pyrimidin-4-yl |
| 687 | 5-OCH₂OCH₃-pyrimidin-4-yl |
| 688 | 6-OCH₂OCH₃-pyrimidin-4-yl |
| 689 | 2-OCH₂OCH₂CH₃-pyrimidin-4-yl |
| 690 | 5-OCH₂OCH₂CH₃-pyrimidin-4-yl |
| 691 | 6-OCH₂OCH₂CH₃-pyrimidin-4-yl |
| 692 | 2-OCH(CH₃)OCH₃-pyrimidin-4-yl |
| 693 | 5-OCH(CH₃)OCH₃-pyrimidin-4-yl |
| 694 | 6-OCH(CH₃)OCH₃-pyrimidin-4-yl |
| 695 | 2-OCH(CH₃)OCH₂CH₃-pyrimidin-4-yl |
| 696 | 5-OCH(CH₃)OCH₂CH₃-pyrimidin-4-yl |
| 697 | 6-OCH(CH₃)OCH₂CH₃-pyrimidin-4-yl |
| 698 | 2-OCH₂CH₂OCH₃-pyrimidin-4-yl |
| 699 | 5-OCH₂CH₂OCH₃-pyrimidin-4-yl |
| 700 | 6-OCH₂CH₂OCH₃-pyrimidin-4-yl |
| 701 | 2-OCH₂CH₂OCH₂CH₃-pyrimidin-4-yl |
| 702 | 5-OCH₂CH₂OCH₂CH₃-pyrimidin-4-yl |
| 703 | 6-OCH₂CH₂OCH₂CH₃-pyrimidin-4-yl |
| 704 | 2-OCH₂CH₂OCH(CH₃)₂-pyrimidin-4-yl |
| 705 | 5-OCH₂CH₂OCH(CH₃)₂-pyrimidin-4-yl |
| 706 | 6-OCH₂CH₂OCH(CH₃)₂-pyrimidin-4-yl |
| 707 | 2-OCH₂CH₂SCH₃-pyrimidin-4-yl |
| 708 | 5-OCH₂CH₂SCH₃-pyrimidin-4-yl |
| 709 | 6-OCH₂CH₂SCH₃-pyrimidin-4-yl |
| 710 | 2-OCH₂CH₂SO₂CH₃-pyrimidin-4-yl |
| 711 | 5-OCH₂CH₂SO₂CH₃-pyrimidin-4-yl |
| 712 | 6-OCH₂CH₂SO₂CH₃-pyrimidin-4-yl |
| 713 | 2-OCH₂CH₂SCH(CH₃)₂-pyrimidin-4-yl |
| 714 | 5-OCH₂CH₂SCH(CH₃)₂-pyrimidin-4-yl |
| 715 | 6-OCH₂CH₂SCH(CH₃)₂-pyrimidin-4-yl |
| 716 | 2-OCH₂CH₂CN-pyrimidin-4-yl |
| 717 | 5-OCH₂CH₂CN-pyrimidin-4-yl |
| 718 | 6-OCH₂CH₂CN-pyrimidin-4-yl |
| 719 | 2-OCH₂CH₂SCH₂CH₂CN-pyrimidin-4-yl |
| 720 | 5-OCH₂CH₂SCH₂CH₂CN-pyrimidin-4-yl |
| 721 | 6-OCH₂CH₂SCH₂CH₂CN-pyrimidin-4-yl |
| 722 | 2-OCH₂CH₂OC₆H₅-pyrimidin-4-yl |
| 723 | 5-OCH₂CH₂OC₆H₅-pyrimidin-4-yl |
| 724 | 6-OCH₂CH₂OC₆H₅-pyrimidin- 4-yl |
| 725 | 2-OCH₂CH₂OCH₂C₆H₅-pyrimidin-4-yl |
| 726 | 5-OCH₂CH₂OCH₂C₆H₅-pyrimidin-4-yl |
| 727 | 6-OCH₂CH₂OCH₂C₆H₅-pyrimidin-4-yl |
| 728 | 2-OCH₂CH₂N(CH₃)₂-pyrimidin-4-yl |
| 729 | 5-OCH₂CH₂N(CH₃)₂-pyrimidin-4-yl |
| 730 | 6-OCH₂CH₂N(CH₃)₂-pyrimidin-4-yl |
| 731 | 2-OCH₂CH₂CONH₂-pyrimidin-4-yl |
| 732 | 5-OCH₂CH₂CONH₂-pyrimidin-4-yl |
| 733 | 6-OCH₂CH₂CONH₂-pyrimidin-4-yl |
| 734 | 2-OCH₂CH₂CO₂CH₂CH₂CH₃-pyrimidin-4-yl |
| 735 | 5-OCH₂CH₂CO₂CH₂CH₂CH₃-pyrimidin-4-yl |
| 736 | 6-OCH₂CH₂CO₂CH₂CH₂CH₃-pyrimidin-4-yl |

TABLE A-continued

| No. | R⁴ |
|---|---|
| 737 | 2-OCH(CH₃)CH₂OCH₃-pyrimidin-4-yl |
| 738 | 5-OCH(CH₃)CH₂OCH₃-pyrimidin-4-yl |
| 739 | 6-OCH(CH₃)CH₂OCH₃-pyrimidin-4-yl |
| 740 | 2-OCH(CH₃)CH₂CO₂CH₃-pyrimidin-4-yl |
| 741 | 5-OCH(CH₃)CH₂CO₂CH₃-pyrimidin-4-yl |
| 742 | 6-OCH(CH₃)CH₂CO₂CH₃-pyrimidin-4-yl |
| 743 | 2-OCH(CH₃)CH₂CO₂CH₂CH₃-pyrimidin-4-yl |
| 744 | 5-OCH(CH₃)CH₂CO₂CH₂CH₃-pyrimidin-4-yl |
| 745 | 6-OCH(CH₃)CH₂CO₂CH₂CH₃-pyrimidin-4-yl |
| 746 | 2-OCH₂CH(CH₃)CO₂CH₃-pyrimidin-4-yl |
| 747 | 5-OCH₂CH(CH₃)CO₂CH₃-pyrimidin-4-yl |
| 748 | 6-OCH₂CH(CH₃)CO₂CH₃-pyrimidin-4-yl |
| 749 | 2-OCH₂C(=O)CH₃-pyrimidin-4-yl |
| 750 | 5-OCH₂C(=O)CH₃-pyrimidin-4-yl |
| 751 | 6-OCH₂C(=O)CH₃-pyrimidin-4-yl |
| 752 | 2-OCH₂C(=O)CH₂CH₃-pyrimidin-4-yl |
| 753 | 5-OCH₂C(=O)CH₂CH₃-pyrimidin-4-yl |
| 744 | 6-OCH₂C(=O)CH₂CH₃-pyrimidin-4-yl |
| 755 | 2-OCH₂CO₂CH₃-pyrimidin-4-yl |
| 756 | 5-OCH₂CO₂CH₃-pyrimidin-4-yl |
| 757 | 6-OCH₂CO₂CH₃-pyrimidin-4-yl |
| 758 | 2-OCH₂CO₂CH₂CH₃-pyrimidin-4-yl |
| 759 | 4-OCH₂CO₂CH₂CH₃-pyrimidin-4-yl |
| 760 | 6-OCH₂CO₂CH₂CH₃-pyrimidin-4-yl |
| 761 | 2-OCH₂C(=O)NH₂-pyrimidin-4-yl |
| 762 | 5-OCH₂C(=O)NH₂-pyrimidin-4-yl |
| 763 | 6-OCH₂C(=O)NH₂-pyrimidin-4-yl |
| 764 | 2-OCH₂C(=O)NHCH₃-pyrimidin-4-yl |
| 765 | 5-OCH₂C(=O)NHCH₃-pyrimidin-4-yl |
| 766 | 6-OCH₂C(=O)NHCH₃-pyrimidin-4-yl |
| 767 | 2-OCH₂C(=O)SCH₃-pyrimidin-4-yl |
| 768 | 5-OCH₂C(=O)SCH₃-pyrimidin-4-yl |
| 769 | 6-OCH₂C(=O)SCH₃-pyrimidin-4-yl |
| 770 | 2-OCH(CH₃)C(=O)NH₂-pyrimidin-4-yl |
| 771 | 5-OCH(CH₃)C(=O)NH₂-pyrimidin-4-yl |
| 772 | 6-OCH(CH₃)C(=O)NH₂-pyrimidin-4-yl |
| 773 | 2-OCH(CH₃)C(=O)NHCH₃-pyrimidin-4-yl |
| 774 | 5-OCH(CH₃)C(=O)NHCH₃-pyrimidin-4-yl |
| 775 | 6-OCH(CH₃)C(=O)NHCH₃-pyrimidin-4-yl |
| 776 | 2-OCH(CH₃)C(=O)NHNH₂-pyrimidin-4-yl |
| 777 | 5-OCH(CH₃)C(=O)NHNH₂-pyrimidin-4-yl |
| 778 | 6-OCH(CH₃)C(=O)NHNH₂-pyrimidin-4-yl |
| 779 | 2-OCH(CH₃)CO₂CH₃-pyrimidin-4-yl |
| 780 | 5-OCH(CH₃)CO₂CH₃-pyrimidin-4-yl |
| 781 | 6-OCH(CH₃)CO₂CH₃-pyrimidin-4-yl |
| 782 | 2-OCH(CH₃)CO₂CH₂CH₃-pyrimidin-4-yl |
| 783 | 5-OCH(CH₃)CO₂CH₂CH₃-pyrimidin-4-yl |
| 784 | 6-OCH(CH₃)CO₂CH₂CH₃-pyrimidin-4-yl |
| 785 | 2-OCH(CH₃)C(=O)CH₃-pyrimidin-4-yl |
| 786 | 5-OCH(CH₃)C(=O)CH₃-pyrimidin-4-yl |
| 787 | 6-OCH(CH₃)C(=O)CH₃-pyrimidin-4-yl |
| 788 | 2-OCH(CH₃)C(=O)CH₂CH₃-pyrimidin-4-yl |
| 789 | 5-OCH(CH₃)C(=O)CH₂CH₃-pyrimidin-4-yl |
| 790 | 6-OCH(CH₃)C(=O)CH₂CH₃-pyrimidin-4-yl |
| 791 | 2-OCH(CH₃)CH₂C(=O)CH₃-pyrimidin-4-yl |
| 792 | 5-OCH(CH₃)CH₂C(=O)CH₃-pyrimidin-4-yl |
| 793 | 6-OCH(CH₃)CH₂C(=O)CH₃-pyrimidin-4-yl |
| 794 | 2-OCH(CH₃)CH₂OC(CH₃)₃-pyrimidin-4-yl |
| 795 | 5-OCH(CH₃)CH₂OC(CH₃)₃-pyrimidin-4-yl |
| 796 | 6-OCH(CH₃)CH₂OC(CH₃)₃-pyrimidin-4-yl |
| 797 | 2-OCH(CH₃)CH₂OCH₂CH₃-pyrimidin-4-yl |
| 798 | 5-OCH(CH₃)CH₂OCH₂CH₃-pyrimidin-4-yl |
| 799 | 6-OCH(CH₃)CH₂OCH₂CH₃-pyrimidin-4-yl |
| 800 | 2-OCH(CH₃)CH₂O(CH₃)₂CH₃-pyrimidin-4-yl |
| 801 | 5-OCH(CH₃)CH₂O(CH₃)₂CH₃-pyrimidin-4-yl |
| 802 | 6-OCH(CH₃)CH₂O(CH₃)₂CH₃-pyrimidin-4-yl |
| 803 | 2-OCH(CH₃)CH₂OCH₂CH=CH₂-pyrimidin-4-yl |
| 804 | 5-OCH(CH₃)CH₂OCH₂CH=CH₂-pyrimidin-4-yl |
| 805 | 6-OCH(CH₃)CH₂OCH₂CH=CH₂-pyrimidin-4-yl |
| 806 | 2-O(CH₂)₃OCH₃-pyrimidin-4-yl |
| 807 | 5-O(CH₂)₃OCH₃-pyrimidin-4-yl |
| 808 | 6-O(CH₂)₃OCH₃-pyrimidin-4-yl |
| 809 | 2-O(CH₂)₃OCH₂CH₃-pyrimidin-4-yl |
| 810 | 5-O(CH₂)₃OCH₂CH₃-pyrimidin-4-yl |
| 811 | 6-O(CH₂)₃OCH₂CH₃-pyrimidin-4-yl |
| 812 | 2-O(CH₂)₃OCH(CH₃)₂-pyrimidin-4-yl |
| 813 | 5-O(CH₂)₃OCH(CH₃)₂-pyrimidin-4-yl |
| 814 | 6-O(CH₂)₃OCH(CH₃)₂-pyrimidin-4-yl |
| 815 | 2-O(CH₂)₃OC₆H₅-pyrimidin-4-yl |
| 816 | 5-O(CH₂)₃OC₆H₅-pyrimidin-4-yl |
| 817 | 6-O(CH₂)₃OC₆H₅-pyrimidin-4-yl |
| 818 | 2-O(CH₂)₃OCH₂C₆H₅-pyrimidin-4-yl |
| 819 | 5-O(CH₂)₃OCH₂C₆H₅-pyrimidin-4-yl |
| 820 | 6-O(CH₂)₃OCH₂C₆H₅-pyrimidin-4-yl |
| 821 | 2-OCH(CH₂CH₃)CH₂OCH₃-pyrimidin-4-yl |
| 822 | 5-OCH(CH₂CH₃)CH₂OCH₃-pyrimidin-4-yl |
| 823 | 6-OCH(CH₂CH₃)CH₂OCH₃-pyrimidin-4-yl |
| 824 | 2-OCH(CH₂CH₃)CH₂CH₂OCH₃-pyrimidin-4-yl |
| 825 | 5-OCH(CH₂CH₃)CH₂CH₂OCH₃-pyrimidin-4-yl |
| 826 | 6-OCH(CH₂CH₃)CH₂CH₂OCH₃-pyrimidin-4-yl |
| 827 | 2-OCH(CH₂CH₃)CH₂CH₂OCH₂CH₃-pyrimidin-4-yl |
| 828 | 5-OCH(CH₂CH₃)CH₂CH₂OCH₂CH₃-pyrimidin-4-yl |
| 829 | 6-OCH(CH₂CH₃)CH₂CH₂OCH₂CH₃-pyrimidin-4-yl |
| 830 | 2-O[(CH₂)₃O]₂CH₃-pyrimidin-4-yl |
| 831 | 5-O[(CH₂)₃O]₂CH₃-pyrimidin-4-yl |
| 832 | 6-O[(CH₂)₃O]₂CH₃-pyrimidin-4-yl |
| 833 | 2-OCH₂CH(CH₃)CH₂OCH₃-pyrimidin-4-yl |
| 834 | 5-OCH₂CH(CH₃)CH₂OCH₃-pyrimidin-4-yl |
| 835 | 6-OCH₂CH(CH₃)CH₂OCH₃-pyrimidin-4-yl |
| 836 | 2-OCH₂CH(CH₃)CH₂OCH₂CH₃-pyrimidin-4-yl |
| 837 | 5-OCH₂CH(CH₃)CH₂OCH₂CH₃-pyrimidin-4-yl |
| 838 | 6-OCH₂CH(CH₃)CH₂OCH₂CH₃-pyrimidin-4-yl |
| 839 | 2-OCH(CH₂Cl)CH₂OCH₃-pyrimidin-4-yl |
| 840 | 5-OCH(CH₂Cl)CH₂OCH₃-pyrimidin-4-yl |
| 841 | 6-OCH(CH₂Cl)CH₂OCH₃-pyrimidin-4-yl |
| 842 | 2-OCH(CH₂Cl)CH₂OCH₂CH₃-pyrimidin-4-yl |
| 843 | 5-OCH(CH₂Cl)CH₂OCH₂CH₃-pyrimidine-4-yl |
| 844 | 6-OCH(CH₂Cl)CH₂OCH₂CH₃-pyrimidin-4-yl |
| 845 | 2-OCH(CH₂Cl)CH₂OCH(CH₃)₂-pyrimidin-4-yl |
| 846 | 5-OCH(CH₂Cl)CH₂OCH(CH₃)₂-pyrimidin-4-yl |
| 847 | 6-OCH(CH₂Cl)CH₂OCH(CH₃)₂-pyrimidin-4-yl |
| 848 | 2-OCH(CH₂Cl)CH₂OCH₂CH=CH₂-pyrimidin-4-yl |
| 849 | 5-OCH(CH₂Cl)CH₂OCH₂CH=CH₂-pyrimidin-4-yl |
| 850 | 6-OCH(CH₂Cl)CH₂OCH₂CH=CH₂-pyrimidin-4-yl |
| 851 | 2-OCH[CH₂OCH₃]₂-pyrimidin-4-yl |
| 852 | 5-OCH[CH₂OCH₃]₂-pyrimidin-4-yl |
| 853 | 6-OCH[CH₂OCH₃]₂-pyrimidin-4-yl |
| 854 | 2-OCH(CH₂OCH₂CH₃)₂-pyrimidin-4-yl |
| 855 | 5-OCH(CH₂OCH₂CH₃)₂-pyrimidin-4-yl |
| 856 | 6-OCH(CH₂OCH₂CH₃)₂-pyrimidin-4-yl |
| 857 | 2-OCCl₃-pyrimidin-4-yl |
| 858 | 5-OCCl₃-pyrimidin-4-yl |
| 859 | 6-OCCl₃-pyrimidin-4-yl |
| 860 | 2-OCHF₂-pyrimidin-4-yl |
| 861 | 5-OCHF₂-pyrimidin-4-yl |
| 862 | 6-OCHF₂-pyrimidin-4-yl |
| 863 | 2-OCF₃-pyrimidin-4-yl |
| 864 | 5-OCF₃-pyrimidin-4-yl |
| 865 | 6-OCF₃-pyrimidin-4-yl |
| 866 | 2-OCF₂CHF₂-pyrimidin-4-yl |
| 867 | 5-OCF₂CHF₂-pyrimidin-4-yl |
| 868 | 6-OCF₂CHF₂-pyrimidin-4-yl |
| 869 | 2-OCH₂CF₃-pyrimidin-4-yl |
| 870 | 5-OCH₂CF₃-pyrimidin-4-yl |
| 871 | 6-OCH₂CF₃-pyrimidin-4-yl |
| 872 | 2-OCH₂CHF₂-pyrimidin-4-yl |
| 873 | 5-OCH₂CHF₂-pyrimidin-4-yl |
| 874 | 6-OCH₂CHF₂-pyrimidin-4-yl |
| 875 | 2-O(CH₂)₃F-pyrimidin-4-yl |
| 876 | 5-O(CH₂)₃F-pyrimidin-4-yl |
| 877 | 6-O(CH₂)₃F-pyrimidin-4-yl |
| 878 | 2-OCH(CH₃)CF₃-pyrimidin-4-yl |
| 879 | 5-OCH(CH₃)CF₃-pyrimidin-4-yl |
| 880 | 6-OCH(CH₃)CF₃-pyrimidin-4-yl |
| 881 | 2-O(CH₂)₄F-pyrimidin-4-yl |
| 882 | 5-O(CH₂)₄F-pyrimidin-4-yl |
| 883 | 6-O(CH₂)4F-pyrimidin-4-yl |
| 884 | 2-O(CH₂)₃CF₃-pyrimidin-4-yl |
| 865 | 5-O(CH₂)₃CF₃-pyrimidin-4-yl |
| 886 | 6-O(CH₂)₃CF₃-pyrimidin-4-yl |
| 887 | 2-OCH(CH₃)CF₂CF₃-pyrimidin-4-yl |
| 888 | 5-OCH(CH₃)CF₂CF₃-pyrimidin-4-yl |
| 889 | 6-OCH(CH₃)CF₂CF₃-pyrimidin-4-yl |
| 890 | 2-OCH(CH₃)CF₂CHF₂-pyrimidin-4-yl |

TABLE A-continued

| No. | R⁴ |
|---|---|
| 891 | 5-OCH(CH₃)CF₂CHF₂-pyrimidin-4-yl |
| 892 | 6-OCH(CH₃)CF₂CHF₂-pyrimidin-4-yl |
| 893 | 2-OCH₂CF₂CHFCH₃-pyrimidin-4-yl |
| 894 | 5-OCH₂CF₂CHFCH₃-pyrimidin-4-yl |
| 895 | 6-OCH₂CF₂CHFCH₃-pyrimidin-4-yl |
| 896 | 2-OCH₂(CF₂)₂CF₃-pyrimidin-4-yl |
| 897 | 5-OCH₂(CF₂)₂CF₃-pyrimidin-4-yl |
| 898 | 6-OCH₂(CF₂)₂CF₃-pyrimidin-4-yl |
| 899 | 2-O(CF₂)₃CF₃-pyrimidin-4-yl |
| 900 | 5-O(CF₂)₃CF₃-pyrimidin-4-yl |
| 901 | 6-O(CF₂)₃CF₃-pyrimidin-4-yl |
| 902 | 2-OCH₂CF₂CHF₂-pyrimidin-4-yl |
| 903 | 5-OCH₂CF₂CHF₂-pyrimidin-4-yl |
| 904 | 6-OCH₂CF₂CHF₂-pyrimidin-4-yl |
| 905 | 2-CH₂CH=CH₂-pyrimidin-4-yl |
| 906 | 5-CH₂CH=CH₂-pyrimidin-4-yl |
| 907 | 6-CH₂CH=CH₂-pyrimidin-4-yl |
| 908 | 2-CH₂C(CH₃)=CH₂-pyrimidin-4-yl |
| 909 | 5-CH₂C(CH₃)=CH₂-pyrimidin-4-yl |
| 910 | 6-CH₂C(CH₃)=CH₂-pyrimidin-4-yl |
| 911 | 2-OCH₂CH=CHCH₃-pyrimidin-4-yl |
| 912 | 5-OCH₂CH=CHCH₃-pyrimidin-4-yl |
| 913 | 6-OCH₂CH=CHCH₃-pyrimidin-4-yl |
| 914 | 2-O(CH₂)₂CH=CH₂-pyrimidin-4-yl |
| 915 | 5-O(CH₂)₂CH=CH₂-pyrimidin-4-yl |
| 916 | 6-O(CH₂)₂CH=CH₂-pyrimidin-4-yl |
| 917 | 2-OCH₂C(CH₃)=CH₂-pyrimidin-4-yl |
| 918 | 5-OCH₂C(CH₃)=CH₂-pyrimidin-4-yl |
| 919 | 6-OCH₂C(CH₃)=CH₂-pyrimidin-4-yl |
| 920 | 2-OCH(CH₃)CH=CH₂-pyrimidin-4-yl |
| 921 | 5-OCH(CH₃)CH=CH₂-pyrimidin-4-yl |
| 922 | 6-OCH(CH₃)CH=CH₂-pyrimidin-4-yl |
| 923 | 2-OCH₂C≡CH-pyrimidin-4-yl |
| 924 | 5-OCH₂C≡CH-pyrimidin-4-yl |
| 925 | 6-OCH₂C≡CH-pyrimidin-4-yl |
| 926 | 2-OCH₂C≡CCH₃-pyrimidin-4-yl |
| 927 | 5-OCH₂C≡CCH₃-pyrimidin-4-yl |
| 928 | 6-OCH₂C≡CCH₃-pyrimidin-4-yl |
| 929 | 2-O(CH₂)₂C≡CH-pyrimidin-4-yl |
| 930 | 5-O(CH₂)₂C≡CH-pyrimidin-4-yl |
| 931 | 6-O(CH₂)₂C≡CH-pyrimidin-4-yl |
| 932 | 2-SCH₃-pyrimidin-4-yl |
| 933 | 5-SCH₃-pyrimidin-4-yl |
| 934 | 6-SCH₃-pyrimidin-4-yl |
| 935 | 2-SCH₂CH₃-pyrimidin-4-yl |
| 936 | 5-SCH₂CH₃-pyrimidin-4-yl |
| 937 | 6-SCH₂CH₃-pyrimidin-4-yl |
| 938 | 2-OC₆H₅-pyrimidin-4-yl |
| 939 | 5-OC₆H₅-pyrimidin-4-yl |
| 940 | 6-OC₆H₅-pyrimidin-4-yl |
| 941 | 2-OCH₂C₆H₅-pyrimidin-4-yl |
| 942 | 5-OCH₂C₆H₅-pyrimidin-4-yl |
| 943 | 6-OCH₂C₆H₅-pyrimidin-4-Yl |
| 944 | 2-NO₂-pyrimidin-4-yl |
| 945 | 5-NO₂-pyrimidin-4-yl |
| 946 | 6-NO₂-pyrimidin-4-yl |
| 947 | 2-NHCH₃-pyrimidin-4-yl |
| 948 | 5-NHCH₃-pyrimidin-4-yl |
| 949 | 6-NHCH₃-pyrimidin-4-yl |
| 950 | 2-N(CH₃)₂-pyrimidin-4-yl |
| 951 | 5-N(CH₃)₂-pyrimidin-4-yl |
| 952 | 6-N(CH₃)₂-pyrimidin-4-yl |
| 953 | 2-N(CH₃)C₂H₅-pyrimidin-4-yl |
| 954 | 5-N(CH₃)C₂H₅-pyrimidin-4-yl |
| 955 | 6-N(CH₃)C₂H₅-pyrimidin-4-yl |
| 956 | 2-NHCH₂CF₃-pyrimidin-4-yl |
| 957 | 5-NHCH₂CF₃-pyrimidin-4-yl |
| 958 | 6-NHCH₂CF₃-pyrimidin-4-yl |
| 959 | 2-F-pyrimidin-4-yl |
| 960 | 5-F-pyrimidin-4-yl |
| 961 | 6-F-pyrimidin-4-yl |
| 962 | 2-Cl-pyrimidin-4-yl |
| 963 | 5-Cl-pyrimidin-4-yl |
| 964 | 6-Cl-pyrimidin-4-yl |
| 965 | 2-OH-pyrimidin-4-yl |
| 966 | 5-OH-pyrimidin-4-yl |
| 967 | 6-OH-pyrimidin-4-yl |
| 968 | 2-CN-pyrimidin-4-yl |
| 969 | 5-CN-pyrimidin-4-yl |
| 970 | 6-CN-pyrimidin-4-yl |
| 971 | 2-C(O)NH₂-pyrimidin-4-yl |
| 972 | 5-C(O)NH₂-pyrimidin-4-yl |
| 973 | 6-C(O)NH₂-pyrimidin-4-yl |
| 974 | 2-C(S)NH₂-pyrimidin-4-yl |
| 975 | 5-C(S)NH₂-pyrimidin-4-yl |
| 976 | 6-C(S)NH₂-pyrimidin-4-yl |
| 977 | 2-CO₂CH₃-pyrimidin-4-yl |
| 978 | 5-CO₂CH₃-pyrimidin-4-yl |
| 979 | 6-CO₂CH₃-pyrimidin-4-yl |
| 980 | 2-ON=C(CH₃)₂-pyrimidin-4-yl |
| 981 | 5-ON=C(CH₃)₂-pyrimidin-4-yl |
| 982 | 6-ON=C(CH₃)₂-pyrimidin-4-yl |
| 983 | 2-[O-cyclopropyl]pyrimidin-4-yl |
| 984 | 5-[O-cyclopropyl]pyrimidin-4-yl |
| 985 | 6-[O-cyclopropyl]pyrimidin-4-yl |
| 986 | 2-[O-cyclobutyl]pyrimidin-4-yl |
| 987 | 5-[O-cyclobutyl]pyrimidin-4-yl |
| 988 | 6-[O-cyclobutyl]pyrimidin-4-yl |
| 989 | 2-[O-cyclopentyl]pyrimidin-4-yl |
| 990 | 5-[O-cyclopentyl]pyrimidin-4-yl |
| 991 | 6-[O-cyclopentyl]pyrimidin-4-yl |
| 992 | 2-[O-cyclohexyl]pyrimidin-4-yl |
| 993 | 5-[O-cyclohexyl]pyrimidin-4-yl |
| 994 | 6-[O-cyclohexyl]pyrimidin-4-yl |
| 995 | 2-(OCH₂-cyclopropyl]pyrimidin-4-yl |
| 996 | 5-(OCH₂-cyclopropyl]pyrimidin-4-yl |
| 997 | 6-(OCH₂-cyclopropyl]pyrimidin-4-yl |
| 998 | 6-F, 2-(OCH₂-cyclopropyl]pyrimidin-4-yl |
| 999 | 2-F, 6-(OCH₂-cyclopropyl]pyrimidin-4-yl |
| 1000 | 5-F, 2-(OCH₂-cyclopropyl]pyrimidin-4-yl |
| 1001 | 6-CH₃, 2-(OCH₂-cyclopropyl]pyrimidin-4-yl |
| 1002 | 2-CH₃, 6-(OCH₂-cyclopropyl]pyrimidin-4-yl |
| 1003 | 5-CH₃, 2-(OCH₂-cyclopropyl]pyrimidin-4-yl |
| 1004 | 6-CF₃, 2-(OCH₂-cyclopropyl]pyrimidin-4-yl |
| 1005 | 2-CF₃, 6-(OCH₂-cyclopropyl]pyrimidin-4-yl |
| 1006 | 5-CF₃, 2-[OCH₂-cyclopropyl]pyrimidin-4-yl |
| 1007 | 2-[OCH(CH₃)-cyclopropyl)]pyrimidin-4-yl |
| 1008 | 5-[OCH(CH₃)-cyclopropyl]pyrimidin-4-yl |
| 1009 | 6-[OCH(CH₃)-cyclopropyl]pyrimidin-4-yl |
| 1010 | 6-F, 2-[OCH(CH₃)-cyclopropyl]pyrimidin-4-yl |
| 1011 | 2-F, 6-[OCH(CH₃)-cyclopropyl]pyrimidin-4-yl |
| 1012 | 5-F, 2-[OCH(CH₃)-cyclopropyl]pyrimidin-4-yl |
| 1013 | 6-CH₃, 2-[OCH(CH₃)-cyclopropyl]pyrimidin-4-yl |
| 1014 | 2-CH₃, 6-[OCH(CH₃)-cyclopropyl]pyrimidin-4-yl |
| 1015 | 5-CH₃, 2-[OCH(CH₃)-cyclopropyl]pyrimidin-4-yl |
| 1016 | 6-CF₃, 2-[OCH(CH₃)-cyclopropyl]pyrimidin-4-yl |
| 1017 | 2-CF₃, 6-[OCH(CH₃)-cyclopropyl]pyrimidin-4-yl |
| 1018 | 5-CF₃, 2-[OCH(CH₃)-cyclopropyl]pyrimidin-4-yl |
| 1019 | 2-[O-(1-CH₃-cyclopropyl]pyrimidin-4-yl |
| 1020 | 5-[O-(1-CH₃-cyclopropyl]pyrimidin-4-yl |
| 1021 | 6-[O-(1-CH₃-cyclopropyl]pyrimidin-4-yl |
| 1022 | 6-F, 2-[O-(1-CH₃-cyclopropyl)]pyrimidin-4-yl |
| 1023 | 2-F, 6-[O-(1-CH₃-cyclopropyl)]pyrimidin-4-yl |
| 1024 | 5-F, 2-[O-(1-CH₃-cyclopropyl)]pyrimidin-4-yl |
| 1025 | 6-CH₃, 2-[O-(1-CH₃-cyclopropyl)]pyrimidin-4-yl |
| 1026 | 2-CH₃, 6-[O-(1-CH₃-cyclopropyl)]pyrimidin-4-yl |
| 1027 | 5-CH₃, 2-[O-(1-CH₃-cyclopropyl)]pyrimidin-4-yl |
| 1028 | 6-CF₃, 2-[O-(1-CH₃-cyclopropyl)]pyrimidin-4-yl |
| 1029 | 2-CF₃, 6-[O-(1-CH₃-cyclopropyl)]pyrimidin-4-yl |
| 1030 | 5-CF₃, 2-[O-(1-CH₃-cyclopropyl)]pyrimidin-4-yl |
| 1031 | 2-[OCH₂-(1-CH₃-cyclopropyl)]pyrimidin-4-yl |
| 1032 | 5-[OCH₂-(1-CH₃-cyclopropyl)]pyrimidin-4-yl |
| 1033 | 6-[OCH₂-(1-CH₃-cyclopropyl)]pyrimidin-4-yl |
| 1034 | 6-F, 2-[OCH₂-(1-CH₃-cyclopropyl)]pyrimidin-4-yl |
| 1035 | 2-F, 6-[OCH₂-(1-CH₃-cyclopropyl)]pyrimidin-4-yl |
| 1036 | 5-F, 2-[OCH₂-(1-CH₃-cyclopropyl)]pyrimidin-4-yl |
| 1037 | 6-CH₃, 2-[OCH₂-(1-CH₃-cyclopropyl)]pyrimidin-4-yl |
| 1038 | 2-CH₃, 6-[OCH₂-(1-CH₃-cyclopropyl)]pyrimidin-4-yl |
| 1039 | 5-CH₃, 2-[OCH₂-(1-CH₃-cyclopropyl)]pyrimidin-4-yl |
| 1040 | 6-CF₃, 2-[OCH₂-(1-CH₃-cyclopropyl)]pyrimidin-4-yl |
| 1041 | 2-CF₃, 6-[OCH₂-(1-CH₃-cyclopropyl)]pyrimidin-4-yl |
| 1042 | 5-CF₃, 2-[OCH₂-(1-CH₃-cyclopropyl)]pyrimidin-4-yl |
| 1043 | 2-[OCH₂-(2-CH₃-cyclopropyl]pyrimidin-4-yl |
| 1044 | 5-[OCH₂-(2-CH₃-cyclopropyl]pyrimidin-4-yl |

TABLE A-continued

| No. | R⁴ |
|---|---|
| 1045 | 6-[OCH₂-(2-CH₃-cyclopropyl)]pyrimidin-4-yl |
| 1046 | 6-F, 2-[OCH₂-(2-CH₃-cyclopropyl)]pyrimidin-4-yl |
| 1047 | 2-F, 6-[OCH₂-(2-CH₃-cyclopropyl)]pyrimidin-4-yl |
| 1048 | 5-F, 2-[OCH₂-(2-CH₃-cyclopropyl)]pyrimidin-4-yl |
| 1049 | 6-CH₃, 2-[OCH₂-(2-CH₃-cyclopropyl)]pyrimidin-4-yl |
| 1050 | 2-CH₃, 6-[OCH₂-(2-CH₃-cyclopropyl)]pyrimidin-4-yl |
| 1051 | 5-CH₃, 2-[OCH₂-(2-CH₃-cyclopropyl)]pyrimidin-4-yl |
| 1052 | 6-CF₃, 2-[OCH₂-(2-CH₃-cyclopropyl)]pyrimidin-4-yl |
| 1053 | 2-CF₃, 6-[OCH₂-(2-CH₃-cyclopropyl)]pyrimidin-4-yl |
| 1054 | 5-CF₃, 2-[OCH₂-(2-CH₃-cyclopropyl)]pyrimidin-4-yl |
| 1055 | 2-[OCH₂-(tetrahydropyran-2-yl)]pyrimidin-4-yl |
| 1056 | 5-[OCH₂-(tetrahydropyran-2-yl)]pyrimidin-4-yl |
| 1057 | 6-[OCH₂-(tetrahydropyran-2-yl)]pyrimidin-4-yl |
| 1058 | 6-F, 2-[OCH₂-(tetrahydropyran-2-yl)]pyrimidin-4-yl |
| 1059 | 2-F, 6-[OCH₂-(tetrahydropyran-2-yl)]pyrimidin-4-yl |
| 1060 | 5-F, 2-[OCH₂-(tetrahydropyran-2-yl)]pyrimidin-4-yl |
| 1061 | 6-CH₃, 2-[OCH₂-(tetrahydropyran-2-yl)]pyrimidin-4-yl |
| 1062 | 2-CH₃, 6-[OCH₂-(tetrahydropyran-2-yl)]pyrimidin-4-yl |
| 1063 | 5-CH₃, 2-[OCH₂-(tetrahydropyran-2-yl)]pyrimidin-4-yl |
| 1064 | 6-CF₃, 2-[OCH₂-(tetrahydropyran-2-yl)]pyrimidin-4-yl |
| 1065 | 2-CF₃, 6-[OCH₂-(tetrahydropyran-2-yl)]pyrimidin-4-yl |
| 1066 | 5-CF₃, 2-[OCH₂-(tetrahydropyran-2-yl)]pyrimidin-4-yl |
| 1067 | 2-[OCH₂-(furan-2-yl)]pyrimidin-4-yl |
| 1068 | 5-[OCH₂-(furan-2-yl)]pyrimidin-4-yl |
| 1069 | 6-[OCH₂-(furan-2-yl)]pyrimidin-4-yl |
| 1070 | 6-F, 2-[OCH₂-(furan-2-yl)]pyrimidin-4-yl |
| 1071 | 2-F, 6-[OCH₂-(furan-2-yl)]pyrimidin-4-yl |
| 1072 | 5-F, 2-[OCH₂-(furan-2-yl)]pyrimidin-4-yl |
| 1073 | 6-CH₃, 2-(OCH₂-(furan-2-yl)]pyrimidin-4-yl |
| 1074 | 2-CH₃, 6-[OCH₂-(furan-2-yl)]pyrimidin-4-yl |
| 1075 | 5-CH₃, 2-[OCH₂-(furan-2-yl)]pyrimidin-4-yl |
| 1076 | 6-CF₃, 2-[OCH₂-(furan-2-yl)]pyrimidin-4-yl |
| 1077 | 2-CF₃, 6-[OCH₂-(furan-2-yl)]pyrimidin-4-yl |
| 1078 | 5-CF₃, 2-[OCH₂-(furan-2-yl)]pyrimidin-4-yl |
| 1079 | 2-[OCH₂-(furan-3-yl)]pyrimidin-4-yl |
| 1080 | 5-[OCH₂-(furan-3-yl)]pyrimidin-4-yl |
| 1081 | 6-[OCH₂-(furan-3-yl)]pyrimidin-4-yl |
| 1082 | 6-F, 2-[OCH₂-(furan-3-yl)]pyrimidin-4-yl |
| 1083 | 2-F, 6-[OCH₂-(furan-3-yl)]pyrimidin-4-yl |
| 1084 | 5-F, 2-[OCH₂-(furan-3-yl)]pyrimidin-4-yl |
| 1085 | 6-CH₃, 2-[OCH₂-(furan-3-yl)]pyrimidin-4-yl |
| 1086 | 2-CH₃, 6-[OCH₂-(furan-3-yl)]pyrimidin-4-yl |
| 1087 | 5-CH₃, 2-[OCH₂-(furan-3-yl)]pyrimidin-4-yl |
| 1088 | 6-CF₃, 2-[OCH₂-(furan-3-yl)]pyrimidin-4-yl |
| 1089 | 2-CF₃, 6-[OCH₂-(furan-3-yl)]pyrimidin-4-yl |
| 1090 | 5-CF₃, 2-[OCH₂-(furan-3-yl)]pyrimidin-4-yl |
| 1091 | 2-[OCH₂-(tetrahydrofuran-3-yl)]pyrimidin-4-yl |
| 1092 | 5-[OCH₂-(tetrahydrofuran-3-yl)]pyrimidin-4-yl |
| 1093 | 6-[OCH₂-(tetrahydrofuran-3-yl)]pyrimidin-4-yl |
| 1094 | 6-F, 2-[OCH₂-(tetrahydrofuran-3-yl)]pyrimidin-4-yl |
| 1095 | 2-F, 6-[OCH₂-(tetrahydrofuran-3-yl)]pyrimidin-4-yl |
| 1096 | 5-F, 2-[OCH₂-(tetrahydrofuran-3-yl)]pyrimidin-4-yl |
| 1097 | 6-CH₃, 2-[OCH₂-(tetrahydrofuran-3-yl)]pyrimidin-4-yl |
| 1098 | 2-CH₃, 6-[OCH₂-(tetrahydrofuran-3-yl)]pyrimidin-4-yl |
| 1099 | 5-CH₃, 2-[OCH₂-(tetrahydrofuran-3-yl)]pyrimidin-4-yl |
| 1100 | 6-CF₃, 2-[OCH₂-(tetrahydrofuran-3-yl)]pyrimidin-4-yl |
| 1101 | 2-CF₃, 6-[OCH₂-(tetrahydrofuran-3-yl)]pyrimidin-4-yl |
| 1102 | 5-CF₃, 2-[OCH₂-(tetrahydrofuran-3-yl)]pyrimidin-4-yl |
| 1103 | 2-[OCH₂-(tetrahydrofuran-2-yl)]pyrimidin-4-yl |
| 1104 | 5-[OCH₂-(tetrahydrofuran-2-yl)]pyrimidin-4-yl |
| 1105 | 6-[OCH₂-(tetrahydrofuran-2-yl)]pyrimidin-4-yl |
| 1106 | 6-F, 2-[OCH₂-(tetrahydrofuran-2-yl)]pyrimidin-4-yl |
| 1107 | 2-F, 6-[OCH₂-(tetrahydrofuran-2-yl)]pyrimidin-4-yl |
| 1108 | 5-F, 2-[OCH₂-(tetrahydrofuran-2-yl)]pyrimidin-4-yl |
| 1109 | 6-CH₃, 2-[OCH₂-(tetrahydrofuran-2-yl)]pyrimidin-4-yl |
| 1110 | 2-CH₃, 6-[OCH₂-(tetrahydrofuran-2-yl)]pyrimidin-4-yl |
| 1111 | 4-CH₃, 2-[OCH₂-(tetrahydrofuran-2-yl)]pyrimidin-4-yl |
| 1112 | 6-CF₃, 2-[OCH₂-(tetrahydrofuran-2-yl)]pyrimidin-4-yl |
| 1113 | 2-CF₃, 6-[OCH₂-(tetrahydrofuran-2-yl)]pyrimidin-4-yl |
| 1114 | 5-CF₃, 2-[OCH₂-(tetrahydrofuran-2-yl)]pyrimidin-4-yl |
| 1115 | 2-[O-(tetrahydropyran-2-yl)]pyrimidin-4-yl |
| 1116 | 5-[O-(tetrahydropyran-2-yl)]pyrimidin-4-yl |
| 1117 | 6-[O-(tetrahydropyran-2-yl)]pyrimidin-4-yl |
| 1118 | 6-F, 2-[O-(tetrahydropyran-2-yl)]pyrimidin-4-yl |
| 1119 | 2-F, 6-[O-(tetrahydropyran-2-yl)]pyrimidin-4-yl |
| 1120 | 5-F, 2-[O-(tetrahydropyran-2-yl)]pyrimidin-4-yl |
| 1121 | 6-CH₃, 2-[O-(tetrahydropyran-2-yl)]pyrimidin-4-yl |
| 1122 | 2-CH₃, 6-[O-(tetrahydropyran-2-yl)]pyrimidin-4-yl |
| 1123 | 5-CH₃, 2-[O-(tetrahydropyran-2-yl)]pyrimidin-4-yl |
| 1124 | 6-CF₃, 2-[O-(tetrahydropyran-2-yl)]pyrimidin-4-yl |
| 1125 | 2-CF₃, 6-[O-(tetrahydropyran-2-yl)]pyrimidin-4-yl |
| 1126 | 5-CF₃, 2-[O-(tetrahydropyran-2-yl)]pyrimidin-4-yl |
| 1127 | 2-[2-Cl—C₆H₄]pyrimidin-4-yl |
| 1128 | 5-[2-Cl—C₆H₄]pyrimidin-4-yl |
| 1129 | 6-[2-Cl—C₆H₄]pyrimidin-4-yl |
| 1130 | 6-F, 2-[2-Cl—C₆H₄]pyrimidin-4-yl |
| 1131 | 2-F, 6-[2-Cl—C₆H₄]pyrimidin-4-yl |
| 1132 | 5-F, 2-[2-Cl—C₆H₄]pyrimidin-4-yl |
| 1133 | 6-CH₃, 2-[2-Cl—C₆H₄]pyrimidin-4-yl |
| 1134 | 2-CH₃, 6-[2-Cl—C₆H₄]pyrimidin-4-yl |
| 1135 | 5-CH₃, 2-[2-Cl—C₆H₄]pyrimidin-4-yl |
| 1136 | 6-CF₃, 2-[2-Cl—C₆H₄]pyrimidin-4-yl |
| 1137 | 2-CF₃, 6-[2-Cl—C₆H₄]pyrimidin-4-yl |
| 1138 | 5-CF₃, 2-[2-Cl—C₆H₄]pyrimidin-4-yl |
| 1139 | 2-[OCH₂-(pyridin-4-yl)]pyrimidin-4-yl |
| 1140 | 5-[OCH₂-(pyridin-4-yl)]pyrimidin-4-yl |
| 1141 | 6-[OCH₂-(pyridin-4-yl)]pyrimidin-4-yl |
| 1142 | 6-F, 2-[OCH₂-(pyridin-4-yl)]pyrimidin-4-yl |
| 1143 | 2-F, 6-[OCH₂-(pyridin-4-yl)]pyrimidin-4-yl |
| 1144 | 5-F, 2-[OCH₂-(pyridin-4-yl)]pyrimidin-4-yl |
| 1145 | 6-CH₃, 2-[OCH₂-(pyridin-4-yl)]pyrimidin-4-yl |
| 1146 | 2-CH₃, 6-[OCH₂-(pyridin-4-yl)]pyrimidin-4-yl |
| 1147 | 5-CH₃, 2-[OCH₂-(pyridin-4-yl)]pyrimidin-4-yl |
| 1148 | 6-CH₃, 2-[OCH₂-(pyridin-4-yl)]pyrimidin-4-yl |
| 1149 | 2-CF₃, 6-[OCH₂-(pyridin-4-yl)]pyrimidin-4-yl |
| 1150 | 5-CF₃, 2-[OCH₂-(pyridin-4-yl)]pyrimidin-4-yl |
| 1151 | 2-[OCH₂-(pyridin-3-yl)]pyrimidin-4-yl |
| 1152 | 5-[OCH₂-(pyridin-3-yl)]pyrimidin-4-yl |
| 1153 | 6-[OCH₂-(pyridin-3-yl)]pyrimidin-4-yl |
| 1154 | 6-F, 2-[OCH₂-(pyridin-3-yl)]pyrimidin-4-yl |
| 1155 | 2-F, 6-[OCH₂-(pyridin-3-yl)]pyrimidin-4-yl |
| 1156 | 5-F, 2-[OCH₂-(pyridin-3-yl)]pyrimidin-4-yl |
| 1157 | 6-CH₃, 2-[OCH₂-(pyridin-3-yl)]pyrimidin-4-yl |
| 1158 | 2-CH₃, 6-[OCH₂-(pyridin-3-yl)]pyrimidin-4-yl |
| 1159 | 5-CH₃, 2-[OCH₂-(pyridin-3-yl)]pyrimidin-4-yl |
| 1160 | 6-CH₃, 2-[OCH₂-(pyridin-3-yl)]pyrimidin-4-yl |
| 1161 | 2-CF₃, 6-[OCH₂-(pyridin-3-yl)]pyrimidin-4-yl |
| 1162 | 5-CF₃, 2-[OCH₂-(pyridin-3-yl)]pyrimidin-4-yl |
| 1163 | 2-[morpholin-2-yl)]pyrimidin-4-yl |
| 1164 | 5-[morpholin-2-yl)]pyrimidin-4-yl |
| 1165 | 6-[morpholin-2-yl)]pyrimidin-4-yl |
| 1166 | 2-[1-CH₃-imidazol-2-yl)]pyrimidin-4-yl |
| 1167 | 5-[1-CH₃-imidazol-2-yl)]pyrimidin-4-yl |
| 1168 | 6-[1-CH₃-imidazol-2-yl)]pyrimidin-4-yl |
| 1169 | 6-F, 2-[1-CH₃-imidazol-2-yl]pyrimidin-4-yl |
| 1170 | 2-F, 6-[1-CH₃-imidazol-2-yl]pyrimidin-4-yl |
| 1171 | 5-F, 2-[1-CH₃-imidazol-2-yl]pyrimidin-4-yl |
| 1172 | 6-CH₃, 2-[1-CH₃-imidazol-2-yl)]pyrimidin-4-yl |
| 1173 | 2-CH₃, 6-[1-CH₃-imidazol-2-yl]pyrimidin-4-yl |
| 1174 | 5-CH₃, 2-[1-CH₃-imidazol-2-yl]pyrimidin-4-yl |
| 1175 | 6-CF₃, 2-[1-CH₃-imidazol-2-yl]pyrimidin-4-yl |
| 1176 | 2-CF₃, 6-[1-CH₃-imidazol-2-yl]pyrimidin-4-yl |
| 1177 | 5-CF₃, 2-[1-CH₃-imidazol-2-yl]pyrimidin-4-yl |
| 1178 | 2-[1,2,2-triazol-1-yl]pyrimidin-4-yl |
| 1179 | 5-[1,2,2-triazol-1-yl]pyrimidin-4-yl |
| 1180 | 6-[1,2,2-triazol-1-yl]pyrimidin-4-yl |
| 1181 | 6-F, 2-[1,2,2-triazol-1-yl]pyrimidin-4-yl |
| 1182 | 2-F, 6-[1,2,2-triazol-1-yl]pyrimidin-4-yl |
| 1183 | 5-F, 2-[1,2,2-triazol-1-yl]pyrimidin-4-yl |
| 1184 | 6-CH₃, 2-[1,2,2-triazol-1-yl)]pyrimidin-4-yl |
| 1185 | 2-CH₃, 6-[1,2,2-triazol-1-yl]pyrimidin-4-yl |
| 1186 | 5-CH₃, 2-[1,2,2-triazol-1-yl]pyrimidin-4-yl |
| 1187 | 6-CF₃, 2-[1,2,2-triazol-1-yl]pyrimidin-4-yl |
| 1188 | 2-CF₃, 6-[1,2,2-triazol-1-yl]pyrimidin-4-yl |
| 1189 | 5-CF₃, 2-[1,2,2-triazol-1-yl]pyrimidin-4-yl |
| 1190 | 2,5-Cl₂-pyrimidin-4-yl |
| 1191 | 2,6-Cl₂-pyrimidin-4-yl |
| 1192 | 5,6-Cl₂-pyrimidin-4-yl |
| 1193 | 2,5-(CH₃)₂-pyrimidin-4-yl |
| 1194 | 2,6-(CH₃)₂-pyrimidin-4-yl |
| 1195 | 5,6-(CH₃)₂-pyrimidin-4-yl |
| 1196 | 2,5-(OCH₃)₂-pyrimidin-4-yl |
| 1197 | 2,6-(OCH₃)₂-pyrimidin-4-yl |
| 1198 | 5,6-(OCH₃)₂-pyrimidin-4-yl |

TABLE A-continued

| No. | R⁴ |
|---|---|
| 1199 | 2,5-(OCH₂CH₃)₂-pyrimidin-4-yl |
| 1200 | 2,6-(OCH₂CH₃)₂-pyrimidin-4-yl |
| 1201 | 5,6-(OCH₂CH₃)₂-pyrimidin-4-yl |
| 1202 | 2-F, 5-CH₃-pyrimidin-4-yl |
| 1203 | 2-F, 6-CH₃-pyrimidin-4-yl |
| 1204 | 5-F, 6-CH₃-pyrimidin-4-yl |
| 1205 | 5-F, 2-CH₃-pyrimidin-4-yl |
| 1206 | 6-F, 2-CH₃-pyrimidin-4-yl |
| 1207 | 6-F, 5-CH₃-pyrimidin-4-yl |
| 1208 | 2-F, 5-OCH₃-pyrimidin-4-yl |
| 1209 | 2-F, 6-OCH₃-pyrimidin-4-yl |
| 1210 | 5-F, 6-OCH₃-pyrimidin-4-yl |
| 1211 | 5-F, 2-OCH₃-pyrimidin-4-yl |
| 1212 | 6-F, 2-OCH₃-pyrimidin-4-yl |
| 1213 | 6-F, 5-OCH₃-pyrimidin-4-yl |
| 1214 | 2-F, 5-OCH₂CH₃-pyrimidin-4-yl |
| 1215 | 2-F, 6-OCH₂CH₃-pyrimidin-4-yl |
| 1216 | 5-F, 6-OCH₂CH₃-pyrimidin-4-yl |
| 1217 | 5-F, 2-OCH₂CH₃-pyrimidin-4-yl |
| 1218 | 6-F, 2-OCH₂CH₃-pyrimidin-4-yl |
| 1219 | 6-F, 5-OCH₂CH₃-pyrimidin-4-yl |
| 1220 | 2-F, 5-OCH₂CF₃-pyrimidin-4-yl |
| 1221 | 2-F, 6-OCH₂CF₃-pyrimidin-4-yl |
| 1222 | 5-F, 6-OCH₂CF₃-pyrimidin-4-yl |
| 1223 | 5-F, 2-OCH₂CF₃-pyrimidin-4-yl |
| 1224 | 6-F, 2-OCH₂CF₃-pyrimidin-4-yl |
| 1225 | 6-F, 5-OCH₂CF₃-pyrimidin-4-yl |
| 1226 | 2-F, 5-OCH(CH₃)₂-pyrimidin-4-yl |
| 1227 | 2-F, 6-OCH(CH₃)₂-pyrimidin-4-yl |
| 1228 | 5-F, 6-OCH(CH₃)₂-pyrimidin-4-yl |
| 1229 | 5-F, 2-OCH(CH₃)₂-pyrimidin-4-yl |
| 1230 | 6-F, 2-OCH(CH₃)₂-pyrimidin-4-yl |
| 1231 | 6-F, 5-OCH(CH₃)₂-pyrimidin-4-yl |
| 1232 | 2-Cl, 5-CH₃-pyrimidin-4-yl |
| 1233 | 2-Cl, 6-CH₃-pyrimidin-4-yl |
| 1234 | 5-Cl, 6-CH₃-pyrimidin-4-yl |
| 1235 | 5-Cl, 2-CH₃-pyrimidin-4-yl |
| 1236 | 6-Cl, 2-CH₃-pyrimidin-4-yl |
| 1237 | 6-Cl, 5-CH₃-pyrimidin-4-yl |
| 1238 | 2-Cl, 5-OCH₃-pyrimidin-4-yl |
| 1239 | 2-Cl, 6-OCH₃-pyrimidin-4-yl |
| 1240 | 5-Cl, 6-OCH₃-pyrimidin-4-yl |
| 1241 | 5-Cl, 2-OCH₃-pyrimidin-4-yl |
| 1242 | 6-Cl, 2-OCH₃-pyrimidin-4-yl |
| 1243 | 6-Cl, 5-OCH₃-pyrimidin-4-yl |
| 1244 | 2-Cl, 5-OCH₂CH₃-pyrimidin-4-yl |
| 1245 | 2-Cl, 6-OCH₂CH₃-pyrimidin-4-yl |
| 1246 | 5-Cl, 6-OCH₂CH₃-pyrimidin-4-yl |
| 1247 | 5-Cl, 2-OCH₂CH₃-pyrimidin-4-yl |
| 1248 | 6-Cl, 2-OCH₂CH₃-pyrimidin-4-yl |
| 1249 | 6-Cl, 5-OCH₂CH₃-pyrimidin-4-yl |
| 1250 | 2-Cl, 5-OCH₂CF₃-pyrimidin-4-yl |
| 1251 | 2-Cl, 6-OCH₂CF₃-pyrimidin-4-yl |
| 1252 | 5-Cl, 6-OCH₂CF₃-pyrimidin-4-yl |
| 1253 | 5-Cl, 2-OCH₂CF₃-pyrimidin-4-yl |
| 1254 | 6-Cl, 2-OCH₂CF₃-pyrimidin-4-yl |
| 1255 | 6-Cl, 5-OCH₂CF₃-pyrimidin-4-yl |
| 1256 | 2-Cl, 5-OCH(CH₃)-pyrimidin-4-yl |
| 1257 | 2-Cl, 6-OCH(CH₃)-pyrimidin-4-yl |
| 1258 | 5-Cl, 6-OCH(CH₃)-pyrimidin-4-yl |
| 1259 | 5-Cl, 2-OCH(CH₃)-pyrimidin-4-yl |
| 1260 | 6-Cl, 2-OCH(CH₃)-pyrimidin-4-yl |
| 1261 | 6-Cl, 5-OCH(CH₃)-pyrimidin-4-yl |
| 1262 | 2-CH₃, 5-OCH₃-pyrimidin-4-yl |
| 1263 | 2-CH₃, 6-OCH₃-pyrimidin-4-yl |
| 1264 | 5-CH₃, 6-OCH₃-pyrimidin-4-yl |
| 1265 | 5-CH₃, 2-OCH₃-pyrimidin-4-yl |
| 1266 | 6-CH₃, 2-OCH₃-pyrimidin-4-yl |
| 1267 | 6-CH₃, 5-OCH₃-pyrimidin-4-yl |
| 1268 | 2-CH₃, 5-OCH₂CH₃-pyrimidin-4-yl |
| 1269 | 2-CH₃, 6-OCH₂CH₃-pyrimidin-4-yl |
| 1270 | 5-CH₃, 6-OCH₂CH₃-pyrimidin-4-yl |
| 1271 | 5-CH₃, 2-OCH₂CH₃-pyrimidin-4-yl |
| 1272 | 6-CH₃, 2-OCH₂CH₃-pyrimidin-4-yl |
| 1273 | 6-CH₃, 5-OCH₂CH₃-pyrimidin-4-yl |
| 1274 | 2-CH₃, 5-OCH₂CF₃-pyrimidin-4-yl |
| 1275 | 2-CH₃, 6-OCH₂CF₃-pyrimidin-4-yl |
| 1276 | 5-CH₃, 6-OCH₂CF₃-pyrimidin-4-yl |
| 1277 | 5-CH₃, 2-OCH₂CF₃-pyrimidin-4-yl |
| 1278 | 6-CH₃, 2-OCH₂CF₃-pyrimidin-4-yl |
| 1279 | 6-CH₃, 5-OCH₂CF₃-pyrimidin-4-yl |
| 1280 | 2-CH₃, 5-OCH(CH₃)₂-pyrimidin-4-yl |
| 1281 | 2-CH₃, 5-OCH(CH₃)₂-pyrimidin-4-yl |
| 1282 | 5-CH₃, 6-OCH(CH₃)₂-pyrimidin-4-yl |
| 1283 | 5-CH₃, 2-OCH(CH₃)₂-pyrimidin-4-yl |
| 1284 | 6-CH₃, 2-OCH(CH₃)₂-pyrimidin-4-yl |
| 1285 | 6-CH₃, 5-OCH(CH₃)₂-pyrimidin-4-yl |
| 1286 | 2-CH₃, 5-OCH₂CH=CH₂-pyrimidin-4-yl |
| 1287 | 2-CH₃, 6-OCH₂CH=CH₂-pyrimidin-4-yl |
| 1288 | 5-CH₃, 6-OCH₂CH=CH₂-pyrimidin-4-yl |
| 1289 | 5-CH₃, 2-OCH₂CH=CH₂-pyrimidin-4-yl |
| 1290 | 6-CH₃, 2-OCH₂CH=CH₂-pyrimidin-4-yl |
| 1291 | 6-CH₃, 5-OCH₂CH=CH₂-pyrimidin-4-yl |
| 1292 | 2-CH₃, 5-CO₂CH₃-pyrimidin-4-yl |
| 1293 | 2-CH₃, 6-CO₂CH₃-pyrimidin-4-yl |
| 1294 | 5-CH₃, 6-CO₂CH₃-pyrimidin-4-yl |
| 1295 | 2-CH₃, 5-CF₃-pyrimidin-4-yl |
| 1296 | 2-CH₃, 6-CF₃-pyrimidin-4-yl |
| 1297 | 5-CH₃, 6-CF₃-pyrimidin-4-yl |
| 1298 | 5-CH₃, 2-CF₃-pyrimidin-4-yl |
| 1299 | 6-CH₃, 6-CF₃-pyrimidin-4-yl |
| 1300 | 6-CH₃, 5-CF₃-pyrimidin-4-yl |
| 1301 | 2-CF₃, 5-CH₂CH₃-pyrimidin-4-yl |
| 1302 | 2-CF₃, 6-CH₂CH₃-pyrimidin-4-yl |
| 1303 | 5-CF₃, 6-CH₂CH₃-pyrimidin-4-yl |
| 1304 | 5-CF₃, 2-CH₂CH₃-pyrimidin-4-yl |
| 1305 | 6-CF₃, 2-CH₂CH₃-pyrimidin-4-yl |
| 1306 | 6-CF₃, 5-CH₂CH₃-pyrimidin-4-yl |
| 1307 | 2-CF₃, 5-OCH₃-pyrimidin-4-yl |
| 1308 | 2-CF₃, 6-OCH₃-pyrimidin-4-yl |
| 1309 | 5-CF₃, 6-OCH₃-pyrimidin-4-yl |
| 1310 | 5-CF₃, 2-OCH₃-pyrimidin-4-yl |
| 1311 | 6-CF₃, 2-OCH₃-pyrimidin-4-yl |
| 1312 | 6-CF₃, 5-OCH₃-pyrimidin-4-yl |
| 1313 | 2-CF₃, 5-OCH₂CH₃-pyrimidin-4-yl |
| 1314 | 2-CF₃, 6-OCH₂CH₃-pyrimidin-4-yl |
| 1315 | 5-CF₃, 6-OCH₂CH₃-pyrimidin-4-yl |
| 1316 | 5-CF₃, 2-OCH₂CH₃-pyrimidin-4-yl |
| 1317 | 6-CF₃, 2-OCH₂CH₃-pyrimidin-4-yl |
| 1318 | 6-CF₃, 5-OCH₂CH₃-pyrimidin-4-yl |
| 1319 | 2-CF₃, 5-OCH₂CF₃-pyrimidin-4-yl |
| 1320 | 2-CF₃, 6-OCH₂CF₃-pyrimidin-4-yl |
| 1321 | 5-CF₃, 6-OCH₂CF₃-pyrimidin-4-yl |
| 1322 | 5-CF₃, 2-OCH₂CF₃-pyrimidin-4-yl |
| 1323 | 6-CF₃, 2-OCH₂CF₃-pyrimidin-4-yl |
| 1324 | 6-CF₃, 5-OCH₂CF₃-pyrimidin-4-yl |
| 1325 | 2-OCH₃, 5-OCH₂CH₃-pyrimidin-4-yl |
| 1326 | 2-OCH₃, 6-OCH₂CH₃-pyrimidin-4-yl |
| 1327 | 5-OCH₃, 6-OCH₂CH₃-pyrimidin-4-yl |
| 1328 | 5-OCH₃, 2-OCH₂CH₃-pyrimidin-4-yl |
| 1329 | 6-OCH₃, 6-OCH₂CH₃-pyrimidin-4-yl |
| 1330 | 6-OCH₃, 6-OCH₂CH₃-pyrimidin-4-yl |
| 1331 | 2-OCH₃, 5-OCH₂CF₃-pyrimidin-4-yl |
| 1332 | 2-OCH₃, 6-OCH₂CF₃-pyrimidin-4-yl |
| 1333 | 5-OCH₃, 6-OCH₂CF₃-pyrimidin-4-yl |
| 1334 | 5-OCH₃, 2-OCH₂CF₃-pyrimidin-4-yl |
| 1335 | 6-OCH₃, 2-OCH₂CF₃-pyrimidin-4-yl |
| 1336 | 6-OCH₃, 5-OCH₂CF₃-pyrimidin-4-yl |
| 1337 | 2-OCH₃, 5-OCH(CH₃)pyrimidin-4-yl |
| 1338 | 2-OCH₃, 6-OCH(CH₃)pyrimidin-4-yl |
| 1339 | 5-OCH₃, 6-OCH(CH₃)pyrimidin-4-yl |
| 1340 | 5-OCH₃, 2-OCH(CH₃)pyrimidin-4-yl |
| 1341 | 6-OCH₃, 2-OCH(CH₃)pyrimidin-4-yl |
| 1342 | 6-OCH₃, 5-OCH(CH₃)pyrimidin-4-yl |
| 1343 | 2-OCH₂CH₃, 5-CH₂OCH₂CH₃-pyrimidin-4-yl |
| 1344 | 2-OCH₂CH₃, 6-CH₂OCH₂CH₃-pyrimidin-4-yl |
| 1345 | 5-OCH₂CH₃, 5-CH₂OCH₂CH₃-pyrimidin-4-yl |
| 1346 | 5-OCH₂CH₃, 2-CH₂OCH₂CH₃-pyrimidin-4-yl |
| 1347 | 6-OCH₂CH₃, 2-CH₂OCH₂CH₃-pyrimidin-4-yl |
| 1348 | 6-OCH₂CH₃, 5-CH₂OCH₂CH₃-pyrimidin-4-yl |
| 1349 | 2-NO₂, 5-CH₃-pyrimidin-4-yl |
| 1350 | 2-NO₂, 6-CH₃-pyrimidin-4-yl |
| 1351 | 5-NO₂, 6-CH₃-pyrimidin-4-yl |
| 1352 | 2-NO₂, 2-CH₃-pyrimidin-4-yl |

TABLE A-continued

| No. | R⁴ |
|---|---|
| 1353 | 6-NO₂, 2-CH₃-pyrimidin-4-yl |
| 1354 | 6-NO₂, 5-CH₃-pyrimidin-4-yl |
| 1355 | 2-NO₂, 5-OCH₃-pyrimidin-4-yl |
| 1356 | 2-NO₂, 6-OCH₃-pyrimidin-4-yl |
| 1357 | 5-NO₂, 6-OCH₃-pyrimidin-4-yl |
| 1358 | 5-NO₂, 2-OCH₃-pyrimidin-4-yl |
| 1359 | 6-NO₂, 2-OCH₃-pyrimidin-4-yl |
| 1360 | 6-NO₂, 5-OCH₃-pyrimidin-4-yl |
| 1361 | 2-NO₂, 5-OCH₂CH₃-pyrimidin-4-yl |
| 1362 | 2-NO₂, 6-OCH₂CH₃-pyrimidin-4-yl |
| 1363 | 5-NO₂, 6-OCH₂CH₃-pyrimidin-4-yl |
| 1364 | 5-NO₂, 2-OCH₂CH₃-pyrimidin-4-yl |
| 1365 | 6-NO₂, 2-OCH₂CH₃-pyrimidin-4-yl |
| 1366 | 6-NO₂, 5-OCH₂CH₃-pyrimidin-4-yl |
| 1367 | 2-NO₂, 5-OCH(CH₃)₂-pyrimidin-4-yl |
| 1368 | 2-NO₂, 6-OCH(CH₃)₂-pyrimidin-4-yl |
| 1369 | 5-NO₂, 6-OCH(CH₃)₂-pyrimidin-4-yl |
| 1370 | 5-NO₂, 2-OCH(CH₃)₂-pyrimidin-4-yl |
| 1371 | 6-NO₂, 2-OCH(CH₃)₂-pyrimidin-4-yl |
| 1372 | 6-NO₂, 5-OCH(CH₃)₂-pyrimidin-4-yl |
| 1373 | 2-NO₂, 5-OCH₂CF₃-pyrimidin-4-yl |
| 1374 | 2-NO₂, 6-OCH₂CF₃-pyrimidin-4-yl |
| 1375 | 5-NO₂, 6-OCH₂CF₃-pyrimidin-4-yl |
| 1376 | 5-NO₂, 2-OCH₂CF₃-pyrimidin-4-yl |
| 1377 | 6-NO₂, 2-OCH₂CF₃-pyrimidin-4-yl |
| 1378 | 6-NO₂, 5-OCH₂CF₃-pyrimidin-4-yl |
| 1379 | 2-CN, 5-CH₃-pyrimidin-4-yl |
| 1380 | 2-CN, 6-CH₃-pyrimidin-4-yl |
| 1381 | 5-CN, 6-CH₃-pyrimidin-4-yl |
| 1382 | 5-CN, 2-CH₃-pyrimidin-4-yl |
| 1383 | 6-CN, 2-CH₃-pyrimidin-4-yl |
| 1384 | 6-CN, 5-CH₃-pyrimidin-4-yl |
| 1385 | 2-CN, 5-OCH₃-pyrimidin-4-yl |
| 1386 | 2-CN, 6-OCH₃-pyrimidin-4-yl |
| 1387 | 5-CN, 6-OCH₃-pyrimidin-4-yl |
| 1388 | 5-CN, 2-OCH₃-pyrimidin-4-yl |
| 1389 | 6-CN, 2-OCH₃-pyrimidin-4-yl |
| 1390 | 6-CN, 5-OCH₃-pyrimidin-4-yl |
| 1391 | 2-CN, 5-OCH₂CH₃-pyrimidin-4-yl |
| 1392 | 2-CN, 6-OCH₂CH₃-pyrimidin-4-yl |
| 1393 | 5-CN, 6-OCH₂CH₃-pyrimidin-4-yl |
| 1394 | 5-CN, 2-OCH₂CH₃-pyrimidin-4-yl |
| 1395 | 6-CN, 2-OCH₂CH₃-pyrimidin-4-yl |
| 1396 | 6-CN, 5-OCH₂CH₃-pyrimidin-4-yl |
| 1397 | 2-CN, 5-OCH(CH₃)₂-pyrimidin-4-yl |
| 1398 | 2-CN, 6-OCH(CH₃)₂-pyrimidin-4-yl |
| 1399 | 5-CN, 6-OCH(CH₃)₂-pyrimidin-4-yl |
| 1400 | 2-CN, 2-OCH(CH₃)₂-pyrimidin-4-yl |
| 1401 | 6-CN, 2-OCH(CH₃)₂-pyrimidin-4-yl |
| 1402 | 6-CN, 5-OCH(CH₃)₂-pyrimidin-4-yl |
| 1403 | 2-CN, 5-OCH₂CF₃-pyrimidin-4-yl |
| 1404 | 2-CN, 6-OCH₂CF₃-pyrimidin-4-yl |
| 1405 | 5-CN, 6-OCH₂CF₃-pyrimidin-4-yl |
| 1406 | 5-CN, 2-OCH₂CF₃-pyrimidin-4-yl |
| 1407 | 6-CN, 2-OCH₂CF₃-pyrimidin-4-yl |
| 1408 | 6-CN, 5-OCH₂CF₃-pyrimidin-4-yl |
| 1409 | 2,5-(CH₃)₂, 6-OCH₃-pyrimidin-4-yl |
| 1410 | 2,6-(CH₃)₂, 5-OCH₃-pyrimidin-4-yl |
| 1411 | 5,6-(CH₃)₂, 2-OCH₃-pyrimidin-4-yl |
| 1412 | 4-CH₃-pyrimidin-5-yl |
| 1413 | 2-CH₃-pyrimidin-5-yl |
| 1414 | 4-CH₂CH₃-pyrimidin-5-yl |
| 1415 | 2-CH₂CH₃-pyrimidin-5-yl |
| 1416 | 4-CH(CH₃)₂-pyrimidin-5-yl |
| 1417 | 2-CH(CH₃)₂-pyrimidin-5-yl |
| 1418 | 4-CH(CH₃)CH₂CH₃-pyrimidin-5-yl |
| 1419 | 2-CH(CH₃)CH₂CH₃-pyrimidin-5-yl |
| 1420 | 4-CF₃-pyrimidin-5-yl |
| 1421 | 2-CF₃-pyrimidin-5-yl |
| 1422 | 4-CH=CH₂-pyrimidin-5-yl |
| 1423 | 2-CH=CH₂-pyrimidin-5-yl |
| 1424 | 4-CH=CHCH₃-pyrimidin-5-yl |
| 1425 | 2-CH=CHCH₃-pyrimidin-5-yl |
| 1426 | 4-CH=CHCl-pyrimidin-5-yl |
| 1427 | 2-CH=CHCl-pyrimidin-5-yl |
| 1428 | 4-C≡CH-pyrimidin-5-yl |
| 1429 | 2-C≡CH-pyrimidin-5-yl |
| 1430 | 4-CH₂C≡CH-pyrimidin-5-yl |
| 1431 | 2-CH₂C≡CH-pyrimidin-5-yl |
| 1432 | 4-CH₂C≡CCH₃-pyrimidin-5-yl |
| 1433 | 2-CH₂C≡CCH₃-pyrimidin-5-yl |
| 1434 | 4-cyclopropyl-pyrimidin-5-yl |
| 1435 | 2-cyclopropyl-pyrimidin-5-yl |
| 1436 | 4-cyclopentyl-pyrimidin-5-yl |
| 1437 | 2-cyclopropyl-pyrimidin-5-yl |
| 1438 | 4-OCH₃-pyrimidin-5-yl |
| 1439 | 2-OCH₃-pyrimidin-5-yl |
| 1440 | 4-OCH₂CH₃-pyrimidin-5-yl |
| 1441 | 2-OCH₂CH₃-pyrimidin-5-yl |
| 1442 | 4-OCH₂CH₃-pyrimidin-5-yl |
| 1443 | 2-OCH₂CH₂CH₃-pyrimidin-5-yl |
| 1444 | 4-OCH(CH₃)₂-pyrimidin-5-yl |
| 1445 | 2-OCH(CH₃)₂-pyrimidin-5-yl |
| 1446 | 4-OCH₂CH₂CH₃-pyrimidin-5-yl |
| 1447 | 2-OCH₂CH₂CH₃-pyrimidin-5-yl |
| 1448 | 4-OCH(CH₃)CH₂CH₃-pyrimidin-5-yl |
| 1449 | 2-OCH(CH₃)CH₂CH₃-pyrimidin-5-yl |
| 1450 | 4-OCH(CH₃)₂-pyrimidin-5-yl |
| 1451 | 2-OCH(CH₃)₂-pyrimidin-5-yl |
| 1452 | 4-OC(CH₃)₃-pyrimidin-5-yl |
| 1453 | 2-OC(CH₃)₃-pyrimidin-5-yl |
| 1454 | 4-OCH(CH₃)CH₂CH₂CH₃-pyrimidin-5-yl |
| 1455 | 2-OCH(CH₃)CH₂CH₂CH₃-pyrimidin-5-yl |
| 1456 | 4-OCH₂OCH₃-pyrimidin-5-yl |
| 1457 | 2-OCH₂OCH₃-pyrimidin-5-yl |
| 1458 | 4-OCH₂OCH₂CH₃-pyrimidin-5-yl |
| 1459 | 2-OCH₂OCH₂CH₃-pyrimidin-5-yl |
| 1460 | 4-OCH(CH₃)OCH₃-pyrimidin-5-yl |
| 1461 | 2-OCH(CH₃)OCH₃-pyrimidin-5-yl |
| 1462 | 4-OCH(CH₃)OCH₂CH₃-pyrimidin-5-yl |
| 1463 | 2-OCH(CH₃)OCH₂CH₃-pyrimidin-5-yl |
| 1464 | 4-OCH₂CH₂OCH₃-pyrimidin-5-yl |
| 1465 | 2-OCH₂CH₂OCH₃-pyrimidin-5-yl |
| 1466 | 4-OCH₂CH₂OCH₂CH₃-pyrimidin-5-yl |
| 1467 | 2-OCH₂CH₂OCH₂CH₃-pyrimidin-5-yl |
| 1468 | 4-OCH₂CH₂OCH(CH₃)₂-pyrimidin-5-yl |
| 1469 | 2-OCH₂CH₂OCH(CH₃)₂-pyrimidin-5-yl |
| 1470 | 4-OCH₂CH₂SCH₃-pyrimidin-5-yl |
| 1471 | 2-OCH₂CH₂SCH₃-pyrimidin-5-yl |
| 1472 | 4-OCH₂CH₂SO₂CH₃-pyrimidin-5-yl |
| 1473 | 2-OCH₂CH₂SO₂CH₃-pyrimidin-5-yl |
| 1474 | 4-OCH₂CH₂SCH(CH₃)₂-pyrimidin-5-yl |
| 1475 | 2-OCH₂CH₂SCH(CH₃)₂-pyrimidin-5-yl |
| 1476 | 4-OCH₂CH₂CN-pyrimidin-5-yl |
| 1477 | 2-OCH₂CH₂CN-pyrimidin-5-yl |
| 1478 | 4-OCH₂CH₂SCH₂CH₂CN-pyrimidin-5-yl |
| 1479 | 2-OCH₂CH₂SCH₂CH₂CN-pyrimidin-5-yl |
| 1480 | 4-OCH₂CH₂OC₆H₂-pyrimidin-5-yl |
| 1481 | 2-OCH₂CH₂OC₆H₂-pyrimidin-5-yl |
| 1482 | 4-OCH₂CH₂OCH₂C₆H₂-pyrimidin-5-yl |
| 1483 | 2-OCH₂CH₂OCH₂C₆H₂-pyrimidin-5-yl |
| 1484 | 4-OCH₂CH₂N(CH₃)₂-pyrimidin-5-yl |
| 1485 | 2-OCH₂CH₂N(CH₃)₂-pyrimidin-5-yl |
| 1486 | 4-OCH₂CH₂CONH₂-pyrimidin-5-yl |
| 1487 | 2-OCH₂CH₂CONH₂-pyrimidin-5-yl |
| 1488 | 4-OCH₂CH₂CO₂CH₂CH₂CH₃-pyrimidin-5-yl |
| 1489 | 2-OCH₂CH₂CO₂CH₂CH₂CH₃-pyrimidin-5-yl |
| 1490 | 4-OCH(CH₃)CH₂OCH₃-pyrimidin-5-yl |
| 1491 | 2-OCH(CH₃)CH₂OCH₃-pyrimidin-5-yl |
| 1492 | 4-OCH(CH₃)CH₂CO₂CH₃-pyrimidin-5-yl |
| 1493 | 2-OCH(CH₃)CH₂CO₂CH₃-pyrimidin-5-yl |
| 1494 | 4-OCH(CH₃)CH₂CO₂CH₂CH₃-pyrimidin-5-yl |
| 1495 | 2-OCH(CH₃)CH₂CO₂CH₂CH₃-pyrimidin-5-yl |
| 1496 | 4-OCH₂CH(CH₃)CO₂CH₃-pyrimidin-5-yl |
| 1497 | 2-OCH₂CH(CH₃)CO₂CH₃-pyrimidin-5-yl |
| 1498 | 4-OCH₂C(=O)CH₃-pyrimidin-5-yl |
| 1499 | 2-OCH₂C(=O)CH₃-pyrimidin-5-yl |
| 1500 | 4-OCH₂C(=O)CH₂CH₃-pyrimidin-5-yl |
| 1501 | 2-OCH₂C(=O)CH₂CH₃-pyrimidin-5-yl |
| 1502 | 4-OCH₂CO₂CH₃-pyrimidin-5-yl |
| 1503 | 2-OCH₂CO₂CH₃-pyrimidin-5-yl |
| 1504 | 4-OCH₂CO₂CH₂CH₃-pyrimidin-5-yl |
| 1505 | 2-OCH₂CO₂CH₂CH₃-pyrimidin-5-yl |
| 1506 | 4-OCH₂C(=O)NH₂-pyrimidin-5-yl |

TABLE A-continued

| No. | R⁴ |
|---|---|
| 1507 | 2-OCH$_2$C(=O)NH$_2$-pyrimidin-5-yl |
| 1508 | 4-OCH$_2$C(=O)NHCH$_3$-pyrimidin-5-yl |
| 1509 | 2-OCH$_2$C(=O)NHCH$_3$-pyrimidin-5-yl |
| 1510 | 4-OCH$_2$C(=O)SCH$_3$-pyrimidin-5-yl |
| 1511 | 2-OCH$_2$C(=O)SCH$_3$-pyrimidin-5-yl |
| 1512 | 4-OCH(CH$_3$)C(=O)NH$_2$-pyrimidin-5-yl |
| 1513 | 2-OCH(CH$_3$)C(=O)NH$_2$-pyrimidin-5-yl |
| 1514 | 4-OCH(CH$_3$)C(=O)NHCH$_3$-pyrimidin-5-yl |
| 1515 | 2-OCH(CH$_3$)C(=O)NHCH$_3$-pyrimidin-5-yl |
| 1516 | 4-OCH(CH$_3$)C(=O)NHNH$_2$-pyrimidin-5-yl |
| 1517 | 2-OCH(CH$_3$)C(=O)NHNH$_2$-pyrimidin-5-yl |
| 1518 | 4-OCH(CH$_3$)CO$_2$CH$_3$-pyrimidin-5-yl |
| 1519 | 2-OCH(CH$_3$)CO$_2$CH$_3$-pyrimidin-5-yl |
| 1520 | 4-OCH(CH$_3$)CO$_2$CH$_2$CH$_3$-pyrimidin-5-yl |
| 1521 | 2-OCH(CH$_3$)CO$_2$CH$_2$CH$_3$-pyrimidin-5-yl |
| 1522 | 4-OCH(CH$_3$)C(=O)CH$_3$-pyrimidin-5-yl |
| 1523 | 2-OCH(CH$_3$)C(=O)CH$_3$-pyrimidin-5-yl |
| 1524 | 4-OCH(CH$_3$)C(=O)CH$_2$CH$_3$-pyrimidin-5-yl |
| 1525 | 2-OCH(CH$_3$)C(=O)CH$_2$CH$_3$-pyrimidin-5-yl |
| 1526 | 4-OCH(CH$_3$)CH$_2$C(=O)CH$_3$-pyrimidin-5-yl |
| 1527 | 2-OCH(CH$_3$)CH$_2$C(=O)CH$_3$-pyrimidin-5-yl |
| 1528 | 4-OCH(CH$_3$)CH$_2$OC(CH$_3$)$_3$-pyrimidin-5-yl |
| 1529 | 2-OCH(CH$_3$)CH$_2$OC(CH$_3$)$_3$-pyrimidin-5-yl |
| 1530 | 4-OCH(CH$_3$)CH$_2$OCH$_2$CH$_3$-pyrimidin-5-yl |
| 1531 | 2-OCH(CH$_3$)CH$_2$OCH$_2$CH$_3$-pyrimidin-5-yl |
| 1532 | 4-OCH(CH$_3$)CH$_2$O(CH$_3$)$_2$CH$_3$-pyrimidin-5-yl |
| 1533 | 2-OCH(CH$_3$)CH$_2$O(CH$_3$)$_2$CH$_3$-pyrimidin-5-yl |
| 1534 | 4-OCH(CH$_3$)CH$_2$OCH$_2$CH=CH$_2$-pyrimidin-5-yl |
| 1535 | 2-OCH(CH$_3$)CH$_2$OCH$_2$CH=CH$_2$-pyrimidin-5-yl |
| 1536 | 4-O(CH$_2$)$_3$OCH$_3$-pyrimidin-5-yl |
| 1537 | 2-O(CH$_2$)$_3$OCH$_3$-pyrimidin-5-yl |
| 1538 | 4-O(CH$_2$)$_3$OCH$_2$CH$_3$-pyrimidin-5-yl |
| 1539 | 2-O(CH$_2$)$_3$OCH$_2$CH$_3$-pyrimidin-5-yl |
| 1540 | 4-O(CH$_2$)$_3$OCH(CH$_3$)$_2$-pyrimidin-5-yl |
| 1541 | 2-O(CH$_2$)$_3$OCH(CH$_3$)$_2$-pyrimidin-5-yl |
| 1542 | 4-O(CH$_2$)$_3$OC$_6$H$_2$-pyrimidin-5-yl |
| 1543 | 2-O(CH$_2$)$_3$OC$_6$H$_2$-pyrimidin-5-yl |
| 1544 | 4-O(CH$_2$)$_3$OCH$_2$C$_6$H$_2$-pyrimidin-5-yl |
| 1545 | 2-O(CH$_2$)$_3$OCH$_2$C$_6$H$_2$-pyrimidin-5-yl |
| 1546 | 4-OCH(CH$_2$CH$_3$)CH$_2$OCH$_3$-pyrimidin-5-yl |
| 1547 | 2-OCH(CH$_2$CH$_3$)CH$_2$OCH$_3$-pyrimidin-5-yl |
| 1548 | 4-OCH(CH$_2$CH$_3$)CH$_2$CH$_2$OCH$_3$-pyrimidin-5-yl |
| 1549 | 2-OCH(CH$_2$CH$_3$)CH$_2$CH$_2$OCH$_3$-pyrimidin-5-yl |
| 1550 | 4-OCH(CH$_2$CH$_3$)CH$_2$CH$_2$OCH$_2$CH$_3$-pyrimidin-5-yl |
| 1551 | 2-OCH(CH$_2$CH$_3$)CH$_2$CH$_2$OCH$_2$CH$_3$-pyrimidin-5-yl |
| 1552 | 4-O[(CH$_2$)$_3$O]$_2$CH$_3$-pyrimidin-5-yl |
| 1553 | 2-O[(CH$_2$)$_3$O]$_2$CH$_3$-pyrimidin-5-yl |
| 1554 | 4-OCH$_2$CH(CH$_3$)CH$_2$OCH$_3$-pyrimidin-5-yl |
| 1555 | 2-OCH$_2$CH(CH$_3$)CH$_2$OCH$_3$-pyrimidin-5-yl |
| 1556 | 4-OCH$_2$CH(CH$_3$)CH$_2$OCH$_2$CH$_3$-pyrimidin-5-yl |
| 1557 | 2-OCH$_2$CH(CH$_3$)CH$_2$OCH$_2$CH$_3$-pyrimidin-5-yl |
| 1558 | 4-OCH(CH$_2$Cl)CH$_2$OCH$_3$-pyrimidin-5-yl |
| 1559 | 2-OCH(CH$_2$Cl)CH$_2$OCH$_3$-pyrimidin-5-yl |
| 1560 | 4-OCH(CH$_2$Cl)CH$_2$OCH$_2$CH$_3$-pyrimidin-5-yl |
| 1561 | 2-OCH(CH$_2$Cl)CH$_2$OCH$_2$CH$_3$-pyrimidin-5-yl |
| 1562 | 4-OCH(CH$_2$Cl)CH$_2$OCH(CH$_3$)$_2$-pyrimidin-5-yl |
| 1563 | 4-OCH(CH$_2$Cl)CH$_2$OCH(CH$_3$)$_2$-pyrimidin-5-yl |
| 1564 | 4-OCH(CH$_2$Cl)CH$_2$OCH$_2$CH=CH$_2$-pyrimidin-5-yl |
| 1565 | 2-OCH(CH$_2$Cl)CH$_2$OCH$_2$CH=CH$_2$-pyrimidin-5-yl |
| 1566 | 4-OCH[CH$_2$OCH$_3$]$_2$-pyrimidin-5-yl |
| 1567 | 2-OCH[CH$_2$OCH$_3$]$_2$-pyrimidin-5-yl |
| 1568 | 4-OCH[CH$_2$OCH$_2$CH$_3$]$_2$-pyrimidin-5-yl |
| 1569 | 2-OCH[CH$_2$OCH$_2$CH$_3$]$_2$-pyrimidin-5-yl |
| 1570 | 4-OCCl$_3$-pyrimidin-5-yl |
| 1571 | 2-OCCl$_3$-pyrimidin-5-yl |
| 1572 | 4-OCHF$_2$-pyrimidin-5-yl |
| 1573 | 2-OCHF$_2$-pyrimidin-5-yl |
| 1574 | 4-OCF$_3$-pyrimidin-5-yl |
| 1575 | 2-OCF$_3$-pyrimidin-5-yl |
| 1576 | 4-OCF$_2$CHF$_2$-pyrimidin-5-yl |
| 1577 | 2-OCF$_2$CHF$_2$-pyrimidin-5-yl |
| 1578 | 4-OCF$_2$CF$_3$-pyrimidin-5-yl |
| 1579 | 2-OCF$_2$CF$_3$-pyrimidin-5-yl |
| 1580 | 4-OCH$_2$CHF$_2$-pyrimidin-5-yl |
| 1581 | 2-OCH$_2$CHF$_2$-pyrimidin-5-yl |
| 1582 | 4-O(CH$_2$)$_3$F-pyrimidin-5-yl |
| 1583 | 2-O(CH$_2$)$_3$F-pyrimidin-5-yl |
| 1584 | 4-OCH(CH$_3$)CF$_3$-pyrimidin-5-yl |
| 1585 | 2-OCH(CH$_3$)CF$_3$-pyrimidin-5-yl |
| 1586 | 4-O(CH$_2$)$_4$F-pyrimidin-5-yl |
| 1587 | 2-O(CH$_2$)$_4$F-pyrimidin-5-yl |
| 1588 | 4-O(CH$_2$)$_3$CF$_3$-pyrimidin-5-yl |
| 1589 | 2-O(CH$_2$)$_3$CF$_3$-pyrimidin-5-yl |
| 1590 | 4-OCH(CH$_3$)CF$_2$CF$_3$-pyrimidin-5-yl |
| 1591 | 2-OCH(CH$_3$)CF$_2$CF$_3$-pyrimidin-5-yl |
| 1592 | 4-OCH(CH$_3$)CF$_2$CHF$_2$-pyrimidin-5-yl |
| 1593 | 2-OCH(CH$_3$)CF$_2$CHF$_2$-pyrimidin-5-yl |
| 1594 | 4-OCH$_2$CF$_2$CHFCH$_3$-pyrimidin-5-yl |
| 1595 | 2-OCH$_2$CF$_2$CHFCH$_3$-pyrimidin-5-yl |
| 1596 | 4-OCH$_2$(CF$_2$)$_2$CF$_3$-pyrimidin-5-yl |
| 1597 | 2-OCH$_2$(CF$_2$)$_2$CF$_3$-pyrimidin-5-yl |
| 1598 | 4-O(CF$_2$)$_3$CF$_3$-pyrimidin-5-yl |
| 1599 | 2-O(CF$_2$)$_3$CF$_3$-pyrimidin-5-yl |
| 1600 | 4-OCH$_2$CF$_2$CHF$_2$-pyrimidin-5-yl |
| 1601 | 2-OCH$_2$CF$_2$CHF$_2$-pyrimidin-5-yl |
| 1602 | 4-CH$_2$CH=CH$_2$-pyrimidin-5-yl |
| 1603 | 2-CH$_2$CH=CH$_2$-pyrimidin-5-yl |
| 1604 | 4-CH$_2$C(CH$_3$)=CH$_2$-pyrimidin-5-yl |
| 1605 | 2-CH$_2$C(CH$_3$)=CH$_2$-pyrimidin-5-yl |
| 1606 | 4-OCH$_2$CH=CHCH$_3$-pyrimidin-5-yl |
| 1607 | 2-OCH$_2$CH=CHCH$_3$-pyrimidin-5-yl |
| 1608 | 4-O(CH$_2$)$_2$CH=CH$_2$-pyrimidin-5-yl |
| 1609 | 2-O(CH$_2$)$_2$CH=CH$_2$-pyrimidin-5-yl |
| 1610 | 4-OCH$_2$C(CH$_3$)=CH$_2$-pyrimidin-5-yl |
| 1611 | 2-OCH$_2$C(CH$_3$)=CH$_2$-pyrimidin-5-yl |
| 1612 | 4-OCH(CH$_3$)CH=CH$_2$-pyrimidin-5-yl |
| 1613 | 2-OCH(CH$_3$)CH=CH$_2$-pyrimidin-5-yl |
| 1614 | 4-OCH$_2$C≡CH-pyrimidin-5-yl |
| 1615 | 2-OCH$_2$C≡CH-pyrimidin-5-yl |
| 1616 | 4-OCH$_2$C≡CCH$_3$-pyrimidin-5-yl |
| 1617 | 2-OCH$_2$C≡CCH$_3$-pyrimidin-5-yl |
| 1618 | 4-O(CH$_2$)$_2$C≡CH-pyrimidin-5-yl |
| 1619 | 2-O(CH$_2$)$_2$C≡CH-pyrimidin-5-yl |
| 1620 | 4-SCH$_3$-pyrimidin-5-yl |
| 1621 | 2-SCH$_3$-pyrimidin-5-yl |
| 1622 | 4-SCH$_2$CH$_3$-pyrimidin-5-yl |
| 1623 | 2-SCH$_2$CH$_3$-pyrimidin-5-yl |
| 1624 | 4-OC$_6$H$_2$-pyrimidin-5-yl |
| 1625 | 2-OC$_6$H$_2$-pyrimidin-5-yl |
| 1626 | 4-OCH$_2$C$_6$H$_2$-pyrimidin-5-yl |
| 1627 | 2-OCH$_2$C$_6$H$_2$-pyrimidin-5-yl |
| 1628 | 4-NO$_2$-pyrimidin-5-yl |
| 1629 | 2-NO$_2$-pyrimidin-5-yl |
| 1630 | 4-NHCH$_3$-pyrimidin-5-yl |
| 1631 | 2-NHCH$_3$-pyrimidin-5-yl |
| 1632 | 4-N(CH$_3$)$_2$-pyrimidin-5-yl |
| 1633 | 2-N(CH$_3$)$_2$-pyrimidin-5-yl |
| 1634 | 4-N(CH$_3$)C$_2$H$_2$-pyrimidin-5-yl |
| 1635 | 2-N(CH$_3$)C$_2$H$_2$-pyrimidin-5-yl |
| 1636 | 4-NHCH$_2$CF$_3$-pyrimidin-5-yl |
| 1637 | 2-NHCH$_2$CF$_3$-pyrimidin-5-yl |
| 1638 | 4-F-pyrimidin-5-yl |
| 1639 | 2-F-pyrimidin-5-yl |
| 1640 | 4-Cl-pyrimidin-5-yl |
| 1641 | 2-Cl-pyrimidin-5-yl |
| 1642 | 4-OH-pyrimidin-5-yl |
| 1643 | 2-OH-pyrimidin-5-yl |
| 1644 | 4-CN-pyrimidin-5-yl |
| 1645 | 2-CN-pyrimidin-5-yl |
| 1646 | 4-C(O)NH$_2$-pyrimidin-5-yl |
| 1647 | 2-C(O)NH$_2$-pyrimidin-5-yl |
| 1648 | 4-C(S)NH$_2$-pyrimidin-5-yl |
| 1649 | 2-C(S)NH$_2$-pyrimidin-5-yl |
| 1650 | 4-CO$_2$CH$_3$-pyrimidin-5-yl |
| 1651 | 2-CO$_2$CH$_3$-pyrimidin-5-yl |
| 1652 | 4-ON=C(CH$_3$)$_2$-pyrimidin-5-yl |
| 1653 | 2-ON=C(CH$_3$)$_2$-pyrimidin-5-yl |
| 1654 | 4-[O-cyclopropyl]pyrimidin-5-yl |
| 1655 | 2-[O-cyclopropyl]pyrimidin-5-yl |
| 1656 | 4-[O-cyclobutyl]pyrimidin-5-yl |
| 1657 | 2-[O-cyclobutyl]pyrimidin-5-yl |
| 1658 | 4-[O-cyclopentyl]pyrimidin-5-yl |
| 1659 | 2-[O-cyclopentyl]pyrimidin-5-yl |
| 1660 | 4-[O-cyclohexyl]pyrimidin-5-yl |

TABLE A-continued

| No. | R⁴ |
|---|---|
| 1661 | 2-[O-cyclohexyl]pyrimidin-5-yl |
| 1662 | 4-[OCH₂-cyclopropyl]pyrimidin-5-yl |
| 1663 | 2-[OCH₂-cyclopropyl]pyrimidin-5-yl |
| 1664 | 2-F, 4-[OCH₂-cyclopropyl]pyrimidin-5-yl |
| 1665 | 4-F, 2-[OCH₂-cyclopropyl]pyrimidin-5-yl |
| 1666 | 2-CH₃, 4-[OCH₂-cyclopropyl]pyrimidin-5-yl |
| 1667 | 4-CH₃, 2-[OCH₂-cyclopropyl]pyrimidin-5-yl |
| 1668 | 2-CF₃, 4-[OCH₂-cyclopropyl]pyrimidin-5-yl |
| 1669 | 4-CF₃, 2-[OCH₂-cyclopropyl]pyrimidin-5-yl |
| 1670 | 4-[OCH(CH₃)-cyclopropyl]pyrimidin-5-yl |
| 1671 | 2-[OCH(CH₃)-cyclopropyl]pyrimidin-5-yl |
| 1672 | 2-F, 4-[OCH(CH₃)-cyclopropyl]pyrimidin-5-yl |
| 1673 | 4-F, 2-[OCH(CH₃)-cyclopropyl]pyrimidin-5-yl |
| 1674 | 2-CH₃, 4-[OCH(CH₃)-cyclopropyl]pyrimidin-5-yl |
| 1675 | 4-CH₃, 2-[OCH(CH₃)-cyclopropyl]pyrimidin-5-yl |
| 1676 | 2-CF₃, 4-[OCH(CH₃)-cyclopropyl]pyrimidin-5-yl |
| 1677 | 4-CF₃, 2-[OCH(CH₃)-cyclopropyl]pyrimidin-5-yl |
| 1678 | 4-[O-(1-CH₃-cyclopropyl)]pyrimidin-5-yl |
| 1679 | 2-[O-(1-CH₃-cyclopropyl)]pyrimidin-5-yl |
| 1680 | 2-F, 4-[O-(1-CH₃-cyclopropyl)]pyrimidin-5-yl |
| 1681 | 4-F, 2-[O-(1-CH₃-cyclopropyl)]pyrimidin-5-yl |
| 1682 | 2-CH₃, 4-[O-(1-CH₃-cyclopropyl)]pyrimidin-5-yl |
| 1683 | 4-CH₃, 2-[O-(1-CH₃-cyclopropyl)]pyrimidin-5-yl |
| 1684 | 2-CF₃, 4-[O-(1-CH₃-cyclopropyl)]pyrimidin-5-yl |
| 1685 | 4-CF₃, 2-[O-(1-CH₃-cyclopropyl)]pyrimidin-5-yl |
| 1686 | 4-[OCH₂-(1-CH₃-cyclopropyl)]pyrimidin-5-yl |
| 1687 | 2-[OCH₂-(1-CH₃-cyclopropyl)]pyrimidin-5-yl |
| 1688 | 2-F, 4-[OCH₂-(1-CH₃-cyclopropyl)]pyrimidin-5-yl |
| 1689 | 4-F, 2-[OCH₂-(1-CH₃-cyclopropyl)]pyrimidin-5-yl |
| 1690 | 2-CH₃, 4-[OCH₂-(1-CH₃-cyclopropyl)]pyrimidin-5-yl |
| 1691 | 4-CH₃, 2-[OCH₂-(1-CH₃-cyclopropyl)]pyrimidin-5-yl |
| 1692 | 2-CF₃, 4-[OCH₂-(1-CH₃-cyclopropyl)]pyrimidin-5-yl |
| 1693 | 4-CF₃, 2-[OCH₂-(1-CH₃-cyclopropyl)]pyrimidin-5-yl |
| 1694 | 4-[OCH₂-(2-CH₃-cyclopropyl)]pyrimidin-5-yl |
| 1695 | 2-[OCH₂-(2-CH₃-cyclopropyl)]pyrimidin-5-yl |
| 1696 | 2-F, 4-[OCH₂-(2-CH₃-cyclopropyl)]pyrimidin-5-yl |
| 1697 | 4-F, 2-[OCH₂-(2-CH₃-cyclopropyl)]pyrimidin-5-yl |
| 1698 | 2-CH₃, 4-[OCH₂-(2-CH₃-cyclopropyl)]pyrimidin-5-yl |
| 1699 | 4-CH₃, 2-[OCH₂-(2-CH₃-cyclopropyl)]pyrimidin-5-yl |
| 1700 | 2-CF₃, 4-[OCH₂-(2-CH₃-cyclopropyl)]pyrimidin-5-yl |
| 1701 | 4-CF₃, 2-[OCH₂-(2-CH₃-cyclopropyl)]pyrimidin-5-yl |
| 1702 | 4-[OCH₂-(tetrahydropyran-2-yl)]pyrimidin-5-yl |
| 1703 | 2-[OCH₂-(tetrahydropyran-2-yl)]pyrimidin-5-yl |
| 1704 | 2-F, 4-[OCH₂-(tetrahydropyran-2-yl)]pyrimidin-5-yl |
| 1705 | 4-F, 2-[OCH₂-(tetrahydropyran-2-yl)]pyrimidin-5-yl |
| 1706 | 2-CH₃, 4-[OCH₂-(tetrahydropyran-2-yl)]pyrimidin-5-yl |
| 1707 | 4-CH₃, 2-[OCH₂-(tetrahydropyran-2-yl)]pyrimidin-5-yl |
| 1708 | 2-CF₃, 4-[OCH₂-(tetrahydropyran-2-yl)]pyrimidin-5-yl |
| 1709 | 4-CF₃, 2-[OCH₂-(tetrahydropyran-2-yl)]pyrimidin-5-yl |
| 1710 | 4-[OCH₂-(furan-2-yl)]pyrimidin-5-yl |
| 1711 | 2-[OCH₂-(furan-2-yl)]pyrimidin-5-yl |
| 1712 | 2-F, 4-[OCH₂-(furan-2-yl)]pyrimidin-5-yl |
| 1713 | 4-F, 4-[OCH₂-(furan-2-yl)]pyrimidin-5-yl |
| 1714 | 2-CH₃, 4-[OCH₂-(furan-2-yl)]pyrimidin-5-yl |
| 1715 | 4-CH₃, 2-[OCH₂-(furan-2-yl)]pyrimidin-5-yl |
| 1716 | 2-CF₃, 4-[OCH₂-(furan-2-yl)]pyrimidin-5-yl |
| 1717 | 4-CF₃, 2-[OCH₂-(furan-2-yl)]pyrimidin-5-yl |
| 1718 | 4-[OCH₂-(furan-3-yl)]pyrimidin-5-yl |
| 1719 | 2-[OCH₂-(furan-3-yl)]pyrimidin-5-yl |
| 1720 | 2-F, 4-[OCH₂-(furan-3-yl)]pyrimidin-5-yl |
| 1721 | 4-F, 2-[OCH₂-(furan-3-yl)]pyrimidin-5-yl |
| 1722 | 2-CH₃, 4-[OCH₂-(furan-3-yl)]pyrimidin-5-yl |
| 1723 | 4-CH₃, 2-[OCH₂-(furan-3-yl)]pyrimidin-5-yl |
| 1724 | 2-CF₃, 4-[OCH₂-(furan-3-yl)]pyrimidin-5-yl |
| 1725 | 4-CF₃, 2-[OCH₂-(furan-3-yl)]pyrimidin-5-yl |
| 1726 | 4-[OCH₂-(tetrahydrofuran-3-yl)]pyrimidin-5-yl |
| 1727 | 2-[OCH₂-(tetrahydrofuran-3-yl)]pyrimidin-5-yl |
| 1728 | 2-F, 4-[OCH₂-(tetrahydrofuran-3-yl)]pyrimidin-5-yl |
| 1729 | 4-F, 4-[OCH₂-(tetrahydrofuran-3-yl)]pyrimidin-5-yl |
| 1730 | 2-CH₃, 4-[OCH₂-(tetrahydrofuran-3-yl)]pyrimidin-5-yl |
| 1731 | 4-CH₃, 2-[OCH₂-(tetrahydrofuran-3-yl)]pyrimidin-5-yl |
| 1732 | 2-CF₃, 4-[OCH₂-(tetrahydrofuran-3-yl)]pyrimidin-5-yl |
| 1733 | 4-CF₃, 2-[OCH₂-(tetrahydrofuran-3-yl)]pyrimidin-5-yl |
| 1734 | 4-[OCH₂-(tetrahydrofuran-2-yl)]pyrimidin-5-yl |
| 1735 | 2-[OCH₂-(tetrahydrofuran-2-yl)]pyrimidin-5-yl |
| 1736 | 2-F, 4-[OCH₂-(tetrahydrofuran-2-yl)]pyrimidin-5-yl |
| 1737 | 4-F, 2-[OCH₂-(tetrahydrofuran-2-yl)]pyrimidin-5-yl |
| 1738 | 2-CH₃, 4-[OCH₂-(tetrahydrofuran-2-yl)]pyrimidin-5-yl |
| 1739 | 4-CH₃, 2-[OCH₂-(tetrahydrofuran-2-yl)]pyrimidin-5-yl |
| 1740 | 2-CF₃, 4-[OCH₂-(tetrahydrofuran-2-yl)]pyrimidin-5-yl |
| 1741 | 4-CF₃, 2-[OCH₂-(tetrahydrofuran-2-yl)]pyrimidin-5-yl |
| 1742 | 2-[O-(tetrahydropyran-4-yl)]pyrimidin-5-yl |
| 1743 | 4-[O-(tetrahydropyran-4-yl)]pyrimidin-5-yl |
| 1744 | 2-F, 4-[O-(tetrahydropyran-4-yl)]pyrimidin-5-yl |
| 1745 | 4-F, 2-[O-(tetrahydropyran-4-yl)]pyrimidin-5-yl |
| 1746 | 2-CH₃, 4-[O-(tetrahydropyran-4-yl)]pyrimidin-5-yl |
| 1747 | 4-CH₃, 2-[O-(tetrahydropyran-4-yl)]pyrimidin-5-yl |
| 1748 | 2-CF₃, 4-[O-(tetrahydropyran-4-yl)]pyrimidin-5-yl |
| 1749 | 4-CF₃, 2-[O-(tetrahydropyran-4-yl)]pyrimidin-5-yl |
| 1750 | 4-[2-Cl—C₆H₄]pyrimidin-5-yl |
| 1751 | 2-[2-Cl—C₆H₄]pyrimidin-5-yl |
| 1752 | 2-F, 4-[2-Cl—C₆H₄]pyrimidin-5-yl |
| 1753 | 4-F, 2-[2-Cl—C₆H₄]pyrimidin-5-yl |
| 1754 | 2-CH₃, 4-[2-Cl—C₆H₄]pyrimidin-5-yl |
| 1755 | 4-CH₃, 2-[2-Cl—C₆H₄]pyrimidin-5-yl |
| 1756 | 2-CF₃, 4-[2-Cl—C₆H₄]pyrimidin-5-yl |
| 1757 | 4-CF₃, 2-[2-Cl—C₆H₄]pyrimidin-5-yl |
| 1758 | 4-[OCH₂-(pyridin-5-yl)]pyrimidin-5-yl |
| 1759 | 2-[OCH₂-(pyridin-5-yl)]pyrimidin-5-yl |
| 1760 | 2-F, 4-[OCH₂-(pyridin-5-yl)]pyrimidin-5-yl |
| 1761 | 4-F, 2-[OCH₂-(pyridin-5-yl)]pyrimidin-5-yl |
| 1762 | 2-CH₃, 4-[OCH₂-(pyridin-5-yl)]pyrimidin-5-yl |
| 1763 | 4-CH₃, 2-[OCH₂-(pyridin-5-yl)]pyrimidin-5-yl |
| 1764 | 2-CF₃, 4-[OCH₂-(pyridin-5-yl)]pyrimidin-5-yl |
| 1765 | 4-CF₃, 2-[OCH₂-(pyridin-5-yl)]pyrimidin-5-yl |
| 1766 | 4-[OCH₂-(pyridin-3-yl)]pyrimidin-5-yl |
| 1767 | 2-[OCH₂-(pyridin-3-yl)]pyrimidin-5-yl |
| 1768 | 2-F, 4-[OCH₂-(pyridin-3-yl)]pyrimidin-5-yl |
| 1769 | 4-F, 2-[OCH₂-(pyridin-3-yl)]pyrimidin-5-yl |
| 1770 | 2-CH₃, 4-[OCH₂-(pyridin-3-yl)]pyrimidin-5-yl |
| 1771 | 4-CH₃, 2-[OCH₂-(pyridin-3-yl)]pyrimidin-5-yl |
| 1772 | 2-CF₃, 4-[OCH₂-(pyridin-3-yl)]pyrimidin-5-yl |
| 1773 | 4-CF₃, 2-[OCH₂-(pyridin-3-yl)]pyrimidin-5-yl |
| 1774 | 4-[morpholin-4-yl]pyrimidin-5-yl |
| 1775 | 2-[morpholin-4-yl]pyrimidin-5-yl |
| 1776 | 4-[1-CH₃-imidazol-2-yl]pyrimidin-5-yl |
| 1777 | 2-[1-CH₃-imidazol-2-yl]pyrimidin-5-yl |
| 1778 | 2-F, 4-[1-CH₃-imidazol-2-yl]pyrimidin-5-yl |
| 1779 | 4-F, 2-[1-CH₃-imidazol-2-yl]pyrimidin-5-yl |
| 1780 | 2-CH₃, 4-[1-CH₃-imidazol-2-yl]pyrimidin-5-yl |
| 1781 | 4-CH₃, 2-[1-CH₃-imidazol-2-yl]pyrimidin-5-yl |
| 1782 | 2-CF₃, 4-[1-CH₃-imidazol-2-yl]pyrimidin-5-yl |
| 1783 | 4-CF₃, 2-[1-CH₃-imidazol-2-yl]pyrimidin-5-yl |
| 1784 | 4-[1,2,4-triazol-1-yl]pyrimidin-5-yl |
| 1785 | 2-[1,2,4-triazol-1-yl]pyrimidin-5-yl |
| 1786 | 2-F, 4-[1,2,4-triazol-1-yl]pyrimidin-5-yl |
| 1787 | 4-F, 2-[1,2,4-triazol-1-yl]pyrimidin-5-yl |
| 1788 | 2-CH₃, 4-[1,2,4-triazol-1-yl]pyrimidin-5-yl |
| 1789 | 4-CH₃, 2-[1,2,4-triazol-1-yl]pyrimidin-5-yl |
| 1790 | 2-CF₃, 4-[1,2,4-triazol-1-yl]pyrimidin-5-yl |
| 1791 | 4-CF₃, 2-[1,2,4-triazol-1-yl]pyrimidin-5-yl |
| 1792 | 4,2-Cl₂-pyrimidin-5-yl |
| 1793 | 4,6-Cl₂-pyrimidin-5-yl |
| 1794 | 4,2-(CH₃)₂-pyrimidin-5-yl |
| 1795 | 4,6-(CH₃)₂-pyrimidin-5-yl |
| 1796 | 4,2-(OCH₃)₂-pyrimidin-5-yl |
| 1797 | 4,6-(OCH₃)₂-pyrimidin-5-yl |
| 1798 | 4,2-(OCH₂CH₃)₂-pyrimidin-5-yl |
| 1799 | 4,6-(OCH₂CH₃)₂-pyrimidin-5-yl |
| 1800 | 4-F, 2-CH₃-pyrimidin-5-yl |
| 1801 | 4-F, 6-CH₃-pyrimidin-5-yl |
| 1802 | 2-F, 4-CH₃-pyrimidin-5-yl |
| 1803 | 6-F, 4-CH₃-pyrimidin-5-yl |
| 1804 | 4-F, 2-OCH₃-pyrimidin-5-yl |
| 1805 | 4-F, 6-OCH₃-pyrimidin-5-yl |
| 1806 | 2-F, 4-OCH₃-pyrimidin-5-yl |
| 1807 | 6-F, 4-OCH₃-pyrimidin-5-yl |
| 1808 | 4-F, 2-OCH₂CH₃-pyrimidin-5-yl |
| 1809 | 4-F, 6-OCH₂CH₃-pyrimidin-5-yl |
| 1810 | 2-F, 4-OCH₂CH₃-pyrimidin-5-yl |
| 1811 | 6-F, 4-OCH₂CH₃-pyrimidin-5-yl |
| 1812 | 4-F, 2-OCH₂CF₃-pyrimidin-5-yl |
| 1813 | 4-F, 6-OCH₂CF₃-pyrimidin-5-yl |
| 1814 | 2-F, 4-OCH₂CF₃-pyrimidin-5-yl |

TABLE A-continued

| No. | R⁴ |
|---|---|
| 1815 | 6-F, 4-OCH$_2$CF$_3$-pyrimidin-5-yl |
| 1816 | 4-F, 2-OCH(CH$_3$)$_2$-pyrimidin-5-yl |
| 1817 | 4-F, 6-OCH(CH$_3$)$_2$-pyrimidin-5-yl |
| 1818 | 2-F, 4-OCH(CH$_3$)$_2$-pyrimidin-5-yl |
| 1819 | 6-F, 4-OCH(CH$_3$)$_2$-pyrimidin-5-yl |
| 1820 | 4-Cl, 2-CH$_3$-pyrimidin-5-yl |
| 1821 | 4-Cl, 6-CH$_3$-pyrimidin-5-yl |
| 1822 | 2-Cl, 4-CH$_3$-pyrimidin-5-yl |
| 1823 | 6-Cl, 4-CH$_3$-pyrimidin-5-yl |
| 1824 | 4-Cl, 2-OCH$_3$-pyrimidin-5-yl |
| 1825 | 4-Cl, 6-OCH$_3$-pyrimidin-5-yl |
| 1826 | 2-Cl, 4-OCH$_3$-pyrimidin-5-yl |
| 1827 | 6-Cl, 4-OCH$_3$-pyrimidin-5-yl |
| 1828 | 4-Cl, 2-OCH$_2$CH$_3$-pyrimidin-5-yl |
| 1829 | 4-Cl, 6-OCH$_2$CH$_3$-pyrimidin-5-yl |
| 1830 | 2-Cl, 4-OCH$_2$CH$_3$-pyrimidin-5-yl |
| 1831 | 6-Cl, 4-OCH$_2$CH$_3$-pyrimidin-5-yl |
| 1832 | 4-Cl, 2-OCH$_2$CF$_3$-pyrimidin-5-yl |
| 1833 | 4-Cl, 6-OCH$_2$CF$_3$-pyrimidin-5-yl |
| 1834 | 2-Cl, 4-OCH$_2$CF$_3$-pyrimidin-5-yl |
| 1835 | 6-Cl, 4-OCH$_2$CF$_3$-pyrimidin-5-yl |
| 1836 | 4-Cl, 2-OCH(CH$_3$)$_2$-pyrimidin-5-yl |
| 1837 | 4-Cl, 6-OCH(CH$_3$)$_2$-pyrimidin-5-yl |
| 1838 | 2-Cl, 4-OCH(CH$_3$)$_2$-pyrimidin-5-yl |
| 1839 | 6-Cl, 4-OCH(CH$_3$)$_2$-pyrimidin-5-yl |
| 1840 | 4-CH$_3$, 2-OCH$_3$-pyrimidin-5-yl |
| 1841 | 4-CH$_3$, 6-OCH$_3$-pyrimidin-5-yl |
| 1842 | 2-CH$_3$, 4-OCH$_3$-pyrimidin-5-yl |
| 1843 | 6-CH$_3$, 4-OCH$_3$-pyrimidin-5-yl |
| 1844 | 4-CH$_3$, 6-OCH$_2$CH$_3$-pyrimidin-5-yl |
| 1845 | 2-CH$_3$, 4-OCH$_2$CH$_3$-pyrimidin-5-yl |
| 1846 | 4-CH$_3$, 2-OCH$_2$CH$_3$-pyrimidin-5-yl |
| 1847 | 4-CH$_3$, 6-OCH$_2$CH$_3$-pyrimidin-5-yl |
| 1848 | 4-CH$_3$, 2-OCH$_2$CF$_3$-pyrimidin-5-yl |
| 1849 | 4-CH$_3$, 6-OCH$_2$CF$_3$-pyrimidin-5-yl |
| 1850 | 2-CH$_3$, 4-OCH$_2$CF$_3$-pyrimidin-5-yl |
| 1851 | 6-CH$_3$, 4-OCH$_2$CF$_3$-pyrimidin-5-yl |
| 1852 | 4-CH$_3$, 2-OCH(CH$_3$)$_2$-pyrimidin-5-yl |
| 1853 | 4-CH$_3$, 6-OCH(CH$_3$)$_2$-pyrimidin-5-yl |
| 1854 | 2-CH$_3$, 4-OCH(CH$_3$)$_2$-pyrimidin-5-yl |
| 1855 | 6-CH$_3$, 4-OCH(CH$_3$)$_2$-pyrimidin-5-yl |
| 1856 | 4-CH$_3$, 2-OCH$_2$CH=CH$_2$-pyrimidin-5-yl |
| 1857 | 4-CH$_3$, 6-OCH$_2$CH=CH$_2$-pyrimidin-5-yl |
| 1858 | 2-CH$_3$, 4-OCH$_2$CH=CH$_2$-pyrimidin-5-yl |
| 1859 | 6-CH$_3$, 4-OCH$_2$CH=CH$_2$-pyrimidin-5-yl |
| 1860 | 4-CH$_3$, 2-CO$_2$CH$_3$-pyrimidin-5-yl |
| 1861 | 4-CH$_3$, 6-CO$_2$CH$_3$-pyrimidin-5-yl |
| 1862 | 4-CH$_3$, 2-CF$_3$-pyrimidin-5-yl |
| 1863 | 4-CH$_3$, 6-CF$_3$-pyrimidin-5-yl |
| 1864 | 2-CH$_3$, 4-CF$_3$-pyrimidin-5-yl |
| 1865 | 6-CH$_3$, 4-CF$_3$-pyrimidin-5-yl |
| 1866 | 4-CF$_3$, 2-CH$_2$CH$_3$-pyrimidin-5-yl |
| 1867 | 4-CF$_3$, 6-CH$_2$CH$_3$-pyrimidin-5-yl |
| 1868 | 2-CF$_3$, 4-CH$_2$CH$_3$-pyrimidin-5-yl |
| 1869 | 6-CF$_3$, 4-CH$_2$CH$_3$-pyrimidin-5-yl |
| 1870 | 4-CF$_3$, 2-OCH$_3$-pyrimidin-5-yl |
| 1871 | 4-CF$_3$, 6-OCH$_3$-pyrimidin-5-yl |
| 1872 | 2-CF$_3$, 4-OCH$_3$-pyrimidin-5-yl |
| 1873 | 6-CF$_3$, 4-OCH$_3$-pyrimidin-5-yl |
| 1874 | 4-CF$_3$, 2-OCH$_2$CH$_3$-pyrimidin-5-yl |
| 1875 | 4-CF$_3$, 6-OCH$_2$CH$_3$-pyrimidin-5-yl |
| 1876 | 2-CF$_3$, 4-OCH$_2$CH$_3$-pyrimidin-5-yl |
| 1877 | 2-CF$_3$, 4-OCH$_2$CH$_3$-pyrimidin-5-yl |
| 1878 | 4-CF$_3$, 2-OCH$_2$CF$_3$-pyrimidin-5-yl |
| 1879 | 4-CF$_3$, 6-OCH$_2$CF$_3$-pyrimidin-5-yl |
| 1880 | 2-CF$_3$, 4-OCH$_2$CF$_3$-pyrimidin-5-yl |
| 1881 | 6-CF$_3$, 4-OCH$_2$CF$_3$-pyrimidin-5-yl |
| 1882 | 4-OCH$_3$, 2-OCH$_2$CH$_3$-pyrimidin-5-yl |
| 1883 | 4-OCH$_3$, 6-OCH$_2$CH$_3$-pyrimidin-5-yl |
| 1884 | 2-OCH$_3$, 4-OCH$_2$CH$_3$-pyrimidin-5-yl |
| 1885 | 6-OCH$_3$, 4-OCH$_2$CH$_3$-pyrimidin-5-yl |
| 1886 | 4-OCH$_3$, 2-OCH$_2$CF$_3$-pyrimidin-5-yl |
| 1887 | 4-OCH$_3$, 6-OCH$_2$CF$_3$-pyrimidin-5-yl |
| 1888 | 2-OCH$_3$, 4-OCH$_2$CF$_3$-pyrimidin-5-yl |
| 1889 | 6-OCH$_3$, 4-OCH$_2$CF$_3$-pyrimidin-5-yl |
| 1890 | 4-OCH$_3$, 2-OCH(CH$_3$)pyrimidin-5-yl |
| 1891 | 4-OCH$_3$, 6-OCH(CH$_3$)pyrimidin-5-yl |
| 1892 | 6-OCH$_3$, 4-OCH(CH$_3$)pyrimidin-5-yl |
| 1893 | 6-OCH$_3$, 4-OCH(CH$_3$)pyrimidin-5-yl |
| 1894 | 4-OCH$_2$CH$_3$, 2-CH$_2$OCH$_2$CH$_3$-pyrimidin-5-yl |
| 1895 | 4-OCH$_2$CH$_3$, 6-CH$_2$OCH$_2$CH$_3$-pyrimidin-5-yl |
| 1896 | 2-OCH$_2$CH$_3$, 4-CH$_2$OCH$_2$CH$_3$-pyrimidin-5-yl |
| 1897 | 6-OCH$_2$CH$_3$, 4-CH$_2$OCH$_2$CH$_3$-pyrimidin-5-yl |
| 1898 | 4-NO$_2$, 2-CH$_3$-pyrimidin-5-yl |
| 1899 | 4-NO$_2$, 6-CH$_3$-pyrimidin-5-yl |
| 1900 | 2-NO$_2$, 4-CH$_3$-pyrimidin-5-yl |
| 1901 | 6-NO$_2$, 4-CH$_3$-pyrimidin-5-yl |
| 1902 | 4-NO$_2$, 2-OCH$_3$-pyrimidin-5-yl |
| 1903 | 4-NO$_2$, 6-OCH$_3$-pyrimidin-5-yl |
| 1904 | 2-NO$_2$, 4-OCH$_3$-pyrimidin-5-yl |
| 1905 | 6-NO$_2$, 4-OCH$_3$-pyrimidin-5-yl |
| 1906 | 4-NO$_2$, 2-OCH$_2$CH$_3$-pyrimidin-5-yl |
| 1907 | 4-NO$_2$, 6-OCH$_2$CH$_3$-pyrimidin-5-yl |
| 1908 | 2-NO$_2$, 4-OCH$_2$CH$_3$-pyrimidin-5-yl |
| 1909 | 6-NO$_2$, 4-OCH$_2$CH$_3$-pyrimidin-5-yl |
| 1910 | 4-NO$_2$, 2-OCH(CH$_3$)$_2$-pyrimidin-5-yl |
| 1911 | 4-NO$_2$, 6-OCH(CH$_3$)$_2$-pyrimidin-5-yl |
| 1912 | 2-NO$_2$, 4-OCH(CH$_3$)$_2$-pyrimidin-5-yl |
| 1913 | 6-NO$_2$, 4-OCH(CH$_3$)$_2$-pyrimidin-5-yl |
| 1914 | 4-NO$_2$, 2-OCH$_2$CF$_3$-pyrimidin-5-yl |
| 1915 | 4-NO$_2$, 6-OCH$_2$CF$_3$-pyrimidin-5-yl |
| 1916 | 2-NO$_2$, 4-OCH$_2$CF$_3$-pyrimidin-5-yl |
| 1917 | 6-NO$_2$, 4-OCH$_2$CF$_3$-pyrimidin-5-yl |
| 1918 | 4-CN, 2-CH$_3$-pyrimidin-5-yl |
| 1919 | 4-CN, 6-CH$_3$-pyrimidin-5-yl |
| 1920 | 2-CN, 4-CH$_3$-pyrimidin-5-yl |
| 1921 | 6-CN, 4-CH$_3$-pyrimidin-5-yl |
| 1922 | 4-CN, 2-OCH$_3$-pyrimidin-5-yl |
| 1923 | 4-CN, 6-OCH$_3$-pyrimidin-5-yl |
| 1924 | 2-CN, 4-OCH$_3$-pyrimidin-5-yl |
| 1925 | 6-CN, 4-OCH$_3$-pyrimidin-5-yl |
| 1926 | 4-CN, 2-OCH$_2$CH$_3$-pyrimidin-5-yl |
| 1927 | 4-CN, 6-OCH$_2$CH$_3$-pyrimidin-5-yl |
| 1928 | 2-CN, 4-OCH$_2$CH$_3$-pyrimidin-5-yl |
| 1929 | 6-CN, 4-OCH$_2$CH$_3$-pyrimidin-5-yl |
| 1930 | 4-CN, 2-OCH(CH$_3$)$_2$-pyrimidin-5-yl |
| 1931 | 4-CN, 6-OCH(CH$_3$)$_2$-pyrimidin-5-yl |
| 1932 | 2-CN, 4-OCH(CH$_3$)$_2$-pyrimidin-5-yl |
| 1933 | 6-CN, 4-OCH(CH$_3$)$_2$-pyrimidin-5-yl |
| 1934 | 4-CN, 2-OCH$_2$CF$_3$-pyrimidin-5-yl |
| 1935 | 4-CN, 6-OCH$_2$CF$_3$-pyrimidin-5-yl |
| 1936 | 2-CN, 4-OCH$_2$CF$_3$-pyrimidin-5-yl |
| 1937 | 6-CN, 4-OCH$_2$CF$_3$-pyrimidin-5-yl |
| 1938 | 2,6-(CH$_3$)$_2$, 4-OCH$_3$-pyrimidin-5-yl |
| 1939 | 4-CH$_3$-pyridazin-3-yl |
| 1940 | 6-CH$_3$-pyridazin-3-yl |
| 1941 | 4-CH$_2$CH$_3$-pyridazin-3-yl |
| 1942 | 6-CH$_2$CH$_3$-pyridazin-3-yl |
| 1943 | 4-CH(CH$_3$)$_2$-pyridazin-3-yl |
| 1944 | 6-CH(CH$_3$)$_2$-pyridazin-3-yl |
| 1945 | 4-CH(CH$_3$)CH$_2$CH$_3$-pyridazin-3-yl |
| 1946 | 6-CH(CH$_3$)CH$_2$CH$_3$-pyridazin-3-yl |
| 1947 | 4-CF$_3$-pyridazin-3-yl |
| 1948 | 6-CF$_3$-pyridazin-3-yl |
| 1949 | 4-CH=CH$_2$-pyridazin-3-yl |
| 1950 | 6-CH=CH$_2$-pyridazin-3-yl |
| 1951 | 4-CH=CHCH$_3$-pyridazin-3-yl |
| 1952 | 6-CH=CHCH$_3$-pyridazin-3-yl |
| 1953 | 4-CH=CHCl-pyridazin-3-yl |
| 1954 | 6-CH=CHCl-pyridazin-3-yl |
| 1955 | 4-C≡CH-pyridazin-3-yl |
| 1956 | 6-C≡CH-pyridazin-3-yl |
| 1957 | 4-CH$_2$C≡CH-pyridazin-3-yl |
| 1958 | 6-CH$_2$C≡CH-pyridazin-3-yl |
| 1959 | 4-CH$_2$C≡CCH$_3$-pyridazin-3-yl |
| 1960 | 6-CH$_2$C≡CCH$_3$-pyridazin-3-yl |
| 1961 | 4-cyclopropyl-pyridazin-3-yl |
| 1962 | 6-cyclopropyl-pyridazin-3-yl |
| 1963 | 4-cyclopentyl-pyridazin-3-yl |
| 1964 | 6-cyclopentyl-pyridazin-3-yl |
| 1965 | 4-OCH$_3$-pyridazin-3-yl |
| 1966 | 6-OCH$_3$-pyridazin-3-yl |
| 1967 | 4-OCH$_2$CH$_3$-pyridazin-3-yl |
| 1968 | 6-OCH$_2$CH$_3$-pyridazin-3-yl |

TABLE A-continued

| No. | R⁴ |
|---|---|
| 1969 | 4-OCH₂CH₂CH₃-pyridazin-3-yl |
| 1970 | 6-OCH₂CH₂CH₃-pyridazin-3-yl |
| 1971 | 4-OCH(CH₃)₂-pyridazin-3-yl |
| 1972 | 6-OCH(CH₃)₂-pyridazin-3-yl |
| 1973 | 4-OCH₂CH₂CH₂CH₃-pyridazin-3-yl |
| 1974 | 6-OCH₂CH₂CH₂CH₃-pyridazin-3-yl |
| 1975 | 4-OCH(CH₃)CH₂CH₃-pyridazin-3-yl |
| 1976 | 6-OCH(CH₃)CH₂CH₃-pyridazin-3-yl |
| 1977 | 4-OCH₂CH(CH₃)₂-pyridazin-3-yl |
| 1978 | 6-OCH₂CH(CH₃)₂-pyridazin-3-yl |
| 1979 | 4-OC(CH₃)₃-pyridazin-3-yl |
| 1980 | 6-OC(CH₃)₃-pyridazin-3-yl |
| 1981 | 4-OCH(CH₃)CH₂CH₂CH₃-pyridazin-3-yl |
| 1982 | 6-OCH(CH₃)CH₂CH₂CH₃-pyridazin-3-yl |
| 1983 | 4-OCH₂OCH₃-pyridazin-3-yl |
| 1984 | 6-OCH₂OCH₃-pyridazin-3-yl |
| 1985 | 4-OCH₂OCH₂CH₃-pyridazin-3-yl |
| 1986 | 6-OCH₂OCH₂CH₃-pyridazin-3-yl |
| 1987 | 4-OCH(CH₃)OCH₃-pyridazin-3-yl |
| 1988 | 6-OCH(CH₃)OCH₃-pyridazin-3-yl |
| 1989 | 4-OCH(CH₃)OCH₂CH₃-pyridazin-3-yl |
| 1990 | 6-OCH(CH₃)OCH₂CH₃-pyridazin-3-yl |
| 1991 | 4-OCH₂CH₂OCH₃-pyridazin-3-yl |
| 1992 | 6-OCH₂CH₂OCH₃-pyridazin-3-yl |
| 1993 | 4-OCH₂CH₂OCH₂CH₃-pyridazin-3-yl |
| 1994 | 6-OCH₂CH₂OCH₂CH₃-pyridazin-3-yl |
| 1995 | 4-OCH₂CH₂OCH(CH₃)₂-pyridazin-3-yl |
| 1996 | 6-OCH₂CH₂OCH(CH₃)₂-pyridazin-3-yl |
| 1997 | 4-OCH₂CH₂SCH₃-pyridazin-3-yl |
| 1998 | 6-OCH₂CH₂SCH₃-pyridazin-3-yl |
| 1999 | 4-OCH₂CH₂SO₂CH₃-pyridazin-3-yl |
| 2000 | 6-OCH₂CH₂SO₂CH₃-pyridazin-3-yl |
| 2001 | 4-OCH₂CH₂SCH(CH₃)₂-pyridazin-3-yl |
| 2002 | 6-OCH₂CH₂SCH(CH₃)₂-pyridazin-3-yl |
| 2003 | 4-OCH₂CH₂CN-pyridazin-3-yl |
| 2004 | 6-OCH₂CH₂CN-pyridazin-3-yl |
| 2005 | 4-OCH₂CH₂SCH₂CH₂CN-pyridazin-3-yl |
| 2006 | 6-OCH₂CH₂SCH₂CH₂CN-pyridazin-3-yl |
| 2007 | 4-OCH₂CH₂OC₅H₆-pyridazin-3-yl |
| 2008 | 6-OCH₂CH₂OC₅H₆-pyridazin-3-yl |
| 2009 | 4-OCH₂CH₂OCH₂C₅H₆-pyridazin-3-yl |
| 2010 | 6-OCH₂CH₂OCH₂C₅H₆-pyridazin-3-yl |
| 2011 | 4-OCH₂CH₂N(CH₃)₂-pyridazin-3-yl |
| 2012 | 6-OCH₂CH₂N(CH₃)₂-pyridazin-3-yl |
| 2013 | 4-OCH₂CH₂CONH₂-pyridazin-3-yl |
| 2014 | 6-OCH₂CH₂CONH₂-pyridazin-3-yl |
| 2015 | 4-OCH₂CH₂CO₂CH₂CH₂CH₃-pyridazin-3-yl |
| 2016 | 6-OCH₂CH₂CO₂CH₂CH₂CH₃-pyridazin-3-yl |
| 2017 | 4-OCH(CH₃)CH₂OCH₃-pyridazin-3-yl |
| 2018 | 6-OCH(CH₃)CH₂OCH₃-pyridazin-3-yl |
| 2019 | 4-OCH(CH₃)CH₂CO₂CH₃-pyridazin-3-yl |
| 2020 | 6-OCH(CH₃)CH₂CO₂CH₃-pyridazin-3-yl |
| 2021 | 4-OCH(CH₃)CH₂CO₂CH₂CH₃-pyridazin-3-yl |
| 2022 | 6-OCH(CH₃)CH₂CO₂CH₂CH₃-pyridazin-3-yl |
| 2023 | 4-OCH₂CH(CH₃)CO₂CH₃-pyridazin-3-yl |
| 2024 | 6-OCH₂CH(CH₃)CO₂CH₃-pyridazin-3-yl |
| 2025 | 4-OCH₂C(=O)CH₃-pyridazin-3-yl |
| 2026 | 6-OCH₂C(=O)CH₃-pyridazin-3-yl |
| 2027 | 4-OCH₂C(=O)CH₂CH₃-pyridazin-3-yl |
| 2028 | 6-OCH₂C(=O)CH₂CH₃-pyridazin-3-yl |
| 2029 | 4-OCH₂CO₂CH₃-pyridazin-3-yl |
| 2030 | 6-OCH₂CO₂CH₃-pyridazin-3-yl |
| 2031 | 4-OCH₂CO₂CH₂CH₃-pyridazin-3-yl |
| 2032 | 6-OCH₂CO₂CH₂CH₃-pyridazin-3-yl |
| 2033 | 4-OCH₂C(=O)NH₂-pyridazin-3-yl |
| 2034 | 6-OCH₂C(=O)NH₂-pyridazin-3-yl |
| 2035 | 4-OCH₂C(=O)NHCH₃-pyridazin-3-yl |
| 2036 | 6-OCH₂C(=O)NHCH₃-pyridazin-3-yl |
| 2037 | 4-OCH₂C(=O)SCH₃-pyridazin-3-yl |
| 2038 | 6-OCH₂C(=O)SCH₃-pyridazin-3-yl |
| 2039 | 4-OCH(CH₃)C(=O)NH₂-pyridazin-3-yl |
| 2040 | 6-OCH(CH₃)C(=O)NH₂-pyridazin-3-yl |
| 2041 | 4-OCH(CH₃)C(=O)NHCH₃-pyridazin-3-yl |
| 2042 | 6-OCH(CH₃)C(=O)NHCH₃-pyridazin-3-yl |
| 2043 | 4-OCH(CH₃)C(=O)NHNH₂-pyridazin-3-yl |
| 2044 | 6-OCH(CH₃)C(=O)NHNH₂-pyridazin-3-yl |
| 2045 | 4-OCH(CH₃)CO₂CH₃-pyridazin-3-yl |
| 2046 | 6-OCH(CH₃)CO₂CH₃-pyridazin-3-yl |
| 2047 | 4-OCH(CH₃)CO₂CH₂CH₃-pyridazin-3-yl |
| 2048 | 6-OCH(CH₃)CO₂CH₂CH₃-pyridazin-3-yl |
| 2049 | 4-OCH(CH₃)C(=O)CH₃-pyridazin-3-yl |
| 2050 | 6-OCH(CH₃)C(=O)CH₃-pyridazin-3-yl |
| 2051 | 4-OCH(CH₃)C(=O)CH₂CH₃-pyridazin-3-yl |
| 2052 | 6-OCH(CH₃)C(=O)CH₂CH₃-pyridazin-3-yl |
| 2053 | 4-OCH(CH₃)CH₂C(=O)CH₃-pyridazin-3-yl |
| 2054 | 6-OCH(CH₃)CH₂C(=O)CH₃-pyridazin-3-yl |
| 2055 | 4-OCH(CH₃)CH₂OC(CH₃)₃-pyridazin-3-yl |
| 2056 | 6-OCH(CH₃)CH₂OC(CH₃)₃-pyridazin-3-yl |
| 2057 | 4-OCH(CH₃)CH₂OCH₂CH₃-pyridazin-3-yl |
| 2058 | 6-OCH(CH₃)CH₂OCH₂CH₃-pyridazin-3-yl |
| 2059 | 4-OCH(CH₃)CH₂O(CH₃)₂CH₃-pyridazin-3-yl |
| 2060 | 6-OCH(CH₃)CH₂O(CH₃)₂CH₃-pyridazin-3-yl |
| 2061 | 4-OCH(CH₃)CH₂OCH₂CH=CH₂-pyridazin-3-yl |
| 2062 | 6-OCH(CH₃)CH₂OCH₂CH=CH₂-pyridazin-3-yl |
| 2063 | 4-O(CH₂)₃OCH₃-pyridazin-3-yl |
| 2064 | 6-O(CH₂)₃OCH₃-pyridazin-3-yl |
| 2065 | 4-O(CH₂)₃OCH₂CH₃-pyridazin-3-yl |
| 2066 | 6-O(CH₂)₃OCH₂CH₃-pyridazin-3-yl |
| 2067 | 4-O(CH₂)₃OCH(CH₃)₂-pyridazin-3-yl |
| 2068 | 6-O(CH₂)₃OCH(CH₃)₂-pyridazin-3-yl |
| 2069 | 4-O(CH₂)₃OC₅H₆-pyridazin-3-yl |
| 2070 | 6-O(CH₂)₃OC₅H₆-pyridazin-3-yl |
| 2071 | 4-O(CH₂)₃OCH₂C₅H₆-pyridazin-3-yl |
| 2072 | 6-O(CH₂)₃OCH₂C₅H₆-pyridazin-3-yl |
| 2073 | 4-OCH(CH₂CH₃)CH₂OCH₃-pyridazin-3-yl |
| 2074 | 6-OCH(CH₂CH₃)CH₂OCH₃-pyridazin-3-yl |
| 2075 | 4-OCH(CH₂CH₃)CH₂CH₂OCH₃-pyridazin-3-yl |
| 2076 | 6-OCH(CH₂CH₃)CH₂CH₂OCH₃-pyridazin-3-yl |
| 2077 | 4-OCH(CH₂CH₃)CH₂CH₂OCH₂CH₃-pyridazin-3-yl |
| 2078 | 6-OCH(CH₂CH₃)CH₂CH₂OCH₂CH₃-pyridazin-3-yl |
| 2079 | 4-O[(CH₂)₃O]₂CH₃-pyridazin-3-yl |
| 2080 | 6-O[(CH₂)₃O]₂CH₃-pyridazin-3-yl |
| 2081 | 4-OCH₂CH(CH₃)CH₂OCH₃-pyridazin-3-yl |
| 2082 | 6-OCH₂CH(CH₃)CH₂OCH₃-pyridazin-3-yl |
| 2083 | 4-OCH₂CH(CH₃)CH₂OCH₂CH₃-pyridazin-3-yl |
| 2084 | 6-OCH₂CH(CH₃)CH₂OCH₂CH₃-pyridazin-3-yl |
| 2085 | 4-OCH(CH₂Cl)CH₂OCH₃-pyridazin-3-yl |
| 2086 | 6-OCH(CH₂Cl)CH₂OCH₃-pyridazin-3-yl |
| 2087 | 4-OCH(CH₂Cl)CH₂OCH₂CH₃-pyridazin-3-yl |
| 2088 | 6-OCH(CH₂Cl)CH₂OCH₂CH₃-pyridazin-3-yl |
| 2089 | 4-OCH(CH₂Cl)CH₂OCH(CH₃)₂-pyridazin-3-yl |
| 2090 | 6-OCH(CH₂Cl)CH₂OCH(CH₃)₂-pyridazin-3-yl |
| 2091 | 4-OCH(CH₂Cl)CH₂OCH₂CH=CH₂-pyridazin-3-yl |
| 2092 | 6-OCH(CH₂Cl)CH₂OCH₂CH=CH₂-pyridazin-3-yl |
| 2093 | 4-OCH[CH₂OCH₃]₂-pyridazin-3-yl |
| 2094 | 6-OCH[CH₂OCH₃]₂-pyridazin-3-yl |
| 2095 | 4-OCH[CH₂OCH₂CH₃]₂-pyridazin-3-yl |
| 2096 | 6-OCH[CH₂OCH₂CH₃]₂-pyridazin-3-yl |
| 2097 | 4-OCCl₃-pyridazin-3-yl |
| 2098 | 6-OCCl₃-pyridazin-3-yl |
| 2099 | 4-OCHF₂-pyridazin-3-yl |
| 2100 | 6-OCHF₂-pyridazin-3-yl |
| 2101 | 4-OCF₃-pyridazin-3-yl |
| 2102 | 6-OCF₃-pyridazin-3-yl |
| 2103 | 4-OCF₂CHF₂-pyridazin-3-yl |
| 2104 | 6-OCF₂CHF₂-pyridazin-3-yl |
| 2105 | 4-OCH₂CF₃-pyridazin-3-yl |
| 2106 | 6-OCH₂CF₃-pyridazin-3-yl |
| 2107 | 4-OCH₂CHF₂-pyridazin-3-yl |
| 2108 | 6-OCH₂CHF₂-pyridazin-3-yl |
| 2109 | 4-O(CH₂)₃F-pyridazin-3-yl |
| 2110 | 6-O(CH₂)₃F-pyridazin-3-yl |
| 2111 | 4-OCH(CH₃)CF₃-pyridazin-3-yl |
| 2112 | 6-OCH(CH₃)CF₃-pyridazin-3-yl |
| 2113 | 4-O(CH₂)₄F-pyridazin-3-yl |
| 2114 | 6-O(CH₂)₄F-pyridazin-3-yl |
| 2115 | 4-O(CH₂)₃CF₃-pyridazin-3-yl |
| 2116 | 6-O(CH₂)₃CF₃-pyridazin-3-yl |
| 2117 | 4-OCH(CH₃)CF₂CF₃-pyridazin-3-yl |
| 2118 | 4-OCH(CH₃)CF₂CF₃-pyridazin-3-yl |
| 2119 | 4-OCH(CH₃)CF₂CHF₂-pyridazin-3-yl |
| 2120 | 6-OCH(CH₃)CF₂CHF₂-pyridazin-3-yl |
| 2121 | 4-OCH₂CF₂CHFCH₃-pyridazin-3-yl |
| 2122 | 6-OCH₂CF₂CHFCH₃-pyridazin-3-yl |

TABLE A-continued

| No. | R[4] |
|---|---|
| 2123 | 4-OCH$_2$(CF$_2$)$_2$CF$_3$-pyridazin-3-yl |
| 2124 | 6-OCH$_2$(CF$_2$)$_2$CF$_3$-pyridazin-3-yl |
| 2125 | 4-O(CF$_2$)$_3$CF$_3$-pyridazin-3-yl |
| 2126 | 6-O(CF$_2$)$_3$CF$_3$-pyridazin-3-yl |
| 2127 | 4-OCH$_2$CF$_2$CHF$_2$-pyridazin-3-yl |
| 2128 | 6-OCH$_2$CF$_2$CHF$_2$-pyridazin-3-yl |
| 2129 | 4-CH$_2$CH=CH$_2$-pyridazin-3-yl |
| 2130 | 6-CH$_2$CH=CH$_2$-pyridazin-3-yl |
| 2131 | 4-CH$_2$C(CH$_3$)=CH$_2$-pyridazin-3-yl |
| 2132 | 6-CH$_2$C(CH$_3$)=CH$_2$-pyridazin-3-yl |
| 2133 | 4-OCH$_2$CH=CHCH$_3$-pyridazin-3-yl |
| 2134 | 6-OCH$_2$CH=CHCH$_3$-pyridazin-3-yl |
| 2135 | 4-O(CH$_2$)$_2$CH=CH$_2$-pyridazin-3-yl |
| 2136 | 6-O(CH$_2$)$_2$CH=CH$_2$-pyridazin-3-yl |
| 2137 | 4-OCH$_2$C(CH$_3$)=CH$_2$-pyridazin-3-yl |
| 2138 | 6-OCH$_2$C(CH$_3$)=CH$_2$-pyridazin-3-yl |
| 2139 | 4-OCH(CH$_3$)CH=CH$_2$-pyridazin-3-yl |
| 2140 | 6-OCH(CH$_3$)CH=CH$_2$-pyridazin-3-yl |
| 2141 | 4-OCH$_2$C≡CH-pyridazin-3-yl |
| 2142 | 6-OCH$_2$C≡CH-pyridazin-3-yl |
| 2143 | 4-OCH$_2$C≡CCH$_3$-pyridazin-3-yl |
| 2144 | 6-OCH$_2$C≡CCH$_3$-pyridazin-3-yl |
| 2145 | 4-O(CH$_2$)$_2$C≡CH-pyridazin-3-yl |
| 2146 | 6-O(CH$_2$)$_2$C≡CH-pyridazin-3-yl |
| 2147 | 4-SCH$_2$-pyridazin-3-yl |
| 2148 | 6-SCH$_2$-pyridazin-3-yl |
| 2149 | 4-SCH$_2$CH$_3$-pyridazin-3-yl |
| 2150 | 6-SCH$_2$CH$_3$-pyridazin-3-yl |
| 2151 | 4-OC$_5$H$_6$-pyridazin-3-yl |
| 2152 | 6-OC$_5$H$_6$-pyridazin-3-yl |
| 2153 | 4-OCH$_2$C$_5$H$_6$-pyridazin-3-yl |
| 2154 | 6-OCH$_2$C$_5$H$_6$-pyridazin-3-yl |
| 2155 | 4-NO$_2$-pyridazin-3-yl |
| 2156 | 6-NO$_2$-pyridazin-3-yl |
| 2157 | 4-NHCH$_3$-pyridazin-3-yl |
| 2158 | 6-NHCH$_3$-pyridazin-3-yl |
| 2159 | 4-N(CH$_3$)$_2$-pyridazin-3-yl |
| 2160 | 6-N(CH$_3$)$_2$-pyridazin-3-yl |
| 2161 | 4-N(CH$_3$)C$_2$H$_6$-pyridazin-3-yl |
| 2162 | 6-N(CH$_3$)C$_2$H$_6$-pyridazin-3-yl |
| 2163 | 4-NHCH$_2$CF$_3$-pyridazin-3-yl |
| 2164 | 6-NHCH$_2$CF$_3$-pyridazin-3-yl |
| 2165 | 4-F-pyridazin-3-yl |
| 2166 | 6-F-pyridazin-3-yl |
| 2167 | 4-Cl-pyridazin-3-yl |
| 2168 | 6-Cl-pyridazin-3-yl |
| 2169 | 4-OH-pyridazin-3-yl |
| 2170 | 6-OH-pyridazin-3-yl |
| 2171 | 4-CN-pyridazin-3-yl |
| 2172 | 6-CN-pyridazin-3-yl |
| 2173 | 4-C(O)NH$_2$-pyridazin-3-yl |
| 2174 | 6-C(O)NH$_2$-pyridazin-3-yl |
| 2175 | 4-C(S)NH$_2$-pyridazin-3-yl |
| 2176 | 6-C(S)NH$_2$-pyridazin-3-yl |
| 2177 | 4-CO$_2$CH$_3$-pyridazin-3-yl |
| 2178 | 6-CO$_2$CH$_3$-pyridazin-3-yl |
| 2179 | 4-ON=C(CH$_3$)$_2$-pyridazin-3-yl |
| 2180 | 6-ON=C(CH$_3$)$_2$-pyridazin-3-yl |
| 2181 | 4-[O-cyclopropyl]pyridazin-3-yl |
| 2182 | 6-[O-cyclopropyl]pyridazin-3-yl |
| 2183 | 4-[O-cyclobutyl]pyridazin-3-yl |
| 2184 | 6-[O-cyclobutyl]pyridazin-3-yl |
| 2185 | 4-[O-cyclopentyl]pyridazin-3-yl |
| 2186 | 6-[O-cyclopentyl]pyridazin-3-yl |
| 2187 | 4-[O-cyclohexyl]pyridazin-3-yl |
| 2188 | 6-[O-cyclohexyl]pyridazin-3-yl |
| 2189 | 4-[OCH$_2$-cyclopropyl]pyridazin-3-yl |
| 2190 | 6-[OCH$_2$-cyclopropyl]pyridazin-3-yl |
| 2191 | 6-F, 4-[OCH$_2$-cyclopropyl]pyridazin-3-yl |
| 2192 | 4-F, 6-[OCH$_2$-cyclopropyl]pyridazin-3-yl |
| 2193 | 6-CH$_3$, 4-[OCH$_2$-cyclopropyl]pyridazin-3-yl |
| 2194 | 4-CH$_3$, 6-[OCH$_2$-cyclopropyl]pyridazin-3-yl |
| 2195 | 6-CF$_3$, 4-[OCH$_2$-cyclopropyl]pyridazin-3-yl |
| 2196 | 4-CH$_3$, 6-[OCH$_2$-cyclopropyl]pyridazin-3-yl |
| 2197 | 4-[OCH(CH$_3$)-cyclopropyl]pyridazin-3-yl |
| 2198 | 6-[OCH(CH$_3$)-cyclopropyl]pyridazin-3-yl |
| 2199 | 6-F, 4-[OCH(CH$_3$)-cyclopropyl]pyridazin-3-yl |
| 2200 | 4-F, 6-[OCH(CH$_3$)-cyclopropyl]pyridazin-3-yl |
| 2201 | 6-CH$_3$, 4-[OCH(CH$_3$)-cyclopropyl]pyridazin-3-yl |
| 2202 | 4-CH$_3$, 6-[OCH(CH$_3$)-cyclopropyl]pyridazin-3-yl |
| 2203 | 6-CF$_3$, 4-[OCH(CH$_3$)-cyclopropyl]pyridazin-3-yl |
| 2204 | 4-CF$_3$, 6-[OCH(CH$_3$)-cyclopropyl]pyridazin-3-yl |
| 2205 | 4-[O-(1-CH$_3$-cyclopropyl)]pyridazin-3-yl |
| 2206 | 6-[O-(1-CH$_3$-cyclopropyl)]pyridazin-3-yl |
| 2207 | 6-F, 4-[O-(1-CH$_3$-cyclopropyl)]pyridazin-3-yl |
| 2208 | 4-F, 6-[O-(1-CH$_3$-cyclopropyl)]pyridazin-3-yl |
| 2209 | 6-CH$_3$, 4-[O-(1-CH$_3$-cyclopropyl)]pyridazin-3-yl |
| 2210 | 4-CH$_3$, 6-[O-(1-CH$_3$-cyclopropyl)]pyridazin-3-yl |
| 2211 | 6-CF$_3$, 4-[O-(1-CH$_3$-cyclopropyl)]pyridazin-3-yl |
| 2212 | 4-CF$_3$, 6-[O-(1-CH$_3$-cyclopropyl)]pyridazin-3-yl |
| 2213 | 4-[OCH$_2$-(1-CH$_3$-cyclopropyl)]pyridazin-3-yl |
| 2214 | 6-[OCH$_2$-(1-CH$_3$-cyclopropyl)]pyridazin-3-yl |
| 2215 | 6-F, 4-[OCH$_2$-(1-CH$_3$-cyclopropyl)]pyridazin-3-yl |
| 2216 | 4-F, 6-[OCH$_2$-(1-CH$_3$-cyclopropyl)]pyridazin-3-yl |
| 2217 | 6-CH$_3$, 4-[OCH$_2$-(1-CH$_3$-cyclopropyl)]pyridazin-3-yl |
| 2218 | 4-CH$_3$, 4-[OCH$_2$-(1-CH$_3$-cyclopropyl)]pyridazin-3-yl |
| 2219 | 6-CF$_3$, 4-[OCH$_2$-(1-CH$_3$-cyclopropyl)]pyridazin-3-yl |
| 2220 | 4-CF$_3$, 6-[OCH$_2$-(1-CH$_3$-cyclopropyl)]pyridazin-3-yl |
| 2221 | 4-[OCH$_2$-(2-CH$_3$-cyclopropyl)]pyridazin-3-yl |
| 2222 | 6-[OCH$_2$-(2-CH$_3$-cyclopropyl)]pyridazin-3-yl |
| 2223 | 6-F, 4-[OCH$_2$-(2-CH$_3$-cyclopropyl)]pyridazin-3-yl |
| 2224 | 4-F, 6-[OCH$_2$-(2-CH$_3$-cyclopropyl)]pyridazin-3-yl |
| 2225 | 6-CH$_3$, 4-[OCH$_2$-(2-CH$_3$-cyclopropyl)]pyridazin-1-yl |
| 2226 | 4-CH$_3$, 6-[OCH$_2$-(2-CH$_3$-cyclopropyl)]pyridazin-1-yl |
| 2227 | 6-CF$_3$, 4-[OCH$_2$-(2-CH$_3$-cyclopropyl)]pyridazin-1-yl |
| 2228 | 4-CF$_3$, 6-[OCH$_2$-(2-CH$_3$-cyclopropyl)]pyridazin-1-yl |
| 2229 | 4-[OCH$_2$-(tetrahydropyran-2-yl)]pyridazin-3-yl |
| 2230 | 6-[OCH$_2$-(tetrahydropyran-2-yl)]pyridazin-3-yl |
| 2231 | 6-F, 4-[OCH$_2$-(tetrahydropyran-2-yl)]pyridazin-3-yl |
| 2232 | 4-F, 6-[OCH$_2$-(tetrahydropyran-2-yl)]pyridazin-3-yl |
| 2233 | 6-CH$_3$, 4-[OCH$_2$-(tetrahydropyran-2-yl)]pyridazin-3-yl |
| 2234 | 4-CH$_3$, 6-[OCH$_2$-(tetrahydropyran-2-yl)]pyridazin-3-yl |
| 2235 | 6-CF$_3$, 4-[OCH$_2$-(tetrahydropyran-2-yl)]pyridazin-3-yl |
| 2236 | 4-CF$_3$, 6-[OCH$_2$-(tetrahydropyran-2-yl)]pyridazin-3-yl |
| 2237 | 4-[OCH$_2$-(furan-2-yl)]pyridazin-3-yl |
| 2238 | 6-[OCH$_2$-(furan-2-yl)]pyridazin-3-yl |
| 2239 | 6-F, 4-[OCH$_2$-(furan-2-yl)]pyridazin-3-yl |
| 2240 | 4-F, 6-[OCH$_2$-(furan-2-yl)]pyridazin-3-yl |
| 2241 | 6-CH$_3$, 4-[OCH$_2$-(furan-2-yl)]pyridazin-3-yl |
| 2242 | 4-CH$_3$, 6-[OCH$_2$-(furan-2-yl)]pyridazin-3-yl |
| 2243 | 6-CF$_3$, 4-[OCH$_2$-(furan-2-yl)]pyridazin-3-yl |
| 2244 | 4-CF$_3$, 6-[OCH$_2$-(furan-2-yl)]pyridazin-3-yl |
| 2245 | 4-[OCH$_2$-(furan-3-yl)]pyridazin-3-yl |
| 2246 | 6-[OCH$_2$-(furan-3-yl)]pyridazin-3-yl |
| 2247 | 6-F, 4-[OCH$_2$-(furan-3-yl)]pyridazin-3-yl |
| 2248 | 4-F, 6-[OCH$_2$-(furan-3-yl)]pyridazin-3-yl |
| 2249 | 6-CH$_3$, 4-[OCH$_2$-(furan-3-yl)]pyridazin-1-yl |
| 2250 | 4-CH$_3$, 6-[OCH$_2$-(furan-3-yl)]pyridazin-1-yl |
| 2251 | 6-CF$_3$, 4-[OCH$_2$-(furan-3-yl)]pyridazin-1-yl |
| 2252 | 4-CF$_3$, 6-[OCH$_2$-(furan-3-yl)]pyridazin-1-yl |
| 2253 | 4-[OCH$_2$-(tetrahydrofuran-3-yl)]pyridazin-3-yl |
| 2254 | 6-[OCH$_2$-(tetrahydrofuran-3-yl)]pyridazin-3-yl |
| 2255 | 6-F, 4-[OCH$_2$-(tetrahydrofuran-3-yl)]pyridazin-3-yl |
| 2256 | 4-F, 6-[OCH$_2$-(tetrahydrofuran-3-yl)]pyridazin-3-yl |
| 2257 | 6-CH$_3$, 4-[OCH$_2$-(tetrahydrofuran-3-yl)]pyridazin-3-yl |
| 2258 | 4-CH$_3$, 6-[OCH$_2$-(tetrahydrofuran-3-yl)]pyridazin-3-yl |
| 2259 | 6-CF$_3$, 4-[OCH$_2$-(tetrahydrofuran-3-yl)]pyridazin-3-yl |
| 2260 | 4-CF$_3$, 6-[OCH$_2$-(tetrahydrofuran-3-yl)]pyridazin-3-yl |
| 2261 | 4-[OCH$_2$-(tetrahydrofuran-2-yl)]pyridazin-3-yl |
| 2262 | 6-[OCH$_2$-(tetrahydrofuran-2-yl)]pyridazin-3-yl |
| 2263 | 6-F, 4-[OCH$_2$-(tetrahydrofuran-2-yl)]pyridazin-3-yl |
| 2264 | 4-F, 6-[OCH$_2$-(tetrahydrofuran-2-yl)]pyridazin-3-yl |
| 2265 | 6-CH$_3$, 4-[OCH$_2$-(tetrahydrofuran-2-yl)]pyridazin-3-yl |
| 2266 | 4-CH$_3$, 6-[OCH$_2$-(tetrahydrofuran-2-yl)]pyridazin-3-yl |
| 2267 | 6-CF$_3$, 4-[OCH$_2$-(tetrahydrofuran-2-yl)]pyridazin-3-yl |
| 2268 | 4-CF$_3$, 6-[OCH$_2$-(tetrahydrofuran-2-yl)]pyridazin-3-yl |
| 2269 | 4-[O-(tetrahydropyran-4-yl)]pyridazin-3-yl |
| 2270 | 6-[O-(tetrahydropyran-4-yl)]pyridazin-3-yl |
| 2271 | 6-F, 4-[O-(tetrahydropyran-4-yl)]pyridazin-3-yl |
| 2272 | 4-F, 6-[O-(tetrahydropyran-4-yl)]pyridazin-3-yl |
| 2273 | 6-CH$_3$, 4-[O-(tetrahydropyran-4-yl)]pyridazin-3-yl |
| 2274 | 4-CH$_3$, 6-[O-(tetrahydropyran-4-yl)]pyridazin-3-yl |
| 2275 | 6-CF$_3$, 4-[O-(tetrahydropyran-4-yl)]pyridazin-3-yl |
| 2276 | 4-CF$_3$, 6-[O-(tetrahydropyran-4-yl)]pyridazin-3-yl |

TABLE A-continued

| No. | R⁴ |
|---|---|
| 2277 | 4-[2-Cl—C₅H₄]pyridazin-3-yl |
| 2278 | 6-[2-Cl—C₅H₄]pyridazin-3-yl |
| 2279 | 6-F, 4-[2-Cl—C₅H₄]pyridazin-3-yl |
| 2280 | 4-F, 6-[2-Cl—C₅H₄]pyridazin-3-yl |
| 2281 | 6-CH₃, 4-[2-Cl—C₅H₄]pyridazin-3-yl |
| 2282 | 4-CH₃, 6-[2-Cl—C₅H₄]pyridazin-3-yl |
| 2283 | 6-CF₃, 4-[2-Cl—C₅H₄]pyridazin-3-yl |
| 2284 | 4-CF₃, 6-[2-Cl—C₅H₄]pyridazin-3-yl |
| 2285 | 4-[OCH₂-(pyridin-2-yl)]pyridazin-3-yl |
| 2286 | 6-[OCH₂-(pyridin-2-yl)]pyridazin-3-yl |
| 2287 | 6-F, 4-[OCH₂-(pyridin-2-yl)]pyridazin-3-yl |
| 2288 | 4-F, 6-[OCH₂-(pyridin-2-yl)]pyridazin-3-yl |
| 2289 | 6-CH₃, 4-[OCH₂-(pyridin-2-yl)]pyridazin-3-yl |
| 2290 | 4-CH₃, 6-[OCH₂-(pyridin-2-yl)]pyridazin-3-yl |
| 2291 | 6-CF₃, 4-[OCH₂-(pyridin-2-yl)]pyridazin-3-yl |
| 2292 | 4-CF₃, 6-[OCH₂-(pyridin-2-yl)]pyridazin-3-yl |
| 2293 | 4-[OCH₂-(pyridin-3-yl)]pyridazin-3-yl |
| 2294 | 6-[OCH₂-(pyridin-3-yl)]pyridazin-3-yl |
| 2295 | 6-F, 4-[OCH₂-(pyridin-3-yl)]pyridazin-3-yl |
| 2296 | 4-F, 6-[OCH₂-(pyridin-3-yl)]pyridazin-3-yl |
| 2297 | 6-CH₃, 4-[OCH₂-(pyridin-3-yl)]pyridazin-3-yl |
| 2298 | 4-CH₃, 6-[OCH₂-(pyridin-3-yl)]pyridazin-3-yl |
| 2299 | 6-CF₃, 4-[OCH₂-(pyridin-3-yl)]pyridazin-3-yl |
| 2300 | 4-CF₃, 6-[OCH₂-(pyridin-3-yl)]pyridazin-3-yl |
| 2301 | 4-[morpholin-4-yl]pyridazin-3-yl |
| 2302 | 6-[morpholin-4-yl]pyridazin-3-yl |
| 2303 | 4-[1-CH₃-imidazol-2-yl]pyridazin-3-yl |
| 2304 | 6-[1-CH₃-imidazol-2-yl]pyridazin-3-yl |
| 2305 | 6-F, 4-[1-CH₃-imidazol-2-yl]pyridazin-3-yl |
| 2306 | 4-F, 6-[1-CH₃-imidazol-2-yl]pyridazin-3-yl |
| 2307 | 6-CH₃, 4-[1-CH₃-imidazol-2-yl]pyridazin-1-yl |
| 2308 | 4-CH₃, 6-[1-CH₃-imidazol-2-yl]pyridazin-1-yl |
| 2309 | 6-CF₃, 4-[1-CH₃-imidazol-2-yl]pyridazin-1-yl |
| 2310 | 4-CF₃, 6-[1-CH₃-imidazol-2-yl]pyridazin-1-yl |
| 2311 | 4-[1,2,4-triazol-1-yl]pyridazin-3-yl |
| 2312 | 6-[1,2,4-triazol-1-yl]pyridazin-3-yl |
| 2313 | 6-F, 4-[1,2,4-triazol-1-yl]pyridazin-3-yl |
| 2314 | 4-F, 6-[1,2,4-triazol-1-yl]pyridazin-3-yl |
| 2315 | 6-CH₃, 4-[1,2,4-triazol-1-yl]pyridazin-1-yl |
| 2316 | 4-CH₃, 6-[1,2,4-triazol-1-yl]pyridazin-1-yl |
| 2317 | 6-CF₃, 4-[1,2,4-triazol-1-yl]pyridazin-1-yl |
| 2318 | 4-CF₃, 6-[1,2,4-triazol-1-yl]pyridazin-1-yl |
| 2319 | 4,6-Cl₂-pyridazin-3-yl |
| 2320 | 4,5-Cl₂-pyridazin-3-yl |
| 2321 | 4,6-(CH₃)₂-pyridazin-3-yl |
| 2322 | 4,5-(CH₃)₂-pyridazin-3-yl |
| 2323 | 4,6-(OCH₃)₂-pyridazin-3-yl |
| 2324 | 4,5-(OCH₃)₂-pyridazin-3-yl |
| 2325 | 4,6-(OCH₂CH₃)₂-pyridazin-3-yl |
| 2326 | 4,5-(OCH₂CH₃)₂-pyridazin-3-yl |
| 2327 | 4-F, 6-CH₃-pyridazin-3-yl |
| 2328 | 4-F, 5-CH₃-pyridazin-3-yl |
| 2329 | 6-F, 4-CH₃-pyridazin-3-yl |
| 2330 | 5-F, 4-CH₃-pyridazin-3-yl |
| 2331 | 4-F, 6-OCH₃-pyridazin-3-yl |
| 2332 | 4-F, 5-OCH₃-pyridazin-3-yl |
| 2333 | 6-F, 4-OCH₃-pyridazin-3-yl |
| 2334 | 5-F, 4-OCH₃-pyridazin-3-yl |
| 2335 | 4-F, 6-OCH₂CH₃-pyridazin-3-yl |
| 2336 | 4-F, 5-OCH₂CH₃-pyridazin-3-yl |
| 2337 | 6-F, 4-OCH₂CH₃-pyridazin-3-yl |
| 2338 | 5-F, 4-OCH₂CH₃-pyridazin-3-yl |
| 2339 | 4-F, 6-OCH₂CF₃-pyridazin-3-yl |
| 2340 | 4-F, 5-OCH₂CF₃-pyridazin-3-yl |
| 2341 | 6-F, 4-OCH₂CF₃-pyridazin-3-yl |
| 2342 | 5-F, 4-OCH₂CF₃-pyridazin-3-yl |
| 2343 | 4-F, 6-OCH(CH₃)₂-pyridazin-3-yl |
| 2344 | 4-F, 5-OCH(CH₃)₂-pyridazin-3-yl |
| 2345 | 6-F, 4-OCH(CH₃)₂-pyridazin-3-yl |
| 2346 | 5-F, 4-OCH(CH₃)₂-pyridazin-3-yl |
| 2347 | 4-Cl, 6-CH₃-pyridazin-3-yl |
| 2348 | 4-Cl, 5-CH₃-pyridazin-3-yl |
| 2349 | 6-Cl, 4-CH₃-pyridazin-3-yl |
| 2350 | 5-Cl, 4-CH₃-pyridazin-3-yl |
| 2351 | 4-Cl, 6-OCH₃-pyridazin-3-yl |
| 2352 | 4-Cl, 5-OCH₃-pyridazin-3-yl |
| 2353 | 6-Cl, 4-OCH₃-pyridazin-3-yl |
| 2354 | 5-Cl, 4-OCH₃-pyridazin-3-yl |
| 2355 | 4-Cl, 6-OCH₂CH₃-pyridazin-3-yl |
| 2356 | 4-Cl, 5-OCH₂CH₃-pyridazin-3-yl |
| 2357 | 6-Cl, 4-OCH₂CH₃-pyridazin-3-yl |
| 2358 | 5-Cl, 4-OCH₂CH₃-pyridazin-3-yl |
| 2359 | 4-Cl, 6-OCH₂CF₃-pyridazin-3-yl |
| 2360 | 4-Cl, 5-OCH₂CF₃-pyridazin-3-yl |
| 2361 | 6-Cl, 4-OCH₂CF₃-pyridazin-3-yl |
| 2362 | 5-Cl, 4-OCH₂CF₃-pyridazin-3-yl |
| 2363 | 4-Cl, 6-OCH(CH₃)₂-pyridazin-3-yl |
| 2364 | 4-Cl, 5-OCH(CH₃)₂-pyridazin-3-yl |
| 2365 | 6-Cl, 4-OCH(CH₃)₂-pyridazin-3-yl |
| 2366 | 5-Cl, 4-OCH(CH₃)₂-pyridazin-3-yl |
| 2367 | 4-CH₃, 6-OCH₃-pyridazin-3-yl |
| 2368 | 4-CH₃, 5-OCH₃-pyridazin-3-yl |
| 2369 | 6-CH₃, 4-OCH₃-pyridazin-3-yl |
| 2370 | 5-CH₃, 4-OCH₃-pyridazin-3-yl |
| 2371 | 5-CH₃, 4-OCH₂CH₃-pyridazin-3-yl |
| 2372 | 6-CH₃, 4-OCH₂CH₃-pyridazin-3-yl |
| 2373 | 4-CH₃, 6-OCH₂CH₃-pyridazin-3-yl |
| 2374 | 4-CH₃, 5-OCH₂CH₃-pyridazin-3-yl |
| 2375 | 4-CH₃, 6-OCH₂CF₃-pyridazin-3-yl |
| 2376 | 4-CH₃, 5-OCH₂CF₃-pyridazin-3-yl |
| 2377 | 6-CH₃, 4-OCH₂CF₃-pyridazin-3-yl |
| 2378 | 5-CH₃, 4-OCH₂CF₃-pyridazin-3-yl |
| 2379 | 4-CH₃, 6-OCH(CH₃)₂-pyridazin-3-yl |
| 2380 | 4-CH₃, 5-OCH(CH₃)₂-pyridazin-3-yl |
| 2381 | 6-CH₃, 4-OCH(CH₃)₂-pyridazin-3-yl |
| 2382 | 5-CH₃, 4-OCH(CH₃)₂-pyridazin-3-yl |
| 2383 | 4-CH₃, 6-OCH₂CH=CH₂-pyridazin-3-yl |
| 2384 | 4-CH₃, 5-OCH₂CH=CH₂-pyridazin-3-yl |
| 2385 | 6-CH₃, 4-OCH₂CH=CH₂-pyridazin-3-yl |
| 2386 | 5-CH₃, 4-OCH₂CH=CH₂-pyridazin-3-yl |
| 2387 | 4-CH₃, 6-CO₂CH₃-pyridazin-3-yl |
| 2388 | 4-CH₃, 5-CO₂CH₃-pyridazin-3-yl |
| 2389 | 4-CH₃, 6-CF₃-pyridazin-3-yl |
| 2390 | 4-CH₃, 5-CF₃-pyridazin-3-yl |
| 2391 | 6-CH₃, 4-CF₃-pyridazin-3-yl |
| 2392 | 5-CH₃, 4-CF₃-pyridazin-3-yl |
| 2393 | 4-CF₃, 6-CH₂CH₃-pyridazin-3-yl |
| 2394 | 4-CF₃, 5-CH₂CH₃-pyridazin-3-yl |
| 2395 | 6-CF₃, 4-CH₂CH₃-pyridazin-3-yl |
| 2396 | 5-CF₃, 4-CH₂CH₃-pyridazin-3-yl |
| 2397 | 4-CF₃, 6-OCH₃-pyridazin-3-yl |
| 2398 | 4-CF₃, 5-OCH₃-pyridazin-3-yl |
| 2399 | 6-CF₃, 4-OCH₃-pyridazin-3-yl |
| 2400 | 5-CF₃, 4-OCH₃-pyridazin-3-yl |
| 2401 | 4-CF₃, 6-OCH₂CH₃-pyridazin-3-yl |
| 2402 | 4-CF₃, 5-OCH₂CH₃-pyridazin-3-yl |
| 2403 | 6-CF₃, 4-OCH₂CH₃-pyridazin-3-yl |
| 2404 | 5-CF₃, 4-OCH₂CH₃-pyridazin-3-yl |
| 2405 | 4-CF₃, 6-OCH₂CF₃-pyridazin-3-yl |
| 2406 | 4-CF₃, 5-OCH₂CF₃-pyridazin-3-yl |
| 2407 | 6-CF₃, 4-OCH₂CF₃-pyridazin-3-yl |
| 2408 | 5-CF₃, 4-OCH₂CF₃-pyridazin-3-yl |
| 2409 | 4-OCH₃, 6-OCH₂CH₃-pyridazin-3-yl |
| 2410 | 4-OCH₃, 5-OCH₂CH₃-pyridazin-3-yl |
| 2411 | 6-OCH₃, 4-OCH₂CH₃-pyridazin-3-yl |
| 2412 | 5-OCH₃, 4-OCH₂CH₃-pyridazin-3-yl |
| 2413 | 4-OCH₃, 6-OCH₂CF₃-pyridazin-3-yl |
| 2414 | 4-OCH₃, 6-OCH₂CF₃-pyridazin-3-yl |
| 2415 | 6-OCH₃, 4-OCH₂CF₃-pyridazin-3-yl |
| 2416 | 5-OCH₃, 4-OCH₂CF₃-pyridazin-3-yl |
| 2417 | 4-OCH₃, 6-OCH(CH₃)pyridazin-3-yl |
| 2418 | 4-OCH₃, 5-OCH(CH₃)pyridazin-3-yl |
| 2419 | 6-OCH₃, 4-OCH(CH₃)pyridazin-3-yl |
| 2420 | 5-OCH₃, 4-OCH(CH₃)pyridazin-3-yl |
| 2421 | 4-OCH₂CH₃, 6-CH₂OCH₂CH₃-pyridazin-3-yl |
| 2422 | 4-OCH₂CH₃, 5-CH₂OCH₂CH₃-pyridazin-3-yl |
| 2423 | 6-OCH₂CH₃, 4-CH₂OCH₂CH₃-pyridazin-3-yl |
| 2424 | 5-OCH₂CH₃, 4-CH₂OCH₂CH₃-pyridazin-3-yl |
| 2425 | 4-NO₂, 6-CH₃-pyridazin-3-yl |
| 2426 | 4-NO₂, 5-CH₃-pyridazin-3-yl |
| 2427 | 6-NO₂, 4-CH₃-pyridazin-3-yl |
| 2428 | 5-NO₂, 4-CH₃-pyridazin-3-yl |
| 2429 | 4-NO₂, 6-OCH₃-pyridazin-3-yl |
| 2430 | 4-NO₂, 5-OCH₃-pyridazin-3-yl |

TABLE A-continued

| No. | R⁴ |
|---|---|
| 2431 | 6-NO₂, 4-OCH₃-pyridazin-3-yl |
| 2432 | 5-NO₂, 4-OCH₃-pyridazin-3-yl |
| 2433 | 4-NO₂, 6-OCH₂CH₃-pyridazin-3-yl |
| 2434 | 4-NO₂, 5-OCH₂CH₃-pyridazin-3-yl |
| 2435 | 6-NO₂, 4-OCH₂CH₃-pyridazin-3-yl |
| 2436 | 5-NO₂, 4-OCH₂CH₃-pyridazin-3-yl |
| 2437 | 4-NO₂, 6-OCH(CH₃)₂-pyridazin-3-yl |
| 2438 | 4-NO₂, 5-OCH(CH₃)₂-pyridazin-3-yl |
| 2439 | 6-NO₂, 4-OCH(CH₃)₂-pyridazin-3-yl |
| 2440 | 5-NO₂, 4-OCH(CH₃)₂-pyridazin-3-yl |
| 2441 | 4-NO₂, 6-OCH₂CF₃-pyridazin-3-yl |
| 2442 | 4-NO₂, 5-OCH₂CF₃-pyridazin-3-yl |
| 2443 | 6-NO₂, 4-OCH₂CF₃-pyridazin-3-yl |
| 2444 | 5-NO₂, 4-OCH₂CF₃-pyridazin-3-yl |
| 2445 | 4-CN, 6-CH₃-pyridazin-3-yl |
| 2446 | 4-CN, 5-CH₃-pyridazin-3-yl |
| 2447 | 6-CN, 4-CH₃-pyridazin-3-yl |
| 2448 | 5-CN, 4-CH₃-pyridazin-3-yl |
| 2449 | 4-CN, 6-OCH₃-pyridazin-3-yl |
| 2450 | 4-CN, 5-OCH₃-pyridazin-3-yl |
| 2451 | 6-CN, 4-OCH₃-pyridazin-3-yl |
| 2452 | 5-CN, 4-OCH₃-pyridazin-3-yl |
| 2453 | 4-CN, 6-OCH₂CH₃-pyridazin-3-yl |
| 2454 | 4-CN, 5-OCH₂CH₃-pyridazin-3-yl |
| 2455 | 6-CN, 4-OCH₂CH₃-pyridazin-3-yl |
| 2456 | 5-CN, 4-OCH₂CH₃-pyridazin-3-yl |
| 2457 | 4-CN, 6-OCH(CH₃)₂-pyridazin-3-yl |
| 2458 | 4-CN, 5-OCH(CH₃)₂-pyridazin-3-yl |
| 2459 | 6-CN, 4-OCH(CH₃)₂-pyridazin-3-yl |
| 2460 | 5-CN, 4-OCH(CH₃)₂-pyridazin-3-yl |
| 2461 | 4-CN, 6-OCH₂CF₃-pyridazin-3-yl |
| 2462 | 4-CN, 5-OCH₂CF₃-pyridazin-3-yl |
| 2463 | 6-CN, 4-OCH₂CF₃-pyridazin-3-yl |
| 2464 | 5-CN, 4-OCH₂CF₃-pyridazin-3-yl |
| 2465 | 5,6-(CH₃)₂, 4-OCH₃-pyridazin-3-yl |
| 2466 | 3-CH₃-pyridazin-4-yl |
| 2467 | 6-CH₃-pyridazin-4-yl |
| 2468 | 3-CH₂CH₃-pyridazin-4-yl |
| 2469 | 6-CH₂CH₃-pyridazin-4-yl |
| 2470 | 3-CH(CH₃)₂-pyridazin-4-yl |
| 2471 | 6-CH(CH₃)₂-pyridazin-4-yl |
| 2472 | 3-CH(CH₃)CH₂CH₃-pyridazin-4-yl |
| 2473 | 6-CH(CH₃)CH₂CH₃-pyridazin-4-yl |
| 2474 | 3-CF₃-pyridazin-4-yl |
| 2475 | 6-CF₃-pyridazin-4-yl |
| 2476 | 3-CH=CH₂-pyridazin-4-yl |
| 2477 | 6-CH=CH₂-pyridazin-4-yl |
| 2478 | 3-CH=CHCH₃-pyridazin-4-yl |
| 2479 | 6-CH=CHCH₃-pyridazin-4-yl |
| 2480 | 3-CH=CHCl-pyridazin-4-yl |
| 2481 | 6-CH=CHCl-pyridazin-4-yl |
| 2482 | 3-C≡CH-pyridazin-4-yl |
| 2483 | 6-C≡CH-pyridazin-4-yl |
| 2484 | 3-CH₂C≡CH-pyridazin-4-yl |
| 2485 | 6-CH₂C≡CH-pyridazin-4-yl |
| 2486 | 3-CH₂C≡CCH₃-pyridazin-4-yl |
| 2487 | 6-CH₂C≡CCH₃-pyridazin-4-yl |
| 2488 | 3-cyclopropyl-pyridazin-4-yl |
| 2489 | 6-cyclopropyl-pyridazin-4-yl |
| 2490 | 3-cyclopentyl-pyridazin-4-yl |
| 2491 | 6-cyclopentyl-pyridazin-4-yl |
| 2492 | 3-OCH₃-pyridazin-4-yl |
| 2493 | 6-OCH₃-pyridazin-4-yl |
| 2494 | 3-OCH₂CH₃-pyridazin-4-yl |
| 2495 | 6-OCH₂CH₃-pyridazin-4-yl |
| 2496 | 3-OCH₂CH₂CH₃-pyridazin-4-yl |
| 2497 | 6-OCH₂CH₂CH₃-pyridazin-4-yl |
| 2498 | 3-OCH(CH₃)₂-pyridazin-4-yl |
| 2499 | 6-OCH(CH₃)₂-pyridazin-4-yl |
| 2500 | 3-OCH₂CH₂CH₂CH₃-pyridazin-4-yl |
| 2501 | 6-OCH₂CH₂CH₂CH₃-pyridazin-4-yl |
| 2502 | 3-OCH(CH₃)CH₂CH₃-pyridazin-4-yl |
| 2503 | 6-OCH(CH₃)CH₂CH₃-pyridazin-4-yl |
| 2504 | 3-OCH₂CH(CH₃)₂-pyridazin-4-yl |
| 2505 | 6-OCH₂CH(CH₃)₂-pyridazin-4-yl |
| 2506 | 3-OC(CH₃)₃-pyridazin-4-yl |
| 2507 | 6-OC(CH₃)₃-pyridazin-4-yl |
| 2508 | 3-OCH(CH₃)CH₂CH₂CH₃-pyridazin-4-yl |
| 2509 | 6-OCH(CH₃)CH₂CH₂CH₃-pyridazin-4-yl |
| 2510 | 3-OCH₂OCH₃-pyridazin-4-yl |
| 2511 | 6-OCH₂OCH₃-pyridazin-4-yl |
| 2512 | 3-OCH₂OCH₂CH₃-pyridazin-4-yl |
| 2513 | 6-OCH₂OCH₂CH₃-pyridazin-4-yl |
| 2514 | 3-OCH(CH₃)OCH₃-pyridazin-4-yl |
| 2515 | 6-OCH(CH₃)OCH₃-pyridazin-4-yl |
| 2516 | 3-OCH(CH₃)OCH₂CH₃-pyridazin-4-yl |
| 2517 | 6-OCH(CH₃)OCH₂CH₃-pyridazin-4-yl |
| 2518 | 3-OCH₂CH₂OCH₃-pyridazin-4-yl |
| 2519 | 6-OCH₂CH₂OCH₃-pyridazin-4-yl |
| 2520 | 3-OCH₂CH₂OCH₂CH₃-pyridazin-4-yl |
| 2521 | 6-OCH₂CH₂OCH₂CH₃-pyridazin-4-yl |
| 2522 | 3-OCH₂CH₂OCH(CH₃)₂-pyridazin-4-yl |
| 2523 | 6-OCH₂CH₂OCH(CH₃)₂-pyridazin-4-yl |
| 2524 | 3-OCH₂CH₂SCH₃-pyridazin-4-yl |
| 2525 | 6-OCH₂CH₂SCH₃-pyridazin-4-yl |
| 2526 | 3-OCH₂CH₂SO₂CH₃-pyridazin-4-yl |
| 2527 | 6-OCH₂CH₂SO₂CH₃-pyridazin-4-yl |
| 2528 | 3-OCH₂CH₂SCH(CH₃)₂-pyridazin-4-yl |
| 2529 | 6-OCH₂CH₂SCH(CH₃)₂-pyridazin-4-yl |
| 2530 | 3-OCH₂CH₂CN-pyridazin-4-yl |
| 2531 | 6-OCH₂CH₂CN-pyridazin-4-yl |
| 2532 | 3-OCH₂CH₂SCH₂CH₂CN-pyridazin-4-yl |
| 2533 | 6-OCH₂CH₂SCH₂CH₂CN-pyridazin-4-yl |
| 2534 | 3-OCH₂CH₂OC₅H₆-pyridazin-4-yl |
| 2535 | 6-OCH₂CH₂OC₅H₆-pyridazin-4-yl |
| 2536 | 3-OCH₂CH₂OCH₂C₅H₆-pyridazin-4-yl |
| 2537 | 6-OCH₂CH₂OCH₂C₅H₆-pyridazin-4-yl |
| 2538 | 3-OCH₂CH₂N(CH₃)₂-pyridazin-4-yl |
| 2539 | 6-OCH₂CH₂N(CH₃)₂-pyridazin-4-yl |
| 2540 | 3-OCH₂CH₂CONH₂-pyridazin-4-yl |
| 2541 | 6-OCH₂CH₂CONH₂-pyridazin-4-yl |
| 2542 | 3-OCH₂CH₂CO₂CH₂CH₂CH₃-pyridazin-4-yl |
| 2543 | 6-OCH₂CH₂CO₂CH₂CH₂CH₃-pyridazin-4-yl |
| 2544 | 3-OCH(CH₃)CH₂OCH₃-pyridazin-4-yl |
| 2545 | 6-OCH(CH₃)CH₂OCH₃-pyridazin-4-yl |
| 2546 | 3-OCH(CH₃)CH₂CO₂CH₃-pyridazin-4-yl |
| 2547 | 6-OCH(CH₃)CH₂CO₂CH₃-pyridazin-4-yl |
| 2548 | 3-OCH(CH₃)CH₂CO₂CH₂CH₃-pyridazin-4-yl |
| 2549 | 6-OCH(CH₃)CH₂CO₂CH₂CH₃-pyridazin-4-yl |
| 2550 | 3-OCH₂CH(CH₃)CO₂CH₂CH₃-pyridazin-4-yl |
| 2551 | 6-OCH₂CH(CH₃)CO₂CH₂CH₃-pyridazin-4-yl |
| 2552 | 3-OCH₂C(=O)CH₃-pyridazin-4-yl |
| 2553 | 6-OCH₂C(=O)CH₃-pyridazin-4-yl |
| 2554 | 3-OCH₂C(=O)CH₂CH₃-pyridazin-4-yl |
| 2555 | 6-OCH₂C(=O)CH₂CH₃-pyridazin-4-yl |
| 2556 | 3-OCH₂CO₂CH₃-pyridazin-4-yl |
| 2557 | 6-OCH₂CO₂CH₃-pyridazin-4-yl |
| 2558 | 3-OCH₂CO₂CH₂CH₃-pyridazin-4-yl |
| 2559 | 6-OCH₂CO₂CH₂CH₃-pyridazin-4-yl |
| 2560 | 3-OCH₂C(=O)NH₂-pyridazin-4-yl |
| 2561 | 6-OCH₂C(=O)NH₂-pyridazin-4-yl |
| 2562 | 3-OCH₂C(=O)NHCH₃-pyridazin-4-yl |
| 2563 | 6-OCH₂C(=O)NHCH₃-pyridazin-4-yl |
| 2564 | 3-OCH₂C(=O)SCH₃-pyridazin-4-yl |
| 2565 | 6-OCH₂C(=O)SCH₃-pyridazin-4-yl |
| 2566 | 3-OCH(CH₃)C(=O)NH₂-pyridazin-4-yl |
| 2567 | 6-OCH(CH₃)C(=O)NH₂-pyridazin-4-yl |
| 2568 | 3-OCH(CH₃)C(=O)NHCH₃-pyridazin-4-yl |
| 2569 | 6-OCH(CH₃)C(=O)NHCH₃-pyridazin-4-yl |
| 2570 | 3-OCH(CH₃)C(=O)NHNH₂-pyridazin-4-yl |
| 2571 | 6-OCH(CH₃)C(=O)NHNH₂-pyridazin-4-yl |
| 2572 | 3-OCH(CH₃)CO₂CH₃-pyridazin-4-yl |
| 2573 | 6-OCH(CH₃)CO₂CH₃-pyridazin-4-yl |
| 2574 | 3-OCH(CH₃)CO₂CH₂CH₃-pyridazin-4-yl |
| 2575 | 6-OCH(CH₃)CO₂CH₂CH₃-pyridazin-4-yl |
| 2576 | 3-OCH(CH₃)C(=O)CH₃-pyridazin-4-yl |
| 2577 | 6-OCH(CH₃)C(=O)CH₃-pyridazin-4-yl |
| 2578 | 3-OCH(CH₃)C(=O)CH₂CH₃-pyridazin-4-yl |
| 2579 | 6-OCH(CH₃)C(=O)CH₂CH₃-pyridazin-4-yl |
| 2580 | 3-OCH(CH₃)CH₂C(=O)CH₃-pyridazin-4-yl |
| 2581 | 6-OCH(CH₃)CH₂C(=O)CH₃-pyridazin-4-yl |
| 2582 | 3-OCH(CH₃)CH₂OC(CH₃)₃-pyridazin-4-yl |
| 2583 | 6-OCH(CH₃)CH₂OC(CH₃)₃-pyridazin-4-yl |
| 2584 | 3-OCH(CH₃)CH₂OCH₂CH₃-pyridazin-4-yl |

TABLE A-continued

| No. | R⁴ |
|---|---|
| 2585 | 6-OCH(CH₃)CH₂OCH₂CH₃-pyridazin-4-yl |
| 2586 | 3-OCH(CH₃)CH₂O(CH₃)₂CH₃-pyridazin-4-yl |
| 2587 | 6-OCH(CH₃)CH₂O(CH₃)₂CH₃-pyridazin-4-yl |
| 2588 | 3-OCH(CH₃)CH₂OCH₂CH=CH₂-pyridazin-4-yl |
| 2589 | 6-OCH(CH₃)CH₂OCH₂CH=CH₂-pyridazin-4-yl |
| 2590 | 3-O(CH₂)₃OCH₃-pyridazin-4-yl |
| 2591 | 6-O(CH₂)₃OCH₃-pyridazin-4-yl |
| 2592 | 3-O(CH₂)₃OCH₂CH₃-pyridazin-4-yl |
| 2593 | 6-O(CH₂)₃OCH₂CH₃-pyridazin-4-yl |
| 2594 | 3-O(CH₂)₃OCH(CH₃)₂-pyridazin-4-yl |
| 2595 | 6-O(CH₂)₃OCH(CH₃)₂-pyridazin-4-yl |
| 2596 | 3-O(CH₂)₃OC₅H₆-pyridazin-4-yl |
| 2597 | 6-O(CH₂)₃OC₅H₆-pyridazin-4-yl |
| 2598 | 3-O(CH₂)₃OCH₂C₅H₆-pyridazin-4-yl |
| 2599 | 6-O(CH₂)₃OCH₂C₅H₆-pyridazin-4-yl |
| 2600 | 3-OCH(CH₂CH₃)CH₂OCH₃-pyridazin-4-yl |
| 2601 | 6-OCH(CH₂CH₃)CH₂OCH₃-pyridazin-4-yl |
| 2602 | 3-OCH(CH₂CH₃)CH₂CH₂OCH₃-pyridazin-4-yl |
| 2603 | 6-OCH(CH₂CH₃)CH₂CH₂OCH₃-pyridazin-4-yl |
| 2604 | 3-OCH(CH₂CH₃)CH₂CH₂OCH₂CH₃-pyridazin-4-yl |
| 2605 | 6-OCH(CH₂CH₃)CH₂CH₂OCH₂CH₃-pyridazin-4-yl |
| 2606 | 3-O[(CH₂)₃O]₂CH₃-pyridazin-4-yl |
| 2607 | 6-O[(CH₂)₃O]₂CH₃-pyridazin-4-yl |
| 2608 | 3-OCH₂CH(CH₃)CH₂OCH₃-pyridazin-4-yl |
| 2609 | 6-OCH₂CH(CH₃)CH₂OCH₃-pyridazin-4-yl |
| 2610 | 3-OCH₂CH(CH₃)CH₂OCH₂CH₃-pyridazin-4-yl |
| 2611 | 6-OCH₂CH(CH₃)CH₂OCH₂CH₃-pyridazin-4-yl |
| 2612 | 3-OCH(CH₂Cl)CH₂OCH₃-pyridazin-4-yl |
| 2613 | 6-OCH(CH₂Cl)CH₂OCH₃-pyridazin-4-yl |
| 2614 | 3-OCH(CH₂Cl)CH₂OCH₂CH₃-pyridazin-4-yl |
| 2615 | 6-OCH(CH₂Cl)CH₂OCH₂CH₃-pyridazin-4-yl |
| 2616 | 3-OCH(CH₂Cl)CH₂OCH(CH₃)₂-pyridazin-4-yl |
| 2617 | 6-OCH(CH₂Cl)CH₂OCH(CH₃)₂-pyridazin-4-yl |
| 2618 | 3-OCH(CH₂Cl)CH₂OCH₂CH=CH₂-pyridazin-4-yl |
| 2619 | 6-OCH(CH₂Cl)CH₂OCH₂CH=CH₂-pyridazin-4-yl |
| 2620 | 3-OCH[CH₂OCH₃]₂-pyridazin-4-yl |
| 2621 | 6-OCH[CH₂OCH₃]₂-pyridazin-4-yl |
| 2622 | 3-OCH[CH₂OCH₂CH₃]₂-pyridazin-4-yl |
| 2623 | 6-OCH[CH₂OCH₂CH₃]₂-pyridazin-4-yl |
| 2624 | 3-OCCl₃-pyridazin-4-yl |
| 2625 | 6-OCCl₃-pyridazin-4-yl |
| 2626 | 3-OCHF₂-pyridazin-4-yl |
| 2627 | 6-OCHF₂-pyridazin-4-yl |
| 2628 | 3-OCF₃-pyridazin-4-yl |
| 2629 | 6-OCF₃-pyridazin-4-yl |
| 2630 | 3-OCF₂CHF₂-pyridazin-4-yl |
| 2631 | 6-OCF₂CHF₂-pyridazin-4-yl |
| 2632 | 3-OCH₂CF₃-pyridazin-4-yl |
| 2633 | 6-OCH₂CF₃-pyridazin-4-yl |
| 2634 | 3-OCH₂CHF₂-pyridazin-4-yl |
| 2635 | 6-OCH₂CHF₂-pyridazin-4-yl |
| 2636 | 3-O(CH₂)₃F-pyridazin-4-yl |
| 2637 | 6-O(CH₂)₃F-pyridazin-4-yl |
| 2638 | 3-OCH(CH₃)CF₃-pyridazin-4-yl |
| 2639 | 6-OCH(CH₃)CF₃-pyridazin-4-yl |
| 2640 | 3-O(CH₂)₄F-pyridazin-4-yl |
| 2641 | 6-O(CH₂)₄F-pyridazin-4-yl |
| 2642 | 3-O(CH₂)₃CF₃-pyridazin-4-yl |
| 2643 | 6-O(CH₂)₃CF₃-pyridazin-4-yl |
| 2644 | 3-OCH(CH₃)CF₂CF₃-pyridazin-4-yl |
| 2645 | 6-OCH(CH₃)CF₂CF₃-pyridazin-4-yl |
| 2646 | 3-OCH(CH₃)CF₂CHF₂-pyridazin-4-yl |
| 2647 | 6-OCH(CH₃)CF₂CHF₂-pyridazin-4-yl |
| 2648 | 3-OCH₂CF₂CHFCH₃-pyridazin-4-yl |
| 2649 | 6-OCH₂CF₂CHFCH₃-pyridazin-4-yl |
| 2650 | 3-OCH₂(CF₂)₂CF₃-pyridazin-4-yl |
| 2651 | 6-OCH₂(CF₂)₂CF₃-pyridazin-4-yl |
| 2652 | 3-O(CF₂)₃CF₃-pyridazin-4-yl |
| 2653 | 6-O(CF₂)₃CF₃-pyridazin-4-yl |
| 2654 | 3-OCH₂CF₂CHF₂-pyridazin-4-yl |
| 2655 | 6-OCH₂CF₂CHF₂-pyridazin-4-yl |
| 2656 | 3-CH₂CH=CH₂-pyridazin-4-yl |
| 2657 | 6-CH₂CH=CH₂-pyridazin-4-yl |
| 2658 | 3-CH₂C(CH₃)=CH₂-pyridazin-4-yl |
| 2659 | 6-CH₂C(CH₃)=CH₂-pyridazin-4-yl |
| 2660 | 3-OCH₂CH=CHCH₃-pyridazin-4-yl |
| 2661 | 6-OCH₂CH=CHCH₃-pyridazin-4-yl |
| 2662 | 3-O(CH₂)₂CH=CH₂-pyridazin-4-yl |
| 2663 | 6-O(CH₂)₂CH=CH₂-pyridazin-4-yl |
| 2664 | 3-OCH₂C(CH₃)=CH₂-pyridazin-4-yl |
| 2665 | 6-OCH₂C(CH₃)=CH₂-pyridazin-4-yl |
| 2666 | 3-OCH(CH₃)CH=CH₂-pyridazin-4-yl |
| 2667 | 6-OCH(CH₃)CH=CH₂-pyridazin-4-yl |
| 2668 | 3-OCH₂C≡CH-pyridazin-4-yl |
| 2669 | 6-OCH₂C≡CH-pyridazin-4-yl |
| 2670 | 3-OCH₂C≡CCH₃-pyridazin-4-yl |
| 2671 | 6-OCH₂C≡CCH₃-pyridazin-4-yl |
| 2672 | 3-O(CH₂)₂C≡CH-pyridazin-4-yl |
| 2673 | 6-O(CH₂)₂C≡CH-pyridazin-4-yl |
| 2674 | 3-SCH₃-pyridazin-4-yl |
| 2675 | 6-SCH₃-pyridazin-4-yl |
| 2676 | 3-SCH₂CH₃-pyridazin-4-yl |
| 2677 | 6-SCH₂CH₃-pyridazin-4-yl |
| 2678 | 3-OC₅H₆-pyridazin-4-yl |
| 2679 | 6-OC₅H₆-pyridazin-4-yl |
| 2680 | 3-OCH₂C₅H₆-pyridazin-4-yl |
| 2681 | 6-OCH₂C₅H₆-pyridazin-4-yl |
| 2682 | 3-NO₂-pyridazin-4-yl |
| 2683 | 6-NO₂-pyridazin-4-yl |
| 2684 | 3-NHCH₃-pyridazin-4-yl |
| 2685 | 6-NHCH₃-pyridazin-4-yl |
| 2686 | 3-N(CH₃)₂-pyridazin-4-yl |
| 2687 | 6-N(CH₃)₂-pyridazin-4-yl |
| 2688 | 3-N(CH₃)C₂H₆-pyridazin-4-yl |
| 2689 | 6-N(CH₃)C₂H₆-pyridazin-4-yl |
| 2690 | 3-NHCH₂CF₃-pyridazin-4-yl |
| 2691 | 6-NHCH₂CF₃-pyridazin-4-yl |
| 2692 | 3-F-pyridazin-4-yl |
| 2693 | 6-F-pyridazin-4-yl |
| 2694 | 3-Cl-pyridazin-4-yl |
| 2695 | 6-Cl-pyridazin-4-yl |
| 2696 | 3-OH-pyridazin-4-yl |
| 2697 | 6-OH-pyridazin-4-yl |
| 2698 | 3-CN-pyridazin-4-yl |
| 2699 | 6-CN-pyridazin-4-yl |
| 2700 | 3-C(O)NH₂-pyridazin-4-yl |
| 2701 | 6-C(O)NH₂-pyridazin-4-yl |
| 2702 | 3-C(S)NH₂-pyridazin-4-yl |
| 2703 | 6-C(S)NH₂-pyridazin-4-yl |
| 2704 | 3-CO₂CH₃-pyridazin-4-yl |
| 2705 | 6-CO₂CH₃-pyridazin-4-yl |
| 2706 | 3-ON=C(CH₃)₂-pyridazin-4-yl |
| 2707 | 6-ON=C(CH₃)₂-pyridazin-4-yl |
| 2708 | 3-[O-cyclopropyl]pyridazin-4-yl |
| 2709 | 6-[O-cyclopropyl]pyridazin-4-yl |
| 2710 | 3-[O-cyclobutyl]pyridazin-4-yl |
| 2711 | 6-[O-cyclobutyl]pyridazin-4-yl |
| 2712 | 3-[O-cyclopentyl]pyridazin-4-yl |
| 2713 | 6-[O-cyclopentyl]pyridazin-4-yl |
| 2714 | 3-[O-cyclohexyl]pyridazin-4-yl |
| 2715 | 6-[O-cyclohexyl]pyridazin-4-yl |
| 2716 | 3-[OCH₂-cyclopropyl]pyridazin-4-yl |
| 2717 | 6-[OCH₂-cyclopropyl]pyridazin-4-yl |
| 2718 | 6-F, 3-[OCH₂-cyclopropyl]pyridazin-4-yl |
| 2719 | 3-F, 6-[OCH₂-cyclopropyl]pyridazin-4-yl |
| 2720 | 6-CH₃, 3-[OCH₂-cyclopropyl]pyridazin-4-yl |
| 2721 | 3-CH₃, 6-[OCH₂-cyclopropyl]pyridazin-4-yl |
| 2722 | 6-CF₃, 3-[OCH₂-cyclopropyl]pyridazin-4-yl |
| 2723 | 3-CF₃, 6-[OCH₂-cyclopropyl]pyridazin-4-yl |
| 2724 | 3-[OCH(CH₃)-cyclopropyl]pyridazin-4-yl |
| 2725 | 6-[OCH(CH₃)-cyclopropyl]pyridazin-4-yl |
| 2726 | 6-F, 3-[OCH(CH₃)cyclopropyl]pyridazin-4-yl |
| 2727 | 3-F, 6-[OCH(CH₃)cyclopropyl]pyridazin-4-yl |
| 2728 | 6-CH₃, 3-[OCH(CH₃)cyclopropyl]pyridazin-4-yl |
| 2729 | 3-CH₃, 6-[OCH(CH₃)cyclopropyl]pyridazin-4-yl |
| 2730 | 4-CF₃, 3-[OCH(CH₃)cyclopropyl]pyridazin-4-yl |
| 2731 | 3-CF₃, 6-[OCH(CH₃)cyclopropyl]pyridazin-4-yl |
| 2732 | 3-[O-(1-CH₃-cyclopropyl)]pyridazin-4-yl |
| 2733 | 6-[O-(1-CH₃-cyclopropyl)]pyridazin-4-yl |
| 2734 | 6-F, 3-[O-(1-CH₃-cyclopropyl)]pyridazin-4-yl |
| 2735 | 3-F, 6-[O-(1-CH₃-cyclopropyl)]pyridazin-4-yl |
| 2736 | 6-CH₃, 3-[O-(1-CH₃-cyclopropyl)]pyridazin-4-yl |
| 2737 | 3-CH₃, 6-[O-(1-CH₃-cyclopropyl)]pyridazin-4-yl |
| 2738 | 6-CF₃, 3-[O-(1-CH₃-cyclopropyl)]pyridazin-4-yl |

TABLE A-continued

| No. | R⁴ |
|---|---|
| 2739 | 3-CF₃, 6-[O-(1-CH₃-cyclopropyl)]pyridazin-4-yl |
| 2740 | 3-[OCH₂-(1-CH₃-cyclopropyl)]pyridazin-4-yl |
| 2741 | 6-[OCH₂-(1-CH₃-cyclopropyl)]pyridazin-4-yl |
| 2742 | 6-F, 3-[OCH₂-(1-CH₃-cyclopropyl)]pyridazin-4-yl |
| 2743 | 6-F, 3-[OCH₂-(1-CH₃-cyclopropyl)]pyridazin-4-yl |
| 2744 | 6-CH₃, 3-[OCH₂-(1-CH₃-cyclopropyl)]pyridazin-4-yl |
| 2745 | 3-CH₃, 6-[OCH₂-(1-CH₃-cyclopropyl)]pyridazin-4-yl |
| 2746 | 6-CF₃, 3-[OCH₂-(1-CH₃-cyclopropyl)]pyridazin-4-yl |
| 2747 | 3-CF₃, 6-[OCH₂-(1-CH₃-cyclopropyl)]pyridazin-4-yl |
| 2748 | 3-[OCH₂-(2-CH₃-cyclopropyl)]pyridazin-4-yl |
| 2749 | 6-[OCH₂-(2-CH₃-cyclopropyl)]pyridazin-4-yl |
| 2750 | 6-F, 3-[OCH₂-(2-CH₃-cyclopropyl)]pyridazin-4-yl |
| 2751 | 3-F, 6-[OCH₂-(2-CH₃-cyclopropyl)]pyridazin-4-yl |
| 2752 | 6-CH₃, 3-[OCH₂-(2-CH₃-cyclopropyl)]pyridazin-4-yl |
| 2753 | 3-CH₃, 6-[OCH₂-(2-CH₃-cyclopropyl)]pyridazin-4-yl |
| 2754 | 6-CF₃, 3-[OCH₂-(2-CH₃-cyclopropyl)]pyridazin-4-yl |
| 2755 | 3-CF₃, 6-[OCH₂-(2-CH₃-cyclopropyl)]pyridazin-4-yl |
| 2756 | 3-[OCH₂-(tetrahydropyran-2-yl)]pyridazin-4-yl |
| 2757 | 6-[OCH₂-(tetrahydropyran-2-yl)]pyridazin-4-yl |
| 2758 | 6-F, 3-[OCH₂-(tetrahydropyran-2-yl)]pyridazin-4-yl |
| 2759 | 3-F, 6-[OCH₂-(tetrahydropyran-2-yl)]pyridazin-4-yl |
| 2760 | 6-CH₃, 3-[OCH₂-(tetrahydropyran-2-yl)]pyridazin-4-yl |
| 2761 | 3-CH₃, 6-[OCH₂-(tetrahydropyran-2-yl)]pyridazin-4-yl |
| 2762 | 6-CF₃, 3-[OCH₂-(tetrahydropyran-2-yl)]pyridazin-4-yl |
| 2763 | 3-CF₃, 6-[OCH₂-(tetrahydropyran-2-yl)]pyridazin-4-yl |
| 2764 | 3-[OCH₂-(furan-2-yl)]pyridazin-4-yl |
| 2765 | 6-[OCH₂-(furan-2-yl)]pyridazin-4-yl |
| 2766 | 6-F, 3-[OCH₂-(furan-2-yl)]pyridazin-4-yl |
| 2767 | 3-F, 6-[OCH₂-(furan-2-yl)]pyridazin-4-yl |
| 2768 | 6-CH₃, 3-[OCH₂-(furan-2-yl)]pyridazin-4-yl |
| 2769 | 3-CH₃, 6-[OCH₂-(furan-2-yl)]pyridazin-4-yl |
| 2770 | 6-CF₃, 3-[OCH₂-(furan-2-yl)]pyridazin-4-yl |
| 2771 | 3-CF₃, 6-[OCH₂-(furan-2-yl)]pyridazin-4-yl |
| 2772 | 3-[OCH₂-(furan-3-yl)]pyridazin-4-yl |
| 2773 | 6-[OCH₂-(furan-3-yl)]pyridazin-4-yl |
| 2774 | 6-F, 3-[OCH₂-(furan-3-yl)]pyridazin-4-yl |
| 2775 | 3-F, 3-[OCH₂-(furan-3-yl)]pyridazin-4-yl |
| 2776 | 6-CH₃, 3-[OCH₂-(furan-3-yl)]pyridazin-4-yl |
| 2777 | 3-CH₃, 6-[OCH₂-(furan-3-yl)]pyridazin-4-yl |
| 2778 | 6-CF₃, 3-[OCH₂-(furan-3-yl)]pyridazin-4-yl |
| 2779 | 3-CF₃, 6-[OCH₂-(furan-3-yl)]pyridazin-4-yl |
| 2780 | 3-[OCH₂-(tetrahydrofuran-3-yl)]pyridazin-4-yl |
| 2781 | 6-[OCH₂-(tetrahydrofuran-3-yl)]pyridazin-4-yl |
| 2782 | 6-F, 3-[OCH₂-(tetrahydrofuran-3-yl)]pyridazin-4-yl |
| 2783 | 3-F, 6-[OCH₂-(tetrahydrofuran-3-yl)]pyridazin-4-yl |
| 2784 | 6-CH₃, 3-[OCH₂-(tetrahydrofuran-3-yl)]pyridazin-4-yl |
| 2785 | 3-CH₃, 6-[OCH₂-(tetrahydrofuran-3-yl)]pyridazin-4-yl |
| 2786 | 6-CF₃, 3-[OCH₂-(tetrahydrofuran-3-yl)]pyridazin-4-yl |
| 2787 | 3-CF₃, 6-[OCH₂-(tetrahydrofuran-3-yl)]pyridazin-4-yl |
| 2788 | 3-[OCH₂-(tetrahydrofuran-2-yl)]pyridazin-4-yl |
| 2789 | 6-[OCH₂-(tetrahydrofuran-2-yl)]pyridazin-4-yl |
| 2790 | 6-F, 3-[OCH₂-(tetrahydrofuran-2-yl)]pyridazin-4-yl |
| 2791 | 3-F, 6-[OCH₂-(tetrahydrofuran-2-yl)]pyridazin-4-yl |
| 2792 | 6-CH₃, 3-[OCH₂-(tetrahydrofuran-2-yl)]pyridazin-4-yl |
| 2793 | 3-CH₃, 6-[OCH₂-(tetrahydrofuran-2-yl)]pyridazin-4-yl |
| 2794 | 6-CF₃, 3-[OCH₂-(tetrahydrofuran-2-yl)]pyridazin-4-yl |
| 2795 | 3-CF₃, 6-[OCH₂-(tetrahydrofuran-2-yl)]pyridazin-4-yl |
| 2796 | 3-[O-(tetrahydropyran-3-yl)]pyridazin-4-yl |
| 2797 | 6-[O-(tetrahydropyran-3-yl)]pyridazin-4-yl |
| 2798 | 6-F, 3-[O-(tetrahydropyran-3-yl)]pyridazin-4-yl |
| 2799 | 3-F, 6-[O-(tetrahydropyran-3-yl)]pyridazin-4-yl |
| 2800 | 6-CH₃, 3-[O-(tetrahydropyran-3-yl)]pyridazin-4-yl |
| 2801 | 3-CH₃, 3-[O-(tetrahydropyran-3-yl)]pyridazin-4-yl |
| 2802 | 6-CF₃, 3-[O-(tetrahydropyran-3-yl)]pyridazin-4-yl |
| 2803 | 3-CF₃, 6-[O-(tetrahydropyran-3-yl)]pyridazin-4-yl |
| 2804 | 3-[2-Cl—C₅H₄]pyridazin-4-yl |
| 2805 | 6-[2-Cl—C₅H₄]pyridazin-4-yl |
| 2806 | 6-F, 3-[2-Cl—C₅H₄]pyridazin-4-yl |
| 2807 | 3-F, 6-[2-Cl—C₅H₄]pyridazin-4-yl |
| 2808 | 6-CH₃, 3-[2-Cl—C₅H₄]pyridazin-4-yl |
| 2809 | 3-CH₃, 6-[2-Cl—C₅H₄]pyridazin-4-yl |
| 2810 | 6-CF₃, 3-[2-Cl—C₅H₄]pyridazin-4-yl |
| 2811 | 3-CF₃, 6-[2-Cl—C₅H₄]pyridazin-4-yl |
| 2812 | 3-[OCH₂-(pyridin-2-yl)]pyridazin-4-yl |
| 2813 | 6-[OCH₂-(pyridin-2-yl)]pyridazin-4-yl |
| 2814 | 6-F, 3-[OCH₂-(pyridin-2-yl)]pyridazin-4-yl |
| 2815 | 3-F, 6-[OCH₂-(pyridin-2-yl)]pyridazin-4-yl |
| 2816 | 6-CH₃, 3-[OCH₂-(pyridin-2-yl)]pyridazin-4-yl |
| 2817 | 3-CH₃, 6-[OCH₂-(pyridin-2-yl)]pyridazin-4-yl |
| 2818 | 6-CF₃, 3-[OCH₂-(pyridin-2-yl)]pyridazin-4-yl |
| 2819 | 3-CH₃, 6-[OCH₂-(pyridin-2-yl)]pyridazin-4-yl |
| 2820 | 3-[OCH₂-(pyridin-4-yl)]pyridazin-4-yl |
| 2821 | 6-[OCH₂-(pyridin-4-yl)]pyridazin-4-yl |
| 2822 | 6-F, 3-[OCH₂-(pyridin-4-yl)]pyridazin-4-yl |
| 2823 | 3-F, 6-[OCH₂-(pyridin-4-yl)]pyridazin-4-yl |
| 2824 | 6-CH₃, 3-[OCH₂-(pyridin-4-yl)]pyridazin-4-yl |
| 2825 | 3-CH₃, 6-[OCH₂-(pyridin-4-yl)]pyridazin-4-yl |
| 2826 | 6-CF₃, 3-[OCH₂-(pyridin-4-yl)]pyridazin-4-yl |
| 2827 | 3-CF₃, 6-[OCH₂-(pyridin-4-yl)]pyridazin-4-yl |
| 2828 | 3-[morpholin-4-yl]pyridazin-4-yl |
| 2829 | 6-[morpholin-4-yl]pyridazin-4-yl |
| 2830 | 3-[1-CH₃-imidazol-2-yl]pyridazin-4-yl |
| 2831 | 6-[1-CH₃-imidazol-2-yl]pyridazin-4-yl |
| 2832 | 6-F, 3-[1-CH₃-imidazol-2-yl]pyridazin-4-yl |
| 2833 | 3-F, 6-[1-CH₃-imidazol-2-yl]pyridazin-4-yl |
| 2834 | 6-CH₃, 3-[1-CH₃-imidazol-2-yl]pyridazin-4-yl |
| 2835 | 3-CH₃, 6-[1-CH₃-imidazol-2-yl]pyridazin-4-yl |
| 2836 | 6-CF₃, 3-[1-CH₃-imidazol-2-yl]pyridazin-4-yl |
| 2837 | 3-CF₃, 6-[1-CH₃-imidazol-2-yl]pyridazin-4-yl |
| 2838 | 3-[1,2,3-triazol-1-yl]pyridazin-4-yl |
| 2839 | 6-[1,2,3-triazol-1-yl]pyridazin-4-yl |
| 2840 | 6-F, 3-[1,2,3-triazol-1-yl]pyridazin-4-yl |
| 2841 | 3-F, 6-[1,2,3-triazol-1-yl]pyridazin-4-yl |
| 2842 | 6-CH₃, 3-[1,2,3-triazol-1-yl]pyridazin-4-yl |
| 2843 | 3-CH₃, 3-[1,2,3-triazol-1-yl]pyridazin-4-yl |
| 2844 | 6-CF₃, 3-[1,2,3-triazol-1-yl]pyridazin-4-yl |
| 2845 | 3-CF₃, 6-[1,2,3-triazol-1-yl]pyridazin-4-yl |
| 2846 | 3,6-Cl₂-pyridazin-4-yl |
| 2847 | 3,5-Cl₂-pyridazin-4-yl |
| 2848 | 3,6-(CH₃)₂-pyridazin-4-yl |
| 2849 | 3,5-(CH₃)₂-pyridazin-4-yl |
| 2850 | 3,6-(OCH₃)₂-pyridazin-4-yl |
| 2851 | 3,5-(OCH₃)₂-pyridazin-4-yl |
| 2852 | 3,6-(OCH₂CH₃)₂-pyridazin-4-yl |
| 2853 | 3,5-(OCH₂CH₃)₂-pyridazin-4-yl |
| 2854 | 3-F, 6-CH₃-pyridazin-4-yl |
| 2855 | 3-F, 5-CH₃-pyridazin-4-yl |
| 2856 | 6-F, 3-CH₃-pyridazin-4-yl |
| 2857 | 5-F, 3-CH₃-pyridazin-4-yl |
| 2858 | 3-F, 6-OCH₃-pyridazin-4-yl |
| 2859 | 3-F, 5-OCH₃-pyridazin-4-yl |
| 2860 | 6-F, 3-OCH₃-pyridazin-4-yl |
| 2861 | 5-F, 3-OCH₃-pyridazin-4-yl |
| 2862 | 3-F, 6-OCH₂CH₃-pyridazin-4-yl |
| 2863 | 3-F, 5-OCH₂CH₃-pyridazin-4-yl |
| 2864 | 6-F, 3-OCH₂CH₃-pyridazin-4-yl |
| 2865 | 5-F, 3-OCH₂CH₃-pyridazin-4-yl |
| 2866 | 3-F, 6-OCH₂CF₃-pyridazin-4-yl |
| 2867 | 3-F, 5-OCH₂CF₃-pyridazin-4-yl |
| 2868 | 6-F, 3-OCH₂CF₃-pyridazin-4-yl |
| 2869 | 5-F, 3-OCH₂CF₃-pyridazin-4-yl |
| 2870 | 3-F, 6-OCH(CH₃)₂-pyridazin-4-yl |
| 2871 | 3-F, 5-OCH(CH₃)₂-pyridazin-4-yl |
| 2872 | 6-F, 3-OCH(CH₃)₂-pyridazin-4-yl |
| 2873 | 5-F, 3-OCH(CH₃)₂-pyridazin-4-yl |
| 2874 | 3-Cl, 6-CH₃-pyridazin-4-yl |
| 2875 | 3-Cl, 5-CH₃-pyridazin-4-yl |
| 2876 | 6-Cl, 3-CH₃-pyridazin-4-yl |
| 2877 | 5-Cl, 3-CH₃-pyridazin-4-yl |
| 2878 | 3-Cl, 6-OCH₃-pyridazin-4-yl |
| 2879 | 3-Cl, 5-OCH₃-pyridazin-4-yl |
| 2880 | 6-Cl, 3-OCH₃-pyridazin-4-yl |
| 2881 | 5-Cl, 3-OCH₃-pyridazin-4-yl |
| 2882 | 3-Cl, 6-OCH₂CH₃-pyridazin-4-yl |
| 2883 | 3-Cl, 5-OCH₂CH₃-pyridazin-4-yl |
| 2884 | 6-Cl, 6-OCH₃CH₃-pyridazin-4-yl |
| 2885 | 5-Cl, 3-OCH₂CH₃-pyridazin-4-yl |
| 2886 | 3-Cl, 6-OCH₂CF₃-pyridazin-4-yl |
| 2887 | 3-Cl, 5-OCH₂CF₃-pyridazin-4-yl |
| 2888 | 6-Cl, 3-OCH₂CF₃-pyridazin-4-yl |
| 2889 | 5-Cl, 3-OCH₂CF₃-pyridazin-4-yl |
| 2890 | 3-Cl, 6-OCH(CH₃)₂-pyridazin-4-yl |
| 2891 | 3-Cl, 5-OCH(CH₃)₂-pyridazin-4-yl |
| 2892 | 6-Cl, 3-OCH(CH₃)₂-pyridazin-4-yl |

TABLE A-continued

| No. | R⁴ |
|---|---|
| 2893 | 5-Cl, 3-OCH(CH₃)₂-pyridazin-4-yl |
| 2894 | 3-CH₃, 6-OCH₃-pyridazin-4-yl |
| 2895 | 3-CH₃, 5-OCH₃-pyridazin-4-yl |
| 2896 | 6-CH₃, 3-OCH₃-pyridazin-4-yl |
| 2897 | 5-CH₃, 3-OCH₃-pyridazin-4-yl |
| 2898 | 3-CH₃, 6-OCH₂CH₃-pyridazin-4-yl |
| 2899 | 6-CH₃, 3-OCH₂CH₃-pyridazin-4-yl |
| 2900 | 3-CH₃, 6-OCH₂CH₃-pyridazin-4-yl |
| 2901 | 3-CH₃, 5-OCH₂CH₃-pyridazin-4-yl |
| 2902 | 3-CH₃, 6-OCH₂CF₃-pyridazin-4-yl |
| 2903 | 3-CH₃, 5-OCH₂CF₃-pyridazin-4-yl |
| 2904 | 6-CH₃, 3-OCH₂CF₃-pyridazin-4-yl |
| 2905 | 5-CH₃, 3-OCH₂CF₃-pyridazin-4-yl |
| 2906 | 3-CH₃, 6-OCH(CH₃)₂-pyridazin-4-yl |
| 2907 | 3-CH₃, 6-OCH(CH₃)₂-pyridazin-4-yl |
| 2908 | 6-CH₃, 3-OCH(CH₃)₂-pyridazin-4-yl |
| 2909 | 5-CH₃, 3-OCH(CH₃)₂-pyridazin-4-yl |
| 2910 | 3-CH₃, 6-OCH₂CH=CH₂-pyridazin-4-yl |
| 2911 | 3-CH₃, 5-OCH(CH₃)₂-pyridazin-4-yl |
| 2912 | 6-CH₃, 3-OCH(CH₃)₂-pyridazin-4-yl |
| 2913 | 5-CH₃, 3-OCH(CH₃)₂-pyridazin-4-yl |
| 2914 | 3-CH₃, 6-CO₂CH₃-pyridazin-4-yl |
| 2915 | 3-CH₃, 5-CO₂CH₃-pyridazin-4-yl |
| 2916 | 3-CH₃, 6-CF₃-pyridazin-4-yl |
| 2917 | 3-CH₃, 5-CF₃-pyridazin-4-yl |
| 2918 | 6-CH₃, 3-CF₃-pyridazin-4-yl |
| 2919 | 5-CH₃, 3-CF₃-pyridazin-4-yl |
| 2920 | 3-CF₃, 6-CH₂CH₃-pyridazin-4-yl |
| 2921 | 3-CF₃, 5-CH₂CH₃-pyridazin-4-yl |
| 2922 | 6-CF₃, 3-CH₂CH₃-pyridazin-4-yl |
| 2923 | 5-CF₃, 3-CH₂CH₃-pyridazin-4-yl |
| 2924 | 3-CF₃, 6-OCH₃-pyridazin-4-yl |
| 2925 | 3-CF₃, 5-OCH₃-pyridazin-4-yl |
| 2926 | 6-CF₃, 3-OCH₃-pyridazin-4-yl |
| 2927 | 5-CF₃, 3-OCH₃-pyridazin-4-yl |
| 2928 | 3-CF₃, 3-OCH₂CH₃-pyridazin-4-yl |
| 2929 | 3-CF₃, 5-OCH₂CH₃-pyridazin-4-yl |
| 2930 | 6-CF₃, 3-OCH₂CH₃-pyridazin-4-yl |
| 2931 | 5-CF₃, 3-OCH₂CH₃-pyridazin-4-yl |
| 2932 | 3-CF₃, 6-OCH₂CF₃-pyridazin-4-yl |
| 2933 | 3-CF₃, 5-OCH₂CF₃-pyridazin-4-yl |
| 2934 | 6-CF₃, 3-OCH₂CH₃-pyridazin-4-yl |
| 2935 | 5-CF₃, 3-OCH₂CH₃-pyridazin-4-yl |
| 2936 | 3-OCH₃, 6-OCH₂CH₃-pyridazin-4-yl |
| 2937 | 3-OCH₃, 5-OCH₂CH₃-pyridazin-4-yl |
| 2938 | 6-OCH₃, 3-OCH₂CH₃-pyridazin-4-yl |
| 2939 | 5-OCH₃, 3-OCH₂CH₃-pyridazin-4-yl |
| 2940 | 3-OCH₃, 6-OCH₂CF₃-pyridazin-4-yl |
| 2941 | 3-OCH₃, 5-OCH₂CF₃-pyridazin-4-yl |
| 2942 | 6-OCH₃, 3-OCH₂CF₃-pyridazin-4-yl |
| 2943 | 5-OCH₃, 3-OCH₂CF₃-pyridazin-4-yl |
| 2944 | 3-OCH₃, 6-OCH(CH₃)-pyridazin-4-yl |
| 2945 | 3-OCH₃, 5-OCH(CH₃)-pyridazin-4-yl |
| 2946 | 6-OCH₃, 3-OCH(CH₃)-pyridazin-4-yl |
| 2947 | 5-OCH₃, 3-OCH(CH₃)-pyridazin-4-yl |
| 2948 | 3-OCH₂CH₃, 6-CH₂OCH₂CH₃-pyridazin-4-yl |
| 2949 | 3-OCH₂CH₃, 5-CH₂OCH₂CH₃-pyridazin-4-yl |
| 2950 | 6-OCH₂CH₃, 3-CH₂OCH₂CH₃-pyridazin-4-yl |
| 2951 | 5-OCH₂CH₃, 3-CH₂OCH₂CH₃-pyridazin-4-yl |
| 2952 | 3-NO₂, 6-CH₃-pyridazin-4-yl |
| 2953 | 3-NO₂, 5-CH₃-pyridazin-4-yl |
| 2954 | 6-NO₂, 3-CH₃-pyridazin-4-yl |
| 2955 | 5-NO₂, 3-CH₃-pyridazin-4-yl |
| 2956 | 3-NO₂, 6-OCH₃-pyridazin-4-yl |
| 2957 | 3-NO₂, 5-OCH₃-pyridazin-4-yl |
| 2958 | 6-NO₂, 3-OCH₃-pyridazin-4-yl |
| 2959 | 5-NO₂, 3-OCH₃-pyridazin-4-yl |
| 2960 | 3-NO₂, 6-OCH₂CH₃-pyridazin-4-yl |
| 2961 | 3-NO₂, 5-OCH₂CH₃-pyridazin-4-yl |
| 2962 | 6-NO₂, 3-OCH₂CH₃-pyridazin-4-yl |
| 2963 | 5-NO₂, 6-OCH₂CH₃-pyridazin-4-yl |
| 2964 | 6-NO₂, 3-OCH(CH₃)₂-pyridazin-4-yl |
| 2965 | 3-NO₂, 5-OCH(CH₃)₂-pyridazin-4-yl |
| 2966 | 6-NO₂, 3-OCH(CH₃)₂-pyridazin-4-yl |
| 2967 | 5-NO₂, 3-OCH(CH₃)₂-pyridazin-4-yl |
| 2968 | 3-NO₂, 6-OCH₂CF₃-pyridazin-4-yl |
| 2969 | 3-NO₂, 5-OCH₂CF₃-pyridazin-4-yl |
| 2970 | 6-NO₂, 3-OCH₂CF₃-pyridazin-4-yl |
| 2971 | 5-NO₂, 3-OCH₂CF₃-pyridazin-4-yl |
| 2972 | 3-CN, 6-CH₃-pyridazin-4-yl |
| 2973 | 3-CN, 5-CH₃-pyridazin-4-yl |
| 2974 | 6-CN, 3-CH₃-pyridazin-4-yl |
| 2975 | 5-CN, 3-CH₃-pyridazin-4-yl |
| 2976 | 3-CN, 6-OCH₃-pyridazin-4-yl |
| 2977 | 3-CN, 5-OCH₃-pyridazin-4-yl |
| 2978 | 6-CN, 3-OCH₃-pyridazin-4-yl |
| 2979 | 5-CN, 3-OCH₃-pyridazin-4-yl |
| 2980 | 3-CN, 6-OCH₂CH₃-pyridazin-4-yl |
| 2981 | 3-CN, 5-OCH₂CH₃-pyridazin-4-yl |
| 2982 | 6-CN, 3-OCH₂CH₃-pyridazin-4-yl |
| 2983 | 5-CN, 3-OCH₂CH₃-pyridazin-4-yl |
| 2984 | 3-CN, 6-OCH(CH₃)₂-pyridazin-4-yl |
| 2985 | 3-CN, 5-OCH(CH₃)₂-pyridazin-4-yl |
| 2986 | 6-CN, 3-OCH(CH₃)₂-pyridazin-4-yl |
| 2987 | 5-CN, 3-OCH(CH₃)₂-pyridazin-4-yl |
| 2988 | 3-CN, 6-OCH₂CF₃-pyridazin-4-yl |
| 2989 | 3-CN, 5-OCH₂CF₃-pyridazin-4-yl |
| 2990 | 6-CN, 3-OCH₂CF₃-pyridazin-4-yl |
| 2991 | 5-CN, 3-OCH₂CF₃-pyridazin-4-yl |
| 2992 | 5,6-(CH₃)₂, 3-OCH₃-pyridazin-4-yl |
| 2993 | 3-CH₃-pyrazin-2-yl |
| 2994 | 6-CH₃-pyrazin-2-yl |
| 2995 | 3-CH₂CH₃-pyrazin-2-yl |
| 2996 | 6-CH₂CH₃-pyrazin-2-yl |
| 2997 | 3-CH(CH₃)₂-pyrazin-2-yl |
| 2998 | 3-CH(CH₃)₂-pyrazin-2-yl |
| 2999 | 3-CH(CH₃)CH₂CH₃-pyrazin-2-yl |
| 3000 | 6-CH(CH₃)CH₂CH₃-pyrazin-2-yl |
| 3001 | 3-CF₃-pyrazin-2-yl |
| 3002 | 6-CF₃-pyrazin-2-yl |
| 3003 | 3-CH=CH₂-pyrazin-2-yl |
| 3004 | 6-CH=CH₂-pyrazin-2-yl |
| 3005 | 3-CH=CHCH₃-pyrazin-2-yl |
| 3006 | 6-CH=CHCH₃-pyrazin-2-yl |
| 3007 | 3-CH=CHCl-pyrazin-2-yl |
| 3008 | 6-CH=CHCl-pyrazin-2-yl |
| 3009 | 3-C≡CH-pyrazin-2-yl |
| 3010 | 6-C≡CH-pyrazin-2-yl |
| 3011 | 3-CH₂C≡CH-pyrazin-2-yl |
| 3012 | 6-CH₂C≡CH-pyrazin-2-yl |
| 3013 | 3-CH₂C≡CCH₃-pyrazin-2-yl |
| 3014 | 6-CH₂C≡CCH₃-pyrazin-2-yl |
| 3015 | 3-cyclopropyl-pyrazin-2-yl |
| 3016 | 6-cyclopropyl-pyrazin-2-yl |
| 3017 | 3-cyclopentyl-pyrazin-2-yl |
| 3018 | 6-cyclopentyl-pyrazin-2-yl |
| 3019 | 3-OCH₃-pyrazin-2-yl |
| 3020 | 6-OCH₃-pyrazin-2-yl |
| 3021 | 3-OCH₂CH₃-pyrazin-2-yl |
| 3022 | 6-OCH₂CH₃-pyrazin-2-yl |
| 3023 | 3-OCH₂CH₂CH₃-pyrazin-2-yl |
| 3024 | 6-OCH₂CH₂CH₃-pyrazin-2-yl |
| 3025 | 3-OCH(CH₃)₂-pyrazin-2-yl |
| 3026 | 6-OCH(CH₃)₂-pyrazin-2-yl |
| 3027 | 3-OCH₂CH₂CH₂CH₃-pyrazin-2-yl |
| 3028 | 6-OCH₂CH₂CH₂CH₃-pyrazin-2-yl |
| 3029 | 3-OCH(CH₃)CH₂CH₃-pyrazin-2-yl |
| 3030 | 6-OCH(CH₃)CH₂CH₃-pyrazin-2-yl |
| 3031 | 3-OCH₂CH(CH₃)₂-pyrazin-2-yl |
| 3032 | 6-OCH₂CH(CH₃)₂-pyrazin-2-yl |
| 3033 | 3-OC(CH₃)₃-pyrazin-2-yl |
| 3034 | 6-OC(CH₃)₃-pyrazin-2-yl |
| 3035 | 3-OCH(CH₃)CH₂CH₂CH₃-pyrazin-2-yl |
| 3036 | 6-OCH(CH₃)CH₂CH₂CH₃-pyrazin-2-yl |
| 3037 | 3-OCH₂OCH₃-pyrazin-2-yl |
| 3038 | 6-OCH₂OCH₃-pyrazin-2-yl |
| 3039 | 3-OCH₂OCH₂CH₃-pyrazin-2-yl |
| 3040 | 6-OCH₂OCH₂CH₃-pyrazin-2-yl |
| 3041 | 3-OCH(CH₃)OCH₃-pyrazin-2-yl |
| 3042 | 6-OCH(CH₃)OCH₃-pyrazin-2-yl |
| 3043 | 3-OCH(CH₃)OCH₂CH₃-pyrazin-2-yl |
| 3044 | 6-OCH(CH₃)OCH₂CH₃-pyrazin-2-yl |
| 3045 | 3-OCH₂CH₂OCH₃-pyrazin-2-yl |
| 3046 | 6-OCH₂CH₂OCH₃-pyrazin-2-yl |

TABLE A-continued

| No. | R⁴ |
|---|---|
| 3047 | 3-OCH₂CH₂OCH₂CH₃-pyrazin-2-yl |
| 3048 | 6-OCH₂CH₂OCH₂CH₃-pyrazin-2-yl |
| 3049 | 3-OCH₂CH₂OCH(CH₃)₂-pyrazin-2-yl |
| 3050 | 6-OCH₂CH₂OCH(CH₃)₂-pyrazin-2-yl |
| 3051 | 3-OCH₂CH₂SCH₃-pyrazin-2-yl |
| 3052 | 6-OCH₂CH₂SCH₃-pyrazin-2-yl |
| 3053 | 3-OCH₂CH₂SO₂CH₃-pyrazin-2-yl |
| 3054 | 6-OCH₂CH₂SO₂CH₃-pyrazin-2-yl |
| 3055 | 3-OCH₂CH₂SCH(CH₃)₂-pyrazin-2-yl |
| 3056 | 6-OCH₂CH₂SCH(CH₃)₂-pyrazin-2-yl |
| 3057 | 3-OCH₂CH₂CN-pyrazin-2-yl |
| 3058 | 6-OCH₂CH₂CN-pyrazin-2-yl |
| 3059 | 3-OCH₂CH₂SCH₂CH₂CN-pyrazin-2-yl |
| 3060 | 6-OCH₂CH₂SCH₂CH₂CN-pyrazin-2-yl |
| 3061 | 3-OCH₂CH₂OC₅H₆-pyrazin-2-yl |
| 3062 | 6-OCH₂CH₂OC₅H₆-pyrazin-2-yl |
| 3063 | 3-OCH₂CH₂OCH₂C₅H₆-pyrazin-2-yl |
| 3064 | 6-OCH₂CH₂OCH₂C₅H₆-pyrazin-2-yl |
| 3065 | 3-OCH₂CH₂N(CH₃)₂-pyrazin-2-yl |
| 3066 | 6-OCH₂CH₂N(CH₃)₂-pyrazin-2-yl |
| 3067 | 3-OCH₂CH₂CONH₂-pyrazin-2-yl |
| 3068 | 6-OCH₂CH₂CONH₂-pyrazin-2-yl |
| 3069 | 3-OCH₂CH₂CO₂CH₂CH₂CH₃-pyrazin-2-yl |
| 3070 | 6-OCH₂CH₂CO₂CH₂CH₂CH₃-pyrazin-2-yl |
| 3071 | 3-OCH(CH₃)CH₂OCH₃-pyrazin-2-yl |
| 3072 | 6-OCH(CH₃)CH₂OCH₃-pyrazin-2-yl |
| 3073 | 3-OCH(CH₃)CH₂CO₂CH₃-pyrazin-2-yl |
| 3074 | 6-OCH(CH₃)CH₂CO₂CH₃-pyrazin-2-yl |
| 3075 | 3-OCH(CH₃)CH₂CO₂CH₂CH₃-pyrazin-2-yl |
| 3076 | 6-OCH(CH₃)CH₂CO₂CH₂CH₃-pyrazin-2-yl |
| 3077 | 3-OCH₂CH(CH₃)CO₂CH₃-pyrazin-2-yl |
| 3078 | 6-OCH₂CH(CH₃)CO₂CH₃-pyrazin-2-yl |
| 3079 | 3-OCH₂C(=O)CH₃-pyrazin-2-yl |
| 3080 | 6-OCH₂C(=O)CH₃-pyrazin-2-yl |
| 3081 | 3-OCH₂C(=O)CH₂CH₃-pyrazin-2-yl |
| 3082 | 6-OCH₂C(=O)CH₂CH₃-pyrazin-2-yl |
| 3083 | 3-OCH₂CO₂CH₃-pyrazin-2-yl |
| 3084 | 6-OCH₂CO₂CH₃-pyrazin-2-yl |
| 3085 | 3-OCH₂CO₂CH₂CH₃-pyrazin-2-yl |
| 3086 | 6-OCH₂CO₂CH₂CH₃-pyrazin-2-yl |
| 3087 | 3-OCH₂C(=O)NH₂-pyrazin-2-yl |
| 3088 | 6-OCH₂C(=O)NH₂-pyrazin-2-yl |
| 3089 | 3-OCH₂C(=O)NHCH₃-pyrazin-2-yl |
| 3090 | 6-OCH₂C(=O)NHCH₃-pyrazin-2-yl |
| 3091 | 3-OCH₂C(=O)SCH₃-pyrazin-2-yl |
| 3092 | 6-OCH₂C(=O)SCH₃-pyrazin-2-yl |
| 3093 | 3-OCH(CH₃)C(=O)NH₂-pyrazin-2-yl |
| 3094 | 6-OCH(CH₃)C(=O)NH₂-pyrazin-2-yl |
| 3095 | 3-OCH(CH₃)C(=O)NHCH₃-pyrazin-2-yl |
| 3096 | 6-OCH(CH₃)C(=O)NHCH₃-pyrazin-2-yl |
| 3097 | 3-OCH(CH₃)C(=O)NHNH₂-pyrazin-2-yl |
| 3098 | 6-OCH(CH₃)C(=O)NHNH₂-pyrazin-2-yl |
| 3099 | 3-OCH(CH₃)CO₂CH₃-pyrazin-2-yl |
| 3100 | 6-OCH(CH₃)CO₂CH₃-pyrazin-2-yl |
| 3101 | 3-OCH(CH₃)CO₂CH₂CH₃-pyrazin-2-yl |
| 3102 | 6-OCH(CH₃)CO₂CH₂CH₃-pyrazin-2-yl |
| 3103 | 3-OCH(CH₃)C(=O)CH₃-pyrazin-2-yl |
| 3104 | 6-OCH(CH₃)C(=O)CH₃-pyrazin-2-yl |
| 3105 | 3-OCH(CH₃)C(=O)CH₂CH₃-pyrazin-2-yl |
| 3106 | 6-OCH(CH₃)C(=O)CH₂CH₃-pyrazin-2-yl |
| 3107 | 3-OCH(CH₃)CH₂C(=O)CH₃-pyrazin-2-yl |
| 3108 | 6-OCH(CH₃)CH₂C(=O)CH₃-pyrazin-2-yl |
| 3109 | 3-OCH(CH₃)CH₂OC(CH₃)₃-pyrazin-2-yl |
| 3110 | 6-OCH(CH₃)CH₂OC(CH₃)₃-pyrazin-2-yl |
| 3111 | 3-OCH(CH₃)CH₂OCH₂CH₃-pyrazin-2-yl |
| 3112 | 6-OCH(CH₃)CH₂OCH₂CH₃-pyrazin-2-yl |
| 3113 | 3-OCH(CH₃)CH₂O(CH₃)₂CH₃-pyrazin-2-yl |
| 3114 | 6-OCH(CH₃)CH₂O(CH₃)₂CH₃-pyrazin-2-yl |
| 3115 | 3-OCH(CH₃)CH₂OCH₂CH=CH₂-pyrazin-2-yl |
| 3116 | 6-OCH(CH₃)CH₂OCH₂CH=CH₂-pyrazin-2-yl |
| 3117 | 3-O(CH₂)₃OCH₃-pyrazin-2-yl |
| 3118 | 6-O(CH₂)₃OCH₃-pyrazin-2-yl |
| 3119 | 3-O(CH₂)₃OCH₂CH₃-pyrazin-2-yl |
| 3120 | 6-O(CH₂)₃OCH₂CH₃-pyrazin-2-yl |
| 3121 | 3-O(CH₂)₃OCH(CH₃)₂-pyrazin-2-yl |
| 3122 | 6-O(CH₂)₃OCH(CH₃)₂-pyrazin-2-yl |
| 3123 | 3-O(CH₂)₃OC₅H₆-pyrazin-2-yl |
| 3124 | 6-O(CH₂)₃OC₅H₆-pyrazin-2-yl |
| 3125 | 3-O(CH₂)₃OCH₂C₅H₆-pyrazin-2-yl |
| 3126 | 6-O(CH₂)₃OCH₂C₅H₆-pyrazin-2-yl |
| 3127 | 3-OCH(CH₂CH₃)CH₂OCH₃-pyrazin-2-yl |
| 3128 | 6-OCH(CH₂CH₃)CH₂OCH₃-pyrazin-2-yl |
| 3129 | 3-OCH(CH₂CH₃)CH₂CH₂OCH₃-pyrazin-2-yl |
| 3130 | 6-OCH(CH₂CH₃)CH₂CH₂OCH₃-pyrazin-2-yl |
| 3131 | 3-OCH(CH₂CH₃)CH₂CH₂OCH₂CH₃-pyrazin-2-yl |
| 3132 | 6-OCH(CH₂CH₃)CH₂CH₂OCH₂CH₃-pyrazin-2-yl |
| 3133 | 3-O[(CH₂)₃O]₂CH₃-pyrazin-2-yl |
| 3134 | 6-O[(CH₂)₃O]₂CH₃-pyrazin-2-yl |
| 3135 | 3-OCH₂CH(CH₃)CH₂OCH₃-pyrazin-2-yl |
| 3136 | 6-OCH₂CH(CH₃)CH₂OCH₃-pyrazin-2-yl |
| 3137 | 3-OCH₂CH(CH₃)CH₂OCH₂CH₃-pyrazin-2-yl |
| 3138 | 6-OCH₂CH(CH₃)CH₂OCH₂CH₃-pyrazin-2-yl |
| 3139 | 3-OCH(CH₂Cl)CH₂OCH₃-pyrazin-2-yl |
| 3140 | 6-OCH(CH₂Cl)CH₂OCH₃-pyrazin-2-yl |
| 3141 | 3-OCH(CH₂Cl)CH₂OCH₂CH₃-pyrazin-2-yl |
| 3142 | 6-OCH(CH₂Cl)CH₂OCH₂CH₃-pyrazin-2-yl |
| 3143 | 3-OCH(CH₂Cl)CH₂OCH(CH₃)₂-pyrazin-2-yl |
| 3144 | 6-OCH(CH₂Cl)CH₂OCH(CH₃)₂-pyrazin-2-yl |
| 3145 | 3-OCH(CH₂Cl)CH₂OCH₂CH=CH₂-pyrazin-2-yl |
| 3146 | 6-OCH(CH₂Cl)CH₂OCH₂CH=CH₂-pyrazin-2-yl |
| 3147 | 3-OCH[CH₂OCH₃]₂-pyrazin-2-yl |
| 3148 | 6-OCH[CH₂OCH₃]₂-pyrazin-2-yl |
| 3149 | 3-OCH[CH₂OCH₂CH₃]₂-pyrazin-2-yl |
| 3150 | 6-OCH[CH₂OCH₂CH₃]₂-pyrazin-2-yl |
| 3151 | 3-OCCl₃-pyrazin-2-yl |
| 3152 | 6-OCCl₃-pyrazin-2-yl |
| 3153 | 3-OCHF₂-pyrazin-2-yl |
| 3154 | 6-OCHF₂-pyrazin-2-yl |
| 3155 | 3-OCF₃-pyrazin-2-yl |
| 3156 | 6-OCF₃-pyrazin-2-yl |
| 3157 | 3-OCF₂CHF₂-pyrazin-2-yl |
| 3158 | 6-OCF₂CHF₂-pyrazin-2-yl |
| 3159 | 3-OCH₂CF₃-pyrazin-2-yl |
| 3160 | 6-OCH₂CF₃-pyrazin-2-yl |
| 3161 | 3-OCH₂CHF₂-pyrazin-2-yl |
| 3162 | 6-OCH₂CHF₂-pyrazin-2-yl |
| 3163 | 3-O(CH₂)₃F-pyrazin-2-yl |
| 3164 | 6-O(CH₂)₃F-pyrazin-2-yl |
| 3165 | 3-OCH(CH₃)CF₃-pyrazin-2-yl |
| 3166 | 6-OCH(CH₃)CF₃-pyrazin-2-yl |
| 3167 | 3-O(CH₂)₄F-pyrazin-2-yl |
| 3168 | 6-O(CH₂)₄F-pyrazin-2-yl |
| 3169 | 3-O(CH₂)₃CF₃-pyrazin-2-yl |
| 3170 | 6-O(CH₂)₃CF₃-pyrazin-2-yl |
| 3171 | 3-OCH(CH₃)CF₂CF₃-pyrazin-2-yl |
| 3172 | 6-OCH(CH₃)CF₂CF₃-pyrazin-2-yl |
| 3173 | 3-OCH(CH₃)CF₂CH₂-pyrazin-2-yl |
| 3174 | 6-OCH(CH₃)CF₂CH₂-pyrazin-2-yl |
| 3175 | 3-OCH₂CF₂CHFCH₃-pyrazin-2-yl |
| 3176 | 6-OCH₂CF₂CHFCH₃-pyrazin-2-yl |
| 3177 | 3-OCH₂(CF₂)₂CF₃-pyrazin-2-yl |
| 3178 | 6-OCH₂(CF₂)₂CF₃-pyrazin-2-yl |
| 3179 | 3-O(CF₂)₃CF₃-pyrazin-2-yl |
| 3180 | 6-O(CF₂)₃CF₃-pyrazin-2-yl |
| 3181 | 3-OCH₂CF₂CHF₂-pyrazin-2-yl |
| 3182 | 6-OCH₂CF₂CHF₂-pyrazin-2-yl |
| 3183 | 3-CH₂CH=CH₂-pyrazin-2-yl |
| 3184 | 6-CH₂CH=CH₂-pyrazin-2-yl |
| 3185 | 3-CH₂C(CH₃)=CH₂-pyrazin-2-yl |
| 3186 | 6-CH₂C(CH₃)=CH₂-pyrazin-2-yl |
| 3187 | 3-OCH₂CH=CHCH₃-pyrazin-2-yl |
| 3188 | 6-OCH₂CH=CHCH₃-pyrazin-2-yl |
| 3189 | 3-O(CH₂)₂CH=CH₂-pyrazin-2-yl |
| 3190 | 6-O(CH₂)₂CH=CH₂-pyrazin-2-yl |
| 3191 | 3-OCH₂C(CH₃)=CH₂-pyrazin-2-yl |
| 3192 | 6-OCH₂C(CH₃)=CH₂-pyrazin-2-yl |
| 3193 | 3-OCH(CH₃)CH=CH₂-pyrazin-2-yl |
| 3194 | 6-OCH(CH₃)CH=CH₂-pyrazin-2-yl |
| 3195 | 3-OCH₂C≡CH-pyrazin-2-yl |
| 3196 | 6-OCH₂C≡CH-pyrazin-2-yl |
| 3197 | 3-OCH₂C≡CCH₃-pyrazin-2-yl |
| 3198 | 6-OCH₂C≡CCH₃-pyrazin-2-yl |
| 3199 | 3-O(CH₂)₂C≡CH-pyrazin-2-yl |
| 3200 | 6-O(CH₂)₂C≡CH-pyrazin-2-yl |

TABLE A-continued

| No. | R⁴ |
|---|---|
| 3201 | 3-SCH₃-pyrazin-2-yl |
| 3202 | 6-SCH₃-pyrazin-2-yl |
| 3203 | 3-SCH₂CH₃-pyrazin-2-yl |
| 3204 | 6-SCH₂CH₃-pyrazin-2-yl |
| 3205 | 3-OC₅H₆-pyrazin-2-yl |
| 3206 | 6-OC₅H₆-pyrazin-2-yl |
| 3207 | 3-OCH₂C₅H₆-pyrazin-2-yl |
| 3208 | 6-OCH₂C₅H₆-pyrazin-2-yl |
| 3209 | 3-NO₂-pyrazin-2-yl |
| 3210 | 6-NO₂-pyrazin-2-yl |
| 3211 | 3-NHCH₃-pyrazin-2-yl |
| 3212 | 6-NHCH₃-pyrazin-2-yl |
| 3213 | 3-N(CH₃)₂-pyrazin-2-yl |
| 3214 | 6-N(CH₃)₂-pyrazin-2-yl |
| 3215 | 3-N(CH₃)C₂H₆-pyrazin-2-yl |
| 3216 | 6-N(CH₃)C₂H₆-pyrazin-2-yl |
| 3217 | 3-NHCH₂CF₃-pyrazin-2-yl |
| 3218 | 6-NHCH₂CF₃-pyrazin-2-yl |
| 3219 | 3-F-pyrazin-2-yl |
| 3220 | 6-F-pyrazin-2-yl |
| 3221 | 3-Cl-pyrazin-2-yl |
| 3222 | 6-Cl-pyrazin-2-yl |
| 3223 | 3-OH-pyrazin-2-yl |
| 3224 | 6-OH-pyrazin-2-yl |
| 3225 | 3-CN-pyrazin-2-yl |
| 3226 | 6-CN-pyrazin-2-yl |
| 3227 | 3-C(O)NH₂-pyrazin-2-yl |
| 3228 | 6-C(O)NH₂-pyrazin-2-yl |
| 3229 | 3-C(S)NH₂-pyrazin-2-yl |
| 3230 | 6-C(S)NH₂-pyrazin-2-yl |
| 3231 | 3-CO₂CH₃-pyrazin-2-yl |
| 3232 | 6-CO₂CH₃-pyrazin-2-yl |
| 3233 | 3-ON=C(CH₃)₂-pyrazin-2-yl |
| 3234 | 6-ON=C(CH₃)₂-pyrazin-2-yl |
| 3235 | 3-[O-cyclopropyl]pyrazin-2-yl |
| 3236 | 6-[O-cyclopropyl]pyrazin-2-yl |
| 3237 | 3-[O-cyclobutyl]pyrazin-2-yl |
| 3238 | 6-[O-cyclobutyl]pyrazin-2-yl |
| 3239 | 3-[O-cyclopentyl]pyrazin-2-yl |
| 3240 | 6-[O-cyclopentyl]pyrazin-2-yl |
| 3241 | 3-[O-cyclohexyl]pyrazin-2-yl |
| 3242 | 6-[O-cyclohexyl]pyrazin-2-yl |
| 3243 | 3-[OCH₂-cyclopropyl]pyrazin-2-yl |
| 3244 | 6-[OCH₂-cyclopropyl]pyrazin-2-yl |
| 3245 | 6-F, 3-[OCH₂-cyclopropyl]pyrazin-2-yl |
| 3246 | 3-F, 6-[OCH₂-cyclopropyl]pyrazin-2-yl |
| 3247 | 6-CH₃, 3-[OCH₂-cyclopropyl]pyrazin-2-yl |
| 3248 | 3-CH₃, 6-[OCH₂-cyclopropyl]pyrazin-2-yl |
| 3249 | 6-CH₃, 3-[OCH₂-cyclopropyl]pyrazin-2-yl |
| 3250 | 3-CH₃, 6-[OCH₂-cyclopropyl]pyrazin-2-yl |
| 3251 | 3-[OCH(CH₃)-cyclopropyl]pyrazin-2-yl |
| 3252 | 6-[OCH(CH₃)-cyclopropyl]pyrazin-2-yl |
| 3253 | 6-F, 3-[OCH(CH₃)-cyclopropyl]pyrazin-2-yl |
| 3254 | 3-F, 6-[OCH(CH₃)-cyclopropyl]pyrazin-2-yl |
| 3255 | 6-CH₃, 3-[OCH(CH₃)-cyclopropyl]pyrazin-2-yl |
| 3256 | 3-CH₃, 6-[OCH(CH₃)-cyclopropyl]pyrazin-2-yl |
| 3257 | 6-CF₃, 3-[OCH(CH₃)-cyclopropyl]pyrazin-2-yl |
| 3258 | 3-CF₃, 6-[OCH(CH₃)-cyclopropyl]pyrazin-2-yl |
| 3259 | 3-[O-(1-CH₃-cyclopropyl)]pyrazin-2-yl |
| 3260 | 6-[O-(1-CH₃-cyclopropyl)]pyrazin-2-yl |
| 3261 | 6-F, 3-[O-(1-CH₃-cyclopropyl)]pyrazin-2-yl |
| 3262 | 3-F, 6-[O-(1-CH₃-cyclopropyl)]pyrazin-2-yl |
| 3263 | 6-CH₃, 3-[O-(1-CH₃-cyclopropyl)]pyrazin-2-yl |
| 3264 | 3-CH₃, 6-[O-(1-CH₃-cyclopropyl)]pyrazin-2-yl |
| 3265 | 6-CF₃, 3-[O-(1-CH₃-cyclopropyl)]pyrazin-2-yl |
| 3266 | 3-CF₃, 6-[O-(1-CH₃-cyclopropyl)]pyrazin-2-yl |
| 3267 | 3-[OCH₂-(1-CH₃-cyclopropyl)]pyrazin-2-yl |
| 3268 | 6-[OCH₂-(1-CH₃-cyclopropyl)]pyrazin-2-yl |
| 3269 | 6-F, 3-[OCH₂-(1-CH₃-cyclopropyl)]pyrazin-2-yl |
| 3270 | 3-F, 6-[OCH₂-(1-CH₃-cyclopropyl)]pyrazin-2-yl |
| 3271 | 6-CH₃, 3-[OCH₂-(1-CH₃-cyclopropyl)]pyrazin-2-yl |
| 3272 | 3-CH₃, 6-[OCH₂-(1-CH₃-cyclopropyl)]pyrazin-2-yl |
| 3273 | 6-CF₃, 3-[OCH₂-(1-CH₃-cyclopropyl)]pyrazin-2-yl |
| 3274 | 3-CF₃, 6-[OCH₂-(1-CH₃-cyclopropyl)]pyrazin-2-yl |
| 3275 | 3-[OCH₂-(2-CH₃-cyclopropyl)]pyrazin-2-yl |
| 3276 | 6-[OCH₂-(2-CH₃-cyclopropyl)]pyrazin-2-yl |
| 3277 | 6-F, 3-[OCH₂-(2-CH₃-cyclopropyl)]pyrazin-2-yl |
| 3278 | 3-F, 6-[OCH₂-(2-CH₃-cyclopropyl)]pyrazin-2-yl |
| 3279 | 6-CH₃, 3-[OCH₂-(2-CH₃-cyclopropyl)]pyrazin-2-yl |
| 3280 | 3-CH₃, 6-[OCH₂-(2-CH₃-cyclopropyl)]pyrazin-2-yl |
| 3281 | 6-CF₃, 3-[OCH₂-(2-CH₃-cyclopropyl)]pyrazin-2-yl |
| 3282 | 3-CF₃, 6-[OCH₂-(2-CH₃-cyclopropyl)]pyrazin-2-yl |
| 3283 | 3-[OCH₂-(tetrahydropyran-2-yl)]pyrazin-2-yl |
| 3284 | 6-[OCH₂-(tetrahydropyran-2-yl)]pyrazin-2-yl |
| 3285 | 6-F, 3-[OCH₂-(tetrahydropyran-2-yl)]pyrazin-2-yl |
| 3286 | 3-F, 6-[OCH₂-(tetrahydropyran-2-yl)]pyrazin-2-yl |
| 3287 | 6-CH₃, 3-[OCH₂-(tetrahydropyran-2-yl)]pyrazin-2-yl |
| 3288 | 3-CH₃, 6-[OCH₂-(tetrahydropyran-2-yl)]pyrazin-2-yl |
| 3289 | 6-CF₃, 3-[OCH₂-(tetrahydropyran-2-yl)]pyrazin-2-yl |
| 3290 | 3-CF₃, 6-[OCH₂-(tetrahydropyran-2-yl)]pyrazin-2-yl |
| 3291 | 3-[OCH₂-(furan-2-yl)]pyrazin-2-yl |
| 3292 | 6-[OCH₂-(furan-2-yl)]pyrazin-2-yl |
| 3293 | 6-F, 3-[OCH₂-(furan-2-yl)]pyrazin-2-yl |
| 3294 | 3-F, 6-[OCH₂-(furan-2-yl)]pyrazin-2-yl |
| 3295 | 6-CH₃, 3-[OCH₂-(furan-2-yl)]pyrazin-2-yl |
| 3296 | 3-CH₃, 6-[OCH₂-(furan-2-yl)]pyrazin-2-yl |
| 3297 | 6-CF₃, 3-[OCH₂-(furan-2-yl)]pyrazin-2-yl |
| 3298 | 3-CF₃, 6-[OCH₂-(furan-2-yl)]pyrazin-2-yl |
| 3299 | 3-[OCH₂-(furan-3-yl)]pyrazin-2-yl |
| 3300 | 6-[OCH₂-(furan-3-yl)]pyrazin-2-yl |
| 3301 | 6-F, 3-[OCH₂-(furan-3-yl)]pyrazin-2-yl |
| 3302 | 3-F, 6-[OCH₂-(furan-3-yl)]pyrazin-2-yl |
| 3303 | 6-CH₃, 3-[OCH₂-(furan-3-yl)]pyrazin-2-yl |
| 3304 | 3-CH₃, 6-[OCH₂-(furan-3-yl)]pyrazin-2-yl |
| 3305 | 6-CF₃, 3-[OCH₂-(furan-3-yl)]pyrazin-2-yl |
| 3306 | 3-CF₃, 6-[OCH₂-(furan-3-yl)]pyrazin-2-yl |
| 3307 | 3-[OCH₂-(tetrahydrofuran-3-yl)]pyrazin-2-yl |
| 3308 | 6-[OCH₂-(tetrahydrofuran-3-yl)]pyrazin-2-yl |
| 3309 | 6-F, 3-[OCH₂-(tetrahydrofuran-3-yl)]pyrazin-2-yl |
| 3310 | 3-F, 6-[OCH₂-(tetrahydrofuran-3-yl)]pyrazin-2-yl |
| 3311 | 6-CH₃, 3-[OCH₂-(tetrahydrofuran-3-yl)]pyrazin-2-yl |
| 3312 | 3-CH₃, 6-[OCH₂-(tetrahydrofuran-3-yl)]pyrazin-2-yl |
| 3313 | 6-CF₃, 3-[OCH₂-(tetrahydrofuran-3-yl)]pyrazin-2-yl |
| 3314 | 3-CF₃, 6-[OCH₂-(tetrahydrofuran-3-yl)]pyrazin-2-yl |
| 3315 | 3-[OCH₂-(tetrahydrofuran-2-yl)]pyrazin-2-yl |
| 3316 | 6-[OCH₂-(tetrahydrofuran-2-yl)]pyrazin-2-yl |
| 3317 | 6-F, 3-[OCH₂-(tetrahydrofuran-2-yl)]pyrazin-2-yl |
| 3318 | 3-F, 6-[OCH₂-(tetrahydrofuran-2-yl)]pyrazin-2-yl |
| 3319 | 6-CH₃, 3-[OCH₂-(tetrahydrofuran-2-yl)]pyrazin-2-yl |
| 3320 | 3-CH₃, 6-[OCH₂-(tetrahydrofuran-2-yl)]pyrazin-2-yl |
| 3321 | 6-CF₃, 3-[OCH₂-(tetrahydrofuran-2-yl)]pyrazin-2-yl |
| 3322 | 3-CF₃, 6-[OCH₂-(tetrahydrofuran-2-yl)]pyrazin-2-yl |
| 3323 | 3-[O-(tetrahydropyran-3-yl)]pyrazin-2-yl |
| 3324 | 6-[O-(tetrahydropyran-3-yl)]pyrazin-2-yl |
| 3325 | 6-F, 3-[O-(tetrahydropyran-3-yl)]pyrazin-2-yl |
| 3326 | 3-F, 6-[O-(tetrahydropyran-3-yl)]pyrazin-2-yl |
| 3327 | 6-CH₃, 3-[O-(tetrahydropyran-3-yl)]pyrazin-2-yl |
| 3328 | 3-CH₃, 6-[O-(tetrahydropyran-3-yl)]pyrazin-2-yl |
| 3329 | 6-CF₃, 3-[O-(tetrahydropyran-3-yl)]pyrazin-2-yl |
| 3330 | 3-CF₃, 6-[O-(tetrahydropyran-3-yl)]pyrazin-2-yl |
| 3331 | 3-[2-Cl—C₅H₄]pyrazin-2-yl |
| 3332 | 6-[2-Cl—C₅H₄]pyrazin-2-yl |
| 3333 | 6-F, 3-[2-Cl—C₅H₄]pyrazin-2-yl |
| 3334 | 3-F, 6-[2-Cl—C₅H₄]pyrazin-2-yl |
| 3335 | 6-CH₃, 3-[2-Cl—C₅H₄]pyrazin-2-yl |
| 3336 | 3-CH₃, 6-[2-Cl—C₅H₄]pyrazin-2-yl |
| 3337 | 6-CF₃, 3-[2-Cl—C₅H₄]pyrazin-2-yl |
| 3338 | 3-CF₃, 6-[2-Cl—C₅H₄]pyrazin-2-yl |
| 3339 | 3-[OCH₂-(pyridin-2-yl)]pyrazin-2-yl |
| 3340 | 6-[OCH₂-(pyridin-2-yl)]pyrazin-2-yl |
| 3341 | 6-F, 3-[OCH₂-(pyridin-2-yl)]pyrazin-2-yl |
| 3342 | 3-F, 6-[OCH₂-(pyridin-2-yl)]pyrazin-2-yl |
| 3343 | 6-CH₃, 3-[OCH₂-(pyridin-2-yl)]pyrazin-2-yl |
| 3344 | 3-CH₃, 6-[OCH₂-(pyridin-2-yl)]pyrazin-2-yl |
| 3345 | 6-CF₃, 3-[OCH₂-(pyridin-2-yl)]pyrazin-2-yl |
| 3346 | 3-CF₃, 6-[OCH₂-(pyridin-2-yl)]pyrazin-2-yl |
| 3347 | 3-[OCH₂-(pyridin-4-yl)]pyrazin-2-yl |
| 3348 | 6-[OCH₂-(pyridin-4-yl)]pyrazin-2-yl |
| 3349 | 6-F, 3-[OCH₂-(pyridin-4-yl)]pyrazin-2-yl |
| 3350 | 3-F, 6-[OCH₂-(pyridin-4-yl)]pyrazin-2-yl |
| 3351 | 6-CH₃, 3-[OCH₂-(pyridin-4-yl)]pyrazin-2-yl |
| 3352 | 3-CH₃, 6-[OCH₂-(pyridin-4-yl)]pyrazin-2-yl |
| 3353 | 6-CF₃, 3-[OCH₂-(pyridin-4-yl)]pyrazin-2-yl |
| 3354 | 3-CF₃, 6-[OCH₂-(pyridin-4-yl)]pyrazin-2-yl |

TABLE A-continued

| No. | R⁴ |
|---|---|
| 3355 | 3-[morpholin-4-yl]pyrazin-2-yl |
| 3356 | 6-[morpholin-4-yl]pyrazin-2-yl |
| 3357 | 3-[1-CH$_3$-imidazol-2-yl]pyrazin-2-yl |
| 3358 | 6-[1-CH$_3$-imidazol-2-yl]pyrazin-2-yl |
| 3359 | 6-F, 3-[1-CH$_3$-imidazol-2-yl]pyrazin-2-yl |
| 3360 | 3-F, 6-[1-CH$_3$-imidazol-2-yl]pyrazin-2-yl |
| 3361 | 6-CH$_3$, 3-[1-CH$_3$-imidazol-2-yl]pyrazin-2-yl |
| 3362 | 3-CH$_3$, 6-[1-CH$_3$-imidazol-2-yl]pyrazin-2-yl |
| 3363 | 6-CF$_3$, 3-[1-CH$_3$-imidazol-2-yl]pyrazin-2-yl |
| 3364 | 3-CF$_3$, 6-[1-CH$_3$-imidazol-2-yl]pyrazin-2-yl |
| 3365 | 3-[1,2,3-triazol-1-yl]pyrazin-2-yl |
| 3366 | 6-[1,2,3-triazol-1-yl]pyrazin-2-yl |
| 3367 | 6-F, 3-[1,2,3-triazol-1-yl]pyrazin-2-yl |
| 3368 | 3-F, 3-[1,2,3-triazol-1-yl]pyrazin-2-yl |
| 3369 | 6-CH$_3$, 3-[1,2,3-triazol-1-yl]pyrazin-2-yl |
| 3370 | 3-CH$_3$, 3-[1,2,3-triazol-1-yl]pyrazin-2-yl |
| 3371 | 6-CF$_3$, 3-[1,2,3-triazol-1-yl]pyrazin-2-yl |
| 3372 | 3-CF$_3$, 6-[1,2,3-triazol-1-yl]pyrazin-2-yl |
| 3373 | 3,6-Cl$_2$-pyrazin-2-yl |
| 3374 | 3,5-Cl$_2$-pyrazin-2-yl |
| 3375 | 3,6-(CH$_3$)$_2$-pyrazin-2-yl |
| 3376 | 3,5-(CH$_3$)$_2$-pyrazin-2-yl |
| 3377 | 3,6-(OCH$_3$)$_2$-pyrazin-2-yl |
| 3378 | 3,5-(OCH$_3$)$_2$-pyrazin-2-yl |
| 3379 | 3,6-(OCH$_2$CH$_3$)$_2$-pyrazin-2-yl |
| 3380 | 3,5-(OCH$_2$CH$_3$)$_2$-pyrazin-2-yl |
| 3381 | 3-F, 6-CH$_3$-pyrazin-2-yl |
| 3382 | 3-F, 5-CH$_3$-pyrazin-2-yl |
| 3383 | 6-F, 3-CH$_3$-pyrazin-2-yl |
| 3384 | 5-F, 3-CH$_3$-pyrazin-2-yl |
| 3385 | 3-F, 6-OCH$_3$-pyrazin-2-yl |
| 3386 | 3-F, 5-OCH$_3$-pyrazin-2-yl |
| 3387 | 6-F, 3-OCH$_3$-pyrazin-2-yl |
| 3388 | 5-F, 3-OCH$_3$-pyrazin-2-yl |
| 3389 | 3-F, 6-OCH$_2$CH$_3$-pyrazin-2-yl |
| 3390 | 3-F, 5-OCH$_2$CH$_3$-pyrazin-2-yl |
| 3391 | 6-F, 3-OCH$_2$CH$_3$-pyrazin-2-yl |
| 3392 | 5-F, 3-OCH$_2$CH$_3$-pyrazin-2-yl |
| 3393 | 3-F, 6-OCH$_2$CF$_3$-pyrazin-2-yl |
| 3394 | 3-F, 5-OCH$_2$CF$_3$-pyrazin-2-yl |
| 3395 | 6-F, 3-OCH$_2$CF$_3$-pyrazin-2-yl |
| 3396 | 5-F, 3-OCH$_2$CF$_3$-pyrazin-2-yl |
| 3397 | 3-F, 6-OCH(CH$_3$)$_2$-pyrazin-2-yl |
| 3398 | 3-F, 5-OCH(CH$_3$)$_2$-pyrazin-2-yl |
| 3399 | 6-F, 3-OCH(CH$_3$)$_2$-pyrazin-2-yl |
| 3400 | 5-F, 3-OCH(CH$_3$)$_2$-pyrazin-2-yl |
| 3401 | 3-Cl, 6-CH$_3$-pyrazin-2-yl |
| 3402 | 3-Cl, 5-CH$_3$-pyrazin-2-yl |
| 3403 | 6-Cl, 3-CH$_3$-pyrazin-2-yl |
| 3404 | 5-Cl, 3-CH$_3$-pyrazin-2-yl |
| 3405 | 3-Cl, 6-OCH$_3$-pyrazin-2-yl |
| 3406 | 3-Cl, 5-OCH$_3$-pyrazin-2-yl |
| 3407 | 6-Cl, 3-OCH$_3$-pyrazin-2-yl |
| 3408 | 5-Cl, 3-OCH$_3$-pyrazin-2-yl |
| 3409 | 3-Cl, 6-OCH$_2$CH$_3$-pyrazin-2-yl |
| 3410 | 3-Cl, 5-OCH$_2$CH$_3$-pyrazin-2-yl |
| 3411 | 6-Cl, 3-OCH$_2$CH$_3$-pyrazin-2-yl |
| 3412 | 5-Cl, 3-OCH$_2$CH$_3$-pyrazin-2-yl |
| 3413 | 3-Cl, 6-OCH$_2$CF$_3$-pyrazin-2-yl |
| 3414 | 3-Cl, 5-OCH$_2$CF$_3$-pyrazin-2-yl |
| 3415 | 6-Cl, 3-OCH$_2$CF$_3$-pyrazin-2-yl |
| 3416 | 5-Cl, 3-OCH$_2$CF$_3$-pyrazin-2-yl |
| 3417 | 3-Cl, 6-OCH(CH$_3$)$_2$-pyrazin-2-yl |
| 3418 | 3-Cl, 5-OCH(CH$_3$)$_2$-pyrazin-2-yl |
| 3419 | 6-Cl, 3-OCH(CH$_3$)$_2$-pyrazin-2-yl |
| 3420 | 5-Cl, 3-OCH(CH$_3$)$_2$-pyrazin-2-yl |
| 3421 | 3-CH$_3$, 6-OCH$_3$-pyrazin-2-yl |
| 3422 | 3-CH$_3$, 5-OCH$_3$-pyrazin-2-yl |
| 3423 | 6-CH$_3$, 3-OCH$_3$-pyrazin-2-yl |
| 3424 | 5-CH$_3$, 3-OCH$_3$-pyrazin-2-yl |
| 3425 | 5-CH$_3$, 3-OCH$_2$CH$_3$-pyrazin-2-yl |
| 3426 | 6-CH$_3$, 3-OCH$_2$CH$_3$-pyrazin-2-yl |
| 3427 | 3-CH$_3$, 6-OCH$_2$CH$_3$-pyrazin-2-yl |
| 3428 | 3-CH$_3$, 5-OCH$_2$CH$_3$-pyrazin-2-yl |
| 3429 | 3-CH$_3$, 6-OCH$_2$CF$_3$-pyrazin-2-yl |
| 3430 | 3-CH$_3$, 5-OCH$_2$CF$_3$-pyrazin-2-yl |
| 3431 | 6-CH$_3$, 3-OCH$_2$CF$_3$-pyrazin-2-yl |
| 3432 | 5-CH$_3$, 3-OCH$_2$CF$_3$-pyrazin-2-yl |
| 3433 | 3-CH$_3$, 6-OCH(CH$_3$)$_2$-pyrazin-2-yl |
| 3434 | 3-CH$_3$, 6-OCH(CH$_3$)$_2$-pyrazin-2-yl |
| 3435 | 6-CH$_3$, 3-OCH(CH$_3$)$_2$-pyrazin-2-yl |
| 3436 | 5-CH$_3$, 3-OCH(CH$_3$)$_2$-pyrazin-2-yl |
| 3437 | 3-CH$_3$, 6-OCH$_2$CH=CH$_2$-pyrazin-2-yl |
| 3438 | 3-CH$_3$, 5-OCH$_2$CH=CH$_2$-pyrazin-2-yl |
| 3439 | 6-CH$_3$, 3-OCH$_2$CH=CH$_2$-pyrazin-2-yl |
| 3440 | 5-CH$_3$, 3-OCH$_2$CH=CH$_2$-pyrazin-2-yl |
| 3441 | 3-CH$_3$, 6-CO$_2$CH$_3$-pyrazin-2-yl |
| 3442 | 3-CH$_3$, 5-CO$_2$CH$_3$-pyrazin-2-yl |
| 3443 | 3-CH$_3$, 6-CF$_3$-pyrazin-2-yl |
| 3444 | 3-CH$_3$, 5-CF$_3$-pyrazin-2-yl |
| 3445 | 6-CH$_3$, 3-CF$_3$-pyrazin-2-yl |
| 3446 | 5-CH$_3$, 3-CF$_3$-pyrazin-2-yl |
| 3447 | 3-CF$_3$, 6-CH$_2$CH$_3$-pyrazin-2-yl |
| 3448 | 3-CF$_3$, 5-CH$_2$CH$_3$-pyrazin-2-yl |
| 3449 | 6-CF$_3$, 3-CH$_2$CH$_3$-pyrazin-2-yl |
| 3450 | 5-CF$_3$, 3-CH$_2$CH$_3$-pyrazin-2-yl |
| 3451 | 3-CF$_3$, 6-OCH$_3$-pyrazin-2-yl |
| 3452 | 3-CF$_3$, 5-OCH$_3$-pyrazin-2-yl |
| 3453 | 6-CF$_3$, 3-OCH$_3$-pyrazin-2-yl |
| 3454 | 5-CF$_3$, 3-OCH$_3$-pyrazin-2-yl |
| 3455 | 3-CF$_3$, 6-OCH$_2$CH$_3$-pyrazin-2-yl |
| 3456 | 3-CF$_3$, 5-OCH$_2$CH$_3$-pyrazin-2-yl |
| 3457 | 5-CF$_3$, 3-OCH$_2$CH$_3$-pyrazin-2-yl |
| 3458 | 5-CF$_3$, 3-OCH$_2$CH$_3$-pyrazin-2-yl |
| 3459 | 3-CF$_3$, 6-OCH$_2$CF$_3$-pyrazin-2-yl |
| 3460 | 3-CF$_3$, 5-OCH$_2$CF$_3$-pyrazin-2-yl |
| 3461 | 6-CF$_3$, 3-OCH$_2$CF$_3$-pyrazin-2-yl |
| 3462 | 5-CF$_3$, 3-OCH$_2$CF$_3$-pyrazin-2-yl |
| 3463 | 3-OCH$_3$, 6-OCH$_2$CH$_3$-pyrazin-2-yl |
| 3464 | 3-OCH$_3$, 5-OCH$_2$CH$_3$-pyrazin-2-yl |
| 3465 | 6-OCH$_3$, 3-OCH$_2$CH$_3$-pyrazin-2-yl |
| 3466 | 5-OCH$_3$, 3-OCH$_2$CH$_3$-pyrazin-2-yl |
| 3467 | 3-OCH$_3$, 6-OCH$_2$CF$_3$-pyrazin-2-yl |
| 3468 | 3-OCH$_3$, 5-OCH$_2$CF$_3$-pyrazin-2-yl |
| 3469 | 6-OCH$_3$, 3-OCH$_2$CF$_3$-pyrazin-2-yl |
| 3470 | 5-OCH$_3$, 3-OCH$_2$CF$_3$-pyrazin-2-yl |
| 3471 | 3-OCH$_3$, 6-OCH(CH$_3$)-pyrazin-2-yl |
| 3472 | 3-OCH$_3$, 5-OCH(CH$_3$)-pyrazin-2-yl |
| 3473 | 6-OCH$_3$, 3-OCH(CH$_3$)-pyrazin-2-yl |
| 3474 | 5-OCH$_3$, 3-OCH(CH$_3$)-pyrazin-2-yl |
| 3475 | 3-OCH$_2$CH$_3$, 6-CH$_2$OCH$_2$CH$_3$-pyrazin-2-yl |
| 3476 | 3-OCH$_2$CH$_3$, 5-CH$_2$OCH$_2$CH$_3$-pyrazin-2-yl |
| 3477 | 6-OCH$_2$CH$_3$, 3-CH$_2$OCH$_2$CH$_3$-pyrazin-2-yl |
| 3478 | 5-OCH$_2$CH$_3$, 3-CH$_2$OCH$_2$CH$_3$-pyrazin-2-yl |
| 3479 | 3-NO$_2$, 6-CH$_3$-pyrazin-2-yl |
| 3480 | 3-NO$_2$, 5-CH$_3$-pyrazin-2-yl |
| 3481 | 6-NO$_2$, 3-CH$_3$-pyrazin-2-yl |
| 3482 | 5-NO$_2$, 3-CH$_3$-pyrazin-2-yl |
| 3483 | 3-NO$_2$, 6-OCH$_3$-pyrazin-2-yl |
| 3484 | 3-NO$_2$, 5-OCH$_3$-pyrazin-2-yl |
| 3485 | 6-NO$_2$, 3-OCH$_3$-pyrazin-2-yl |
| 3486 | 5-NO$_2$, 3-OCH$_3$-pyrazin-2-yl |
| 3487 | 3-NO$_2$, 6-OCH$_2$CH$_3$-pyrazin-2-yl |
| 3488 | 3-NO$_2$, 5-OCH$_2$CH$_3$-pyrazin-2-yl |
| 3489 | 6-NO$_2$, 3-OCH$_2$CH$_3$-pyrazin-2-yl |
| 3490 | 5-NO$_2$, 3-OCH$_2$CH$_3$-pyrazin-2-yl |
| 3491 | 3-NO$_2$, 6-OCH(CH$_3$)$_2$-pyrazin-2-yl |
| 3492 | 3-NO$_2$, 5-OCH(CH$_3$)$_2$-pyrazin-2-yl |
| 3493 | 6-NO$_2$, 3-OCH(CH$_3$)$_2$-pyrazin-2-yl |
| 3494 | 5-NO$_2$, 3-OCH(CH$_3$)$_2$-pyrazin-2-yl |
| 3495 | 3-NO$_2$, 6-OCH$_2$CF$_3$-pyrazin-2-yl |
| 3496 | 3-NO$_2$, 5-OCH$_2$CF$_3$-pyrazin-2-yl |
| 3497 | 6-NO$_2$, 3-OCH$_2$CF$_3$-pyrazin-2-yl |
| 3498 | 5-NO$_2$, 3-OCH$_2$CF$_3$-pyrazin-2-yl |
| 3499 | 3-CN, 6-CH$_3$-pyrazin-2-yl |
| 3500 | 3-CN, 5-CH$_3$-pyrazin-2-yl |
| 3501 | 6-CN, 3-CH$_3$-pyrazin-2-yl |
| 3502 | 5-CN, 3-CH$_3$-pyrazin-2-yl |
| 3503 | 3-CN, 6-OCH$_3$-pyrazin-2-yl |
| 3504 | 3-CN, 5-OCH$_3$-pyrazin-2-yl |
| 3505 | 6-CN, 3-OCH$_3$-pyrazin-2-yl |
| 3506 | 5-CN, 3-OCH$_3$-pyrazin-2-yl |
| 3507 | 3-CN, 6-OCH$_2$CH$_3$-pyrazin-2-yl |
| 3508 | 3-CN, 5-OCH$_2$CH$_3$-pyrazin-2-yl |

TABLE A-continued

| No. | R⁴ |
|---|---|
| 3509 | 6-CN, 3-OCH₂CH₃-pyrazin-2-yl |
| 3510 | 5-CN, 3-OCH₂CH₃-pyrazin-2-yl |
| 3511 | 3-CN, 6-OCH(CH₃)₂-pyrazin-2-yl |
| 3512 | 3-CN, 5-OCH(CH₃)₂-pyrazin-2-yl |
| 3513 | 6-CN, 3-OCH(CH₃)₂-pyrazin-2-yl |
| 3514 | 5-CN, 3-OCH(CH₃)₂-pyrazin-2-yl |
| 3515 | 3-CN, 6-OCH₂CF₃-pyrazin-2-yl |
| 3516 | 3-CN, 5-OCH₂CF₃-pyrazin-2-yl |
| 3517 | 6-CN, 3-OCH₂CF₃-pyrazin-2-yl |
| 3518 | 5-CN, 3-OCH₂CF₃-pyrazin-2-yl |
| 3519 | 5,6-(CH₃)₂, 3-OCH₃-pyrazin-2-yl |
| 3520 | 4-CH₃-1,3,5-triazin-2-yl |
| 3521 | 4-CH₂CH₃-1,3,5-triazin-2-yl |
| 3522 | 4-CH(CH₃)₂-1,3,5-triazin-2-yl |
| 3523 | 4-CH(CH₃)CH₂CH₃-1,3,5-triazin-2-yl |
| 3524 | 4-CF₃-1,3,5-triazin-2-yl |
| 3525 | 4-CH=CH₂-1,3,5-triazin-2-yl |
| 3526 | 4-CH=CHCH₃-1,3,5-triazin-2-yl |
| 3527 | 4-CH=CHCl-1,3,5-triazin-2-yl |
| 3528 | 4-C≡CH-1,3,5-triazin-2-yl |
| 3529 | 4-CH₂C≡CH-1,3,5-triazin-2-yl |
| 3530 | 4-CH₂C≡CCH₃-1,3,5-triazin-2-yl |
| 3531 | 4-cyclopropyl-1,3,5-triazin-2-yl |
| 3532 | 4-cyclopentyl-1,3,5-triazin-2-yl |
| 3533 | 4-OCH₃-1,3,5-triazin-2-yl |
| 3534 | 4-OCH₂CH₃-1,3,5-triazin-2-yl |
| 3535 | 4-OCH₂CH₂CH₃-1,3,5-triazin-2-yl |
| 3536 | 4-OCH(CH₃)₂-1,3,5-triazin-2-yl |
| 3537 | 4-OCH₂CH₂CH₂CH₃-1,3,5-triazin-2-yl |
| 3538 | 4-OCH(CH₃)CH₂CH₃-1,3,5-triazin-2-yl |
| 3539 | 4-OCH₂CH(CH₃)₂-1,3,5-triazin-2-yl |
| 3540 | 4-OC(CH₃)₄-1,3,5-triazin-2-yl |
| 3541 | 4-OCH(CH₃)CH₂CH₂CH₃-1,3,5-triazin-2-yl |
| 3542 | 4-OCH₂OCH₃-1,3,5-triazin-2-yl |
| 3543 | 4-OCH₂OCH₂CH₃-1,3,5-triazin-2-yl |
| 3544 | 4-OCH(CH₃)OCH₃-1,3,5-triazin-2-yl |
| 3545 | 4-OCH(CH₃OCH₂CH₃-1,3,5-triazin-2-yl |
| 3546 | 4-OCH₂CH₂OCH₃-1,3,5-triazin-2-yl |
| 3547 | 4-OCH₂CH₂OCH₂CH₃-1,3,5-triazin-2-yl |
| 3548 | 4-OCH₂CH₂OCH(CH₃)₂-1,3,5-triazin-2-yl |
| 3549 | 4-OCH₂CH₂SCH₃-1,3,5-triazin-2-yl |
| 3550 | 4-OCH₂CH₂SO₂CH₃-1,3,5-triazin-2-yl |
| 3551 | 4-OCH₂CH₂SCH(CH₃)₂-1,3,5-triazin-2-yl |
| 3552 | 4-OCH₂CH₂CN-1,3,5-triazin-2-yl |
| 3553 | 4-OCH₂CH₂SCH₂CH₂CN-1,3,5-triazin-2-yl |
| 3554 | 4-OCH₂CH₂OC₆H₅-1,3,5-triazin-2-yl |
| 3555 | 4-OCH₂CH₂OCH₂C₆H₅-1,3,5-triazin-2-yl |
| 3556 | 4-OCH₂CH₂N(CH₃)₂-1,3,5-triazin-2-yl |
| 3557 | 4-OCH₂CH₂CONH₂-1,3,5-triazin-2-yl |
| 3558 | 4-OCH₂CH₂CO₂CH₂CH₂CH₃-1,3,5-triazin-2-yl |
| 3559 | 4-OCH(CH₃)CH₂OCH₃-1,3,5-triazin-2-yl |
| 3560 | 4-OCH(CH₃)CH₂CO₂CH₃-1,3,5-triazin-2-yl |
| 3561 | 4-OCH(CH₃)CH₂CO₂CH₂CH₃-1,3,5-triazin-2-yl |
| 3562 | 4-OCH₂CH(CH₃)CO₂CH₃-1,3,5-triazin-2-yl |
| 3563 | 4-OCH₂C(=O)CH₃-1,3,5-triazin-2-yl |
| 3564 | 4-OCH₂C(=O)CH₂CH₃-1,3,5-triazin-2-yl |
| 3565 | 4-OCH₂CO₂CH₃-1,3,5-triazin-2-yl |
| 3566 | 4-OCH₂CO₂CH₂CH₃-1,3-5-triazin-2-yl |
| 3567 | 4-OCH₂C(=O)NH₂-1,3,5-triazin-2-yl |
| 3568 | 4-OCH₂C(=)NHCH₃-1,3,5-triazin-2-yl |
| 3569 | 4-OCH₂C(=O)SCH₃-1,3,5-triazin-2-yl |
| 3570 | 4-OCH(CH₃)C(=O)NH₂-1,3,5-triazin-2-yl |
| 3571 | 4-OCH(CH₃)C(=O)NHCH₃-1,3,5-triazin-2-yl |
| 3572 | 4-OCH(CH₃)C(=O)NHNH₂-1,3,5-triazin-2-yl |
| 3573 | 4-OCH(CH₃)CO₂CH₃-1,3,5-triazin-2-yl |
| 3574 | 4-OCH(CH₃)CO₂CH₂CH₃-1,3,5-triazin-2-yl |
| 3575 | 4-OCH(CH₃)C(=O)CH₂CH₃-1,3,5-triazin-2-yl |
| 3576 | 4-OCH(CH₃)C(=O)CH₂CH₃-1,3,5-triazin-2-yl |
| 3577 | 4-OCH(CH₃)CH₂C(=O)CH₃-1,3,5-triazin-2-yl |
| 3578 | 4-OCH(CH₃)CH₂OC(CH₃)₄-1,3,5-triazin-2-yl |
| 3579 | 4-OCH(CH₃)CH₂OCH₂CH₃-1,3,5-triazin-2-yl |
| 3580 | 4-OCH(CH₃)CH₂O(CH₃)₂CH₃-1,3,5-triazin-2-yl |
| 3581 | 4-OCH(CH₃)CH₂OCH₂CH=CH₂-1,3,5-triazin-2-yl |
| 3582 | 4-O(CH₂)₃OCH₃-1,3,5-triazin-2-yl |
| 3583 | 4-O(CH₂)₃OCH₂CH₃-1,3,5-triazin-2-yl |
| 3584 | 4-O(CH₂)₃OCH(CH₃)₂-1,3,5-triazin-2-yl |
| 3585 | 4-O(CH₂)₃OC₆H₅-1,3,5-triazin-2-yl |
| 3586 | 4-O(CH₂)₃OCH₂C₆H₅-1,3,5-triazin-2-yl |
| 3587 | 4-OCH(CH₂CH₃)CH₂OCH₃-1,3,5-triazin-2-yl |
| 3588 | 4-OCH(CH₂CH₃)CH₂CH₂OCH₃-1,3,5-triazin-2-yl |
| 3589 | 4-OCH(CH₂CH₃)CH₂CH₂OCH₂CH₃-1,3,5-triazin-2-yl |
| 3590 | 4-O[(CH₂)₃O]₂CH₃-1,3,5-triazin-2-yl |
| 3591 | 4-OCH₂CH(CH₃)CH₂OCH₃-1,3,5-triazin-2-yl |
| 3592 | 4-OCH₂CH(CH₃)CH₂OCH₂CH₃-1,3,5-triazin-2-yl |
| 3593 | 4-OCH(CH₂Cl)CH₂OCH₃-1,3,5-triazin-2-yl |
| 3594 | 4-OCH(CH₂Cl)CH₂OCH₂CH₃-1,3,5-triazin-2-yl |
| 3595 | 4-OCH(CH₂Cl)CH₂OCH(CH₃)₂-1,3,5-triazin-2-yl |
| 3596 | 4-OCH(CH₂Cl)CH₂OCH₂CH=CH₂-1,3,5-triazin-2-yl |
| 3597 | 4-OCH[CH₂OCH₃]₂-1,3,5-triazin-2-yl |
| 3598 | 4-OCH[CH₂OCH₂CH₃]₂-1,3,5-triazin-2-yl |
| 3599 | 4-OCCl₄-1,3,5-triazin-2-yl |
| 3600 | 4-OCHF₂-1,3,5-triazin-2-yl |
| 3601 | 4-OCF₃-1,3,5-triazin-2-yl |
| 3602 | 4-OCF₂CHF₂-1,3,5-triazin-2-yl |
| 3603 | 4-OCH₂CF₃-1,3,5-triazin-2-yl |
| 3604 | 4-OCH₂CHF₂-1,3,5-triazin-2-yl |
| 3605 | 4-O(CH₂)₃F-1,3,5-triazin-2-yl |
| 3606 | 4-OCH(CH₃)CF₃-1,3,5-triazin-2-yl |
| 3607 | 4-O(CH₂)₄F-1,3,5-triazin-2-yl |
| 3608 | 4-O(CH₂)₃CF₃-1,3,5-triazin-2-yl |
| 3609 | 4-OCH(CH₃)CF₂CF₃-1,3,5-triazin-2-yl |
| 3610 | 4-OCH(CH₃)CF₂CHF₂-1,3,5-triazin-2-yl |
| 3611 | 4-OCH₂CF₂CHFCH₃-1,3,5-triazin-2-yl |
| 3612 | 4-OCH₂(CF₂)₂CF₃-1,3,5-triazin-2-yl |
| 3613 | 4-O(CF₂)₃CF₃-1,3,5-triazin-2-yl |
| 3614 | 4-OCH₂CF₂CHF₂-1,3,5-triazin-2-yl |
| 3615 | 4-CH₂CH=CH₂-1,3,5-triazin-2-yl |
| 3616 | 4-CH₂C(CH₃)=CH₂-1,3,5-triazin-2-yl |
| 3617 | 4-OCH₂CH=CHCH₃-1,3,5-triazin-2-yl |
| 3618 | 4-O(CH₂)₂CH=CH₂-1,3,5-triazin-2-yl |
| 3619 | 4-OCH₂C(CH₃)=CH₂-1,3,5-triazin-2-yl |
| 3620 | 4-OCH(CH₃)CH=CH₂-1,3,5-triazin-2-yl |
| 3621 | 4-OCH₂C≡CH-1,3,5-triazin-2-yl |
| 3622 | 4-OCH₂C≡CCH₃-1,3,5-triazin-2-yl |
| 3623 | 4-O(CH₂)₂C≡CH-1,3,5-triazin-2-yl |
| 3624 | 4-SCH₃-1,3,5-triazin-2-yl |
| 3625 | 4-SCH₂CH₃-1,3,5-triazin-2-yl |
| 3626 | 4-OC₆H₅-1,3,5-triazin-2-yl |
| 3627 | 4-OCH₂C₆H₅-1,3,5-triazin-2-yl |
| 3628 | 4-NO₂-1,3,5-triazin-2-yl |
| 3629 | 4-NHCH₃-1,3,5-triazin-2-yl |
| 3630 | 4-N(CH₃)₂-1,3,5-triazin-2-yl |
| 3631 | 4-N(CH₃)C₂H₆-1,3,5-triazin-2-yl |
| 3632 | 4-NHCH₂CF₃-1,3,5-triazin-2-yl |
| 3633 | 4-F-1,3,5-triazin-2-yl |
| 3635 | 4-Cl-1,3,5-triazin-2-yl |
| 3636 | 4-CN-1,3,5-triazin-2-yl |
| 3637 | 4-C(O)NH₂-1,3,5-triazin-2-yl |
| 3638 | 4-C(S)NH₂-1,3,5-triazin-2-yl |
| 3639 | 4-CO₂CH₃-1,3,5-triazin-2-yl |
| 3640 | 4-ON=C(CH₃)₂-1,3,5-triazin-2-yl |
| 3641 | 4-[O-cyclopropyl]-1,3,5-triazin-2-yl |
| 3642 | 4-[O-cyclobutyl]-1,3,5-triazin-2-yl |
| 3643 | 4-[O-cyclopentyl]-1,3,5-triazin-2-yl |
| 3644 | 4-[O-cyclohexyl]-1,3,5-triazin-2-yl |
| 3645 | 4-[OCH₂-cyclopropyl]-1,3,5-triazin-2-yl |
| 3646 | 6-F, 4-[OCH₂-cyclopropyl]-1,3,5-triazin-2-yl |
| 3647 | 6-CH₃, 4-[OCH₂-cyclopropyl]-1,3,5-triazin-2-yl |
| 3648 | 6-CF₃, 4-[OCH₂-cyclopropyl]-1,3,5-triazin-2-yl |
| 3649 | 4-[OCH(CH₃)-cyclopropyl]-1,3,5-triazin-2-yl |
| 3650 | 6-F, 4-[OCH(CH₃)-cyclopropyl]-1,3,5-triazin-2-yl |
| 3651 | 6-CH₃, 4-[OCH(CH₃)-cyclopropyl]-1,3,5-triazin-2-yl |
| 3652 | 6-CF₃, 4-[OCH(CH₃)-cyclopropyl]-1,3,5-triazin-2-yl |
| 3653 | 4-[O-(1-CH₃-cyclopropyl)]-1,3,5-triazin-2-yl |
| 3654 | 6-F, 4-[O-(1-CH₃-cyclopropyl)]-1,3,5-triazin-2-yl |
| 3655 | 6-CH₃, 4-[O-(1-CH₃-cyclopropyl)]-1,3,5-triazin-2-yl |
| 3656 | 6-CF₃, 4-[O-(1-CH₃-cyclopropyl)]-1,3,5-triazin-2-yl |
| 3657 | 4-[OCH₂-(1-CH₃-cyclopropyl)]-1,3,5-triazin-2-yl |
| 3658 | 6-F, 4-[OCH₂-(1-CH₃-cyclopropyl)]-1,3,5-triazin-2-yl |
| 3659 | 6-CH₃, 4-[OCH₂-(1-CH₃-cyclopropyl)]-1,3,5-triazin-2-yl |
| 3660 | 6-CF₃, 4-[OCH₂-(1-CH₃-cyclopropyl)]-1,3,5-triazin-2-yl |
| 3661 | 4-[OCH₂-(2-CH₃-cyclopropyl)]-1,3,5-triazin-2-yl |
| 3662 | 6-F, 4-[OCH₂-(2-CH₃-cyclopropyl)]-1,3,5-triazin-2-yl |
| 3663 | 6-CH₃, 4-[OCH₂-(2-CH₃-cyclopropyl)]-1,3,5-triazin-2-yl |

TABLE A-continued

| No. | R⁴ |
|---|---|
| 3664 | 6-CF₃, 4-[OCH₂-(2-CH₃-cyclopropyl)]-1,3,5-triazin-2-yl |
| 3665 | 4-[OCH₂-(tetrahydropyran-2-yl)]-1,3,5-triazin-2-yl |
| 3666 | 6-F, 4-[OCH₂-(tetrahydropyran-2-yl)]-1,3,5-triazin-2-yl |
| 3667 | 6-CH₃, 4-[OCH₂-(tetrahydropyran-2-yl)]-1,3,5-triazin-2-yl |
| 3668 | 6-CF₃, 4-[OCH₂-(tetrahydropyran-2-yl)]-1,3,5-triazin-2-yl |
| 3669 | 4-[OCH₂-(furan-2-yl)]-1,3,5-triazin-2-yl |
| 3670 | 6-F, 4-[OCH₂-(furan-2-yl)]-1,3,5-triazin-2-yl |
| 3671 | 6-CH₃, 4-[OCH₂-(furan-2-yl)]-1,3,5-triazin-2-yl |
| 3672 | 6-CF₃, 4-[OCH₂-(furan-2-yl)]-1,3,5-triazin-2-yl |
| 3673 | 4-[OCH₂-(furan-4-yl)]-1,3,5-triazin-2-yl |
| 3674 | 6-F, 4-[OCH₂-(furan-4-yl)]-1,3,5-triazin-2-yl |
| 3675 | 6-CH₃, 4-[OCH₂-(furan-4-yl)]-1,3,5-triazin-2-yl |
| 3676 | 6-CF₃, 4-[OCH₂-(furan-4-yl)]-1,3,5-triazin-2-yl |
| 3677 | 4-[OCH₂-(tetrahydrofuran-4-yl)]-1,3,5-triazin-2-yl |
| 3678 | 6-F, 4[OCH₂-(tetrahydrofuran-4-yl)]-1,3,5-triazin-2-yl |
| 3679 | 6-CH₃, 4-[OCH₂-(tetrahydrofuran-4-yl)]-1,3,5-triazin-2-yl |
| 3680 | 6-CF₃, 4-[OCH₂-(tetrahydrofuran-4-yl)]-1,3,5-triazin-2-yl |
| 3681 | 4-[OCH₂-(tetrahydrofuran-2-yl)]-1,3,5-triazin-2-yl |
| 3682 | 6-F, 4-[OCH₂-(tetrahydrofuran-2-yl)]-1,3,5-triazin-2-yl |
| 3683 | 6-CH₃, 4-[OCH₂-(tetrahydrofuran-2-yl)]-1,3,5-triazin-2-yl |
| 3684 | 6-CF₃, 4-[OCH₂-(tetrahydrofuran-2-yl)]-1,3,5-triazin-2-yl |
| 3685 | 4-[O-(tetrahydropyran-4-yl)]-1,3,5-triazin-2-yl |
| 3686 | 6-F, 4-[O-(tetrahydropyran-4-yl)]-1,3,5-triazin-2-yl |
| 3687 | 6-CH₃, 4-[O-(tetrahydropyran-4-yl)]-1,3,5-triazin-2-yl |
| 3688 | 6-CF₃, 4-[O-(tetrahydropyran-4-yl)]-1,3,5-triazin-2-yl |
| 3689 | 4-[2-Cl—C₅H₄]-1,3,5-triazin-2-yl |
| 3690 | 6-F, 4-[2-Cl—C₅H₄]-1,3,5-triazin-2-yl |
| 3691 | 6-CH₃, 4-[2-Cl—C₅H₄]-1,3,5-triazin-2-yl |
| 3692 | 6-CF₃, 4-[2-Cl—C₅H₄]-1,3,5-triazin-2-yl |
| 3693 | 4-[OCH₂-(pyridin-2-yl)]-1,3,5-triazin-2-yl |
| 3694 | 6-F, 4-[OCH₂-(pyridin-2-yl)]-1,3,5-triazin-2-yl |
| 3695 | 6-CH₃, 4-[OCH₂-(pyridin-2-yl)]-1,3,5-triazin-2-yl |
| 3696 | 6-CF₃, 4-[OCH₂-(pyridin-2-yl)]-1,3,5-triazin-2-yl |
| 3697 | 4-[OCH₂-(pyridin-4-yl)]-1,3,5-triazin-2-yl |
| 3698 | 6-F, 4-[OCH₂-(pyridin-4-yl)]-1,3,5-triazin-2-yl |
| 3699 | 6-CH₃, 4-[OCH₂-(pyridin-4-yl)]-1,3,5-triazin-2-yl |
| 3700 | 6-CF₃, 4-[OCH₂-(pyridin-4-yl)]-1,3,5-triazin-2-yl |
| 3701 | 4-[morpholin-4-yl]-1,3,5-triazin-2-yl |
| 3702 | 4-[1-CH₃-imidazol-2-yl]-1,3,5-triazin-2-yl |
| 3703 | 6-F, 4-[1-CH₃-imidazol-2-yl]-1,3,5-triazin-2-yl |
| 3704 | 6-CH₃, 4-[1-CH₃-imidazol-2-yl]-1,3,5-triazin-2-yl |
| 3705 | 6-CF₃, 4-[1-CH₃-imidazol-2-yl]-1,3,5-triazin-2-yl |
| 3706 | 4-[1,2,4-triazol-1-yl]-1,3,5-triazin-2-yl |
| 3707 | 6-F, 4-[1,2,4-triazol-1-yl]-1,3,5-triazin-2-yl |
| 3708 | 6-CH₃, 4-[1,2,4-triazol-1-yl]-1,3,5-triazin-2-yl |
| 3709 | 6-CF₃, 4-[1,2,4-triazol-1-yl]-1,3,5-triazin-2-yl |
| 3710 | 4,6-Cl₂-1,3,5-triazin-2-yl |
| 3711 | 4,6-(CH₃)₂-1,3,5-triazin-2-yl |
| 3712 | 4,6-(OCH₃)₂-1,3,5-triazin-2-yl |
| 3713 | 4,6-(OCH₂CH₃)₂-1,3,5-triazin-2-yl |
| 3714 | 4-F, 6-CH₃-1,3,5-triazin-2-yl |
| 3715 | 4-F, 6-OCH₃-1,3,5-triazin-2-yl |
| 3716 | 4-F, 6-OCH₂CH₃-1,3,5-triazin-2-yl |
| 3717 | 4-F, 6-OCH₂CF₃-1,3,5-triazin-2-yl |
| 3718 | 4-F, 6-OCH(CH₃)₂-1,3,5-triazin-2-yl |
| 3719 | 4-Cl, 6-CH₃-1,3,5-triazin-2-yl |
| 3720 | 4-Cl, 6-OCH₃-1,3,5-triazin-2-yl |
| 3721 | 4-Cl, 6-OCH₂CH₃-1,3,5-triazin-2-yl |
| 3722 | 4-Cl, 6-OCH₂CF₃-1,3,5-triazin-2-yl |
| 3723 | 4-Cl, 6-OCH(CH₃)₂-1,3,5-triazin-2-yl |
| 3724 | 4-CH₃, 6-OCH₃-1,3,5-triazin-2-yl |
| 3725 | 4-CH₃, 6-OCH₂CH₃-1,3,5-triazin-2-yl |
| 3726 | 4-CH₃, 6-OCH₂CF₃-1,3,5-triazin-2-yl |
| 3727 | 4-CH₃, 6-OCH(CH₃)₂-1,3,5-triazin-2-yl |
| 3728 | 4-CH₃, 6-OCH₂CH=CH₂-1,3,5-triazin-2-yl |
| 3729 | 4-CH₃, 6-CO₂CH₃-1,3,5-triazin-2-yl |
| 3730 | 4-CH₃, 6-CF₃-1,3,5-triazin-2-yl |
| 3731 | 4-CF₃, 6-CH₂CH₃-1,3,5-triazin-2-yl |
| 3732 | 4-CF₃, 6-OCH₃-1,3,5-triazin-2-yl |
| 3733 | 4-CF₃, 6-OCH₂CH₃-1,3,5-triazin-2-yl |
| 3734 | 4-CF₃, 6-OCH₂CF₃-1,3,5-triazin-2-yl |
| 3735 | 4-OCH₃, 6-OCH₂CH₃-1,3,5-triazin-2-yl |
| 3736 | 4-OCF₃, 6-OCH₂CH₃-1,3,5-triazin-2-yl |
| 3737 | 4-OCH₃, 6-OCH(CH₃)-1,3,5-triazin-2-yl |
| 3738 | 4-OCH₂CH₃, 6-CH₂OCH₂CH₃-1,3,5-triazin-2-yl |
| 3739 | 4-NO₂, 6-CH₃-1,3,5-triazin-2-yl |
| 3740 | 4-NO₂, 6-OCH₃-1,3,5-triazin-2-yl |
| 3741 | 4-NO₂, 6-OCH₂CH₃-1,3,5-triazin-2-yl |
| 3742 | 4-NO₂, 6-OCH(CH₃)₂-1,3,5-triazin-2-yl |
| 3743 | 4-NO₂, 6-OCH₂CF₃-1,3,5-triazin-2-yl |
| 3744 | 4-CN, 6-CH₃-1,3,5-triazin-2-yl |
| 3745 | 4-CN, 6-OCH₃-1,3,5-triazin-2-yl |
| 3746 | 4-CN, 6-OCH₂CH₃-1,3,5-triazin-2-yl |
| 3747 | 4-CN, 6-OCH(CH₃)₂-1,3,5-triazin-2-yl |
| 3748 | 4-CN, 6-OCH₂CF₃-1,3,5-triazin-2-yl |
| 3749 | 1-CH₃, 4-CH₃-indol-2-yl |
| 3750 | 1-CH₃, 4-CH₂CH₃-indol-2-yl |
| 3751 | 1-CH₃, 4-CH(CH₃)₂-indol-2-yl |
| 3752 | 1-CH₃, 4-CH(CH₃)CH₂CH₃-indol-2-yl |
| 3753 | 1-CH₃, 4-CF₃-indol-2-yl |
| 3754 | 1-CH₃, 4-CH=CH₂-indol-2-yl |
| 3755 | 1-CH₃, 4-CH=CHCH₃-indol-2-yl |
| 3756 | 1-CH₃, 4-CH=CHCl-indol-2-yl |
| 3757 | 1-CH₃, 4-C≡CH-indol-2-yl |
| 3758 | 1-CH₃, 4-CH₂C≡CH-indol-2-yl |
| 3759 | 1-CH₃, 4-CH₂C≡CCH₃-indol-2-yl |
| 3760 | 1-CH₃, 4-cyclopropyl-indol-2-yl |
| 3761 | 1-CH₃, 4-cyclopentyl-indol-2-yl |
| 3762 | 1-CH₃, 4-OCH₃-indol-2-yl |
| 3763 | 1-CH₃, 4-OCH₂CH₃-indol-2-yl |
| 3764 | 1-CH₃, 4-OCH₂CH₂CH₃-indol-2-yl |
| 3765 | 1-CH₃, 4-OCH(CH₃)₂-indol-2-yl |
| 3766 | 1-CH₃, 4-OCH₂CH₂CH₂CH₃-indol-2-yl |
| 3767 | 1-CH₃, 4-OCH(CH₃)CH₂CH₃-indol-2-yl |
| 3768 | 1-CH₃, 4-OCH₂CH(CH₃)₂-indol-2-yl |
| 3769 | 1-CH₃, 4-OC(CH₃)₄-indol-2-yl |
| 3770 | 1-CH₃, 4-OCH(CH₂CH₃)CH₂CH₃-indol-2-yl |
| 3771 | 1-CH₃, 4-OCH₂OCH₃-indol-2-yl |
| 3772 | 1-CH₃, 4-OCH₂OCH₂CH₃-indol-2-yl |
| 3773 | 1-CH₃, 4-OCH(CH₃)OCH₃-indol-2-yl |
| 3774 | 1-CH₃, 4-OCH(CH₃)OCH₂CH₃-indol-2-yl |
| 3775 | 1-CH₃, 4-OCH₂CH₂OCH₃-indol-2-yl |
| 3776 | 1-CH₃, 4-OCH₂CH₂OCH₂CH₃-indol-2-yl |
| 3777 | 1-CH₃, 4-OCH₂CH₂OCH(CH₃)₂-indol-2-yl |
| 3778 | 1-CH₃, 4-OCH₂CH₂SCH₃-indol-2-yl |
| 3779 | 1-CH₃, 4-OCH₂CH₂SO₂CH₃-indol-2-yl |
| 3780 | 1-CH₃, 4-OCH₂CH₂SCH(CH₃)₂-indol-2-yl |
| 3781 | 1-CH₃, 4-OCH₂CH₂CN-indol-2-yl |
| 3782 | 1-CH₃, 4-OCH₂CH₂SCH₂CN-indol-2-yl |
| 3783 | 1-CH₃, 4-OCH₂CH₂OC₆H₅-indol-2-yl |
| 3784 | 1-CH₃, 4-OCH₂CH₂OCH₂C₆H₅-indol-2-yl |
| 3785 | 1-CH₃, 4-OCH₂CH₂N(CH₃)₂-indol-2-yl |
| 3786 | 1-CH₃, 4-OCH₂CH₂CONH₂-indol-2-yl |
| 3787 | 1-CH₃, 4-OCH₂CH₂CO₂CH₂CH₃-indol-2-yl |
| 3788 | 1-CH₃, 4-OCH(CH₃)CH₂OCH₃-indol-2-yl |
| 3789 | 1-CH₃, 4-OCH(CH₃)CH₂CO₂CH₃-indol-2-yl |
| 3790 | 1-CH₃, 4-OCH(CH₃(CH₂CO₂CH₂CH₃-indol-2-yl |
| 3791 | 1-CH₃, 4-OCH(CH₃)CO₂CH₃-indol-2-yl |
| 3792 | 1-CH₃, 4-OCH₂C(=O)CH₃-indol-2-yl |
| 3793 | 1-CH₃, 4-OCH₂C(=O)CH₂CH₃-indol-2-yl |
| 3794 | 1-CH₃, 4-OCH₂CO₂CH₃-indol-2-yl |
| 3795 | 1-CH₃, 4-OCH₂CO₂CH₂CH₃-indol-2-yl |
| 3796 | 1-CH₃, 4-OCH₂C(=O)NH₂-indol-2-yl |
| 3797 | 1-CH₃, 4-OCH₂C(=O)NHCH₃-indol-2-yl |
| 3798 | 1-CH₃, 4-OCH₂C(=)SCH₃-indol-2-yl |
| 3799 | 1-CH₃, 4-OCH(CH₃)C(=O)NH₂-indol-2-yl |
| 3800 | 1-CH₃, 4-OCH(CH₃)C(=O)NHCH₃-indol-2-yl |
| 3801 | 1-CH₃, 4-OCH(CH₃)C(=O)NHNH₂-indol-2-yl |
| 3802 | 1-CH₃, 4-OCH(CH₃)CO₂CH₃-indol-2-yl |
| 3803 | 1-CH₃, 4-OCH(CH₃)CO₂CH₂CH₃-indol-2-yl |
| 3804 | 1-CH₃, 4-OCH(CH₃)C(=O)CH₃-indol-2-yl |
| 3805 | 1-CH₃, 4-OCH(CH₃)C(=O)CH₂CH₃-indol-2-yl |
| 3806 | 1-CH₃, 4-OCH(CH₃)CH₂C(=O)CH₃-indol-2-yl |
| 3807 | 1-CH₃, 4-OCH(CH₃)CH₂OC(CH₃)₄-indol-2-yl |
| 3808 | 1-CH₃, 4-OCH(CH₃)CH₂OCH₂CH₃-indol-2-yl |
| 3809 | 1-CH₃, 4-OCH(CH₃)CH₂O(CH₃)₂CH₃-indol-2-yl |
| 3810 | 1-CH₃, 4-OCH(CH₃)CH₂OCH₂CH=CH₂-indol-2-yl |
| 3811 | 1-CH₃, 4-O(CH₂)₃OCH₃-indol-2-yl |
| 3812 | 1-CH₃, 4-O(CH₂)₃OCH₂CH₃-indol-2-yl |
| 3813 | 1-CH₃, 4-O(CH₂)₃OCH(CH₃)₂-indol-2-yl |
| 3814 | 1-CH₃, 4-O(CH₂)₃OC₆H₅-indol-2-yl |
| 3815 | 1-CH₃, 4-O(CH₂)₃OCH₂C₆H₅-indol-2-yl |
| 3816 | 1-CH₃, 4-OCH(CH₂CH₃)CH₂OCH₃-indol-2-yl |
| 3817 | 1-CH₃, 4-OCH(CH₂CH₃)CH₂CH₂OCH₃-indol-2-yl |

TABLE A-continued

| No. | R⁴ |
|---|---|
| 3818 | 1-CH₃, 4-OCH(CH₂CH₃)CH₂CH₂OCH₂CH₃-indol-2-yl |
| 3819 | 1-CH₃, 4-O[(CH₂)₃O]₂CH₃-indol-2-yl |
| 3820 | 1-CH₃, 4-OCH₂CH(CH₃)CH₂OCH₃-indol-2-yl |
| 3821 | 1-CH₃, 4-OCH₂CH(CH₃)CH₂OCH₂CH₃-indol-2-yl |
| 3822 | 1-CH₃, 4-OCH(CH₂Cl)CH₂OCH₃-indol-2-yl |
| 3823 | 1-CH₃, 4-OCH(CH₂Cl)CH₂OCH₂CH₃-indol-2-yl |
| 3824 | 1-CH₃, 4-OCH(CH₂Cl)CH₂OCH(CH₃)₂-indol-2-yl |
| 3825 | 1-CH₃, 4-OCH(CH₂Cl)CH₂OCH₂CH=CH₂-indol-2-yl |
| 3826 | 1-CH₃, 4-OCH[CH₂OCH₃]₂-indol-2-yl |
| 3827 | 1-CH₃, 4-OCH[CH₂OCH₂CH₃]₂-indol-2-yl |
| 3828 | 1-CH₃, 4-OCCl₄-indol-2-yl |
| 3829 | 1-CH₃, 4-OCHF₂-indol-2-yl |
| 3830 | 1-CH₃, 4-OCF₃-indol-2-yl |
| 3831 | 1-CH₃, 4-OCF₂CHF₂-indol-2-yl |
| 3832 | 1-CH₃, 4-OCH₂CF₃-indol-2-yl |
| 3833 | 1-CH₃, 4-OCH₂CHF₂-indol-2-yl |
| 3834 | 1-CH₃, 4-O(CH₂)₃F-indol-2-yl |
| 3835 | 1-CH₃, 4-OCH(CH₃)CF₃-indol-2-yl |
| 3836 | 1-CH₃, 4-O(CH₂)₄F-indol-2-yl |
| 3837 | 1-CH₃, 4-O(CH₂)₃CF₃-indol-2-yl |
| 3838 | 1-CH₃, 4-OCH(CH₃)CF₂CF₃-indol-2-yl |
| 3839 | 1-CH₃, 4-OCH(CH₃)CF₂CHF₂-indol-2-yl |
| 3840 | 1-CH₃, 4-OCH(CH₃)CF₂CHFCH₃-indol-2-yl |
| 3841 | 1-CH₃, 4-OCH₂(CF₂)₂CF₃-indol-2-yl |
| 3842 | 1-CH₃, 4-O(CF₂)₃CF₃-indol-2-yl |
| 3843 | 1-CH₃, 4-OCH₂CF₂CHF₂-indol-2-yl |
| 3844 | 1-CH₃, 4-CH₂CH=CH₂-indol-2-yl |
| 3845 | 1-CH₃, 4-CH₂C(CH₃)=CH₂-indol-2-yl |
| 3846 | 1-CH₃, 4-OCH₂CH=CHCH₃-indol-2-yl |
| 3847 | 1-CH₃, 4-O(CH₂)₂CH=CH₂-indol-2-yl |
| 3848 | 1-CH₃, 4-OCH₂C(CH₃)=CH₂-indol-2-yl |
| 3849 | 1-CH₃, 4-OCH(CH₃)CH=CH₂-indol-2-yl |
| 3850 | 1-CH₃, 4-OCH₂C≡CH-indol-2-yl |
| 3851 | 1-CH₃, 4-OCH₂C≡CCH₃-indol-2-yl |
| 3852 | 1-CH₃, 4-O(CH₂)₂C≡CH-indol-2-yl |
| 3853 | 1-CH₃, 4-SCH₃-indol-2-yl |
| 3854 | 1-CH₃, 4-SCH₂CH₃-indol-2-yl |
| 3855 | 1-CH₃, 4-OC₆H₅-indol-2-yl |
| 3856 | 1-CH₃, 4-OCH₂C₆H₅-indol-2-yl |
| 3857 | 1-CH₃, 4-NO₂-indol-2-yl |
| 3858 | 1-CH₃, 4-NHCH₃-indol-2-yl |
| 3859 | 1-CH₃, 4-N(CH₃)₂-indol-2-yl |
| 3860 | 1-CH₃, 4-N(CH₃)C₂H₆-indol-2-yl |
| 3861 | 1-CH₃, 4-NHCH₂CF₃-indol-2-yl |
| 3862 | 1-CH₃, 4-F-indol-2-yl |
| 3863 | 1-CH₃, 4-Cl-indol-2-yl |
| 3864 | 1-CH₃, 4-OH-indol-2-yl |
| 3865 | 1-CH₃, 4-CN-indol-2-yl |
| 3866 | 1-CH₃, 4-C(O)NH₂-indol-2-yl |
| 3867 | 1-CH₃, 4-C(S)NH₂-indol-2-yl |
| 3868 | 1-CH₃, 4-CO₂CH₃-indol-2-yl |
| 3869 | 1-CH₃, 4-ON=C(CH₃)₂-indol-2-yl |
| 3870 | 1-CH₃, 4-[O-cyclopropyl]indol-2-yl |
| 3871 | 1-CH₃, 4-[O-cyclobutyl]indol-2-yl |
| 3872 | 1-CH₃, 4-[O-cyclopentyl]indol-2-yl |
| 3873 | 1-CH₃, 4-[O-cyclohexyl]indol-2-yl |
| 3874 | 1-CH₃, 4-[OCH₂-cyclopropyl]indol-2-yl |
| 3875 | 1-CH₃, 6-F, 4-[OCH₂-cyclopropyl]indol-2-yl |
| 3876 | 1-CH₃, 6-CH₃, 4-[OCH₂-cyclopropyl]indol-2-yl |
| 3877 | 1-CH₃, 6-CF₃, 4-[OCH₂-cyclopropyl]indol-2-yl |
| 3878 | 1-CH₃, 4-[OCH(CH₃)-cyclopropyl]indol-2-yl |
| 3879 | 1-CH₃, 6-F, 4-[OCH(CH₃)-cyclopropyl]indol-2-yl |
| 3880 | 1-CH₃, 6-CH₃, 4-[OCH(CH₃)-cyclopropyl]indol-2-yl |
| 3881 | 1-CF₃, 6-CH₃, 4-[OCH(CH₃)-cyclopropyl]indol-2-yl |
| 3882 | 1-CH₃, 4-[O-(1-CH₃-cyclopropyl)]indol-2-yl |
| 3883 | 1-CH₃, 6-F, 4-[O-(1-CH₃-cyclopropyl)]indol-2-yl |
| 3884 | 1-CH₃, 6-CH₃, 4-[O-(1-CH₃-cyclopropyl)]indol-2-yl |
| 3885 | 1-CH₃, 6-CF₃, 4-[O-(1-CH₃-cyclopropyl)]indol-2-yl |
| 3886 | 1-CH₃, 4-[OCH₂-(1-CH₃-cyclopropyl)]indol-2-yl |
| 3887 | 1-CH₃, 6-F, 4-[OCH₂-(1-CH₃-cyclopropyl)]indol-2-yl |
| 3888 | 1-CH₃, 6-CH₃, 4-[OCH₂-(1-CH₃-cyclopropyl)]indol-2-yl |
| 3889 | 1-CH₃, 6-CF₃, 4-[OCH₂-(1-CH₃-cyclopropyl)]indol-2-yl |
| 3890 | 1-CH₃, 4-[OCH₂-(2-CH₃-cyclopropyl)]indol-2-yl |
| 3891 | 1-CH₃, 6-F, 4-[OCH₂-(2-CH₃-cyclopropyl)]indol-2-yl |
| 3892 | 1-CH₃, 6-CH₃, 4-[OCH₂-(2-CH₃-cyclopropyl)]indol-2-yl |
| 3893 | 1-CH₃, 6-CF₃, 4-[OCH₂-(2-CH₃-cyclopropyl)]indol-2-yl |
| 3894 | 1-CH₃, 4-[OCH₂-(tetrahydropyran-2-yl)]indol-2-yl |
| 3895 | 1-CH₃, 6-F, 4-[OCH₂-(tetrahydropyran-2-yl)]indol-2-yl |
| 3896 | 1-CH₃, 6-CH₃, 4-[OCH₂-(tetrahydropyran-2-yl)]indol-2-yl |
| 3897 | 1-CH₃, 6-CF₃, 4-[OCH₂-(tetrahydropyran-2-yl)]indol-2-yl |
| 3898 | 1-CH₃, 4-[OCH₂-(furan-2-yl)]indol-2-yl |
| 3899 | 1-CH₃, 6-F, 4-[OCH₂-(furan-2-yl)]indol-2-yl |
| 3900 | 1-CH₃, 6-CH₃, 4-[OCH₂-(furan-2-yl)]indol-2-yl |
| 3901 | 1-CH₃, 6-CF₃, 4-[OCH₂-(furan-2-yl)]indol-2-yl |
| 3902 | 1-CH₃, 4-[OCH₂-(furan-4-yl)]indol-2-yl |
| 3903 | 1-CH₃, 6-F, 4-[OCH₂-(furan-4-yl)]indol-2-yl |
| 3904 | 1-CH₃, 6-CH₃, 4-[OCH₂-(furan-4-yl)]indol-2-yl |
| 3905 | 1-CH₃, 6-CF₃, 4-[OCH₂-(furan-4-yl)]indol-2-yl |
| 3906 | 1-CH₃, 4-[OCH₂-(tetrahydrofuran-4-yl)]indol-2-yl |
| 3907 | 1-CH₃, 6-F, 4-[OCH₂-(tetrahydrofuran-4-yl)]indol-2-yl |
| 3908 | 1-CH₃, 6-CH₃, 4-[OCH₂-(tetrahydrofuran-4-yl)]indol-2-yl |
| 3909 | 1-CH₃, 6-CF₃, 4-[OCH₂-(tetrahydrofuran-4-yl)]indol-2-yl |
| 3910 | 1-CH₃, 4-[OCH₂-(tetrahydrofuran-2-yl)]indol-2-yl |
| 3911 | 1-CH₃, 6-F, 4-[OCH₂-(tetrahydrofuran-2-yl)]indol-2-yl |
| 3912 | 1-CH₃, 6-CH₃, 4-[OCH₂-(tetrahydrofuran-2-yl)]indol-2-yl |
| 3913 | 1-CH₃, 6-CF₃, 4-[OCH₂-(tetrahydrofuran-2-yl)]indol-2-yl |
| 3914 | 1-CH₃, 4-[O-(tetrahydropyran-4-yl)]indol-2-yl |
| 3915 | 1-CH₃, 6-F, 4-[O-(tetrahydropyran-4-yl)]indol-2-yl |
| 3916 | 1-CH₃, 6-CH₃, 4-[O-(tetrahydropyran-4-yl)]indol-2-yl |
| 3917 | 1-CH₃, 6-CF₃, 4-[O-(tetrahydropyran-4-yl)]indol-2-yl |
| 3918 | 1-CH₃, 4-[2-Cl—C₅H₄]indol-2-yl |
| 3919 | 1-CH₃, 6-F, 4-[2-Cl—C₅H₄]indol-2-yl |
| 3920 | 1-CH₃, 6-CH₃, 4-[2-Cl—C₅H₄]indol-2-yl |
| 3921 | 1-CH₃, 6-CF₃, 4-[2-Cl—C₅H₄]indol-2-yl |
| 3922 | 1-CH₃, 4-[OCH₂-(pyridin-2-yl)]indol-2-yl |
| 3923 | 1-CH₃, 6-F, 4-[OCH₂-(pyridin-2-yl)]indol-2-yl |
| 3924 | 1-CH₃, 6-CH₃, 4-[OCH₂-(pyridin-2-yl)]indol-2-yl |
| 3925 | 1-CH₃, 6-CF₃, 4-[OCH₂-(pyridin-2-yl)]indol-2-yl |
| 3926 | 1-CH₃, 4-[OCH₂-(pyridin-4-yl)]indol-2-yl |
| 3927 | 1-CH₃, 6-F, 4-[OCH₂-(pyridin-4-yl)]indol-2-yl |
| 3928 | 1-CH₃, 6-CH₃, 4-[OCH₂-(pyridin-4-yl)]indol-2-yl |
| 3929 | 1-CH₃, 6-CF₃, 4-[OCH₂-(pyridin-4-yl)]indol-2-yl |
| 3930 | 1-CH₃, 4-[morpholin-4-yl]indol-2-yl |
| 3931 | 1-CH₃, 4-[1-CH₃-imidazol-2-yl]indol-2-yl |
| 3932 | 1-CH₃, 6-F, 4-[1-CH₃-imidazol-2-yl]indol-2-yl |
| 3933 | 1-CH₃, 6-CH₃, 4-[1-CH₃-imidazol-2-yl]indol-2-yl |
| 3934 | 1-CH₃, 6-CF₃, 4-[1-CH₃-imidazol-2-yl]indol-2-yl |
| 3935 | 1-CH₃, 4-[1,2,4-triazol-1-yl]indol-2-yl |
| 3936 | 1-CH₃, 6-F, 4-[1,2,4-triazol-1-yl]indol-2-yl |
| 3937 | 1-CH₃, 6-CH₃, 4-[1,2,4-triazol-1-yl]indol-2-yl |
| 3938 | 1-CH₃, 6-CF₃, 4-[1,2,4-triazol-1-yl]indol-2-yl |
| 3939 | 1-CH₃, 4,6-Cl₂-indol-2-yl |
| 3940 | 1-CH₃, 4,6-(CH₃)₂-indol-2-yl |
| 3941 | 1-CH₃, 4,6-(OCH₃)₂-indol-2-yl |
| 3942 | 1-CH₃, 4,6-(OCH₂CH₃)₂-indol-2-yl |
| 3943 | 1-CH₃, 4-F, 6-CH₃-indol-2-yl |
| 3944 | 1-CH₃, 4-F, 6-OCH₃-indol-2-yl |
| 3945 | 1-CH₃, 4-F, 6-OCH₂CH₃-indol-2-yl |
| 3946 | 1-CH₃, 4-F, 6-OCH₂CF₃-indol-2-yl |
| 3947 | 1-CH₃, 4-F, 6-OCH(CH₃)₂-indol-2-yl |
| 3948 | 1-CH₃, 4-Cl, 6-CH₃-indol-2-yl |
| 3949 | 1-CH₃, 4-Cl, 6-OCH₃-indol-2-yl |
| 3950 | 1-CH₃, 4-Cl, 6-OCH₂CH₃-indol-2-yl |
| 3951 | 1-CH₃, 4-Cl, 6-OCH₂CF₃-indol-2-yl |
| 3952 | 1-CH₃, 4-Cl, 6-OCH(CH₃)₂-indol-2-yl |
| 3953 | 1-CH₃, 4-CH₃, 6-CH₃-indol-2-yl |
| 3954 | 1-CH₃, 4-CH₃, 6-OCH₂CH₃-indol-2-yl |
| 3955 | 1-CH₃, 4-CH₃, 6-OCH₂CF₃-indol-2-yl |
| 3956 | 1-CH₃, 4-CH₃, 6-OCH(CH₃)₂-indol-2-yl |
| 3957 | 1-CH₃, 4-CH₃, 6-OCH₂CH=CH₂-indol-2-yl |
| 3958 | 1-CH₃, 4-CH₃, 6-CO₂CH₃-indol-2-yl |
| 3959 | 1-CH₃, 4-CH₃, 6-CF₃-indol-2-yl |
| 3960 | 1-CH₃, 4-CF₃, 6-CH₂CH₃-indol-2-yl |
| 3961 | 1-CH₃, 4-CF₃, 6-OCH₃-indol-2-yl |
| 3962 | 1-CH₃, 4-CF₃, 6-OCH₂CH₃-indol-2-yl |
| 3963 | 1-CH₃, 4-CF₃, 6-OCH₂CF₃-indol-2-yl |
| 3964 | 1-CH₃, 4-OCH₃, 6-OCH₂CH₃-indol-2-yl |
| 3965 | 1-CH₃, 4-OCH₃, 6-OCH₂CF₃-indol-2-yl |
| 3966 | 1-CH₃, 4-OCH₃, 6-OCH(CH₃)₂-indol-2-yl |
| 3967 | 1-CH₃, 4-OCH₂CH₃, 6-CH₂OCH₂CH₃-indol-2-yl |
| 3968 | 1-CH₃, 4-NO₂, 6-CH₃-indol-2-yl |
| 3969 | 1-CH₃, 4-NO₂, 6-OCH₃-indol-2-yl |
| 3970 | 1-CH₃, 4-NO₂, 6-OCH₂CH₃-indol-2-yl |
| 3971 | 1-CH₃, 4-NO₂, 6-OCH(CH₃)₂-indol-2-yl |

TABLE A-continued

| No. | R⁴ |
|---|---|
| 3972 | 1-CH$_3$, 4-NO$_2$, 6-OCH$_2$CF$_3$-indol-2-yl |
| 3973 | 1-CH$_3$, 4-CN, 6-CH$_3$-indol-2-yl |
| 3974 | 1-CH$_3$, 4-CN, 6-OCH$_3$-indol-2-yl |
| 3975 | 1-CH$_3$, 4-CN, 6-OCH$_2$CH$_3$-indol-2-yl |
| 3976 | 1-CH$_3$, 4-CN, 6-OCH(CH$_3$)$_2$-indol-2-yl |
| 3977 | 1-CH$_3$, 4-CN, 6-OCH$_2$CF$_3$-indol-2-yl |
| 3978 | 1-CH$_3$, 4-CH$_3$-indol-3-yl |
| 3979 | 1-CH$_3$, 4-CH$_2$CH$_3$-indol-3-yl |
| 3980 | 1-CH$_3$, 4-CH(CH$_3$)$_2$-indol-3-yl |
| 3981 | 1-CH$_3$, 4-CH(CH$_3$)CH$_2$CH$_3$-indol-3-yl |
| 3982 | 1-CH$_3$, 4-CF$_3$-indol-3-yl |
| 3983 | 1-CH$_3$, 4-CH=CH$_2$-indol-3-yl |
| 3984 | 1-CH$_3$, 4-CH=CHCH$_3$-indol-3-yl |
| 3985 | 1-CH$_3$, 4-CH=CHCl-indol-3-yl |
| 3986 | 1-CH$_3$, 4-C≡CH-indol-3-yl |
| 3987 | 1-CH$_3$, 4-CH$_2$C≡CH-indol-3-yl |
| 3988 | 1-CH$_3$, 4-CH$_2$C≡CCH$_3$-indol-3-yl |
| 3989 | 1-CH$_3$, 4-cyclopropyl-indol-3-yl |
| 3990 | 1-CH$_3$, 4-cyclopentyl-indol-3-yl |
| 3991 | 1-CH$_3$, 4-OCH$_3$-indol-3-yl |
| 3992 | 1-CH$_3$, 4-OCH$_2$CH$_3$-indol-3-yl |
| 3993 | 1-CH$_3$, 4-OCH$_2$CH$_2$CH$_3$-indol-3-yl |
| 3994 | 1-CH$_3$, 4-OCH(CH$_3$)$_2$-indol-3-yl |
| 3995 | 1-CH$_3$, 4-OCH$_2$CH$_2$CH$_2$CH$_3$-indol-3-yl |
| 3996 | 1-CH$_3$, 4-OCH(CH$_3$)CH$_2$CH$_3$-indol-3-yl |
| 3997 | 1-CH$_3$, 4-OCH$_2$CH(CH$_3$)$_2$-indol-3-yl |
| 3998 | 1-CH$_3$, 4-OC(CH$_3$)$_4$-indol-3-yl |
| 3999 | 1-CH$_3$, 4-OCH(CH$_3$)CH$_2$CH$_2$CH$_3$-indol-3-yl |
| 4000 | 1-CH$_3$, 4-OCH$_2$OCH$_3$-indol-3-yl |
| 4001 | 1-CH$_3$, 4-OCH$_2$OCH$_2$CH$_3$-indol-3-yl |
| 4002 | 1-CH$_3$, 4-OCH(CH$_3$)OCH$_3$-indol-3-yl |
| 4003 | 1-CH$_3$, 4-OCH(CH$_3$)OCH$_2$CH$_3$-indol-3-yl |
| 4004 | 1-CH$_3$, 4-OCH$_2$CH$_2$OCH$_3$-indol-3-yl |
| 4005 | 1-CH$_3$, 4-OCH$_2$CH$_2$OCH$_2$CH$_3$-indol-3-yl |
| 4006 | 1-CH$_3$, 4-OCH$_2$CH$_2$OCH(CH$_3$)$_2$-indol-3-yl |
| 4007 | 1-CH$_3$, 4-OCH$_2$CH$_2$SCH$_3$-indol-3-yl |
| 4008 | 1-CH$_3$, 4-OCH$_2$SO$_2$CH$_3$-indol-3-yl |
| 4009 | 1-CH$_3$, 4-OCH$_2$CH$_2$SCH(CH$_3$)$_2$-indol-3-yl |
| 4010 | 1-CH$_3$, 4-OCH$_2$CH$_2$CN-indol-3-yl |
| 4011 | 1-CH$_3$, 4-OCH$_2$CH$_2$SCH$_2$CH$_2$CN-indol-3-yl |
| 4012 | 1-CH$_3$, 4-OCH$_2$CH$_2$OC$_6$H$_5$-indol-3-yl |
| 4013 | 1-CH$_3$, 4-OCH$_2$CH$_2$OCH$_2$C$_6$H$_5$-indol-3-yl |
| 4014 | 1-CH$_3$, 4-OCH$_2$CH$_2$N(CH$_3$)$_2$-indol-3-yl |
| 4015 | 1-CH$_3$, 4-OCH$_2$CH$_2$CONH$_2$-indol-3-yl |
| 4016 | 1-CH$_3$, 4-OCH$_2$CH$_2$CO$_2$CH$_2$CH$_3$-indol-3-yl |
| 4017 | 1-CH$_3$, 4-OCH(CH$_3$)CH$_2$OCH$_3$-indol-3-yl |
| 4018 | 1-CH$_3$, 4-OCH(CH$_3$)CH$_2$CO$_2$CH$_3$-indol-3-yl |
| 4019 | 1-CH$_3$, 4-OCH(CH$_3$)CH$_2$CO$_2$CH$_2$CH$_3$-indol-3-yl |
| 4020 | 1-CH$_3$, 4-OCH$_2$CH(CH$_3$)CO$_2$CH$_3$-indol-3-yl |
| 4021 | 1-CH$_3$, 4-OCH$_2$C(=O)CH$_3$-indol-3-yl |
| 4022 | 1-CH$_3$, 4-OCH$_2$C(=O)CH$_2$CH$_3$-indol-3-yl |
| 4023 | 1-CH$_3$, 4-OCH$_2$CO$_2$CH$_3$-indol-3-yl |
| 4024 | 1-CH$_3$, 4-OCH$_2$CO$_2$CH$_2$CH$_3$-indol-3-yl |
| 4025 | 1-CH$_3$, 4-OCH$_2$C(=O)NH$_2$-indol-3-yl |
| 4026 | 1-CH$_3$, 4-OCH$_2$C(=O)NHCH$_3$-indol-3-yl |
| 4027 | 1-CH$_3$, 4-OCH$_2$C(=O)SCH$_3$-indol-3-yl |
| 4028 | 1-CH$_3$, 4-OCH(CH$_3$)C(=O)NH$_2$-indol-3-yl |
| 4029 | 1-CH$_3$, 4-OCH(CH$_3$)C(=O)NHCH$_3$-indol-3-yl |
| 4030 | 1-CH$_3$, 4-OCH(CH$_3$)C(=O)NHNH$_2$-indol-3-yl |
| 4031 | 1-CH$_3$, 4-OCH(CH$_3$)CO$_2$CH$_3$-indol-3-yl |
| 4032 | 1-CH$_3$, 4-OCH(CH$_3$)CO$_2$CH$_2$CH$_3$-indol-3-yl |
| 4033 | 1-CH$_3$, 4-OCH(CH$_3$)C(=O)CH$_3$-indol-3-yl |
| 4034 | 1-CH$_3$, 4-OCH(CH$_3$)CH$_2$C(=O)CH$_2$CH$_3$-indol-3-yl |
| 4035 | 1-CH$_3$, 4-OCH(CH$_3$)CH$_2$C(=O)CH$_3$-indol-3-yl |
| 4036 | 1-CH$_3$, 4-OCH(CH$_3$)CH$_2$OC(CH$_3$)$_4$-indol-3-yl |
| 4037 | 1-CH$_3$, 4-OCH(CH$_3$)CH$_2$OCH$_2$CH$_3$-indol-3-yl |
| 4038 | 1-CH$_3$, 4-OCH(CH$_3$)CH$_2$O(CH$_3$)$_2$-indol-3-yl |
| 4039 | 1-CH$_3$, 4-OCH(CH$_3$)CH$_2$OCH$_2$CH=CH$_2$-indol-3-yl |
| 4040 | 1-CH$_3$, 4-O(CH$_2$)$_2$OCH$_3$-indol-3-yl |
| 4041 | 1-CH$_3$, 4-O(CH$_2$)$_3$OCH$_2$CH$_3$-indol-3-yl |
| 4042 | 1-CH$_3$, 4-O(CH$_2$)$_3$OCH(CH$_3$)$_2$-indol-3-yl |
| 4043 | 1-CH$_3$, 4-O(CH$_2$)$_3$OC$_6$H$_5$-indol-3-yl |
| 4044 | 1-CH$_3$, 4-O(CH$_2$)$_3$OCH$_2$C$_6$H$_5$-indol-3-yl |
| 4045 | 1-CH$_3$, 4-OCH(CH$_2$CH$_3$)CH$_2$OCH$_3$-indol-3-yl |
| 4046 | 1-CH$_3$, 4-OCH(CH$_2$CH$_3$)CH$_2$CH$_2$OCH$_3$-indol-3-yl |
| 4047 | 1-CH$_3$, 4-OCH(CH$_2$CH$_3$)CH$_2$CH$_2$OCH$_2$CH$_3$-indol-3-yl |
| 4048 | 1-CH$_3$, 4-O[(CH$_2$)$_3$O]$_2$CH$_3$-indol-3-yl |
| 4049 | 1-CH$_3$, 4-OCH$_2$CH(CH$_3$)CH$_2$OCH$_3$-indol-3-yl |
| 4050 | 1-CH$_3$, 4-OCH$_2$CH(CH$_3$)CH$_2$OCH$_2$CH$_3$-indol-3-yl |
| 4051 | 1-CH$_3$, 4-OCH(CH$_2$Cl)CH$_2$OCH$_3$-indol-3-yl |
| 4052 | 1-CH$_3$, 4-OCH(CH$_2$Cl)CH$_2$OCH$_2$CH$_3$-indol-3-yl |
| 4053 | 1-CH$_3$, 4-OCH(CH$_2$Cl)CH$_2$OCH(CH$_3$)$_2$-indol-3-yl |
| 4054 | 1-CH$_3$, 4-OCH(CH$_2$Cl)CH$_2$OCH$_2$CH=CH$_2$-indol-3-yl |
| 4055 | 1-CH$_3$, 4-OCH[CH$_2$OCH$_3$]$_2$-indol-3-yl |
| 4056 | 1-CH$_3$, 4-OCH[CH$_2$OCH$_2$CH$_3$]$_2$-indol-3-yl |
| 4057 | 1-CH$_3$, 4-OCCl$_4$-indol-3-yl |
| 4058 | 1-CH$_3$, 4-OCHF$_2$-indol-3-yl |
| 4059 | 1-CH$_3$, 4-OCF$_3$-indol-3-yl |
| 4060 | 1-CH$_3$, 4-OCF$_2$CHF$_2$-indol-3-yl |
| 4061 | 1-CH$_3$, 4-OCH$_2$CF$_3$-indol-3-yl |
| 4062 | 1-CH$_3$, 4-OCH$_2$CHF$_2$-indol-3-yl |
| 4063 | 1-CH$_3$, 4-O(CH$_2$)$_3$F-indol-3-yl |
| 4064 | 1-CH$_3$, 4-OCH(CH$_3$)CF$_3$-indol-3-yl |
| 4065 | 1-CH$_3$, 4-O(CH$_2$)$_4$F-indol-3-yl |
| 4066 | 1-CH$_3$, 4-O(CH$_2$)$_3$CF$_3$-indol-3-yl |
| 4067 | 1-CH$_3$, 4-OCH(CH$_3$)CF$_2$CF$_3$-indol-3-yl |
| 4068 | 1-CH$_3$, 4-OCH(CH$_3$)CF$_2$CHF$_2$-indol-3-yl |
| 4069 | 1-CH$_3$, 4-OCH$_2$CF$_2$CHFCH$_3$-indol-3-yl |
| 4070 | 1-CH$_3$, 4-OCH$_2$(CF$_2$)$_2$CF$_3$-indol-3-yl |
| 4071 | 1-CH$_3$, 4-O(CF$_2$)$_3$CF$_3$-indol-3-yl |
| 4072 | 1-CH$_3$, 4-OCH$_2$CF$_2$CHF$_2$-indol-3-yl |
| 4073 | 1-CH$_3$, 4-CH$_2$CH=CH$_2$-indol-3-yl |
| 4074 | 1-CH$_3$, 4-CH$_2$C(CH$_3$)=CH$_2$-indol-3-yl |
| 4075 | 1-CH$_3$, 4-OCH$_2$CH=CHCH$_3$-indol-3-yl |
| 4076 | 1-CH$_3$, 4-O(CH$_2$)$_2$CH=CH$_2$-indol-3-yl |
| 4077 | 1-CH$_3$, 4-OCH$_2$C(CH$_3$)=CH$_2$-indol-3-yl |
| 4078 | 1-CH$_3$, 4-OCH(CH$_3$)CH=CH$_2$-indol-3-yl |
| 4079 | 1-CH$_3$, 4-OCH$_2$C≡CH-indol-3-yl |
| 4080 | 1-CH$_3$, 4-OCH$_2$C≡CCH$_3$-indol-3-yl |
| 4081 | 1-CH$_3$, 4-O(CH$_2$)$_2$C≡CH-indol-3-yl |
| 4082 | 1-CH$_3$, 4-SCH$_3$-indol-3-yl |
| 4083 | 1-CH$_3$, 4-SCH$_2$CH$_3$-indol-3-yl |
| 4084 | 1-CH$_3$, 4-OC$_6$H$_5$-indol-3-yl |
| 4085 | 1-CH$_3$, 4-OCH$_2$C$_6$H$_5$-indol-3-yl |
| 4086 | 1-CH$_3$, 4-NO$_2$-indol-3-yl |
| 4087 | 1-CH$_3$, 4-NHCH$_3$-indol-3-yl |
| 4088 | 1-CH$_3$, 4-N(CH$_3$)$_2$-indol-3-yl |
| 4089 | 1-CH$_3$, 4-NHCH$_2$CF$_3$-indol-3-yl |
| 4090 | 1-CH$_3$, 4-NHCH$_2$CF$_3$-indol-3-yl |
| 4091 | 1-CH$_3$, 4-F-indol-3-yl |
| 4092 | 1-CH$_3$, 4-Cl-indol-3-yl |
| 4093 | 1-CH$_3$, 4-OH-indol-3-yl |
| 4094 | 1-CH$_3$, 4-CN-indol-3-yl |
| 4095 | 1-CH$_3$, 4-C(O)NH$_2$-indol-3-yl |
| 4096 | 1-CH$_3$, 4-C(S)NH$_2$-indol-3-yl |
| 4097 | 1-CH$_3$, 4-CO$_2$CH$_3$-indol-3-yl |
| 4098 | 1-CH$_3$, 4-ON=C(CH$_3$)$_2$-indol-3-yl |
| 4099 | 1-CH$_3$, 4-[O-cyclopropyl]indol-3-yl |
| 4100 | 1-CH$_3$, 4-[O-cyclobutyl]indol-3-yl |
| 4101 | 1-CH$_3$, 4-[O-cyclopentyl]indol-3-yl |
| 4102 | 1-CH$_3$, 4-[O-cyclohexyl]indol-3-yl |
| 4103 | 1-CH$_3$, 4-OCH$_2$-cyclopropyl-indol-3-yl |
| 4104 | 1-CH$_3$, 6-F, 4-[OCH$_2$-cyclopropyl]indol-3-yl |
| 4105 | 1-CH$_3$, 6-CH$_3$, 4-[OCH$_2$-cyclopropyl]indol-3-yl |
| 4106 | 1-CH$_3$, 6-CF$_3$, 4-[OCH$_2$-cyclopropyl]indol-3-yl |
| 4107 | 1-CH$_3$, 4-[OCH(CH$_3$)-cyclopropyl]indol-3-yl |
| 4108 | 1-CH$_3$, 6-F, 4-[OCH(CH$_3$)-cyclopropyl]indol-3-yl |
| 4109 | 1-CH$_3$, 6-CH$_3$, 4-[OCH(CH$_3$)-cyclopropyl]indol-3-yl |
| 4110 | 1-CH$_3$, 6-CF$_3$, 4-[OCH(CH$_3$)-cyclopropyl]indol-3-yl |
| 4111 | 1-CH$_3$, 4-[O-(1-CH$_3$-cyclopropyl)]indol-3-yl |
| 4112 | 1-CH$_3$, 6-F, 4-[O-(1-CH$_3$-cyclopropyl)]indol-3-yl |
| 4113 | 1-CH$_3$, 6-CH$_3$, 4-[O-(1-CH$_3$-cyclopropyl)]indol-3-yl |
| 4114 | 1-CH$_3$, 6-CF$_3$, 4-[O-(1-CH$_3$-cyclopropyl)]indol-3-yl |
| 4115 | 1-CH$_3$, 4-[OCH$_2$-(1-CH$_3$-cyclopropyl)]indol-3-yl |
| 4116 | 1-CH$_3$, 6-F, 4-[OCH$_2$-(1-CH$_3$-cyclopropyl)]indol-3-yl |
| 4117 | 1-CH$_3$, 6-CH$_3$, 4-[OCH$_2$-(1-CH$_3$-cyclopropyl)]indol-3-yl |
| 4118 | 1-CH$_3$, 6-CF$_3$, 4-[OCH$_2$-(1-CH$_3$-cyclopropyl)]indol-3-yl |
| 4119 | 1-CH$_3$, 4-[OCH$_2$-(2-CH$_3$-cyclopropyl)]indol-3-yl |
| 4120 | 1-CH$_3$, 6-F, 4-[OCH$_2$-(2-CH$_3$-cyclopropyl)]indol-3-yl |
| 4121 | 1-CH$_3$, 6-CH$_3$, 4-[OCH$_2$-(2-CH$_3$-cyclopropyl)]indol-3-yl |
| 4122 | 1-CH$_3$, 6-CF$_3$, 4-[OCH$_2$-(2-CH$_3$-cyclopropyl)]indol-3-yl |
| 4123 | 1-CH$_3$, 4-[OCH$_2$-(tetrahydropyran-2-yl)]indol-3-yl |
| 4124 | 1-CH$_3$, 6-F, 4-[OCH$_2$-(tetrahydropyran-2-yl)]indol-3-yl |
| 4125 | 1-CH$_3$, 6-CH$_3$, 4-[OCH$_2$-(tetrahydropyran-2-yl)]indol-3-yl |

TABLE A-continued

| No. | R⁴ |
|---|---|
| 4126 | 1-CH₃, 6-CF₃, 4-[OCH₂-(tetrahydropyran-2-yl)]indol-3-yl |
| 4127 | 1-CH₃, 4-[OCH₂-(furan-2-yl)]indol-3-yl |
| 4128 | 1-CH₃, 6-F, 4-[OCH₂-(furan-2-yl)]indol-3-yl |
| 4129 | 1-CH₃, 6-CH₃, 4-[OCH₂-(furan-2-yl)]indol-3-yl |
| 4130 | 1-CH₃, 6-CF₃, 4-[OCH₂-(furan-2-yl)]indol-3-yl |
| 4131 | 1-CH₃, 4-[OCH₂-(furan-4-yl)]indol-3-yl |
| 4132 | 1-CH₃, 6-F, 4-[OCH₂-(furan-4-yl)]indol-3-yl |
| 4133 | 1-CH₃, 6-CH₃, 4-[OCH₂-(furan-4-yl)]indol-3-yl |
| 4134 | 1-CH₃, 6-CF₃, 4-[OCH₂-(furan-4-yl)]indol-3-yl |
| 4135 | 1-CH₃, 4-[OCH₂-(tetrahydrofuran-4-yl)]indol-3-yl |
| 4136 | 1-CH₃, 6-F, 4-[OCH₂-(tetrahydrofuran-4-yl)]indol-3-yl |
| 4137 | 1-CH₃, 6-CH₃, 4-[OCH₂-(tetrahydrofuran-4-yl)]indol-3-yl |
| 4138 | 1-CH₃, 6-CF₃, 4-[OCH₂-(tetrahydrofuran-4-yl)]indol-3-yl |
| 4139 | 1-CH₃, 4-[OCH₂-(tetrahydrofuran-2-yl)]indol-3-yl |
| 4140 | 1-CH₃, 6-F, 4-[OCH₂-(tetrahydrofuran-2-yl)]indol-3-yl |
| 4141 | 1-CH₃, 6-CH₃, 4-[OCH₂-(tetrahydrofuran-2-yl)]indol-3-yl |
| 4142 | 1-CH₃, 6-CF₃, 4-[OCH₂-(tetrahydrofuran-2-yl)]indol-3-yl |
| 4143 | 1-CH₃, 4-[O-tetrahydropyran-4-yl)]indol-3-yl |
| 4144 | 1-CH₃, 6-F, 4-[O-(tetrahydropyran-4-yl)]indol-3-yl |
| 4145 | 1-CH₃, 6-CH₃, 4-[O-(tetrahydropyran-4-yl)]indol-3-yl |
| 4146 | 1-CH₃, 6-CF₃, 4-[O-(tetrahydropyran-4-yl)]indol-3-yl |
| 4147 | 1-CH₃, 4-[2-Cl—C₅H₄]indol-3-yl |
| 4148 | 1-CH₃, 6-F, 4-[2-Cl—C₅H₄]indol-3-yl |
| 4149 | 1-CH₃, 6-CH₃, 4-[2-Cl—C₅H₄]indol-3-yl |
| 4150 | 1-CH₃, 6-CF₃, 4-[2-Cl—C₅H₄]indol-3-yl |
| 4151 | 1-CH₃, 4-[OCH₂-(pyridin-2-yl)]indol-3-yl |
| 4152 | 1-CH₃, 6-F, 4-[OCH₂-(pyridin-2-yl)]indol-3-yl |
| 4153 | 1-CH₃, 6-CH₃, 4-[OCH₂-(pyridin-2-yl)]indol-3-yl |
| 4154 | 1-CH₃, 6-CF₃, 4-[OCH₂-(pyridin-2-yl)]indol-3-yl |
| 4155 | 1-CH₃, 4-[OCH₂-(pyridin-4-yl)]indol-3-yl |
| 4156 | 1-CH₃, 6-F, 4-[OCH₂-(pyridin-4-yl)]indol-3-yl |
| 4157 | 1-CH₃, 6-CH₃, 4-[OCH₂-(pyridin-4-yl)]indol-3-yl |
| 4158 | 1-CH₃, 6-CF₃, 4-[OCH₂-(pyridin-4-yl)]indol-3-yl |
| 4159 | 1-CH₃, 4-[morpholin-4-yl]indol-3-yl |
| 4160 | 1-CH₃, 4-[1-CH₃-imidazol-2-yl]indol-3-yl |
| 4161 | 1-CH₃, 6-F, 4-[1-CH₃-imidazol-2-yl]indol-3-yl |
| 4162 | 1-CH₃, 6-CH₃, 4-[1-CH₃-imidazol-2-yl]indol-3-yl |
| 4163 | 1-CH₃, 6-CF₃, 4-[1-CH₃-imidazol-2-yl]indol-3-yl |
| 4164 | 1-CH₃, 4-[1,2,4-triazol-1-yl]indol-3-yl |
| 4165 | 1-CH₃, 6-F, 4-[1,2,4-triazol-1-yl]indol-3-yl |
| 4166 | 1-CH₃, 6-CH₃, 4-[1,2,4-triazol-1-yl]indol-3-yl |
| 4167 | 1-CH₃, 6-CF₃, 4-[1,2,4-triazol-1-yl]indol-3-yl |
| 4168 | 1-CH₃, 4,6-Cl₂-indol-3-yl |
| 4169 | 1-CH₃, 4,6-(CH₃)₂-indol-3-yl |
| 4170 | 1-CH₃, 4,6-(OCH₃)₂-indol-3-yl |
| 4171 | 1-CH₃, 4,6-(OCH₂CH₃)₂-indol-3-yl |
| 4172 | 1-CH₃, 4-F, 6-CH₃-indol-3-yl |
| 4173 | 1-CH₃, 4-F, 6-OCH₃-indol-3-yl |
| 4174 | 1-CH₃, 4-F, 6-OCH₂CH₃-indol-3-yl |
| 4175 | 1-CH₃, 4-F, 6-OCH₂CF₃-indol-3-yl |
| 4176 | 1-CH₃, 4-F, 6-OCH(CH₃)₂-indol-3-yl |
| 4177 | 1-CH₃, 4-Cl, 6-CH₃-indol-3-yl |
| 4178 | 1-CH₃, 4-Cl, 6-OCH₃-indol-3-yl |
| 4179 | 1-CH₃, 4-Cl, 6-OCH₂CH₃-indol-3-yl |
| 4180 | 1-CH₃, 4-Cl, 6-OCH₂CF₃-indol-3-yl |
| 4181 | 1-CH₃, 4-Cl, 6-OCH(CH₃)₂-indol-3-yl |
| 4182 | 1-CH₃, 4-CH₃, 6-OCH₃-indol-3-yl |
| 4183 | 1-CH₃, 4-CH₃, 6-OCH₂CH₃-indol-3-yl |
| 4184 | 1-CH₃, 4-CH₃, 6-OCH₂CF₃-indol-3-yl |
| 4185 | 1-CH₃, 4-CH₃, 6-OCH(CH₃)₂-indol-3-yl |
| 4186 | 1-CH₃, 4-CH₃, 6-OCH₂CH=CH₂-indol-3-yl |
| 4187 | 1-CH₃, 4-CH₃, 6-CO₂CH₃-indol-3-yl |
| 4188 | 1-CH₃, 4-CH₃, 6-CF₃-indol-3-yl |
| 4189 | 1-CH₃, 4-CH₃, 6-CH₂CH₃-indol-3-yl |
| 4190 | 1-CH₃, 4-CH₃, 6-OCH₃-indol-3-yl |
| 4191 | 1-CH₃, 4-CH₃, 6-OCH₂CH₃-indol-3-yl |
| 4192 | 1-CH₃, 4-CH₃, 6-OCH₂CF₃-indol-3-yl |
| 4193 | 1-CH₃, 4-OCH₃, 6-OCH₂CH₃-indol-3-yl |
| 4194 | 1-CH₃, 4-OCH₃, 6-OCH₂CF₃-indol-3-yl |
| 4195 | 1-CH₃, 4-OCH₃, 6-OCH(CH₃)-indol-3-yl |
| 4196 | 1-CH₃, 4-OCH₂CH₃, 6-CH₂OCH₂CH₃-indol-3-yl |
| 4197 | 1-CH₃, 4-NO₂, 6-CH₃-indol-3-yl |
| 4198 | 1-CH₃, 4-NO₂, 6-OCH₃-indol-3-yl |
| 4199 | 1-CH₃, 4-NO₂, 6-OCH₂CH₃-indol-3-yl |
| 4200 | 1-CH₃, 4-NO₂, 6-OCH(CH₃)₂-indol-3-yl |
| 4201 | 1-CH₃, 4-NO₂, 6-OCH₂CF₃-indol-3-yl |
| 4202 | 1-CH₃, 4-CN, 6-CH₃-indol-3-yl |
| 4203 | 1-CH₃, 4-CN, 6-OCH₃-indol-3-yl |
| 4204 | 1-CH₃, 4-CN, 6-OCH₂CH₃-indol-3-yl |
| 4205 | 1-CH₃, 4-CN, 6-OCH(CH₃)₂-indol-3-yl |
| 4206 | 1-CH₃, 4-CN, 6-OCH₂CF₃-indol-3-yl |
| 4207 | 4-CH₃-quinolin-2-yl |
| 4208 | 4-CH₂CH₃-quinolin-2-yl |
| 4209 | 4-CH(CH₃)₂-quinolin-2-yl |
| 4210 | 4-CH(CH₃)CH₂CH₃-quinolin-2-yl |
| 4211 | 4-CF₃-quinolin-2-yl |
| 4212 | 4-CH=CH₂-quinolin-2-yl |
| 4213 | 4-CH=CHCH₃-quinolin-2-yl |
| 4214 | 4-CH=CHCl-quinolin-2-yl |
| 4215 | 4-C≡CH-quinolin-2-yl |
| 4216 | 4-CH₂C≡CH-quinolin-2-yl |
| 4217 | 4-CH₂C≡CCH₃-quinolin-2-yl |
| 4218 | 4-cyclopropyl-quinolin-2-yl |
| 4219 | 4-cyclopentyl-quinolin-2-yl |
| 4220 | 4-OCH₃-quinolin-2-yl |
| 4221 | 4-OCH₂CH₃-quinolin-2-yl |
| 4222 | 4-OCH₂CH₂CH₃-quinolin-2-yl |
| 4223 | 4-OCH(CH₃)₂-quinolin-2-yl |
| 4224 | 4-OCH₂CH₂CH₂CH₃-quinolin-2-yl |
| 4225 | 4-OCH(CH₃)CH₂CH₃-quinolin-2-yl |
| 4226 | 4-OCH₂CH(CH₃)₂-quinolin-2-yl |
| 4227 | 4-OC(CH₃)₄-quinolin-2-yl |
| 4228 | 4-OCH(CH₃)CH₂CH₂CH₃-quinolin-2-yl |
| 4229 | 4-OCH₂OCH₃-quinolin-2-yl |
| 4230 | 4-OCH₂OCH₂CH₃-quinolin-2-yl |
| 4231 | 4-OCH(CH₃)OCH₃-quinolin-2-yl |
| 4232 | 4-OCH(CH₃)OCH₂CH₃-quinolin-2-yl |
| 4233 | 4-OCH₂CH₂OCH₃-quinolin-2-yl |
| 4234 | 4-OCH₂CH₂OCH₂CH₃-quinolin-2-yl |
| 4235 | 4-OCH₂CH₂OCH(CH₃)₂-quinolin-2-yl |
| 4236 | 4-OCH₂CH₂SCH₃-quinolin-2-yl |
| 4237 | 4-OCH₂CH₂SO₂CH₃-quinolin-2-yl |
| 4238 | 4-OCH₂CH₂SCH(CH₃)₂-quinolin-2-yl |
| 4239 | 4-OCH₂CH₂CN-quinolin-2-yl |
| 4240 | 4-OCH₂CH₂SCH₂CN-quinolin-2-yl |
| 4241 | 4-OCH₂CH₂OC₆H₅-quinolin-2-yl |
| 4242 | 4-OCH₂CH₂OCH₂C₆H₅-quinolin-2-yl |
| 4243 | 4-OCH₂CH₂N(CH₃)₂-quinolin-2-yl |
| 4244 | 4-OCH₂CH₂CONH₂-quinolin-2-yl |
| 4245 | 4-OCH₂CH₂CO₂CH₂CH₂CH₃-quinolin-2-yl |
| 4246 | 4-OCH(CH₃)CH₂OCH₃-quinolin-2-yl |
| 4247 | 4-OCH(CH₃)CH₂CO₂CH₃-quinolin-2-yl |
| 4248 | 4-OCH(CH₃)CH₂CO₂CH₂CH₃-quinolin-2-yl |
| 4249 | 4-OCH₂CH(CH₃)CO₂CH₃-quinolin-2-yl |
| 4250 | 4-OCH₂C(=O)CH₃-quinolin-2-yl |
| 4251 | 4-OCH₂C(=O)CH₃-quinolin-2-yl |
| 4252 | 4-OCH₂CO₂CH₃-quinolin-2-yl |
| 4253 | 4-OCH₂CO₂CH₂CH₃-quinolin-2-yl |
| 4254 | 4-OCH₂C(=O)NH₂-quinolin-2-yl |
| 4255 | 4-OCH₂C(=O)NHCH₃-quinolin-2-yl |
| 4256 | 4-OCH₂C(=O)SCH₃-quinolin-2-yl |
| 4257 | 4-OCH(CH₃)C(=O)NH₂-quinolin-2-yl |
| 4258 | 4-OCH(CH₃)C(=O)NHCH₃-quinolin-2-yl |
| 4259 | 4-OCH(CH₃)C(=O)NHNH₂-quinolin-2-yl |
| 4260 | 4-OCH(CH₃)CO₂CH₃-quinolin-2-yl |
| 4261 | 4-OCH(CH₃)CO₂CH₂CH₃-quinolin-2-yl |
| 4263 | 4-OCH(CH₃)C(=O)CH₂CH₃-quinolin-2-yl |
| 4264 | 4-OCH(CH₃)CH₂C(=O)CH₃-quinolin-2-yl |
| 4265 | 4-OCH(CH₃)CH₂OC(CH₃)₄-quinolin-2-yl |
| 4266 | 4-OCH(CH₃)CH₂OCH₂CH₃-quinolin-2-yl |
| 4267 | 4-OCH(CH₃)CH₂O(CH₃)₂CH₃-quinolin-2-yl |
| 4268 | 4-OCH(CH₃)CH₂OCH₂CH=CH₂-quinolin-2-yl |
| 4269 | 4-O(CH₂)₃OCH₃-quinolin-2-yl |
| 4270 | 4-O(CH₂)₃OCH₂CH₃-quinolin-2-yl |
| 4271 | 4-O(CH₃)₃OCH(CH₃)₂-quinolin-2-yl |
| 4272 | 4-O(CH₂)₃OC₆H₅-quinolin-2-yl |
| 4273 | 4-O(CH₂)₃OCH₂C₆H₅-quinolin-2-yl |
| 4274 | 4-OCH(CH₂CH₃)CH₂CH₃-quinolin-2-yl |
| 4275 | 4-OCH(CH₂CH₃)CH₂OCH₃-quinolin-2-yl |
| 4276 | 4-OCH(CH₂CH₃)CH₂CH₂OCH₂CH₃-quinolin-2-yl |
| 4277 | 4-O[(CH₂)₂O]₂CH₃-quinolin-2-yl |
| 4278 | 4-OCH₂CH(CH₃)CH₂OCH₃-quinolin-2-yl |
| 4279 | 4-OCH₂CH(CH₃)CH₂OCH₂CH₃-quinolin-2-yl |
| 4280 | 4-OCH(CH₂Cl)CH₂OCH₃-quinolin-2-yl |

TABLE A-continued

| No. | R⁴ |
|---|---|
| 4281 | 4-OCH(CH₂Cl)CH₂OCH₂CH₃-quinolin-2-yl |
| 4282 | 4-OCH(CH₂Cl)CH₂OCH(CH₃)₂-quinolin-2-yl |
| 4283 | 4-OCH(CH₂Cl)CH₂OCH₂CH=CH₂-quinolin-2-yl |
| 4284 | 4-OCH[CH₂OCH₃]₂-quinolin-2-yl |
| 4285 | 4-OCH[CH₂OCH₂CH₃]₂-quinolin-2-yl |
| 4286 | 4-OCCl₄-quinolin-2-yl |
| 4287 | 4-OCHF₂-quinolin-2-yl |
| 4288 | 4-OCF₃-quinolin-2-yl |
| 4289 | 4-OCF₂CHF₂-quinolin-2-yl |
| 4290 | 4-OCH₂CF₃-quinolin-2-yl |
| 4291 | 4-OCH₂CHF₂-quinolin-2-yl |
| 4292 | 4-O(CH₂)₃F-quinolin-2-yl |
| 4293 | 4-OCH(CH₃)CF₃-quinolin-2-yl |
| 4294 | 4-O(CH₂)₄F-quinolin-2-yl |
| 4295 | 4-O(CH₂)₃CF₃-quinolin-2-yl |
| 4296 | 4-OCH(CH₃)CF₂CF₃-quinolin-2-yl |
| 4297 | 4-OCH(CH₃)CF₂CHF₂-quinolin-2-yl |
| 4298 | 4-OCH₂CF₂CHFCH₃-quinolin-2-yl |
| 4299 | 4-OCH₂(CF₂)₂CF₃-quinolin-2-yl |
| 4300 | 4-O(CF₂)₃CF₃-quinolin-2-yl |
| 4301 | 4-OCH₂CF₂CHF₂-quinolin-2-yl |
| 4302 | 4-CH₂CH=CH₂-quinolin-2-yl |
| 4303 | 4-CH₂C(CH₃)=CH₂-quinolin-2-yl |
| 4304 | 4-OCH₂CH=CHCH₃-quinolin-2-yl |
| 4305 | 4-O(CH₂)₂CH=CH₂-quinolin-2-yl |
| 4306 | 4-OCH₂C(CH₃)=CH₂-quinolin-2-yl |
| 4307 | 4-OCH(CH₃)CH=CH₂-quinolin-2-yl |
| 4308 | 4-OCH₂C≡CH-quinolin-2-yl |
| 4309 | 4-OCH₂C≡CCH₃-quinolin-2-yl |
| 4310 | 4-O(CH₂)₂C≡CH-quinolin-2-yl |
| 4311 | 4-SCH₃-quinolin-2-yl |
| 4312 | 4-SCH₂CH₃-quinolin-2-yl |
| 4313 | 4-OC₆H₅-quinolin-2-yl |
| 4314 | 4-OCH₂C₆H₅-quinolin-2-yl |
| 4315 | 4-NO₂-quinolin-2-yl |
| 4316 | 4-NHCH₃-quinolin-2-yl |
| 4317 | 4-N(CH₃)₂-quinolin-2-yl |
| 4318 | 4-N(CH₃)C₂H₆-quinolin-2-yl |
| 4319 | 4-NHCF₃-quinolin-2-yl |
| 4320 | 4-F-quinolin-2-yl |
| 4321 | 4-Cl-quinolin-2-yl |
| 4322 | 4-OH-quinolin-2-yl |
| 4323 | 4-CN-quinolin-2-yl |
| 4324 | 4-C(O)NH₂-quinolin-2-yl |
| 4325 | 4-C(S)NH₂-quinolin-2-yl |
| 4326 | 4-CO₂CH₃-quinolin-2-yl |
| 4327 | 4-ON=C(CH₃)₂-quinolin-2-yl |
| 4328 | 4-[O-cyclopropyl]quinolin-2-yl |
| 4329 | 4-[O-cyclobutyl]quinolin-2-yl |
| 4330 | 4-[O-cyclopentyl]quinolin-2-yl |
| 4331 | 4-[O-cyclohexyl]quinolin-2-yl |
| 4332 | 4-[OCH₂-cyclopropyl]quinolin-2-yl |
| 4333 | 6-F, 4-[OCH₂-cyclopropyl]quinolin-2-yl |
| 4334 | 6-CH₃, 4-[OCH₂-cyclopropyl]quinolin-2-yl |
| 4335 | 6-CF₃, 4-[OCH₂-cyclopropyl]quinolin-2-yl |
| 4336 | 4-[OCH(CH₃)-cyclopropyl]quinolin-2-yl |
| 4337 | 6-F, 4-[OCH(CH₃)-cyclopropyl]quinolin-2-yl |
| 4338 | 6-CH₃, 4-[OCH(CH₃)-cyclopropyl]quinolin-2-yl |
| 4339 | 6-CF₃, 4-[OCH(CH₃)-cyclopropyl]quinolin-2-yl |
| 4340 | 4-[O-(1-CH₃-cyclopropyl)]quinolin-2-yl |
| 4341 | 6-F, 4-[O-(1-CH₃-cyclopropyl)]quinolin-2-yl |
| 4342 | 6-CH₃, 4-[O-(1-CH₃-cyclopropyl)]quinolin-2-yl |
| 4343 | 6-CF₃, 4-[O-(1-CH₃-cyclopropyl)]quinolin-2-yl |
| 4344 | 4-[OCH₂-(1-CH₃-cyclopropyl)]quinolin-2-yl |
| 4345 | 6-F, 4-[OCH₂-(1-CH₃-cyclopropyl)]quinolin-2-yl |
| 4346 | 6-CH₃, 4-[OCH₂-(1-CH₃-cyclopropyl)]quinolin-2-yl |
| 4347 | 6-CF₃, 4-[OCH₂-(1-CH₃-cyclopropyl)]quinolin-2-yl |
| 4348 | 4-[OCH₂-(2-CH₃-cyclopropyl)]quinolin-2-yl |
| 4349 | 6-F, 4-[OCH₂-(2-CH₃-cyclopropyl)]quinolin-2-yl |
| 4350 | 6-CH₃, 4-[OCH₂-(2-CH₃-cyclopropyl)]quinolin-2-yl |
| 4351 | 6-CF₃, 4-[OCH₂-(2-CH₃-cyclopropyl)]quinolin-2-yl |
| 4352 | 4-[OCH₂-(tetrahydropyran-2-yl)]quinolin-2-yl |
| 4353 | 6-F, 4-[OCH₂-(tetrahydropyran-2-yl)]quinolin-2-yl |
| 4354 | 6-CH₃, 4-[OCH₂-(tetrahydropyran-2-yl)]quinolin-2-yl |
| 4355 | 6-CF₃, 4-[OCH₂-(tetrahydropyran-2-yl)]quinolin-2-yl |
| 4356 | 4-[OCH₂-(furan-2-yl)]quinolin-2-yl |
| 4357 | 6-F, 4-[OCH₂-(furan-2-yl)]quinolin-2-yl |
| 4358 | 6-CH₃, 4-[OCH₂-(furan-2-yl)]quinolin-2-yl |
| 4359 | 6-CF₃, 4-[OCH₂-(furan-2-yl)]quinolin-2-yl |
| 4360 | 4-[OCH₂-(furan-4-yl)]quinolin-2-yl |
| 4361 | 6-F, 4-[OCH₂-(furan-4-yl)]quinolin-2-yl |
| 4362 | 6-CH₃, 4-[OCH₂-(furan-4-yl)]quinolin-2-yl |
| 4363 | 6-CF₃, 4-[OCH₂-(furan-4-yl)]quinolin-2-yl |
| 4364 | 4-[OCH₂-(tetrahydrofuran-4-yl)]quinolin-2-yl |
| 4365 | 6-F, 4-[OCH₂-(tetrahydrofuran-4-yl)]quinolin-2-yl |
| 4366 | 6-CH₃, 4-[OCH₂-(tetrahydrofuran-4-yl)]quinolin-2-yl |
| 4367 | 6-CF₃, 4-[OCH₂-(tetrahydrofuran-4-yl)]quinolin-2-yl |
| 4368 | 4-[OCH₂-(tetrahydrofuran-2-yl)]quinolin-2-yl |
| 4369 | 6-F, 4-[OCH₂-(tetrahydrofuran-2-yl)]quinolin-2-yl |
| 4370 | 6-CH₃, 4-[OCH₂-(tetrahydrofuran-2-yl)]quinolin-2-yl |
| 4371 | 6-CF₃, 4-[OCH₂-(tetrahydrofuran-2-yl)]quinolin-2-yl |
| 4372 | 4-[O-(tetrahydropyran-4-yl)]quinolin-2-yl |
| 4373 | 6-F, 4-[O-(tetrahydropyran-4-yl)]quinolin-2-yl |
| 4374 | 6-CH₃, 4-[O-(tetrahydropyran-4-yl)]quinolin-2-yl |
| 4375 | 6-CF₃, 4-[O-(tetrahydropyran-4-yl)]quinolin-2-yl |
| 4376 | 4-[2-Cl—C₅H₄]quinolin-2-yl |
| 4377 | 6-F, 4-[2-Cl—C₅H₄]quinolin-2-yl |
| 4378 | 6-CH₃, 4-[2-Cl—C₅H₄]quinolin-2-yl |
| 4379 | 6-CF₃, 4-[2-Cl—C₅H₄]quinolin-2-yl |
| 4380 | 4-[OCH₂-(pyridin-2-yl)]quinolin-2-yl |
| 4381 | 6-F, 4[OCH₂-(pyridin-2-yl)]quinolin-2-yl |
| 4382 | 6-CH₃, 4-[OCH₂-(pyridin-2-yl)]quinolin-2-yl |
| 4383 | 6-CF₃, 4-[OCH₂-(pyridin-2-yl)]quinolin-2-yl |
| 4384 | 4-[OCH₂-(pyridin-4-yl)]quinolin-2-yl |
| 4385 | 6-F, 4-[OCH₂-(pyridin-4-yl)]quinolin-2-yl |
| 4386 | 6-CH₃, 4-[OCH₂-(pyridin-4-yl)]quinolin-2-yl |
| 4387 | 6-CH₃, 4-[OCH₂-(pyridin-4-yl)]quinolin-2-yl |
| 4388 | 4-[morpholin-4-yl]quinolin-2-yl |
| 4389 | 4-[1-CH₃-imidazol-2-yl]quinolin-2-yl |
| 4390 | 6-F, 4-[1-CH₃-imidazol-2-yl]quinolin-2-yl |
| 4391 | 6-CH₃, 4-[1-CH₃-imidazol-2-yl]quinolin-2-yl |
| 4392 | 6-CF₃, 4-[1-CH₃-imidazol-2-yl]quinolin-2-yl |
| 4393 | 4-[1,2,4-triazol-1-yl]quinolin-2-yl |
| 4394 | 6-F, 4-[1,2,4-triazol-1-yl]quinolin-2-yl |
| 4395 | 6-CH₃, 4-[1,2,4-triazol-1-yl]quinolin-2-yl |
| 4396 | 6-CF₃, 4-[1,2,4-triazol-1-yl]quinolin-2-yl |
| 4397 | 4,6-Cl₂-quinolin-2-yl |
| 4398 | 4,6-(CH₃)₂-quinolin-2-yl |
| 4399 | 4,6-OCH₃)₂-quinolin-2-yl |
| 4400 | 4,6-(OCH₂CH₃)₂-quinolin-2-yl |
| 4401 | 4-F, 6-CH₃-quinolin-2-yl |
| 4402 | 4-F, 6-OCH₃-quinolin-2-yl |
| 4403 | 4-F, 6-OCH₂CH₃-quinolin-2-yl |
| 4404 | 4-F, 6-OCH₂CF₃-quinolin-2-yl |
| 4405 | 4-F, 6-OCH(CH₃)₂-quinolin-2-yl |
| 4406 | 4-Cl, 6-CH₃-quinolin-2-yl |
| 4407 | 4-Cl, 6-OCH₃-quinolin-2-yl |
| 4408 | 4-Cl, 6-OCH₂CH₃-quinolin-2-yl |
| 4409 | 4-Cl, 6-OCH₂CF₃-quinolin-2-yl |
| 4410 | 4-Cl, 6-OCH(CH₃)₂-quinolin-2-yl |
| 4411 | 4-CH₃, 6-OCH₃-quinolin-2-yl |
| 4412 | 4-CH₃, 6-OCH₂CH₃-quinolin-2-yl |
| 4413 | 4-CH₃, 6-OCH₂CF₃-quinolin-2-yl |
| 4414 | 4-CH₃, 6-OCH(CH₃)₂-quinolin-2-yl |
| 4415 | 4-CH₃, 6-OCH₂CH=CH₂-quinolin-2-yl |
| 4416 | 4-CH₃, 6-CO₂CH₃-quinolin-2-yl |
| 4417 | 4-CH₃, 6-CF₃-quinolin-2-yl |
| 4418 | 4-CF₃, 6-CH₂CH₃-quinolin-2-yl |
| 4419 | 4-CF₃, 6-OCH₃-quinolin-2-yl |
| 4420 | 4-CF₃, 6-OCH₂CH₃-quinolin-2-yl |
| 4421 | 4-CF₃, 6-OCH₂CF₃-quinolin-2-yl |
| 4422 | 4-OCH₃, 6-OCH₂CH₃-quinolin-2-yl |
| 4423 | 4-OCH₃, 6-OCH₂CF₃-quinolin-2-yl |
| 4424 | 4-OCH₃, 6-OCH(CH₃)₂-quinolin-2-yl |
| 4425 | 4-OCH₂CH₃, 6-CH₂OCH₂CH₃-quinolin-2-yl |
| 4426 | 4-NO₂, 6-CH₃-quinolin-2-yl |
| 4427 | 4-NO₂, 6-OCH₃-quinolin-2-yl |
| 4428 | 4-NO₂, 6-OCH₂CH₃-quinolin-2-yl |
| 4429 | 4-NO₂, 6-OCH(CH₃)₂-quinolin-2-yl |
| 4430 | 4-NO₂, 6-OCH₂CF₃-quinolin-2-yl |
| 4431 | 4-CN, 6-CH₃-quinolin-2-yl |
| 4432 | 4-CN, 6-OCH₃-quinolin-2-yl |
| 4433 | 4-CN, 6-OCH₂CH₃-quinolin-2-yl |
| 4434 | 4-CN, 6-OCH(CH₃)₂-quinolin-2-yl |

TABLE A-continued

| No. | R⁴ |
|---|---|
| 4435 | 4-CN, 6-OCH₂CF₃-quinolin-2-yl |
| 4436 | 4-CH₃-isoquinolin-3-yl |
| 4437 | 4-CH₂CH₃-isoquinolin-3-yl |
| 4438 | 4-CH(CH₃)₂-isoquinolin-3-yl |
| 4439 | 4-CH(CH₃)CH₂CH₃-isoquinolin-3-yl |
| 4440 | 4-CF₃-isoquinolin-3-yl |
| 4441 | 4-CH=CH₂-isoquinolin-3-yl |
| 4442 | 4-CH=CHCH₃-isoquinolin-3-yl |
| 4443 | 4-CH=CHCl-isoquinolin-3-yl |
| 4444 | 4-C≡CH-isoquinolin-3-yl |
| 4445 | 4-CH₂C≡CH-isoquinolin-3-yl |
| 4446 | 4-CH₂C≡CCH₃-isoquinolin-3-yl |
| 4447 | 4-cyclopropyl-isoquinolin-3-yl |
| 4448 | 4-cyclopentyl-isoquinolin-3-yl |
| 4449 | 4-OCH₃-isoquinolin-3-yl |
| 4450 | 4-OCH₂CH₃-isoquinolin-3-yl |
| 4451 | 4-OCH₂CH₂CH₃-isoquinolin-3-yl |
| 4452 | 4-OCH(CH₃)₂-isoquinolin-3-yl |
| 4453 | 4-OCH₂CH₂CH₂CH₃-isoquinolin-3-yl |
| 4454 | 4-OCH(CH₃)CH₂CH₃-isoquinolin-3-yl |
| 4455 | 4-OCH₂CH(CH₃)₂-isoquinolin-3-yl |
| 4456 | 4-OC(CH₃)₄-isoquinolin-3-yl |
| 4457 | 4-OCH(CH₃)CH₂CH₂CH₃-isoquinolin-3-yl |
| 4458 | 4-OCH₂OCH₃-isoquinolin-3-yl |
| 4459 | 4-OCH₂OCH₂CH₃-isoquinolin-3-yl |
| 4460 | 4-OCH(CH₃)OCH₃-isoquinolin-3-yl |
| 4461 | 4-OCH(CH₃)OCH₂CH₃-isoquinolin-3-yl |
| 4462 | 4-OCH₂CH₂OCH₃-isoquinolin-3-yl |
| 4463 | 4-OCH₂CH₂OCH₂CH₃-isoquinolin-3-yl |
| 4464 | 4-OCH₂CH₂OCH(CH₃)₂-isoquinolin-3-yl |
| 4465 | 4-OCH₂CH₂SCH₃-isoquinolin-3-yl |
| 4466 | 4-OCH₂CH₂SO₂CH₃-isoquinolin-3-yl |
| 4467 | 4-OCH₂CH₂SCH(CH₃)₂-isoquinolin-3-yl |
| 4468 | 4-OCH₂CH₂CN-isoquinolin-3-yl |
| 4469 | 4-OCH₂CH₂SCH₂CH₂CN-isoquinolin-3-yl |
| 4470 | 4-OCH₂CH₂OC₆H₅-isoquinolin-3-yl |
| 4471 | 4-OCH₂CH₂OCH₂C₆H₅-isoquinolin-3-yl |
| 4472 | 4-OCH₂CH₂N(CH₃)₂-isoquinolin-3-yl |
| 4473 | 4-OCH₂CH₂CONH₂-isoquinolin-3-yl |
| 4474 | 4-OCH₂CH₂CO₂CH₂CH₃-isoquinolin-3-yl |
| 4475 | 4-OCH(CH₃)CH₂OCH₃-isoquinolin-3-yl |
| 4476 | 4-OCH(CH₃)CH₂CO₂CH₃-isoquinolin-3-yl |
| 4477 | 4-OCH(CH₃)CH₂CO₂CH₂CH₃-isoquinolin-3-yl |
| 4478 | 4-OCH₂CH(CH₃)CO₂CH₃-isoquinolin-3-yl |
| 4479 | 4-OCH₂C(=O)CH₃-isoquinolin-3-yl |
| 4480 | 4-OCH₂C(=O)CH₂CH₃-isoquinolin-3-yl |
| 4481 | 4-OCH₂CO₂CH₃-isoquinolin-3-yl |
| 4482 | 4-OCH₂CO₂CH₂CH₃-isoquinolin-3-yl |
| 4483 | 4-OCH₂C(=O)NH₂-isoquinolin-3-yl |
| 4484 | 4-OCH₂C(=O)NHCH₃-isoquinolin-3-yl |
| 4485 | 4-OCH₂C(=O)SCH₃-isoquinolin-3-yl |
| 4486 | 4-OCH(CH₃)C(=O)NH₂-isoquinolin-3-yl |
| 4487 | 4-OCH(CH₃)C(=O)NHCH₃-isoquinolin-3-yl |
| 4488 | 4-OCH(CH₃)C(=O)NHNH₃-isoquinolin-3-yl |
| 4489 | 4-OCH(CH₃)CO₂CH₃-isoquinolin-3-yl |
| 4490 | 4-OCH(CH₃)CO₂CH₂CH₃-isoquinolin-3-yl |
| 4491 | 4-OCH(CH₃)C(=O)CH₃-isoquinolin-3-yl |
| 4492 | 4-OCH(CH₃)C(=O)CH₂CH₃-isoquinolin-3-yl |
| 4493 | 4-OCH(CH₃)C(=O)CH₂CH₃-isoquinolin-3-yl |
| 4494 | 4-OCH(CH₃)CH₂OC(CH₃)₄-isoquinolin-3-yl |
| 4495 | 4-OCH(CH₃)CH₂OCH₂CH₃-isoquinolin-3-yl |
| 4496 | 4-OCH(CH₃)CH₂O(CH₃)₂CH₃-isoquinolin-3-yl |
| 4497 | 4-OCH(CH₃)CH₂OCH₂CH=CH₂-isoquinolin-3-yl |
| 4498 | 4-O(CH₂)₃OCH₃-isoquinolin-3-yl |
| 4499 | 4-O(CH₂)₃OCH₂CH₃-isoquinolin-3-yl |
| 4500 | 4-O(CH₂)₃OCH(CH₃)₂-isoquinolin-3-yl |
| 4501 | 4-O(CH₂)₃OC₆H₅-isoquinolin-3-yl |
| 4502 | 4-O(CH₂)₃OCH₂C₆H₅-isoquinolin-3-yl |
| 4503 | 4-OCH(CH₂CH₃)CH₂OCH₃-isoquinolin-3-yl |
| 4504 | 4-OCH(CH₂CH₃)CH₂CH₂OCH₃-isoquinolin-3-yl |
| 4505 | 4-OCH(CH₂CH₃)CH₂CH₂OCH₂CH₃-isoquinolin-3-yl |
| 4506 | 4-O[(CH₂)₃O]₂CH₃-isoquinolin-3-yl |
| 4507 | 4-OCH(CH₂OCH₃)CH₂OCH₃-isoquinolin-3-yl |
| 4508 | 4-OCH₂CH(CH₃)CH₂OCH₂CH₃-isoquinolin-3-yl |
| 4509 | 4-OCH(CH₂Cl)CH₂OCH₃-isoquinolin-3-yl |
| 4510 | 4-OCH(CH₂Cl)CH₂OCH₂CH₃-isoquinolin-3-yl |
| 4511 | 4-OCH(CH₂Cl)CH₂OCH(CH₃)₂-isoquinolin-3-yl |
| 4512 | 4-OCH(CH₂Cl)CH₂OCH₂CH=CH₂-isoquinolin-3-yl |
| 4513 | 4-OCH[CH₂OCH₃]₂-isoquinolin-3-yl |
| 4514 | 4-OCH[CH₂OCH₂CH₃]₂-isoquinolin-3-yl |
| 4515 | 4-OCCl₄-isoquinolin-3-yl |
| 4516 | 4-OCHF₂-isoquinolin-3-yl |
| 4517 | 4-OCF₃-isoquinolin-3-yl |
| 4518 | 4-OCF₂CHF₂-isoquinolin-3-yl |
| 4519 | 4-OCH₂CF₃-isoquinolin-3-yl |
| 4520 | 4-OCH₂CHF₂-isoquinolin-3-yl |
| 4521 | 4-O(CH₂)₃F-isoquinolin-3-yl |
| 4522 | 4-OCH(CH₃)CF₃-isoquinolin-3-yl |
| 4523 | 4-O(CH₂)₄F-isoquinolin-3-yl |
| 4524 | 4-O(CH₂)₃CF₃-isoquinolin-3-yl |
| 4525 | 4-OCH(CH₃)CF₂CF₃-isoquinolin-3-yl |
| 4526 | 4-OCH(CH₃)CF₂CHF₂-isoquinolin-3-yl |
| 4527 | 4-OCH₂CF₂CHFCH₃-isoquinolin-3-yl |
| 4528 | 4-OCH₂(CF₂)₂CF₃-isoquinolin-3-yl |
| 4529 | 4-O(CF₂)₃CF₃-isoquinolin-3-yl |
| 4530 | 4-OCH₂CF₂CHF₂-isoquinolin-3-yl |
| 4531 | 4-CH₂CH=CH₂-isoquinolin-3-yl |
| 4532 | 4-CH₂C(CH₃)=CH₂-isoquinolin-3-yl |
| 4533 | 4-OCH₂CH=CHCH₃-isoquinolin-3-yl |
| 4534 | 4-O(CH₂)₂CH=CH₂-isoquinolin-3-yl |
| 4535 | 4-OCH₂C(CH₃)=CH₂-isoquinolin-3-yl |
| 4536 | 4-OCH(CH₃)CH=CH₂-isoquinolin-3-yl |
| 4537 | 4-OCH₂C≡CH-isoquinolin-3-yl |
| 4538 | 4-OCH₂C≡CCH₃-isoquinolin-3-yl |
| 4539 | 4-O(CH₂)₂C≡CH-isoquinolin-3-yl |
| 4540 | 4-SCH₃-isoquinolin-3-yl |
| 4541 | 4-SCH₂CH₃-isoquinolin-3-yl |
| 4542 | 4-OC₆H₅-isoquinolin-3-yl |
| 4543 | 4-OCH₂C₆H₅-isoquinolin-3-yl |
| 4544 | 4-NO₂-isoquinolin-3-yl |
| 4545 | 4-NHCH₃-isoquinolin-3-yl |
| 4546 | 4-N(CH₃)₂-isoquinolin-3-yl |
| 4547 | 4-N(CH₃)C₂H₆-isoquinolin-3-yl |
| 4548 | 4-NHCH₂CF₃-isoquinolin-3-yl |
| 4549 | 4-F-isoquinolin-3-yl |
| 4550 | 4-Cl-isoquinolin-3-yl |
| 4551 | 4-OH-isoquinolin-3-yl |
| 4552 | 4-CN-isoquinolin-3-yl |
| 4553 | 4-C(O)NH₂-isoquinolin-3-yl |
| 4554 | 4-C(S)NH₂-isoquinolin-3-yl |
| 4555 | 4-CO₂CH₃-isoquinolin-3-yl |
| 4556 | 4-ON=C(CH₃)₂-isoquinolin-3-yl |
| 4557 | 4-[O-cyclopropyl]isoquinolin-3-yl |
| 4558 | 4-[O-cyclobutyl]isoquinolin-3-yl |
| 4559 | 4-[O-cyclopentyl]isoquinolin-3-yl |
| 4560 | 4-[O-cyclohexyl]isoquinolin-3-yl |
| 4561 | 4-[OCH₂-cyclopropyl]isoquinolin-3-yl |
| 4562 | 6-F, 4-[OCH₂-cyclopropyl]isoquinolin-3-yl |
| 4563 | 6-CH₃, 4-[OCH₂-cyclopropyl]isoquinolin-3-yl |
| 4564 | 6-CF₃, 4-[OCH₂-cyclopropyl]isoquinolin-3-yl |
| 4565 | 4-[OCH(CH₃)-cyclopropyl]isoquinolin-3-yl |
| 4566 | 6-F, 4-[OCH(CH₃)-cyclopropyl]isoquinolin-3-yl |
| 4567 | 6-CH₃, 4-[OCH(CH₃)-cyclopropyl]isoquinolin-3-yl |
| 4568 | 6-CF₃, 4-[OCH(CH₃)-cyclopropyl]isoquinolin-3-yl |
| 4569 | 4-[O-(1-CH₃-cyclopropyl)]isoquinolin-3-yl |
| 4570 | 6-F, 4-[O-(1-CH₃-cyclopropyl)]isoquinolin-3-yl |
| 4571 | 6-CH₃, 4-[O(1-CH₃-cyclopropyl)]isoquinolin-3-yl |
| 4572 | 6-CF₃, 4-[O(1-CH₃-cyclopropyl)]isoquinolin-3-yl |
| 4573 | 4-[OCH₂-(1-CH₃-cyclopropyl)]isoquinolin-3-yl |
| 4574 | 6-F, 4-[OCH₂-(1-CH₃-cyclopropyl)]isoquinolin-3-yl |
| 4575 | 6-CH₃, 4-[OCH₂-(1-CH₃-cyclopropyl)]isoquinolin-3-yl |
| 4576 | 6-CF₃, 4-[OCH₂-(1-CH₃-cyclopropyl)]isoquinolin-3-yl |
| 4577 | 4-[OCH₂-(2-CH₃cyclopropyl)]isoquinolin-3-yl |
| 4578 | 6-F, 4-[OCH₂-(2-CH₃-cyclopropyl)]isoquinolin-3-yl |
| 4579 | 6-CH₃, 4-[OCH₂-(2-CH₃-cyclopropyl)]isoquinolin-3-yl |
| 4580 | 6-CF₃, 4-[OCH₂-(2-CH₃-cyclopropyl)]isoquinolin-3-yl |
| 4581 | 4-[OCH₂-(tetrahydropyran-2-yl)]isoquinolin-3-yl |
| 4582 | 6-F, 4-[OCH₂-(tetrahydropyran-2-yl)]isoquinolin-3-yl |
| 4583 | 6-CH₃, 4-[OCH₂-(tetrahydropyran-2-yl)]isoquinolin-3-yl |
| 4584 | 6-CF₃, 4-[OCH₂-(tetrahydropyran-2-yl)]isoquinolin-3-yl |
| 4585 | 4-[OCH₂-(furan-2-yl)]isoquinolin-3-yl |
| 4586 | 6-F, 4-[OCH₂-(furan-2-yl)]isoquinolin-3-yl |
| 4587 | 6-CH₃, 4-[OCH₂-(furan-2-yl)]isoquinolin-3-yl |
| 4588 | 6-CF₃, 4-[OCH₂-(furan-2-yl)]isoquinolin-3-yl |

TABLE A-continued

| No. | R⁴ |
|---|---|
| 4589 | 4-[OCH₂-(furan-4-yl)]isoquinolin-3-yl |
| 4590 | 6-F, 4-[OCH₂-(furan-4-yl)]isoquinolin-3-yl |
| 4591 | 6-CH₃, 4-[OCH₂-(furan-4-yl)]isoquinolin-3-yl |
| 4592 | 6-CF₃, 4-[OCH₂-(furan-4-yl)]isoquinolin-3-yl |
| 4593 | 4-[OCH₂-(tetrahydrofuran-4-yl)]isoquinolin-3-yl |
| 4594 | 6-F, 4-[OCH₂-(tetrahydrofuran-4-yl)]isoquinolin-3-yl |
| 4595 | 6-CH₃, 4-[OCH₂(tetrahydrofuran-4-yl)]isoquinolin-3-yl |
| 4596 | 6-CF₃, 4-[OCH₂(tetrahydrofuran-4-yl)]isoquinolin-3-yl |
| 4597 | 4-[OCH₂-(tetrahydrofuran-2-yl)]isoquinolin-3-yl |
| 4598 | 6-F, 4-[OCH₂-(tetrahydrofuran-2-yl)]isoquinolin-3-yl |
| 4599 | 6-CH₃, 4-[OCH₂-(tetrahydrofuran-2-yl)]isoquinolin-3-yl |
| 4600 | 6-CF₃, 4-[OCH₂-(tetrahydrofuran-2-yl)]isoquinolin-3-yl |
| 4601 | 4-[O-(tetrahydropyran-4-yl)]isoquinolin-3-yl |
| 4602 | 6-F, 4-[O-(tetrahydropyran-4-yl)]isoquinolin-3-yl |
| 4603 | 6-CH₃, 4-[O-(tetrahydropyran-4-yl)]isoquinolin-3-yl |
| 4604 | 6-CF₃, 4-[O-(tetrahydropyran-4-yl)]isoquinolin-3-yl |
| 4605 | 4-[2-Cl—C₅H₄]isoquinolin-3-yl |
| 4606 | 6-F, 4-[2-Cl—C₅H₄]isoquinolin-3-yl |
| 4607 | 6-CH₃, 4-[2-Cl—C₅H₄]isoquinolin-3-yl |
| 4608 | 6-CF₃, 4-[2-Cl—C₅H₄]isoquinolin-3-yl |
| 4609 | 4-[OCH₂-(pyridin-2-yl)]isoquinolin-3-yl |
| 4610 | 6-F, 4-[OCH₂-(pyridin-2-yl)]isoquinolin-3-yl |
| 4611 | 6-CH₃, 4-[OCH₂-(pyridin-2-yl)]isoquinolin-3-yl |
| 4612 | 6-CF₃, 4-[OCH₂-(pyridin-2-yl)]isoquinolin-3-yl |
| 4613 | 4-[OCH₂-(pyridin-4-yl)]isoquinolin-3-yl |
| 4614 | 6-F, 4-[OCH₂-(pyridin-4-yl)]isoquinolin-3-yl |
| 4615 | 6-CH₃, 4-[OCH₂-(pyridin-4-yl)]isoquinolin-3-yl |
| 4616 | 6-CF₃, 4-[OCH₂-(pyridin-4-yl)]isoquinolin-3-yl |
| 4617 | 4-[morpholin-4-yl]isoquinolin-3-yl |
| 4618 | 4-[1-CH₃-imidazol-2-yl]isoquinolin-3-yl |
| 4619 | 6-F, 4-[1-CH₃-imidazol-2-yl]isoquinolin-3-yl |
| 4620 | 6-CH₃, 4-[1-CH₃-imidazol-2-yl]isoquinolin-3-yl |
| 4621 | 6-CF₃, 4-[1-CH₃-imidazol-2-yl]isoquinolin-3-yl |
| 4622 | 4-[1,2,4-triazol-1-yl]isoquinolin-3-yl |
| 4623 | 6-F, 4-[1,2,4-triazol-1-yl]isoquinolin-3-yl |
| 4624 | 6-CH₃, 4-[1,2,4-triazol-1-yl]isoquinolin-3-yl |
| 4625 | 6-CF₃, 4-[1,2,4-triazol-1-yl]isoquinolin-3-yl |
| 4626 | 4,6-Cl₂-isoquinolin-3-yl |
| 4627 | 4,6-(CH₃)₂-isoquinolin-3-yl |
| 4628 | 4,6-(OCH₃)₂-isoquinolin-3-yl |
| 4629 | 4,6-(OCH₂CH₃)₂-isoquinolin-3-yl |
| 4630 | 4-F, 6-CH₃-isoquinolin-3-yl |
| 4631 | 4-F, 6-OCH₃-isoquinolin-3-yl |
| 4632 | 4-F, 6-OCH₂CH₃-isoquinolin-3-yl |
| 4633 | 4-F, 6-OCH₂CF₃-isoquinolin-3-yl |
| 4634 | 4-F, 6-OCH(CH₃)₂-isoquinolin-3-yl |
| 4635 | 4-Cl, 6-CH₃-isoquinolin-3-yl |
| 4636 | 4-Cl, 6-OCH₃-isoquinolin-3-yl |
| 4637 | 4-Cl, 6-OCH₂CH₃-isoquinolin-3-yl |
| 4638 | 4-Cl, 6-OCH₂CF₃-isoquinolin-3-yl |
| 4639 | 4-Cl, 6-OCH(CH₃)₂-isoquinolin-3-yl |
| 4640 | 4-CH₃, 6-OCH₃-isoquinolin-3-yl |
| 4641 | 4-CH₃, 6-OCH₂CH₃-isoquinolin-3-yl |
| 4642 | 4-CH₃, 6-OCH₂CF₃-isoquinolin-3-yl |
| 4643 | 4-CH₃, 6-OCH(CH₃)₂-isoquinolin-3-yl |
| 4644 | 4-CH₃, 6-OCH₂CH=CH₂-isoquinolin-3-yl |
| 4645 | 4-CH₃, 6-CO₂CH₃-isoquinolin-3-yl |
| 4646 | 4-CH₃, 6-CF₃-isoquinolin-3-yl |
| 4647 | 4-CF₃, 6-OCH₂CH₃-isoquinolin-3-yl |
| 4648 | 4-CF₃, 6-OCH₃-isoquinolin-3-yl |
| 4649 | 4-CF₃, 6-OCH₂CH₃-isoquinolin-3-yl |
| 4650 | 4-CF₃, 6-OCH₂CF₃-isoquinolin-3-yl |
| 4651 | 4-OCH₃, 6-OCH₂CH₃-isoquinolin-3-yl |
| 4652 | 4-OCH₃, 6-OCH₂CF₃-isoquinolin-3-yl |
| 4653 | 4-OCH₃, 6-OCH(CH₃)-isoquinolin-3-yl |
| 4654 | 4-OCH₂CH₃, 6-CH₂OCH₂CH₃-isoquinolin-3-yl |
| 4655 | 4-NO₂, 6-CH₃-isoquinolin-3-yl |
| 4656 | 4-NO₂, 6-OCH₃-isoquinolin-3-yl |
| 4657 | 4-NO₂, 6-OCH₂CH₃-isoquinolin-3-yl |
| 4658 | 4-NO₂, 6-OCH(CH₃)₂-isoquinolin-3-yl |
| 4659 | 4-NO₂, 6-OCH₂CF₃-isoquinolin-3-yl |
| 4660 | 4-CN, 6-CH₃-isoquinolin-3-yl |
| 4661 | 4-CN, 6-OCH₃-isoquinolin-3-yl |
| 4662 | 4-CN, 6-OCH₂CH₃-isoquinolin-3-yl |
| 4663 | 4-CN, 6-OCH(CH₃)₂-isoquinolin-3-yl |
| 4664 | 4-CN, 6-OCH₂CF₃-isoquinolin-3-yl |
| 4665 | 7-CH₃, 2-CH₃-purin-8-yl |
| 4666 | 7-CH₃, 2-CH₂CH₃-purin-8-yl |
| 4667 | 7-CH₃, 2-CH(CH₃)₂-purin-8-yl |
| 4668 | 7-CH₃, 2-CH(CH₃)CH₂CH₃-purin-8-yl |
| 4669 | 7-CH₃, 2-CF₃-purin-8-yl |
| 4670 | 7-CH₃, 2-CH=CH₂-purin-8-yl |
| 4671 | 7-CH₃, 2-CH=CHCH₃-purin-8-yl |
| 4672 | 7-CH₃, 2-CH=CHCl-purin-8-yl |
| 4673 | 7-CH₃, 2-C≡CH-purin-8-yl |
| 4674 | 7-CH₃, 2-CH₂C≡CH-purin-8-yl |
| 4675 | 7-CH₃, 2-CH₂C≡CCH₃-purin-8-yl |
| 4676 | 7-CH₃, 2-cyclopropyl-purin-8-yl |
| 4677 | 7-CH₃, 2-cyclopentyl-purin-8-yl |
| 4678 | 7-CH₃, 2-OCH₃-purin-8-yl |
| 4679 | 7-CH₃, 2-OCH₂CH₃-purin-8-yl |
| 4680 | 7-CH₃, 2-OCH₂CH₂CH₃-purin-8-yl |
| 4681 | 7-CH₃, 2-OCH(CH₃)₂-purin-8-yl |
| 4682 | 7-CH₃, 2-OCH(CH₃)CH₂CH₃-purin-8-yl |
| 4683 | 7-CH₃, 2-OCH(CH₃)CH₂CH₃-purin-8-yl |
| 4684 | 7-CH₃, 2-OCH₂CH(CH₃)₂-purin-8-yl |
| 4685 | 7-CH₃, 2-OC(CH₃)₃-purin-8-yl |
| 4686 | 7-CH₃, 2-OCH(CH₃)CH₂CH₂CH₃-purin-8-yl |
| 4687 | 7-CH₃, 2-OCH₂OCH₃-purin-8-yl |
| 4688 | 7-CH₃, 2-OCH₂OCH₂CH₃-purin-8-yl |
| 4689 | 7-CH₃, 2-OCH(CH₃)OCH₃-purin-8-yl |
| 4690 | 7-CH₃, 2-OCH(CH₃)OCH₂CH₃-purin-8-yl |
| 4691 | 7-CH₃, 2-OCH₂CH₂OCH₃-purin-8-yl |
| 4692 | 7-CH₃, 2-OCH₂CH₂OCH₂CH₃-purin-8-yl |
| 4693 | 7-CH₃, 2-OCH₂CH₂OCH(CH₃)₂-purin-8-yl |
| 4694 | 7-CH₃, 2-OCH₂CH₂SCH₃-purin-8-yl |
| 4695 | 7-CH₃, 2-OCH₂CH₂SO₂CH₃-purin-8-yl |
| 4696 | 7-CH₃, 2-OCH₂CH₂SCH(CH₃)₂-purin-8-yl |
| 4697 | 7-CH₃, 2-OCH₂CH₂CN-purin-8-yl |
| 4698 | 7-CH₃, 2-OCH₂CH₂SCH₂CH₂CN-purin-8-yl |
| 4699 | 7-CH₃ , 2-OCH₂OC₆H₅-purin-8-yl |
| 4700 | 7-CH₃, 2-OCH₂CH₂OCH₂C₆H₅-purin-8-yl |
| 4701 | 7-CH₃, 2-OCH₂CH₂N(CH₃)₂-purin-8-yl |
| 4702 | 7-CH₃, 2-OCH₂CH₂CONH₂-purin-8-yl |
| 4703 | 7-CH₃, 2-OCH₂CH₂CO₂CH₂CH₂CH₃-purin-8-yl |
| 4704 | 7-CH₃, 2-OCH(CH₃)CH₂OCH₃-purin-8-yl |
| 4705 | 7-CH₃, 2-OCH(CH₃)CH₂CO₂CH₃-purin-8-yl |
| 4706 | 7-CH₃, 2-OCH(CH₃)CH₂CO₂CH₂CH₃-purin-8-yl |
| 4707 | 7-CH₃, 2-OCH(CH₃)CH₂CO₂CH₃-purin-8-yl |
| 4708 | 7-CH₃, 2-OCH₂C(=O)CH₃-purin-8-yl |
| 4709 | 7-CH₃, 2-OCH₂C(=O)CH₂CH₃-purin-8-yl |
| 4710 | 7-CH₃, 2-OCH₂CO₂CH₃-purin-8-yl |
| 4711 | 7-CH₃, 2-OCH₂CO₂CH₂CH₃-purin-8-yl |
| 4712 | 7-CH₃, 2-OCH₂C(=O)NH₂-purin-8-yl |
| 4713 | 7-CH₃, 2-OCH₂C(=O)NHCH₃-purin-8-yl |
| 4714 | 7-CH₃, 2-OCH₂C(=O)SCH₃-purin-8-yl |
| 4715 | 7-CH₃, 2-OCH(CH₃)C(=O)NH₂-purin-8-yl |
| 4716 | 7-CH₃, 2-OCH(CH₃)C(=O)NHCH₃-purin-8-yl |
| 4717 | 7-CH₃, 2-OCH(CH₃)C(=O)NHNH₃-purin-8-yl |
| 4718 | 7-CH₃, 2-OCH(CH₃)CO₂CH₃-purin-8-yl |
| 4719 | 7-CH₃, 2-OCH(CH₃)CO₂CH₂CH₃-purin-8-yl |
| 4720 | 7-CH₃, 2-OCH(CH₃)C(=O)CH₃-purin-8-yl |
| 4721 | 7-CH₃, 2-OCH(CH₃)C(=O)CH₂CH₃-purin-8-yl |
| 4722 | 7-CH₃, 2-OCH(CH₃)CH₂C(=O)CH₃-purin-8-yl |
| 4723 | 7-CH₃, 2-OCH(CH₃)CH₂OC(CH₃)₃-purin-8-yl |
| 4724 | 7-CH₃, 2-OCH(CH₃)CH₂OCH₂CH₃-purin-8-yl |
| 4725 | 7-CH₃, 2-OCH(CH₃)CH₂O(CH₃)₂CH₃-purin-8-yl |
| 4726 | 7-CH₃, 2-OCH(CH₃)CH₂OCH₂CH=CH₂-purin-8-yl |
| 4727 | 7-CH₃, 2-O(CH₂)₃OCH₃-purin-8-yl |
| 4728 | 7-CH₃, 2-O(CH₂)₃OCH₂CH₃-purin-8-yl |
| 4729 | 7-CH₃, 2-O(CH₂)₃OCH(CH₃)₂-purin-8-yl |
| 4730 | 7-CH₃, 2-O(CH₂)₃OC₆H₅-purin-8-yl |
| 4731 | 7-CH₃, 2-O(CH₂)₃OCH₂C₆H₄-purin-8-yl |
| 4732 | 7-CH₃, 2-OCH(CH₂CH₃)CH₂OCH₃-purin-8-yl |
| 4733 | 7-CH₃, 2-OCH(CH₂CH₃)CH₂OCH₃-purin-8-yl |
| 4734 | 7-CH₃, 2-OCH(CH₂CH₃)CH₂CH₂OCH₂CH₃-purin-8-yl |
| 4735 | 7-CH₃, 2-O[(CH₂)₃O]₂CH₃-purin-8-yl |
| 4736 | 7-CH₃, 2-OCH₂CH(CH₃)CH₂OCH₃-purin-8-yl |
| 4737 | 7-CH₃, 2-OCH(CH₂Cl)CH₂OCH₃-purin-8-yl |
| 4738 | 7-CH₃, 2-OCH(CH₂Cl)CH₂OCH₃-purin-8-yl |
| 4739 | 7-CH₃, 2-OCH(CH₂Cl)CH₂OCH₂CH₃-purin-8-yl |
| 4740 | 7-CH₃, 2-OCH(CH₂Cl)CH₂OCH(CH₃)₂-purin-8-yl |
| 4741 | 7-CH₃, 2-OCH(CH₂Cl)CH₂OCH₂CH=CH₂-purin-8-yl |
| 4742 | 7-CH₃, 2-OCH[CH₂OCH₃]₂-purin-8-yl |

TABLE A-continued

| No. | R⁴ |
|---|---|
| 4743 | 7-CH₃, 2-OCH[CH₂OCH₂CH₃]₂-purin-8-yl |
| 4744 | 7-CH₃, 2-OCCl₂-purin-8-yl |
| 4745 | 7-CH₃, 2-OCHF₂-purin-8-yl |
| 4746 | 7-CH₃, 2-OCF₃-purin-8-yl |
| 4747 | 7-CH₃, 2-OCF₂CHF₂-purin-8-yl |
| 4748 | 7-CH₃, 2-OCH₂CF₃-purin-8-yl |
| 4749 | 7-CH₃, 2-OCH₂CHF₂-purin-8-yl |
| 4750 | 7-CH₃, 2-O(CH₂)₃F-purin-8-yl |
| 4751 | 7-CH₃, 2-OCH(CH₃)CF₃-purin-8-yl |
| 4752 | 7-CH₃, 2-O(CH₂)₄F-purin-8-yl |
| 4753 | 7-CH₃, 2-O(CH₂)₃CF₃-purin-8-yl |
| 4754 | 7-CH₃, 2-OCH(CH₃)CF₂CF₃-purin-8-yl |
| 4755 | 7-CH₃, 2-OCH(CH₃)CF₂CHF₂-purin-8-yl |
| 4756 | 7-CH₃, 2-OCH₂CF₂CHFCH₃-purin-8-yl |
| 4757 | 7-CH₃, 2-OCH₂(CF₂)₂CF₃-purin-8-yl |
| 4758 | 7-CH₃, 2-O(CF₂)₃CF₃-purin-8-yl |
| 4759 | 7-CH₃, 2-OCH₂CF₂CHF₂-purin-8-yl |
| 4760 | 7-CH₃, 2-CH₂CH=CH₂-purin-8-yl |
| 4761 | 7-CH₃, 2-CH₂C(CH₃)=CH₂-purin-8-yl |
| 4762 | 7-CH₃, 2-OCH₂CH=CHCH₃-purin-8-yl |
| 4763 | 7-CH₃, 2-O(CH₂)₂CH=CH₂-purin-8-yl |
| 4764 | 7-CH₃, 2-OCH₂C(CH₃)=CH₂-purin-8-yl |
| 4765 | 7-CH₃, 2-OCH(CH₃)CH=CH₂-purin-8-yl |
| 4766 | 7-CH₃, 2-OCH₂C≡CH-purin-8-yl |
| 4767 | 7-CH₃, 2-OCH₂C≡CCH₃-purin-8-yl |
| 4768 | 7-CH₃, 2-O(CH₂)₂C≡CH-purin-8-yl |
| 4769 | 7-CH₃, 2-SCH₃-purin-8-yl |
| 4770 | 7-CH₃, 2-SCH₂CH₃-purin-8-yl |
| 4771 | 7-CH₃, 2-OC₆H₅-purin-8-yl |
| 4772 | 7-CH₃, 2-OCH₂C₆H₅-purin-8-yl |
| 4773 | 7-CH₃, 2-NO₂-purin-8-yl |
| 4774 | 7-CH₃, 2-NHCH₃-purin-8-yl |
| 4775 | 7-CH₃, 2-N(CH₃)₂-purin-8-yl |
| 4776 | 7-CH₃, 2-N(CH₃)C₂H₆-purin-8-yl |
| 4777 | 7-CH₃, 2-NHCH₂CF₃-purin-8-yl |
| 4778 | 7-CH₃, 2-F-purin-8-yl |
| 4779 | 7-CH₃, 2-Cl-purin-8-yl |
| 4780 | 7-CH₃, 2-OH-purin-8-yl |
| 4781 | 7-CH₃, 2-CN-purin-8-yl |
| 4782 | 7-CH₃, 2-C(O)NH₂-purin-8-yl |
| 4783 | 7-CH₃, 2-C(S)NH₂-purin-8-yl |
| 4784 | 7-CH₃, 2-CO₂CH₃-purin-8-yl |
| 4785 | 7-CH₃, 2-ON=C(CH₃)₂-purin-8-yl |
| 4786 | 7-CH₃, 2-[O-cyclopropyl]purin-8-yl |
| 4787 | 7-CH₃, 2-[O-cyclobutyl]purin-8-yl |
| 4788 | 7-CH₃, 2-[O-cyclopentyl]purin-8-yl |
| 4789 | 7-CH₃, 2-[O-cyclohexyl]purin-8-yl |
| 4790 | 7-CH₃, 2-[OCH₂-cyclopropyl]purin-8-yl |
| 4791 | 7-CH₃, 6-F, 2-[OCH₂-cyclopropyl]purin-8-yl |
| 4792 | 7-CH₃, 6-CH₃, 2-[OCH₂-cyclopropyl]purin-8-yl |
| 4793 | 7-CH₃, 6-CF₃, 2-[OCH₂-cyclopropyl]purin-8-yl |
| 4794 | 7-CH₃, 2-[OCH(CH₃)-cyclopropyl]purin-8-yl |
| 4795 | 7-CH₃, 6-F, 2-[OCH(CH₃)-cyclopropyl]purin-8-yl |
| 4796 | 7-CH₃, 6-CH₃, 2-[OCH(CH₃)-cyclopropyl]purin-8-yl |
| 4797 | 7-CH₃, 6-CF₃, 2-[OCH(CH₃)-cyclopropyl]purin-8-yl |
| 4798 | 7-CH₃, 2-[O-(7-CH₃-cyclopropyl)]purin-8-yl |
| 4799 | 7-CH₃, 6-F, 2-[O-(7-CH₃-cyclopropyl)]purin-8-yl |
| 4800 | 7-CH₃, 6-CH₃, 2-[O-(7-CH₃-cyclopropyl)]purin-8-yl |
| 4801 | 7-CH₃, 6-CF₃, 2-[O-(7-CH₃-cyclopropyl)]purin-8-yl |
| 4802 | 7-CH₃, 2-[OCH₂-(7-CH₃-cyclopropyl)]purin-8-yl |
| 4803 | 7-CH₃, 6-F, 2-[OCH₂-(7-CH₃-cyclopropyl)]purin-8-yl |
| 4804 | 7-CH₃, 6-CH₃, 2-[OCH₂-(7-CH₃-cyclopropyl)]purin-8-yl |
| 4805 | 7-CH₃, 6-CF₃, 2-[OCH₂-(7-CH₃-cyclopropyl)]purin-8-yl |
| 4806 | 7-CH₃, 2-[OCH₂-(2-CH₃-cyclopropyl)]purin-8-yl |
| 4807 | 7-CH₃, 6-F, 2-[OCH₂-(2-CH₃-cyclopropyl)]purin-8-yl |
| 4808 | 7-CH₃, 6-CH₃, 2-[OCH₂-(2-CH₃-cyclopropyl)]purin-8-yl |
| 4809 | 7-CH₃, 6-CF₃, 2-[OCH₂-(2-CH₃-cyclopropyl)]purin-8-yl |
| 4810 | 7-CH₃, 2-[OCH₂-(tetrahydropyran-2-yl)]purin-8-yl |
| 4811 | 7-CH₃, 6-F, 2-[OCH₂-(tetrahydropyran-2-yl)]purin-8-yl |
| 4812 | 7-CH₃, 6-CH₃, 2-[OCH₂-(tetrahydropyran-2-yl)]purin-8-yl |
| 4813 | 7-CH₃, 6-CF₃, 2-[OCH₂-(tetrahydropyran-2-yl)]purin-8-yl |
| 4814 | 7-CH₃, 2-[OCH₂-(furan-2-yl)]purin-8-yl |
| 4815 | 7-CH₃, 6-F, 2-[OCH₂-(furan-2-yl)]purin-8-yl |
| 4816 | 7-CH₃, 6-CH₃, 2-[OCH₂-(furan-2-yl)]purin-8-yl |
| 4817 | 7-CH₃, 6-CF₃, 2-[OCH₂-(furan-2-yl)]purin-8-yl |
| 4818 | 7-CH₃, 2-[OCH₂-(furan-2-yl)]purin-8-yl |
| 4819 | 7-CH₃, 6-F, 2-[OCH₂-(furan-2-yl)]purin-8-yl |
| 4820 | 7-CH₃, 6-CH₃, 2-[OCH₂-(furan-2-yl)]purin-8-yl |
| 4821 | 7-CH₃, 6-CF₃, 2-[OCH₂-(furan-2-yl)]purin-8-yl |
| 4822 | 7-CH₃, 2-[OCH₂-(tetrahydrofuran-2-yl)]purin-8-yl |
| 4823 | 7-CH₃, 6-F, 2-[OCH₂-(tetrahydrofuran-2-yl)]purin-8-yl |
| 4824 | 7-CH₃, 6-CH₃, 2-[OCH₂-(tetrahydrofuran-2-yl)]purin-8-yl |
| 4825 | 7-CH₃, 6-CF₃, 2-[OCH₂-(tetrahydrofuran-2-yl)]purin-8-yl |
| 4826 | 7-CH₃, 2-[OCH₂-(tetrahydrofuran-2-yl)]purin-8-yl |
| 4827 | 7-CH₃, 6-F, 2-[OCH₂-(tetrahydrofuran-2-yl)]purin-8-yl |
| 4828 | 7-CH₃, 6-CH₃, 2-[OCH₂-(tetrahydrofuran-2-yl)]purin-8-yl |
| 4829 | 7-CH₃, 6-CF₃, 2-[OCH₂-(tetrahydrofuran-2-yl)]purin-8-yl |
| 4830 | 7-CH₃, 2-[O-tetrahydropyran-2-yl)]purin-8-yl |
| 4831 | 7-CH₃, 6-F, 2-[O-(tetrahydropyran-2-yl)]purin-8-yl |
| 4832 | 7-CH₃, 6-CH₃, 2-[O-tetrahydropyran-2-yl)]purin-8-yl |
| 4833 | 7-CH₃, 6-CF₃, 2-[O-tetrahydropyran-2-yl)]purin-8-yl |
| 4834 | 7-CH₃, 2-[2-Cl—C₅H₄]-purin-8-yl |
| 4835 | 7-CH₃, 6-F, 2-[2-ClC₅H₄]purin-8-yl |
| 4836 | 7-CH₃, 6-CH₃, 2-[2-Cl—C₅H₄]purin-8-yl |
| 4837 | 7-CH₃, 6-CF₃, 2-[2-Cl—C₅H₄]purin-8-yl |
| 4838 | 7-CH₃, 2-[OCH₂-(pyridin-2-yl)]purin-8-yl |
| 4839 | 7-CH₃, 6-F, 2-[OCH₂-(pyridin-2-yl)]purin-8-yl |
| 4840 | 7-CH₃, 6-CH₃, 2-[OCH₂-(pyridin-2-yl)]purin-8-yl |
| 4841 | 7-CH₃, 6-CF₃, 2-[OCH₂-(pyridin-2-yl)]purin-8-yl |
| 4842 | 7-CH₃, 2-[OCH₂-(pyridin-2-yl)]purin-8-yl |
| 4843 | 7-CH₃, 6-F, 2-[OCH₂-(pyridin-2-yl)]purin-8-yl |
| 4844 | 7-CH₃, 6-CH₃, 2-[OCH₂-(pyridin-2-yl)]purin-8-yl |
| 4845 | 7-CH₃, 6-CF₃, 2-[OCH₂-(pyridin-2-yl)]purin-8-yl |
| 4846 | 7-CH₃, 2-[morpholin-2-yl]purin-8-yl |
| 4847 | 7-CH₃, 2-[7-CH₃-imidazol-2-yl]purin-8-yl |
| 4848 | 7-CH₃, 6-F, 2-[7-CH₃-imidazol-2-yl]purin-8-yl |
| 4849 | 7-CH₃, 6-CH₃, 2-[7-CH₃-imidazol-2-yl]purin-8-yl |
| 4850 | 7-CH₃, 6-CF₃, 2-[7-CH₃-imidazol-2-yl]purin-8-yl |
| 4851 | 7-CH₃, 2-[1,2,2-triazol-1-yl]purin-8-yl |
| 4852 | 7-CH₃, 6-F, 2-[1,2,2-triazol-1-yl]purin-8-yl |
| 4853 | 7-CH₃, 6-CH₃, 2-[1,2,2-triazol-1-yl]purin-8-yl |
| 4854 | 7-CH₃, 6-CF₃, 2-[1,2,2-triazol-1-yl]purin-8-yl |
| 4855 | 7-CH₃, 4,6-Cl₂-purin-8-yl |
| 4856 | 7-CH₃, 4,6-(CH₃)₂-purin-8-yl |
| 4857 | 7-CH₃, 4,6-(OCH₃)₂-purin-8-yl |
| 4858 | 7-CH₃, 4,6-(OCH₂CH₃)₂-purin-8-yl |
| 4859 | 7-CH₃, 2-F, 6-CH₃-purin-8-yl |
| 4860 | 7-CH₃, 2-F, 6-OCH₃-purin-8-yl |
| 4861 | 7-CH₃, 2-F, 6-OCH₂CH₃-purin-8-yl |
| 4862 | 7-CH₃, 2-F, 6-OCH₂CF₃-purin-8-yl |
| 4863 | 7-CH₃, 2-F, 6-OCH(CH₃)₂-purin-8-yl |
| 4864 | 7-CH₃, 2-Cl, 6-CH₃-purin-8-yl |
| 4865 | 7-CH₃, 2-Cl, 6-OCH₃-purin-8-yl |
| 4866 | 7-CH₃, 2-Cl, 6-OCH₂CH₃-purin-8-yl |
| 4867 | 7-CH₃, 2-Cl, 6-OCH₂CF₃-purin-8-yl |
| 4868 | 7-CH₃, 2-Cl, 6-OCH(CH₃)₂-purin-8-yl |
| 4869 | 7-CH₃, 2-CH₃, 6-OCH₃-purin-8-yl |
| 4870 | 7-CH₃, 2-CH₃, 6-OCH₂CH₃-purin-8-yl |
| 4871 | 7-CH₃, 2-CH₃, 6-OCH₂CF₃-purin-8-yl |
| 4872 | 7-CH₃, 2-CH₃, 6-OCH(CH₃)₂-purin-8-yl |
| 4873 | 7-CH₃, 2-CH₃, 6-OCH₂CH=CH₂-purin-8-yl |
| 4874 | 7-CH₃, 2-CH₃, 6-CH₂CH₃-purin-8-yl |
| 4875 | 7-CH₃, 2-CH₃, 6-CF₃-purin-8-yl |
| 4876 | 7-CH₃, 2-CF₃, 6-CH₂CH₃-purin-8-yl |
| 4877 | 7-CH₃, 2-CF₃, 6-OCH₃-purin-8-yl |
| 4878 | 7-CH₃, 2-CF₃, 6-OCH₂CH₃-purin-8-yl |
| 4879 | 7-CH₃, 2-CF₃, 6-OCH₂CF₃-purin-8-yl |
| 4880 | 7-CH₃, 2-OCH₃, 6-OCH₂CH₃-purin-8-yl |
| 4881 | 7-CH₃, 2-OCH₃, 6-OCH₂CF₃-purin-8-yl |
| 4882 | 7-CH₃, 2-OCH₃, 6-OCH(CH₃)₂-purin-8-yl |
| 4883 | 7-CH₃, 2-OCH₂CH₃, 6-CH₂OCH₂CH₃-purin-8-yl |
| 4884 | 7-CH₃, 2-NO₂, 6-CH₃-purin-8-yl |
| 4885 | 7-CH₃, 2-NO₂, 6-OCH₃-purin-8-yl |
| 4886 | 7-CH₃, 2-NO₂, 6-OCH₂CH₃-purin-8-yl |
| 4887 | 7-CH₃, 2-NO₂, 6-OCH(CH₃)₂-purin-8-yl |
| 4888 | 7-CH₃, 2-NO₂, 6-OCH₂CF₃-purin-8-yl |
| 4889 | 7-CH₃, 2-CN, 6-CH₃-purin-8-yl |
| 4890 | 7-CH₃, 2-CN, 6-OCH₃-purin-8-yl |
| 4891 | 7-CH₃, 2-CN, 6-OCH₂CH₃-purin-8-yl |
| 4892 | 7-CH₃, 2-CN, 6-OCH(CH₃)₂-purin-8-yl |
| 4893 | 7-CH₃, 2-CN, 6-OCH₂CF₃-purin-8-yl |
| 4894 | 3-CH₂CH₂CH₃-pyridin-2-yl |
| 4895 | 4-CH₂CH₂CH₃-pyridin-2-yl |
| 4896 | 5-CH₂CH₂CH₃-pyridin-2-yl |

TABLE A-continued

| No. | R⁴ |
|---|---|
| 4897 | 6-CH₂CH₂CH₃-pyridin-2-yl |
| 4898 | 3-CH(CH₃)₂-pyridin-2-yl |
| 4899 | 4-CH(CH₃)₂-pyridin-2-yl |
| 4900 | 5-CH(CH₃)₂-pyridin-2-yl |
| 4901 | 6-CH(CH₃)₂-pyridin-2-yl |
| 4902 | 3-CH₂(CH₂)₂CH₃-pyridin-2-yl |
| 4903 | 4-CH₂(CH₂)₂CH₃-pyridin-2-yl |
| 4904 | 5-CH₂(CH₂)₂CH₃-pyridin-2-yl |
| 4905 | 6-CH₂(CH₂)₂CH₃-pyridin-2-yl |
| 4906 | 3-CH(CH₃)CH₂CH₃-pyridin-2-yl |
| 4907 | 4-CH(CH₃)CH₂CH₃-pyridin-2-yl |
| 4908 | 5-CH(CH₃)CH₂CH₃-pyridin-2-yl |
| 4909 | 6-CH(CH₃)CH₂CH₃-pyridin-2-yl |
| 4910 | 3-CH₂CH(CH₃)₂-pyridin-2-yl |
| 4911 | 4-CH₂-H(CH₃)₂-pyridin-2-yl |
| 4912 | 5-CH₂CH(CH₃)₂-pyridin-2-yl |
| 4913 | 6-CH₂CH(CH₃)₂-pyridin-2-yl |
| 4914 | 3-C(CH₃)₃-pyridin-2-yl |
| 4915 | 4-C(CH₃)₃-pyridin-2-yl |
| 4916 | 5-C(CH₃)₃-pyridin-2-yl |
| 4917 | 6-C(CH₃)₃-pyridin-2-yl |
| 4918 | 3-C₂F₅-pyridin-2-yl |
| 4919 | 4-C₂F₅-pyridin-2-yl |
| 4920 | 5-C₂F₅-pyridin-2-yl |
| 4921 | 6-C₂F₅-pyridin-2-yl |
| 4922 | 4-CH₂CH(CH₃)₂-pyrimidin-2-yl |
| 4923 | 5-CH₂CH(CH₃)₂-pyrimidin-2-yl |
| 4924 | 4-C(CH₃)₃-pyrimidin-2-yl |
| 4925 | 5-C(CH₃)₃-pyrimidin-2-yl |
| 4926 | 3-Cl-pyridin-2-yl |
| 4927 | 4-Cl-pyridin-2-yl |
| 4928 | 5-Cl-pyridin-2-yl |
| 4929 | 6-Cl-pyridin-2-yl |
| 4930 | 3-F-pyridin-2-yl |
| 4931 | 4-F-pyridin-2-yl |
| 4932 | 5-F-pyridin-2-yl |
| 4933 | 6-F-pyridin-2-yl |
| 4934 | 3-Br-pyridin-2-yl |
| 4935 | 4-Br-pyridin-2-yl |
| 4936 | 5-Br-pyridin-2-yl |
| 4937 | 6-Br-pyridin-2-yl |

The compounds of the formula I according to the invention are suitable for controlling harmful fungi and animal pests of the insects, arachnids and nematodes classes. They can be employed as fungicides and pesticides in crop protection and in the hygiene, stored material protection and veterinary sectors.

The harmful insects include:
from the order of the butterflies (Lepidoptera), for example, *Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis, further Galleria mellonella and Sitotroga cerealella, Ephestia cautella, Tineola bisselliella;* from the order of the beetles (Coleoptera), for example, *Agriotes lineatus, Agriotes obscurus, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus, further Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus;* from the order of the dipterous insects (Diptera), for example, *Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, Tipula oleracea, Tipula paludosa, further Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia cuprina, Lucilia sericata, Musca domestica, Muscina stabulans, Oestrus ovis, Tabanus bovinus, Simulium damnosum;* from the order of the thrips (Thysanoptera), for example, *Frankliniella fusca, Frankliniella occidentalis, Frankliniella tritici, Haplothrips tritici, Scirtothrips citri, Thrips oryzae, Thrips palmi, Thrips tabaci;* from the order of the hymenopterous insects (Hymenoptera), for example, *Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;* from the order of the bugs (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularism Thyanta perditor;* from the order of the plant-sucking insects (Homoptera), for example, *Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, Viteus vitifolii;* from the order of the termites (Isoptera), for example, *Calotermes flavicollis, Leucotermes flavipes, Macrotermes subhyalinus, Odontotermes formosanus, Reticulitermes lucifugus, Termes natalensis;* from the order of the orthopterous insects (Orthoptera), for example, *Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria,* further *Acheta domestica, Blatta orientalis, Blattella germanica, Periplaneta americana;* from the order of the Arachnoidea, for example, phytophagous mites such as *Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranychus pacificus, Tetranychus urticae,* ticks such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus* and *Rhipicephalus evertsi* as well as animal-parasitic mites such as *Dermanyssus gallinae, Psoroptes ovis* and *Sarcoptes scabiei;* from the class of the nematodes, for example, root gall nematodes, eg. *Meloidogyne hapla, Meloidogyne incognita, Meloidogyne javanica,* cyst-forming nematodes, eg. *Globodera pallida, Globodera rostochiensis, Heterodera avenae, Heterodera glycines, Heterodera schachtii,* migratory endoparasites and semiendoparasitic nematodes, eg. *Heliocotylenchus multicinctus, Hirschmanniella oryzae, Hoplolaimus spp, Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans,* stem and leaf nematodes eg. *Anguina tritici, Aphelenchoides besseyi, Ditylenchus angustus, Ditylenchus dipsaci,* virus vectors, eg. *Longidorus spp., Trichodorus christei, Trichodorus viruliferus, Xiphinema index, Xiphinema mediterraneum.*

The compounds I can be applied as such, in the form of their formulations or the application forms prepared therefrom, eg. in the form of directly sprayable solutions, powders, suspensions or dispersions, emulsions, oil dispersions, pastes, dust compositions, scattering compositions or granules, by spraying, atomizing, dusting, scattering or watering. The application forms depend entirely on the intended uses; in each case they should if possible guarantee the finest dispersion of the active compounds according to the invention.

The compounds of the formula I are in some cases systemically active as fungicides. They can be employed as foliar and soil fungicides against a broad spectrum of phytopathogenic fungi, in particular from the Ascomycetes, Deuteromycetes, Phycomycetes and Basidiomycetes classes.

They are of particular importance for controlling a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and cucurbits, and on the seeds of these plants.

The compounds I are specifically suitable for controlling the following plant diseases:

*Erysiphe graminis* (powdery mildew) in cereals,

*Erysiphe cichoracearum* and *Sphaerotheca fuliginea* on cucurbits,

*Podosphaera leucotricha* on apples,

*Uncinula necator* on vines,

Puccinia species on cereals,

Rhizoctonia species on cotton and grass,

Ustilago species on cereals and sugar cane,

*Venturia inaequalis* (scab) on apples,

Helminthosporium species on cereals,

*Septoria nodorum* on wheat,

*Botrytis cinerea* (gray mold) on strawberries, vines,

*Cercospora arachidicola* on groundnuts,

*Pseudocercosporella herpotrichoides* on wheat, barley,

*Pyricularia oryzae* on rice,

*Phytophthora infestans* on potatoes and tomatoes,

Fusarium and Verticillium species on various plants,

*Plasmopara viticola* on vines,

Alternaria species on vegetables and fruit.

The novel compounds can also be employed in the protection of materials, eg. for the protection of wood, paper and textiles eg. against *Paecilomyces variotii.*

They can be converted into the customary formulations, such as solutions, emulsions, suspensions, dusts, powders, pastes or granules. The use forms here depend on the particular intended use; in each case they should if possible guarantee the finest dispersion of the active compounds.

The formulations are prepared in a known manner, eg. by extending the active compound with solvents and/or carriers, if desired using emulsifiers and dispersants, where if water is used as a diluent other organic solvents can also be used as auxiliary solvents.

Suitable auxiliaries for this purpose are mainly:

solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water;

carriers such as ground natural minerals (eg. kaolins, argillaceous earths, talc, chalk) and ground synthetic minerals (eg. highly disperse silica, silicates);

emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl, lauryl ether and fatty alcohol sulfates, as well as salts of sulfated hexa-, hepta- and octadecanols, and also of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenol or tributylphenylpolyglycol ether, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Aqueous use forms can be prepared from emulsion concentrates, dispersions, pastes, wettable powders or water-dispersible granules by addition of water. To prepare emulsions, pastes or oil dispersions, the substrates can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Powder, broadcasting and dusting compositions can be prepared by mixing or joint grinding of the active substances with a solid carrier.

Granules, eg. coated, impregnated and homogeneous granules, can be prepared by binding the active compounds to solid carriers.

Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as cereal flour, tree bark meal, wood meal and nutshell meal, cellulose powder or other solid carriers. The active compound concentrations in the ready-to-use preparations can be varied within relatively wide ranges.

Very generally, the compositions contain from 0.0001 to 95% by weight of active compound.

Formulations containing more than 95% by weight of active compound can be applied highly successfully in the ultra-low volume process (ULV), it even being possible to use the active compound without additives.

For use as fungicides, concentrations of from 0.01 to 95% by weight, preferably of from 0.5 to 90% by weight, of active compound are recommended. For use as insecticides, formulations containing from 0.0001 to 10% by weight, preferably from 0.01 to 1% by weight, of active compound are suitable.

The active compounds are normally employed in a purity of from 90% to 100%, preferably from 95% to 100% (according to NMR spectrum).

Examples of such preparations are:

I. a solution of 90 parts by weight of a compound I according to the invention and 10 parts by weight of N-methyl-α-pyrrolidone, which is suitable for application in the form of very small drops;

II. a solution of 20 parts by weight of a compound I according to the invention in a mixture of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil; a dispersion is obtained by finely dispersing the formulation in water.

III. a solution of 20 parts by weight of a compound I according to the invention in a mixture of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil; a dispersion is obtained by finely dispersing the formulation in water.

IV. an aqueous dispersion of 20 parts by weight of a compound I according to the invention in a mixture of 25 parts by weight of cyclohexanone, 65 parts by weight of a mineral oil fraction of boiling point from 210° to 280° C. and 10 parts by weight of the addition product of 40 mol of ethylene oxide to 1 mol of castor oil; a dispersion is obtained by finely dispersing the formulation in water.

V. a mixture, ground in a hammer mill, of 20 parts by weight of a compound I according to the invention, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel; a spray mixture is obtained by finely dispersing the mixture in water;

VI. an intimate mixture of 3 parts by weight of a compound I according to the invention and 97 parts by weight of finely divided kaolin; this dusting composition contains 3% by weight of active compound;

VII. an intimate mixture of 30 parts by weight of a compound I according to the invention, 92 parts by weight of powdered silica gel and 8 parts by weight of liquid paraffin which has been sprayed onto the surface of this silica gel; this preparation gives the active compound a good adherence;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of a compound I according to the invention, 2 parts by weight of the calcium salt of dodecylbenzenesulfonic acid, 8 parts by weight of fatty alcohol polyglycol ether, 2 parts by weight of the sodium salt of a phenolsulfonic acid/urea/formaldehyde condensate and 68 parts by weight of a paraffinic mineral oil;

X. a mixture, ground in a hammer mill, of 10 parts by weight of a compound I according to the invention, 4 parts by weight of the sodium salt of diisobutylnaphthalene-α-sulfonic acid, 20 parts by weight of the sodium salt of a lignosulfonic acid from a sulfite waste liquor, 38 parts by weight of silica gel and 38 parts by weight of kaolin. By finely dispersing the mixture in 10,000 parts by weight of water, a spray mixture is obtained which contains 0.1% by weight of the active compound.

The compounds I are applied by treating the fungi or the seed, plants, materials or the soil to be protected from fungal attack with a fungicidally active amount of the active compounds.

They are applied before or after the infection of the materials, plants or seed by the fungi.

Depending on the type of effect desired, the application rates are from 0.02 to 3 kg of active compound per ha, preferably from 0.1 to 1 kg/ha.

In seed treatment, amounts of active compound of from 0.001 to 50 g, preferably from 0.01 to 10 g, per kilogram of seed are in general needed.

The application rate of active compound for controlling pests under outdoor conditions is from 0.02 to 10, preferably from 0.1 to 2.0 kg/ha of active compound.

The compounds I, on their own or in combination with herbicides or fungicides, can also be applied jointly mixed with further crop protection agents, for example with growth regulators or with agents for controlling pests or bacteria. Of interest is also the miscibility with fertilizers or with mineral salt solutions which are employed for eliminating nutritional and trace element deficiencies.

The crop protection agents and fertilizers can be added to the compositions according to the invention in a weight ratio of from 1:10 to 10:1, if appropriate even only immediately before use (tank mix). On mixing with fungicides or insecticides, in many cases an increase in the fungicidal spectrum of action is obtained here.

The following list of fungicides with which the compounds according to the invention can be applied jointly is intended to illustrate the combination possibilities, but not to restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfides, ammonia complex of zinc N,N-ethylenebisdithiocarbamate, ammonia complex of zinc N,N'-propylenebisdithiocarbamate, zinc N,N'-propylenebisdithiocarbamate, N,N'-polypropylenebis (thiocarbamoyl) disulfide; nitro derivatives, such as dinitro-(1-methylheptyl)phenyl crotonate, 2-sec-butyl-4,6-dinitro-phenyl 3,3-dimethylacrylate, 2-sec-butyl-4, 6-dinitrophenyl isopropyl carbonate, diisopropyl 5-nitroisophthalate;

-heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-β-[bis(dimethylamino)-phosphinyl]-3-phenyl-1,2,4-triazole, 2,3-dicyano-1,4-dithio-anthraquinone, 2-thio-1,3-dithiolo-β-[4,5-b] quinoxaline, methyl 1-(butylcarbamoyl)-2-benzimidazolecarbamate, 2-methoxycarbonylaminobenzimidazole, 2-(fur-2-yl) benzimidazole, 2-(thiazol-4-yl)-benzimidazole, N-(1,1, 2,2-tetrachloroethylthio)tetrahydrophthalimide, N-trichloromethylthiotetrahydrophthalimide, N-trichloromethylthiophthalimide, N-dichlorofluoromethylthio-N', N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl))formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2, 4-triazole, 1-[2-(2,4-dichlorophenyl)-4-n-propyl-1,3-dioxolan-2-ylethyl]-1H-1,2,4-triazole, N-(n-propyl)-N-( 2,4,6-trichlorophenoxyethyl)-N'-imidazolylurea, 1-(4-chloro-phenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidine-methanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and also various fungicides, such as dodecylguanidine acetate, 3-[3-(3,5-dimethyl-2-oxycyclohexyl)-2-hydroxyethyl]glutarimide, hexachlorobenzene, DL-methyl-N-(2,6-dimethylphenyl)-N-2-furoyl alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1, 3-oxazolidine-2,4-dione, 3-(3,5-dichlorophenyl)-1-isopropylcarbamoylhydantoin, N-(3,5-dichlorophenyl) -1,2-dimethylcyclopropane-1,2-dicarboximide, 2-cyano-[N-ethylaminocarbonyl-2-methoximino]-acetamide, 1-[2-(2,4-dichlorophenyl)pentyl]-1H-1,2,4-triazole, 2,4-difluoro-α-(1H-1,2,4-triazolyl-1-methyl) benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl) methyl)-1H-1,2,4-triazole.

SYNTHESIS EXAMPLES

The procedures described in the synthesis examples below were used with appropriate modification of the starting compounds to obtain further compounds I. The compounds thus obtained are listed with physical data in the following table.

1. Methyl N-methoxy-N-((2-(4-(2,2,2-trifluoroethoxy) pyrimidin-2-yl)acetiminoxymethyl)phenyl)carbamate

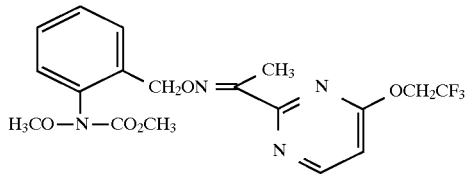

A mixture of 2.3 g (10 mmol) of 4-(2,2,2-trifluoroethoxy)-2-acetylpyrimidine oxime (WO 92/18,487) and 0.3 g (12.5 mmol) of sodium hydride in 20 ml of dimethylformamide is stirred at room temperature for 10 minutes. 3.3 g (10 mmol) of methyl N-methoxy-N-(2-bromomethylphenyl)carbamate (purity about 80%, WO 93/15,046) are then added and the reaction mixture is stirred at room temperature for about 1 hour. It is then diluted with water and the aqueous phase is extracted three times with methyl t-butyl ether. The combined organic phases are extracted once with water, dried over MgSO$_4$ and concentrated. The residue is purified by column chromatography using cyclohexane/ethyl acetate mixtures. 2.7 g (63%) of the title compound are obtained as a pale yellow oil.

$^1$H-NMR (CDCl$_3$; δ in ppm): 8.6 (d,1H,pyrimidinyl); 7.6 (m,1H,phenyl); 7.4 (m,3H;phenyl); 6.85 (d,1H, pyrimidinyl); 5.45 (s,2H,OCH$_2$); 4.9 (q,2H,O—CH$_2$—CF$_3$); 3.8 (s,3H;OCH$_3$); 3.75 (s,3H,OCH$_3$); 2.4 (s,3H,CH$_3$)

2. N-Methyl-N'-methoxy-N'-((2-(4-(2,2,2-trifluoromethoxy)-pyrimidin-2-yl)acetiminoxymethyl)phenyl)urea

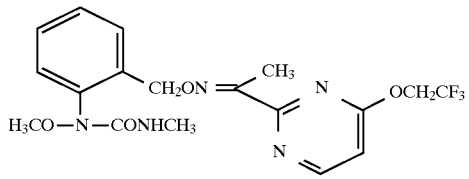

A mixture of 2.3 g (10 mmol) of 4-(2,2,2-trifluoroethoxy)-2-acetylpyrimidine oxime (WO 92/18,487), 1.8 g (13 mmol) of K$_2$CO$_3$ and 3.4 g (10 mmcol) of phenyl N-methoxy-N-(2-bromomethylphenyl)carbamate (prepared in a similar manner to WO 93/15,046) in 30 ml of dimethylformamide is stirred overnight at room temperature. The reaction mixture is then diluted with water and the aqueous phase is extracted three times with methyl t-butyl ether. The combined organic phases are dried over MgSO$_4$ and concentrated. The residue is filtered off with suction through Al$_2$O$_3$ using cyclohexane/ethyl acetate 4:1. The solvent is then evaporated in vacuo.

The residue is treated with 20 ml of 40% strength aqueous methylamine solution and the reaction mixture is stirred at room temperature for 3 hours. It is then extracted with methylene chloride. The combined organic phases are dried over MgSO$_4$ and concentrated. The residue is purified by column chromatography using cyclohexane/ethyl acetate mixtures. The product thus obtained crystallizes and is washed with methyl t-butyl ether/hexane 1:1 with stirring and then sucked dry. 0.4 g (10% of the title compound is obtained as colorless crystals (m.p.:=136° C.).

$^1$H-NMR (CDCl$_3$; δ in ppm): 8.6 (d,1H,pyrimidinyl); 7.55 (m,1H,phenyl); 7.35 (m,3H;phenyl); 6.8 (d,1H, pyrimidinyl); 6.95 (m, 1H, NH); 5.5 (s,2H,OCH$_2$); 4.85 (q,2H,O—CH$_2$—CF$_3$); 3.7 (s,3H;OCH$_3$); 2.9 (s,3H,OCH$_3$); 2.4 (s,3H,CH$_3$)

3. Methyl N-methoxy-N-(2-((4-methoxypyrimidin-2-yl)acetiminoxymethyl)-phenyl)carbamate phenyl )carbamate a) Methyl N-methoxy-N-((2-phthalimidoxymethyl)-phenyl)carbamate

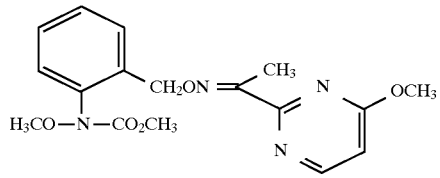

A mixture of 15 g (38 mmol) of methyl N-methoxy-N-(2-bromomethylphenyl)carbamate (purity about 70%; WO 93/15,046), 6.9 g (42 mmol) of N-hydroxyphthalimide and 4.6 g (46 mmol) of triethylamine in 50 ml of dimethylformamide is stirred at 60° C. for about 2 hours. The reaction mixture is then cooled to room temperature and diluted with water. During the course of this a solid precipitates, which is washed with water and i-propanol and dried in vacuo. 10.6 g (78%) of the title compound are obtained as colorless crystals (m.p.:=150° C.).

$^1$H-NMR (CDCl$_3$; δ in ppm): 7.8 (m,5H,phenyl); 7.4 (m,3H,phenyl); 5.25 (s,2H,OCH$_2$); 4.0 (2s, each 3H,2× OCH$_3$).

b) Methyl N-methoxy-N-(2-aminoxymethylphenyl)carbamate

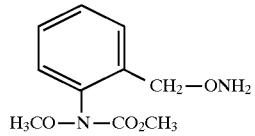

A mixture of 6.8 g (19 mmol) of the subst. phthalimide from Example 3a and 0.8 g (16 mmol) of hydrazine hydrate in 30 ml of methanol is stirred at room temperature for 4 hours. The precipitated solid is then filtered off with suction and the filtrate is concentrated. The partly crystalline residue is washed with ether with stirring. The solid is filtered off with suction and the filtrate is concentrated. As a residue, 4.0 g (99%) of the title compound (purity >90%) are obtained as a yellow oil.

$^1$H-NMR (CDCl$_3$; δ in ppm): 7.5 (m,1H,phenyl); 7.35 (m,3H,phenyl); 5.45 (s,broad,2H,NH$_2$); 4.75 (s,2H,OCH$_2$); 3.8 (s,3H,OCH$_3$); 3.75 (s,3H,OCH$_3$)

c) Methyl N-methoxy-N-(2-((4-methoxypyrimidin-2-yl)-octiminoxymethyl)phenyl)carbamate

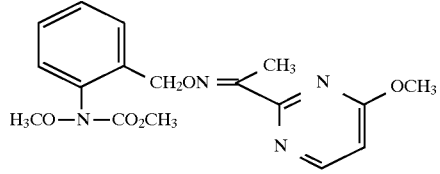

A mixture of 1.0 g (6.4 mmol) of 2-acetyl-4-chloropyrimidine (WO 92/18,487) and 1.4 g (6.4 mmol) of methyl N-methoxy-N-(2-aminoxymethylphenyl)carbamate (Example 3b) in 20 ml of methanol is stirred overnight at room temperature. The reaction mixture is concentrated and the residue is purified by column chromatography using cyclohexane/ethyl acetate mixtures. 0.4 g (17%) of the title compound is obtained as a pale yellow oil.

$^1$H-NMR (CDCl$_3$; δ in ppm): 8.5 (d,1H,pyrimidinyl); 7.6 (m,1H,phenyl); 7.4 (m,3H,phenyl); 6.7 (d,1H,pyrimidinyl); 5.45 (s,2H,OCH$_2$); 4.05 (s,3H,OCH$_3$); 3.8 (s,3H,OCH$_3$); 3.75 (s,3H,OCH$_3$); 2.4 (s,3H,CH$_3$)

Methyl N-methoxy-N-(2-((4-chloropyrimidin-2-yl) acetiminoxymethyl)phenyl)carbamate

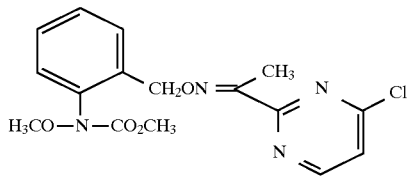

A mixture of 0.7 g (4.4 mmol) of 2-acetyl-4-chloropyrimidine (WO 92/18487) and 1 g (4.4 mmol) of methyl N-methoxy-N-(2-aminoxymethylphenyl)carbamate (Example 3b) in 15 ml of tetrahydrofuran is stirred at room temperature for 2 hours. The reaction mixture is then concentrated and the residue is purified by column chromatography using cyclohexane/ethyl acetate mixtures. 1.2 g (74%) of the title compound are obtained as a pale yellow oil.

$^1$H-NMR (CDCl$_3$; δ in ppm): 8.7 (d,1H,pyrimidinyl); 7.6 (m,1H;phenyl); 7.4 (m,3H,phenyl); 7.3 (d,1H,pyrimidinyl); 5.45 (s,2H;OCH$_2$) 3.8 (s,3H,OCH$_3$); 3.75 (s,3H,OCH$_3$)

fatty alcohols) and diluted with water according to the concentration desired.

The fungicidal action of the compounds according to the invention was determined in comparison with the known active compound A.18/7 (Example No. 18, Table 7 from WO-A 93/15,046) in the manner described below.

*Puccinia recondita* (brown rust of wheat)

Leaves of wheat seedlings (Kanzler variety) were dusted with spores of brown rust (*Puccinia recondita*). The plants treated in this way were incubated for 24 h at 20°–22° C. and a relative atmospheric humidity of 90–95% and then treated with the aqueous active compound preparation. After a further 8 days at 20°–22° C. and 65–70% relative atmospheric humidity, the extent of the fungal development was determined. Assessment was carried out visually.

In this test, the plants treated with the compounds 01 and 02 according to the invention showed no fungal attack, while the plants treated with the known active compound A.18/7 were attacked to 25%. The untreated plants showed an attack of 70%.

In a corresponding test, the plants treated with 250 ppm of the compounds 04, 06, 07, 08, 09, 10, 11 and 12 according to the invention showed a fungal attack of 15% or less while the plants treated with the known active compound A.18/7 were attacked to 25%. The untreated plants showed an attack of 70%.

*Pyricularia oryzae* (rice blast disease)

Rice seedlings (Tai Nong 67 variety) were sprayed with the active compound preparation until dripping wet. After 24 hours, the plants were sprayed with an aqueous spore suspension of fungus *Pyricularia oryzae* and kept at a

TABLE

| No. | R$_n$ | R$^1$ | X | R$^2$ | R$^3$ | R$^4$ | m.p. [°C.]; $^1$H-NMR |
|-----|-------|-------|-----|-------|-------|-------|-----------------------|
| 01 | H | CH$_3$ | O | CH$_3$ | CH$_3$ | 4-OC$_2$H$_5$-pyrimidin-2-yl | 3.8(s, 3H); 3.75(s, 3H) |
| 02 | H | CH$_3$ | O | CH$_3$ | CH$_3$ | 4-OCH$_2$CF$_3$-pyrimidin-2-yl | 3.8(s, 3H); 3.75(s, 3H) |
| 03 | H | CH$_3$ | NH | CH$_3$ | CH$_3$ | 4-OCH$_2$CF$_3$-pyrimidin-2-yl | 136 |
| 04 | H | CH$_3$ | O | CH$_3$ | CH$_3$ | 4-OCH$_3$-pyrimidin-2-yl | 3.8(s, 3H); 3.75(s, 3H) |
| 05 | H | CH$_3$ | O | CH$_3$ | CH$_3$ | 4-Cl-pyrimidin-2-yl | 3.8(s, 3H); 3.75(s, 3H) |
| 06 | H | CH$_3$ | O | CH$_3$ | CH$_3$ | 4-OCH(CH$_3$)$_2$-pyrimidin-2-yl | 3.8(s, 3H); 3.75(s, 3H) |
| 07 | H | CH$_3$ | O | CH$_3$ | CH$_3$ | 4-O(CH$_2$)$_2$CH$_3$-pyrimidin-2-yl | 76 |
| 08 | H | CH$_3$ | O | CH$_3$ | CH$_3$ | 4-OCH$_2$C≡CH-pyrimidin-2-yl | 3.8(s, 3H); 3.75(s, 3H) |
| 09 | H | CH$_3$ | O | CH$_3$ | CH$_3$ | 4-(CH$_2$)$_3$-pyrimidin-2-yl | 3.8(s, 3H); 3.75(s, 3H) |
| 10 | H | CH$_3$ | O | CH$_3$ | CH$_3$ | 4-(CH$_2$)$_4$CH$_3$-pyrimidin-2-yl | 3.8(s, 3H); 3.75(s, 3H) |
| 11 | H | CH$_3$ | O | CH$_3$ | CH$_3$ | 4-C$_6$H$_5$-pyrimidin-2-yl | 3.8(s, 3H); 3.75(s, 3H) |
| 12 | H | CH$_3$ | O | CH$_3$ | CH$_3$ | 4-OC$_6$H$_5$-pyrimidin-2-yl | 3.8(s, 3H); 3.75(s, 3H) |
| 13 | H | CH$_3$ | O | CH$_3$ | CH$_3$ | 4-OCH$_2$CF$_3$, 6-CH$_3$-pyrimidin-2-yl | 3.8(s, 3H); 3.75(s, 3H) |
| 14 | H | CH$_3$ | O | CH$_3$ | CH$_3$ | 6-OCH$_2$CF$_3$-pyrimidin-4-yl | 3.8(s, 3H); 3.75(s, 3H) |
| 15 | H | CH$_3$ | O | CH$_3$ | CH$_3$ | 4-CH$_3$-pyrimidin-2-yl | 123 |
| 16 | H | CH$_3$ | O | CH$_3$ | CH$_3$ | 4-CH$_3$, 6-OCH$_3$-pyrimidin-2-yl | 102 |
| 17 | H | CH$_3$ | O | CH$_3$ | CH$_3$ | 4-CH$_2$CH(CH$_3$)$_2$-pyrimidin-2-yl | 102 |
| 18 | H | CH$_3$ | O | CH$_3$ | CH$_3$ | 6-OCH$_3$-pyrimidin-4-yl | 103 |
| 19 | H | CH$_3$ | O | CH$_3$ | CH$_3$ | 6-OC$_2$H$_5$-pyrimidin-4-yl | 3.8(s, 3H); 3.75(s, 3H) |
| 20 | H | CH$_3$ | O | CH$_3$ | CH$_3$ | 4-CH$_3$, 6-CF$_3$-pyrimidin-2-yl | 3.8(s, 3H); 3.75(s, 3H) |
| 21 | H | CH$_3$ | O | CH$_3$ | CH$_3$ | 4-C(CH$_3$)$_3$-pyrimidin-2-yl | 3.8(s, 3H); 3.75(s, 3H) |
| 22 | H | CH$_3$ | O | CH$_3$ | CH$_3$ | 4,6-(OCH$_3$)$_2$-pyrimidin-2-yl | 3.8(s, 3H); 3.75(s, 3H) |
| 23 | H | CH$_3$ | O | CH$_3$ | CH$_3$ | 5-Cl-pyrimidin-2-yl | 103 |
| 24 | H | CH$_3$ | O | CH$_3$ | CH$_3$ | 4-OCH$_3$, 6-CF$_3$-pyrimidin-2-yl | 90 |

Examples of the action against harmful fungi

It was possible to show the fungicidal action of the compounds of the formula I by the following tests:

The active compounds were prepared as a 20% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated relative atmospheric humidity of 95–99% at 22°–24° C. for 6 days. Assessment was carried out visually.

In this test, the plants treated with the compounds 01 and 02 according to the invention showed no fungal attack, while the plants treated with the known active compound A.18/7 were attacked to 60%. The untreated plants likewise showed an attack of 60%.

In a corresponding test, the plants treated with 16 ppm of the compounds 06, 07, 09, 10 and 11 according to the invention showed a fungal attack of 25% or less while the plants treated with the known active compound A.18/7 were attacked to 60%. The untreated plants showed an attack of 60%.

Examples of the action against animal pests

It was possible to show the action of the compounds of the general formula I against animal pests by the following tests:

The active compounds were prepared a) as a 0.1% strength solution in acetone or b) as a 10% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols)

and diluted with acetone in the case of a) or with water in the case of b) according to the desired concentration.

After conclusion of the tests, the lowest concentration at which the compounds still caused an 80–100% inhibition or mortality in comparison with untreated control tests was determined in each case (activity threshold or minimum concentration).

We claim:

1. An iminooxymethyleneanilide of the formula I

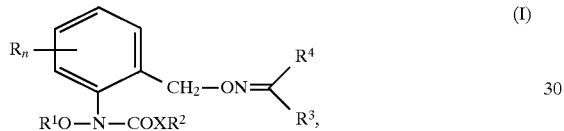

where the index and the substituents have the following meanings:

n is 0, 1, 2, 3 or 4, it being possible for the substituents R to be different if n is greater than 1;

R is nitro, cyano, halogen, $C_1$–$C_{10}$-alkyl, $C_2$–$C_{10}$-alkenyl, $C_2$–$C_{10}$-alkynyl, $C_1$–$C_{10}$-alkoxy, $C_3$–$C_{10}$-alkenyloxy and $C_3$–$C_{10}$-alkynyloxy, it being possible for these groups to be partially or completely halogenated and/or to carry one to three of the following radicals:

cyano, nitro, hydroxyl, amino, formyl, carboxyl, aminocarbonyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylamino, di-$C_1$–$C_6$-alkylamino, $C_1$–$C_6$-alkylcarbonyl, $C_1$–$C_6$-alkoxycarbonyl, $C_1$–$C_6$-alkylcarbonyloxy, $C_1$–$C_6$-alkylaminocarbonyl, di-$C_1$–$C_6$-alkylaminocarbonyl, $C_1$–$C_6$-alkylcarbonylamino, $C_1$–$C_6$-alkoxycarbonylamino, $C_1$–$C_6$-alkylcarbonyl-N-$C_1$–$C_6$-alkylamino, and $CR^{iii}$=$NOR^{iv}$, $R^{iii}$ being hydrogen, $C_1$–$C_6$-alkyl, $C_2$–$C_6$-alkenyl, $C_2$–$C_6$-alkynyl or $C_3$–$C_{12}$-cycloalkyl and $R^{iv}$ being $C_1$–$C_6$-alkyl, $C_3$–$C_6$-alkenyl, $C_3$–$C_6$-alkynyl or aryl-$C_1$–$C_6$-alkyl, $C_3$–$C_{12}$-cycloalkyl, $C_3$–$C_{12}$-cycloalkoxy, $C_3$–$C_{12}$-cycloalkylthio, $C_3$–$C_{12}$-cycloalkylamino, $C_3$–$C_{12}$-cycloalkyl-N-$C_1$–$C_6$-alkylamino, each of which is unsubstituted or substituted by customary groups, 3- to 12-membered heterocyclyl, heterocyclyloxy, heterocyclylthio, heterocyclylamino or heterocyclyl-N-$C_1$–$C_6$-alkylamino, each of which is unsubstituted or substituted by customary groups, aryl, aryloxy, arylthio, arylamino, aryl-N-$C_1$–$C_6$-alkylamino, aryl-$C_1$–$C_6$-alkoxy, aryl-$C_1$–$C_6$-alkylthio, aryl-$C_1$–$C_6$-alkylamino, aryl-$C_1$–$C_6$-alkyl-N-$C_1$–$C_6$-alkylamino, hetaryl, hetaryloxy, hetarylthio, hetarylamino, hetaryl-N-$C_1$–$C_6$-alkylamino, hetaryl-$C_1$–$C_6$-alkoxy, hetaryl-$C_1$–$C_6$-alkylthio, hetaryl-$C_1$–$C_6$-alkylamino, hetaryl-$C_1$–$C_6$-alkyl-N-$C_1$–$C_6$-alkylamino, arylcarbonyl, aryloxycarbonyl, arylcarbonyloxy, arylaminocarbonyl, N-aryl-N-$C_1$–$C_6$-alkylaminocarbonyl, arylcarbonyl-N-$C_1$–$C_6$-alkylamino, aryloxycarbonylamino, hetarylcarbonyl, hetaryloxycarbonyl, hetarylcarbonyloxy, hetarylaminocarbonyl, N-hetaryl-N-$C_1$–$C_6$-alkylaminocarbonyl, hetarylcarbonyl-N-$C_1$–$C_6$-alkylamino and hetaryloxycarbonylamino, each of which is unsubstituted or substituted by customary groups, in the case where n is 2, 3 or 4, additionally an unsubstituted or substituted bridge bonded to two adjacent ring atoms, which contains three or four members from the group consisting of 3 or 4 carbon atoms, and 2 or 3 carbon atoms and 1 or 2 nitrogen, oxygen and/or sulfur atoms, it being possible for this bridge, together with the ring to which it is bonded, to form a partially unsaturated or aromatic radical;

X is a direct bond or $CH_2$, O or $NR^a$;

$R^a$ is hydrogen, $C_1$–$C_{10}$-alkyl, $C_2$–$C_{10}$-alkenyl, $C_2$–$C_{10}$-alkynyl, $C_3$–$C_{10}$-cycloalkyl or $C_5$–$C_{10}$-cycloalkenyl;

$R^1$ is hydrogen, $C_1$–$C_{10}$-alkyl, $C_2$–$C_{10}$-alkenyl, $C_2$–$C_{10}$-alkynyl, $C_3$–$C_{10}$-cycloalkyl, $C_5$–$C_{10}$-cycloalkenyl, $C_1$–$C_{10}$-alkylcarbonyl or $C_1$–$C_{10}$-alkoxycarbonyl, it being possible for these groups to be partially or completely halogenated and/or to carry one to three of the following radicals:

cyano, nitro, hydroxyl, amino, formyl, carboxyl, aminocarbonyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylamino, di-$C_1$–$C_6$-alkylamino, $C_1$–$C_6$-alkylcarbonyl, $C_1$–$C_6$-alkoxycarbonyl, $C_1$–$C_6$-alkylcarbonyloxy, $C_1$–$C_6$-alkylaminocarbonyl, di-$C_1$–$C_6$-alkylaminocarbonyl, $C_1$–$C_6$-alkylcarbonylamino, $C_1$–$C_6$-alkoxycarbonylamino, $C_1$–$C_6$-alkylcarbonyl-N-$C_1$–$C_6$-alkylamino, and $CR^{iii}$=$NOR^{iv}$, $R^{iii}$ being hydrogen, $C_1$–$C_6$-alkyl, $C_2$–$C_6$-alkenyl, $C_2$–$C_6$-alkynyl or $C_3$–$C_{12}$-cycloalkyl and $R^{iv}$ being $C_1$–$C_6$-alkyl, $C_3$–$C_6$-alkenyl, $C_3$–$C_6$-alkynyl or aryl-$C_1$–$C_6$-alkyl, $C_3$–$C_{12}$-cycloalkyl, $C_3$–$C_{12}$-cycloalkoxy, $C_3$–$C_{12}$-cycloalkylthio, $C_3$–$C_{12}$-cycloalkylamino, $C_3$–$C_{12}$-cycloalkyl-N-$C_1$–$C_6$-alkylamino, each of which is unsubstituted or substituted by customary groups, 3- to 12-membered heterocyclyl, heterocyclyloxy, heterocyclylthio, heterocyclylamino or heterocyclyl-N-$C_1$–$C_6$-alkylamino, each of which is unsubstituted or substituted by customary groups, aryl, aryloxy, arylthio, arylamino, aryl-N-$C_1$–$C_6$-alkylamino, aryl-$C_1$–$C_6$-alkoxy, aryl-$C_1$–$C_6$-alkylthio, aryl-$C_1$–$C_6$-alkylamino, aryl-$C_1$–$C_6$-alkyl-N-$C_1$–$C_6$-alkyl-amino, hetaryl, hetaryloxy, hetarylthio, hetarylamino, hetaryl-N-$C_1$–$C_6$-alkylamino, hetaryl-$C_1$–$C_6$-alkoxy, hetaryl-$C_1$–$C_6$-alkylthio, hetaryl-$C_1$–$C_6$-alkylamino, hetaryl-$C_1$–$C_6$-alkyl-N-$C_1$–$C_6$-alkylamino, arylcarbonyl, aryloxycarbonyl, arylcarbonyloxy, arylaminocarbonyl, N-aryl-N-$C_1$–$C_6$-alkylaminocarbonyl, arylcarbonyl-N-$C_1$–$C_6$-alkylamino, aryloxycarbonylamino, hetarylcarbonyl, hetaryloxycarbonyl, hetarylcarbonyloxy, hetarylaminocarbonyl, N-hetaryl-N-$C_1$–$C_6$-alkylaminocarbonyl, hetarylcarbonyl-N-$C_1$–$C_6$-alkylamino and hetaryloxycarbonylamino, each of which is unsubstituted or substituted by customary groups, $R^2$ is $C_1$–$C_{10}$-alkyl, $C_2$–$C_{10}$-alkenyl, $C_2$–$C_{10}$-alkynyl, $C_3$–$C_{10}$-cycloalkyl or $C_5$–$C_{10}$-cycloalkenyl, or in the case where X is $NR^a$, additionally hydrogen;

$R^3$ is hydrogen, cyano, halogen, $C_1$–$C_{10}$alkyl, $C_1$–$C_{10}$haloalkyl, $C_1$–$C_{10}$alkoxy, $C_1$–$C_{10}$haloalkoxy, $C_1$–$C_{10}$alkylthio, $C_1$–$C_4$-haloalkylthio or $C_3$–$C_{10}$-cycloalkyl;

$R^4$ is a 6- to 10-membered mono- or bicyclic, heteroaromatic ring system selected from the group consisting of:
2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, indolyl, quinolinyl, isoquinolinyl and purinyl, which is substituted by customary groups;
it being possible for the radicals substituted by customary groups to be:
partially or completely halogenated,
and/or one to four of the following radicals
cyano, nitro, hydroxyl, amino, carboxyl, aminocarbonyl, $C_1$–$C_6$-alkyl, $C_1$–$C_6$-haloalkyl, $C_2$–$C_8$-alkenyl, $C_2$–$C_8$-haloalkenyl, $C_2$–$C_8$-alkenyloxy, $C_2$–$C_8$-haloalkenyloxy, $C_2$–$C_8$-alkynyl, $C_2$–$C_8$-haloalkynyl, $C_2$–$C_8$-alkynyloxy, $C_2$–$C_8$-haloalkynyloxy, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylamino, di-$C_1$–$C_6$-alkylamino, $C_1$–$C_6$-alkylcarbonyl, $C_1$–$C_6$-alkoxycarbonyl, $C_1$–$C_6$-alkylcarbonyloxy, $C_1$–$C_6$-alkylaminocarbonyl, di-$C_1$–$C_6$-alkylaminocarbonyl, $C_1$–$C_6$-alkylcarbonylamino, $C_1$–$C_6$-alkoxycarbonylamino and $C_1$–$C_6$-alkylcarbonyl-N-$C_1$–$C_6$-alkylamino, and/or one to three of the following radicals
$C_3$–$C_{12}$-cycloalkyl, $C_3$–$C_{12}$-cycloalkoxy, $C_3$–$C_{12}$-cycloalkylthio, $C_3$–$C_{12}$-cycloalkylamino, $C_3$–$C_{12}$-Cycloalkyl-N-$C_1$–$C_6$-alkylamino, 3- to 12-membered heterocyclyl, heterocyclyloxy, heterocyclylthio, heterocyclylamino or heterocyclyl-N-$C_1$–$C_6$-alkylamino, aryl, aryloxy, arylthio, arylamino, aryl-N-$C_1$–$C_6$-alkylamino, aryl-$C_1$–$C_6$-alkoxy, aryl-$C_1$–$C_6$-alkylthio, aryl-$C_1$–$C_6$-alkylamino, aryl-$C_1$–$C_6$-alkyl-N-$C_1$–$C_6$-alkylamino, hetaryl, hetaryloxy, hetarylthio, hetarylamino, hetaryl-N-$C_1$–$C_6$-alkylamino, hetaryl-$C_1$–$C_6$-alkoxy, hetaryl-$C_1$–$C_6$-alkylthio, hetaryl-$C_1$–$C_6$-alkylamino, hetaryl-$C_1$–$C_6$-alkyl-N-$C_1$–$C_6$-alkylamino, arylcarbonyl, aryloxycarbonyl, arylcarbonyloxy, arylaminocarbonyl, N-aryl-N-$C_1$–$C_6$-alkylaminocarbonyl, arylcarbonyl-N-$C_1$–$C_6$-alkylamino, aryloxycarbonylamino, hetarylcarbonyl, hetaryloxycarbonyl, hetarylcarbonyloxy, hetarylaminocarbonyl, N-hetaryl-N-$C_1$–$C_6$-alkylaminocarbonyl, hetarylcarbonyl-N-$C_1$–$C_6$-alkylamino and hetaryloxycarbonylamino, and or one or two of the following radicals formyl or $CR^{iii}$=$NOR^{iv}$, $R^{iii}$ being hydrogen, $C_1$–$C_6$-alkyl, $C_2$–$C_6$-alkenyl, $C_3$–$C_{10}$-cycloalkyl or $C_2$–$C_6$-alkynyl and $R^{iv}$ being $C_1$–$C_6$-alkyl, $C_2$–$C_6$-alkenyl, $C_2$–$C_6$-alkynyl and aryl-$C_1$–$C_6$-alkyl, or a $C_3$–$C_5$-alkylene, $C_3$–$C_5$-alkenylene, oxy-$C_2$–$C_4$-alkylene, oxy-$C_1$–$C_3$-alkyleneoxy, oxy-$C_2$–$C_4$-alkenylene, oxy-$C_2$–$C_4$-alkenyleneoxy or butadienediyl group bonded to two adjacent C atoms, it being possible for these bridges in turn to be partially or completely halogenated and/or to carry one to three of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

2. A compound of the formula I as claimed in claim 1, where n is 0 or 1.

3. A compound of the formula I as claimed in claim 1, where R is fluorine, chlorine, cyano, methyl and methoxy.

4. A compound of the formula I as claimed in claim 1, where X is a direct bond, $CH_2$, oxygen or NH.

5. A compound of the formula I as claimed in claim 1, where $R^1$ is hydrogen, $C_1$–$C_4$-alkyl, allyl, propargyl or methoxymethyl.

6. A compound of the formula I as claimed in claim 1, where $R^4$ is substituted pyridinyl, 2-pyrimidinyl, 4-pyrimidinyl, 5-pyrimidinyl, 1,3,5-triazin-2-yl or isoquinolinyl.

7. A compound of the formula I as claimed in claim 1, where $R^4$ is substituted by pyridin-2-yl, cyano, halogen, $C_1$–$C_6$-alkyl, $C_1$–$C_6$-alkoxy, $C_2$–$C_6$-alkenyl, $C_2$–$C_6$-alkenyloxy, $C_2$–$C_6$-alkynyl, $C_2$–$C_6$-alkynyloxy, $C_1$–$C_6$-haloalkyl, $C_1$–$C_6$-haloalkoxy, $C_2$–$C_6$-haloalkenyl, $C_2$–$C_6$-haloalkenoxy, $C_2$–$C_6$-haloalkynyl, $C_2$–$C_6$-haloalkynyloxy, phenyl, phenoxy, hetaryl or hetaryloxy.

8. A process for preparing the compounds of the formula I as claimed in claim 1, where $R^1$ is not hydrogen, which comprises reacting a methyleneanilide of the formula II

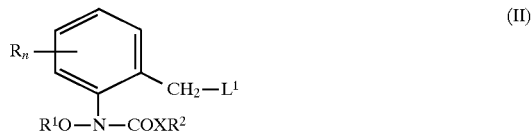

where $L^1$ is a leaving group, with an oxime of the formula III

or its salt.

9. A process for preparing the compounds of the formula I as claimed in claim 1, where $R^1$ is hydrogen, which comprises converting a nitrobenzene of the formula IV

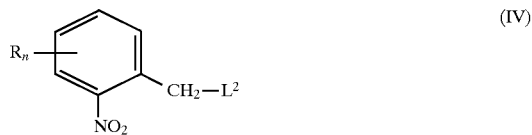

where $L^2$ is a leaving group, with an oxime of the formula HO—N=$CR^3R^4$ or its salts, into the corresponding oxime ether of the formula V

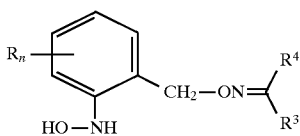 (V)

reducing V in a manner known per se to the hydroxylamine of the formula VI

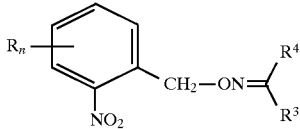 (VI)

and then reacting VI a) with an acylating agent of the formula VIIa

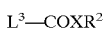 (VIIa)

where $L^3$ is halogen, phenoxy or the group $R^2XCO_2$, or b) with an isocyanate of the formula VIIb

 (VIIb)

or c) with a cyanate of the formula VIIc

 (VIIc)

where $M^+$ is an equivalent of a metal ion, to give a compound according to formula I.

10. A process for preparing the compounds of the formula I as claimed in claim 1, where $R^1$ is not hydrogen, which comprises reacting a compound of the formula I, where $R^1$ is hydrogen, in a manner known per se with a compound of the formula VIII

 (VIII)

where $L^4$ is a leaving group.

11. A process for preparing the compounds of the formula I as claimed in claim 1, which comprises first converting a methyleneanilide of the formula II

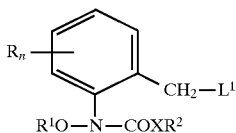 (II)

with N-hydroxyphthalimide (IX)

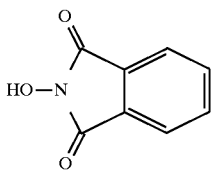 (IX)

into the benzyl ether of the formula X

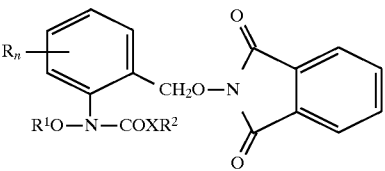 (X)

then hydrolyzing X with ammonia, hydrazine or an amine or with acid catalysis to the hydroxylamine ether of the formula XI

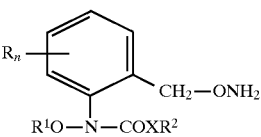 (XI)

and then reacting XI with a carbonyl compound of the formula XII $$O=CR^3R^4 \quad (XII)$$

to give a compound according to formula I.

12. A process for preparing the compounds of the formula I as claimed in claim 1, where X is $NR^a$, which comprises first converting a methyleneanilide of the formula IIa

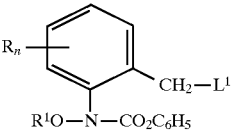 (IIa)

where $L^1$ is a leaving group, with an oxime of the formula $HO-N=CR^3R^4$ or its salts, into the corresponding oxime ether of the formula XIII

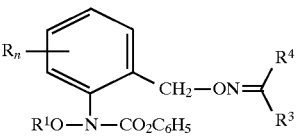 (XIII)

and then reacting XIII with an amine of the formula XIV $$H_2NR^a \quad (XIV)$$

to give a compound according to formula I.

13. An intermediate of the formula XV

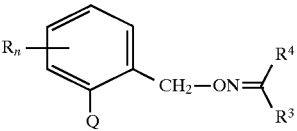 (XV)

where

Q is $NO_2$, NHOH or $N(OR^1)-CO_2C_6H_5$, n is 0, 1, 2, 3 or 4, it being possible for the substituents R to be different if n is greater than 1;

R is nitro, cyano, halogen,
$C_1-C_{10}$-alkyl, $C_2-C_{10}$-alkenyl, $C_2-C_{10}$-alkynyl, $C_1-C_{10}$-alkoxy, $C_3-C_{10}$-alkenyloxy and $C_3-C_{10}$-alkynyloxy, it being possible for these groups to be partially or completely halogenated and/or to carry one to three of the following radicals:
cyano, nitro, hydroxyl, amino, formyl, carboxyl, aminocarbonyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylamino, di-$C_1$–$C_6$-alkylamino, $C_1$–$C_6$-alkylcarbonyl, $C_1$–$C_6$-alkoxycarbonyl, $C_1$–$C_6$-alkylcarbonyloxy, $C_1$–$C_6$-alkylaminocarbonyl, di-$C_1$–$C_6$-alkylaminocarbonyl, $C_1$–$C_6$-alkylcarbonylamino, $C_1$–$C_6$-alkoxycarbonylamino, $C_1$–$C_6$-alkylcarbonyl-N-$C_1$–$C_6$-alkylamino, and $CR^{iii}$=$NOR^{iv}$, $R^{iii}$ being hydrogen, $C_1$–$C_6$-alkyl, $C_2$–$C_6$-alkenyl, $C_2$–$C_6$-alkynyl or $C_3$–$C_{12}$-cycloalkyl and $R^{iv}$ being $C_1$–$C_6$-alkyl, $C_3$–$C_6$-alkenyl, $C_3$–$C_6$-alkynyl or aryl-$C_1$–$C_6$-alkyl, $C_3$–$C_{12}$-cycloalkyl, $C_3$–$C_{12}$-cycloalkoxy, $C_3$–$C_{12}$-cycloalkylthio, $C_3$–$C_{12}$-cycloalkylamino, $C_3$–$C_{12}$-cycloalkyl-N-$C_1$–$C_6$-alkylamino, each of which is unsubstituted or substituted by customary groups, 3- to 12-membered heterocyclyl, heterocyclyloxy, heterocyclylthio, heterocyclylamino or heterocyclyl-N-$C_1$–$C_6$-alkylamino, each of which is unsubstituted or substituted by customary groups, aryl, aryloxy, arylthio, arylamino, aryl-N-$C_1$–$C_6$-alkylamino, aryl-$C_1$–$C_6$-alkoxy, aryl-$C_1$–$C_6$-alkylthio, aryl-$C_1$–$C_6$-alkylamino, aryl-$C_1$–$C_6$-alkyl-N-$C_1$–$C_6$-alkylamino, hetaryl, het-aryloxy, hetarylthio, hetarylamino, hetaryl-N-$C_1$–$C_6$-alkylamino, hetaryl-$C_1$–$C_6$-alkoxy, hetaryl-$C_1$–$C_6$-alkylthio, het-aryl-$C_1$–$C_6$-alkylamino, hetaryl-$C_1$–$C_6$-alkyl-N-$C_1$–$C_6$-alkylamino, arylcarbonyl, aryloxycarbonyl, arylcarbonyloxy, arylaminocarbonyl, N-aryl-N-$C_1$–$C_6$-alkylaminocarbonyl, arylcarbonyl-N-$C_1$–$C_6$-alkylamino, aryloxycarbonylamino, hetarylcarbonyl, hetaryloxycarbonyl, hetarylcarbonyloxy, hetarylaminocarbonyl, N-hetaryl-N-$C_1$–$C_6$-alkylaminocarbonyl, hetarylcarbonyl-N-$C_1$–$C_6$-alkylamino and hetaryloxycarbonylamino, each of which is unsubstituted or substituted by customary groups, or in the case where n is 2, 3 or 4 additionally an unsubstituted or substituted bridge bonded to two adjacent ring atoms, which contains three or four members from the group consisting of 3 or 4 carbon atoms, and 2 or 3 carbon atoms and 1 or 2 nitrogen, oxygen and/or sulfur atoms, it being possible for this bridge, together with the ring to which it is bonded, to form a partially unsaturated or aromatic radical;

X is a direct bond or $CH_2$, O or $NR^a$;

$R^a$ is hydrogen, $C_1$–$C_{10}$-alkyl, $C_2$–$C_{10}$-alkenyl, $C_2$–$C_{10}$-alkynyl, $C_3$–$C_{10}$-cycloalkyl or $C_5$–$C_{10}$-cycloalkenyl;

$R^1$ is hydrogen, $C_1$–$C_{10}$-alkyl, $C_2$–$C_{10}$-alkenyl, $C_2$–$C_{10}$-alkynyl, $C_3$–$C_{10}$-cycloalkyl, $C_5$–$C_{10}$-cycloalkenyl, $C_1$–$C_{10}$-alkylcarbonyl or $C_1$–$C_{10}$-alkoxycarbonyl, it being possible for these groups to be partially or completely halogenated and/or to carry one to three of the following radicals:

cyano, nitro, hydroxyl, amino, formyl, carboxyl, aminocarbonyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylamino, di-$C_1$–$C_6$-alkylamino, $C_1$–$C_6$-alkylcarbonyl, $C_1$–$C_6$-alkoxycarbonyl, $C_1$–$C_6$-alkylcarbonyloxy, $C_1$–$C_6$-alkylaminocarbonyl, di-$C_1$–$C_6$-alkylaminocarbonyl, $C_1$–$C_6$-alkylcarbonylamino, $C_1$–$C_6$-alkoxycarbonylamino, $C_1$–$C_6$-alkylcarbonyl-N-$C_1$–$C_6$-alkylamino, and $CR^{iii}$=$NOR^{iv}$, $R^{iii}$ being hydrogen, $C_1$–$C_6$-alkyl, $C_2$–$C_6$-alkenyl, $C_2$–$C_6$-alkynyl or $C_3$–$C_{12}$-cycloalkyl and $R^{iv}$ being $C_1$–$C_6$-alkyl, $C_3$–$C_6$-alkenyl, $C_3$–$C_6$-alkynyl or aryl-$C_1$–$C_6$-alkyl, $C_3$–$C_{12}$-cycloalkyl, $C_3$–$C_{12}$-cycloalkoxy, $C_3C_{12}$-cycloalkylthio, $C_3$–$C_{12}$-cycloalkylamino, $C_3$–$C_{12}$-cycloalkyl-N-$C_1$–$C_6$-alkylamino, each of which is unsubstituted or substituted by customary groups, 3- to 12-membered heterocyclyl, heterocyclyloxy, heterocyclylthio, heterocyclylamino or heterocyclyl-N-$C_1$–$C_6$-alkylamino, each of which is unsubstituted or substituted by customary groups, aryl, aryloxy, arylthio, arylamino, aryl-N-$C_1$–$C_6$-alkylamino, aryl-$C_1$–$C_6$-alkoxy, aryl-$C_1$–$C_6$-alkylthio, aryl-$C_1$–$C_6$-alkylamino, aryl-$C_1$–$C_6$-alkyl-N-$C_1$–$C_6$-alkyl-amino, hetaryl, hetaryloxy, hetarylthio, hetarylamino, hetaryl-N-$C_1$–$C_6$-alkylamino, hetaryl-$C_1$–$C_6$-alkoxy, hetaryl-$C_1$–$C_6$-alkylthio, hetaryl-$C_1$–$C_6$-alkylamino, hetaryl-$C_1$–$C_6$-alkyl-N-$C_1$–$C_6$-alkylamino, arylcarbonyl, aryloxycarbonyl, arylcarbonyloxy, arylaminocarbonyl, N-aryl-N-$C_1$–$C_6$-alkylaminocarbonyl, arylcarbonyl-N-$C_1$–$C_6$-alkylamino, aryloxycarbonylamino, hetarylcarbonyl, hetaryloxycarbonyl, hetarylcarbonyloxy, hetarylaminocarbonyl, N-hetaryl-N-$C_1$–$C_6$-alkylaminocarbonyl, hetarylcarbonyl-N-$C_1$–$C_6$-alkylamino and hetaryloxycarbonylamino, each of which is unsubstituted or substituted by customary groups, $R^3$ is hydrogen, cyano, halogen, $C_1$–$C_{10}$-alkyl, $C_1$–$C_{10}$-haloalkyl, $C_1$–$C_{10}$-alkoxy, $C_1$–$C_{10}$-haloalkoxy, $C_1$–$C_{10}$-alkylthio, $C_1$–$C_4$-haloalkylthio or $C_3$–$C_{10}$-cycloalkyl;

$R^4$ is a 6- to 10-membered mono- or bicyclic, heteroaromatic ring system selected from the group consisting of:

2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, indolyl, quinolinyl, isoquinolinyl and purinyl, which is substituted by customary groups;

it being possible for the radicals substituted by customary groups to be:

partially or completely halogenated, and/or one to four of the following radicals cyano, nitro, hydroxyl, amino, carboxyl, aminocarbonyl, $C_1$–$C_6$-alkyl, $C_1$–$C_6$-haloalkyl, $C_2$–$C_8$-alkenyl, $C_2$–$C_8$-haloalkenyl, $C_2$–$C_8$-alkenyloxy, $C_2$–$C_8$-haloalkenyloxy, $C_2$–$C_8$-alkynyl, $C_2$–$C_8$-haloalkynyl, $C_2$–$C_8$-alkynyloxy, $C_2$–$C_8$-haloalkynyloxy, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylamino, di-$C_1$–$C_6$-alkylamino, $C_1$–$C_6$-alkylcarbonyl, $C_1$–$C_6$-alkoxycarbonyl, $C_1$–$C_6$-alkylcarbonyloxy, $C_1$–$C_6$-alkylaminocarbonyl, di-$C_1$–$C_6$-alkylaminocarbonyl, $C_1$–$C_6$-alkylcarbonylamino, $C_1$–$C_6$-alkoxycarbonylamino and $C_1$–$C_6$-alkylcarbonyl-N-$C_1$–$C_6$-alkylamino, and/or one to three of the following radicals $C_3$–$C_{12}$-cycloalkyl, $C_3$–$C_{12}$-cycloalkoxy, $C_3$–$C_{12}$-cycloalkylthio, $C_3$–$C_{12}$-cycloalkylamino, $C_3$–$C_{12}$-cycloalkyl-N-$C_1$–$C_6$-alkylamino, 3- to 12-membered heterocyclyl, heterocyclyloxy, heterocyclylthio, heterocyclylamino or heterocyclyl-N-$C_1$–$C_6$-alkylamino, aryl, aryloxy, arylthio, arylamino, aryl-N-$C_1$–$C_6$-alkylamino, aryl-$C_1$–$C_6$-alkoxy, aryl-$C_1$–$C_6$-alkylthio, aryl-$C_1$–$C_6$-alkylamino, aryl-$C_1$–$C_6$-alkyl-N-$C_1$–$C_6$-alkylamino, hetaryl, hetaryloxy, hetarylthio, hetarylamino, hetaryl-N-$C_1$–$C_6$-alkylamino, hetaryl-$C_1$–$C_6$-alkoxy, hetaryl-$C_1$–$C_6$-alkylthio, hetaryl-$C_1$–$C_6$-alkylamino, hetaryl-$C_1$–$C_6$-alkyl-N-$C_1$–$C_6$-alkylamino, arylcarbonyl, aryloxycarbonyl, arylcarbonyloxy, arylaminocarbonyl, N-aryl-N-$C_1$–$C_6$-alkylaminocarbonyl, arylcarbonyl-N-$C_1$–$C_6$-alkylamino, aryloxycarbonylamino, hetarylcarbonyl, hetaryloxycarbonyl, hetarylcarbonyloxy, hetarylaminocarbonyl, N-hetaryl-N-$C_1$–$C_6$-alkylaminocarbonyl, hetarylcarbonyl-N-$C_1$–$C_6$-alkylamino and hetaryloxycarbonylamino,
and or one or two of the following radicals formyl or $CR^{iii}$=$NOR^{iv}$, $R^{iii}$ being hydrogen, $C_1$–$C_6$-alkyl, $C_2$–$C_6$-alkenyl, $C_3$–$C_{10}$-cycloalkyl or $C_2$–$C_6$-alkynyl and $R^{iv}$ being $C_1$–$C_6$-alkyl, $C_2$–$C_6$-alkenyl, $C_2$–$C_6$-alkynyl and aryl-$C_1$–$C_6$-alkyl, or a $C_3$–$C_5$-alkylene, $C_3$–$C_5$-alkenylene, oxy-$C_2$–$C_4$-alkylene, oxy-$C_1$–$C_3$-alkyleneoxy, oxy-$C_2$–$C_4$-alkenylene, oxy-$C_2$–$C_4$-alkenyleneoxy or butadienediyl group bonded to two adjacent C atoms, it being possible for these bridges in turn to be partially or completely halogenated and/or to carry one to three of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

14. A composition suitable for controlling animal pests or harmful fungi, containing a solid or liquid carrier and a compound of the formula I as claimed in claim 1.

15. A method of controlling animal pests or harmful fungi, which comprises treating the fungi or the materials, plants, soil or seed to be protected from fungal attack with an effective amount of a compound of the formula I as claimed in claim 1.

* * * * *

UNITED STATES PATENT AND TRADEMARK OFFICE
CERTIFICATE OF CORRECTION

PATENT NO.: 5,814,633

DATED: September 29, 1998

INVENTOR(S): Müller et al.

It is certified that error appears in the above-identified patent and that said Letters Patent is hereby corrected as shown below:

Col. 126, claim 1, line 17, insert --or,-- after "groups,".

Col. 127, claim 1, line 48, "Cycloalkyl" should be --cycloalkyl--.

Col. 131, claim 13, line 6, "alkvlcarbonylamino" should be --alkylcarbonylamino--.

Signed and Sealed this

Nineteenth Day of January, 1999

*Attest:*

*Attesting Officer*

*Acting Commissioner of Patents and Trademarks*